US008906913B2

(12) United States Patent
Jain et al.

(10) Patent No.: US 8,906,913 B2
(45) Date of Patent: Dec. 9, 2014

(54) AZABICYCLOHEXANES

(75) Inventors: Rajesh Jain, New Delhi (IN); Sanjay Trehan, New Delhi (IN); Jagattaran Das, New Delhi (IN); Gurmeet Kaur, New Delhi (IN); Sandeep Kanwar, New Delhi (IN); Nishan Singh, New Delhi (IN); Gurmeet Kaur Nanda, New Delhi (IN); Sitaram Kumar Magadi, New Delhi (IN); Sudhir Kumar Sharma, New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 156 days.

(21) Appl. No.: 13/380,744

(22) PCT Filed: Jun. 22, 2010

(86) PCT No.: PCT/IN2010/000428
§ 371 (c)(1),
(2), (4) Date: Mar. 19, 2012

(87) PCT Pub. No.: WO2010/150281
PCT Pub. Date: Dec. 29, 2010

(65) Prior Publication Data
US 2012/0165320 A1    Jun. 28, 2012

(30) Foreign Application Priority Data

Jun. 26, 2009 (IN) .......................... 1320/DEL/2009
Mar. 10, 2010 (IN) ............................ 555/DEL/2010
Jun. 3, 2010 (IN) .......................... 1297/DEL/2010

(51) Int. Cl.
| | |
|---|---|
| A61K 31/5355 | (2006.01) |
| C07D 413/10 | (2006.01) |
| C07D 209/52 | (2006.01) |
| C07D 417/14 | (2006.01) |
| C07D 491/08 | (2006.01) |
| C07D 221/22 | (2006.01) |
| C07D 487/04 | (2006.01) |
| C07D 413/14 | (2006.01) |
| C07D 409/04 | (2006.01) |
| C07D 471/04 | (2006.01) |
| C07D 417/10 | (2006.01) |
| C07D 401/10 | (2006.01) |

(52) U.S. Cl.
CPC ............ *C07D 221/22* (2013.01); *C07D 209/52* (2013.01); *C07D 417/14* (2013.01); *C07D 491/08* (2013.01); *C07D 487/04* (2013.01); *C07D 413/14* (2013.01); *C07D 409/04* (2013.01); *C07D 471/04* (2013.01); *C07D 417/10* (2013.01); *C07D 413/10* (2013.01); *C07D 401/10* (2013.01)
USPC ..... 514/235.2; 514/218; 514/221; 514/228.2; 514/343; 514/376; 514/414; 540/492; 540/514; 544/61; 544/143; 546/271.4; 548/231; 548/467

(58) Field of Classification Search
USPC ........... 514/218, 221, 228.2, 235.2, 343, 376, 514/414; 540/492, 514; 544/61, 143; 546/271.4; 548/231, 467
See application file for complete search history.

(56) References Cited

U.S. PATENT DOCUMENTS

| | | | |
|---|---|---|---|
| 5,565,571 A | 10/1996 | Barbachyn et al. | |
| 5,654,428 A | 8/1997 | Barbachyn et al. | |
| 5,654,435 A | 8/1997 | Barbachyn et al. | |
| 5,756,732 A | 5/1998 | Barbachyn et al. | |
| 5,801,246 A | 9/1998 | Barbachyn et al. | |
| 6,689,779 B2 | 2/2004 | Lee et al. | |
| 7,855,298 B2* | 12/2010 | Arista et al. ............... | 548/264.2 |
| 2007/0155798 A1 | 7/2007 | Rhee et al. | |

FOREIGN PATENT DOCUMENTS

| | | |
|---|---|---|
| CN | 101434584 A | 5/2009 |
| WO | WO 93/09103 A1 | 5/1993 |
| WO | WO 95/07272 A1 | 3/1995 |
| WO | WO 96/35691 A1 | 11/1996 |
| WO | WO 00/29396 A1 | 5/2000 |
| WO | WO 00/73301 A1 | 12/2000 |
| WO | WO 01/94342 A1 | 12/2001 |
| WO | WO 02/064547 A2 | 8/2002 |
| WO | WO 02/081469 A1 | 10/2002 |
| WO | WO 02/081470 A1 | 10/2002 |
| WO | WO 02/002095 A2 | 12/2002 |
| WO | WO 03/006447 A2 | 1/2003 |
| WO | WO 03/007870 A2 | 1/2003 |
| WO | WO 03/008389 A1 | 1/2003 |
| WO | WO 03/064415 A1 | 8/2003 |
| WO | WO 03/072553 A1 | 9/2003 |
| WO | WO 03/097059 A1 | 11/2003 |
| WO | WO 2004/009587 A1 | 1/2004 |

(Continued)

OTHER PUBLICATIONS

Arista et al. "Preparation of N-(4H-1,2,4-trazol . . . " CA143:266934 (2005).*
Drug Metabolism, Wikipedia, p. 1-4 (2011).*
Giovannini et al. "Preparation of phenyl . . . " CA158:301984 (2013).*
Hamprecht et al. "Use of azabicyclohexane . . . " CA146:295767 (2007).*
ACPS meeting "Scientific consideration . . . " p 1-5 (2002).*
Prodrug "definition" Am. Hertage dictionary p. 1 (2013).*

(Continued)

*Primary Examiner* — Celia Chang
(74) *Attorney, Agent, or Firm* — Lowe Hauptman & Ham, LLP

(57) ABSTRACT

The present invention relates to novel compounds of Formula I, their pharmaceutically acceptable derivatives, tautomeric forms, stereoisomers including R and S isomers, polymorphs, prodrugs, metabolites, salts or solvates thereof. The invention also relates to processes for the synthesis of novel compounds of Formula I, their pharmaceutically acceptable derivatives, tautomeric forms, stereoisomers, polymorphs, prodrugs, metabolites, salts or solvates thereof.

11 Claims, No Drawings

(56) References Cited

FOREIGN PATENT DOCUMENTS

| | | |
|---|---|---|
| WO | WO 2004/014392 A1 | 2/2004 |
| WO | WO 2004/018439 A1 | 3/2004 |
| WO | WO 2004/033451 A1 | 4/2004 |
| WO | WO 2004/056817 A1 | 7/2004 |
| WO | WO 2004/056818 A1 | 7/2004 |
| WO | WO 2004/089943 A1 | 10/2004 |
| WO | WO 2005/003087 A2 | 1/2005 |
| WO | WO 2005/005399 A1 | 1/2005 |
| WO | WO 2005/058886 A1 | 6/2005 |
| WO | WO 2005/082897 A1 | 9/2005 |
| WO | WO 2005/082900 A2 | 9/2005 |
| WO | WO 2005/116021 A1 | 12/2005 |
| WO | WO 2005/116024 A1 | 12/2005 |
| WO | WO 2006/035283 A1 | 4/2006 |
| WO | WO 2006/043121 A1 | 4/2006 |
| WO | WO 2006/109056 A1 | 10/2006 |
| WO | WO 2007/000432 A1 | 1/2007 |
| WO | WO 2007/004037 A1 | 1/2007 |
| WO | WO 2007/040326 A1 | 4/2007 |
| WO | WO 2007/082910 A1 | 7/2007 |
| WO | WO 2007/093904 A1 | 8/2007 |
| WO | WO 2007/095784 A1 | 8/2007 |
| WO | WO 2007/114326 A1 | 10/2007 |
| WO | WO 2005/005422 A1 | 6/2012 |

OTHER PUBLICATIONS

Salman et al. "Preparation of oxazolidinone . . . " CA143:286414 (2005).*

Seddon "Pweudopolymorph . . . " Crystal growth and design, 4(6) p. 1087 (2004).*

Examination Guidelines Federal Registeer p. 1-34 (2010).*

Alan H. Mutnick et al., "Linezolid Resistance Since 2001: Sentry Antimicrobial Surveillance Program", The Annals of Pharmacotherapy, Jun. 2003, vol. 37, pp. 769-774.

Christopher Walsh et al., "Introduction: Antibiotic Resistance", Chemical Reviews; American Chemical Society, 2005, vol. 105, No. 2, pp. 391-393.

Douglas Hutchinson et al., "Recent advances in oxazolidinone antibacterial agent research", Expert Opinion; Ther. Patents, 2004, vol. 14, No. 9, pp. 1309-1328.

* cited by examiner

AZABICYCLOHEXANES

RELATED APPLICATIONS

The present application is a National Phase of International Application Number PCT/IN2010/000428, filed Jun. 22, 2010 and claims priority from, India Application Numbers 1297/DEL/2010, filed Jun. 3, 2010, 555/DEL/2010, filed Mar. 10, 2010 and 1320/DEL/2009, filed Jun. 26, 2009.

FIELD OF THE INVENTION

The present invention relates to novel compounds of Formula I, their pharmaceutically acceptable derivatives, tautomeric forms, stereoisomers including R and S isomers, polymorphs, prodrugs, metabolites, salts or solvates thereof. The invention also relates to processes for the synthesis of novel compounds of Formula I, their pharmaceutically acceptable derivatives, tautomeric forms, stereoisomers, polymorphs, prodrugs, metabolites, salts or solvates thereof. The present invention also provides pharmaceutical compositions comprising compounds of Formula I, and methods of treating or preventing one or more disorders of the central and/or peripheral nervous system or microbial infections.

BACKGROUND OF THE INVENTION

Azabicyclo[3.1.0] hexane derivatives have been extensively known in the prior art for the treatment of central nervous system disorders, as antimicrobial agents, as having anxiolytic and analgesic activity, as vanilloid receptor ligands and for the treatment of Hepatitis C virus infection. Depending upon the selection of different types of substituents on the main scaffold "3-azabicyclo[3.1.0]hexane", the specificity or affinity for the different targets varies.

For example, U.S. Pat. No. 4,435,419 (American Cyanamid Company) discloses 3-azabicyclo[3.1.0]hexanes exhibiting antidepressant properties. U.S. Pat. No. 4,131,611 (American Cyanamid Company) discloses 3-azabicyclo [3.1.0]hexanes having anxiolytic and analgesic activity.

PCT application WO 2002066427 (DOV pharmaceuticals, Inc.) discloses (+)-1-(3,4-dichlorophenyl)-3-azabicyclo [3.1.0]hexane. PCT application WO 2003017927 (DOV pharmaceuticals, Inc.) discloses (−)-1-(3,4-dichlorophenyl)-3-azabicyclo[3.1.0]hexane. DOV's PCT applications WO 2008153937, WO 2007016155 and WO 2006096810 further disclose substituted 3-azabicyclo[3.2.1]hexanes. PCT application WO 2008057575 (DOV pharmaceuticals, Inc.) discloses arylbicyclo[3.1.0]hexylamines.

Glaxo's following PCT applications disclose 3-azabicyclo [3.1.0]hexane derivatives: WO 2009027293, WO 2008074716, WO 2007113258, WO 2007113232, WO 2007022935, WO 2007022934, WO 2007022936, WO 2007022933, WO 2007136223, WO 2006133945, WO 2006108701, WO 2006108700 and WO 2005080382.

US patent application US 2008/0176860, discloses azabicyclo[3.1.0]hexyl-O-phenyl-oxazolidinone derivatives as antimicrobial agents. WO 05/005398 discloses phenyl oxazolidinone linked to azabicyclo[3.1.0]hexane moiety as antibiotics. PCT publications bearing number WO 03/027083, WO 04/089943, WO 04/033451, WO 05/005399 and WO 05/005422 disclose azabicyclo[3.1.0]hexyl-phenyl-oxazolidinone derivatives as antimicrobial agents. Other references include *J. Med. Chem.* 2005, 48, 5009 disclosing azabicyclo [3.1.0]hexyl-phenyl-oxazolidinones as antibacterials and *J. Med. Chem.* 2008, 51, 6558 disclosing biaryl oxazolidinones bearing azabicyclo[3.1.0]hex-6-yl ring system as antibacterials. Phenyl oxazolidinones linked to the cyclopropyl moiety of azabicyclohexane scaffold have been discussed in *Biorg. Med. Chem. Lett.* 2006, 16, 1126.

PCT patent application WO 05/082899, discloses phenyl oxazolidinones as antibacterial compounds. According to their Markush structure, the invention encompasses phenyl oxazolidinones linked to 3-azabicyclo[3.1.0]hexane core through nitrogen of azabicyclo hexane. However, Compound No. 32, (S)—N-{[3-(3-Fluoro-4-{3-(1α,5α,6α)-6-[N-methyl-N-(5-nitro-furan-2-yl)amino]-3-azabicyclo-[3.1.0] hexyl}phenyl)-2-oxo-oxazolidin-5-yl]methyl}acetamide, representing the Structure A has been wrongly interpreted by the databases (Thomson Pharma and Scifinder) as Structure B.

Structure A

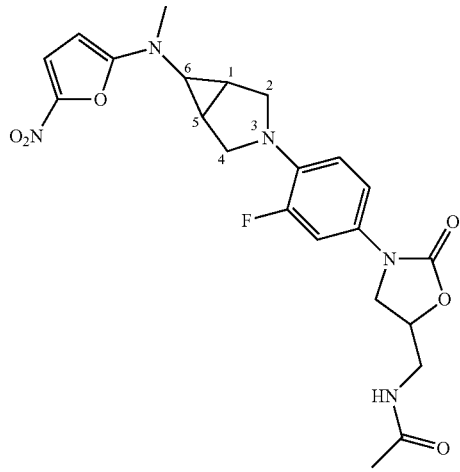

Structure B

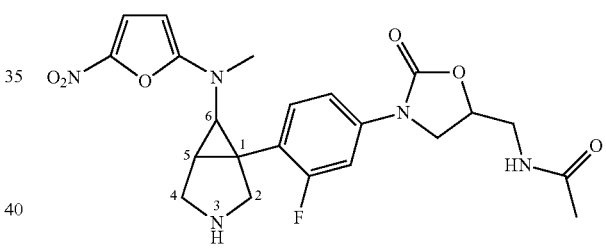

This Compound No. 32 neither falls under the coverage of the Markush of '899 patent application nor it is the actual invention. The synthetic procedure for its preparation and $^1$H NMR data given for it in '899 patent application also suggest Compound No. 32 to be Structure A.

The compounds of the present invention are structurally different from the known 3-azabicyclo[3.1.0]hexane derivatives.

SUMMARY OF THE INVENTION

The present invention relates to the novel compounds of the Formula I,

Formula I

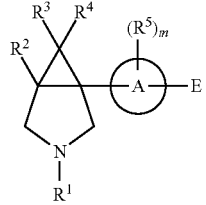

their pharmaceutically acceptable derivatives, tautomeric forms, stereoisomers including R and S isomers, polymorphs, prodrugs, metabolites, salts or solvates thereof, wherein, E represents

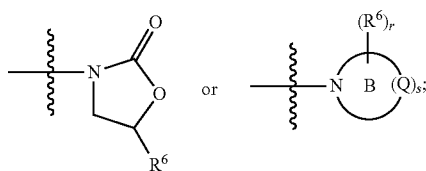

ring A represents either aryl or heteroaryl;
ring B represents heterocyclyl attached to ring A through a nitrogen atom at any available position of ring A, ring B can further be fused to one or more aryl, heteroaryl, cycloalkyl or heterocyclyl rings, with the proviso that ring B cannot be isoxazolyl, —CH$_2$—N-pyrrolyl, 1,1-dioxido-2-isothiazolidinyl, thienyl, thiazolyl, pyridyl or 2-pyrrolidinonyl;

$R^1$, $R^2$ and $R^4$ are independently selected from —H, $C_{1-12}$ alkyl, $C_{2-12}$ alkenyl, $C_{2-12}$ alkynyl, $C_{1-12}$ alkoxyalkyl, $C_{2-12}$ alkoxyalkenyl, $C_{2-12}$ alkoxyalkynyl, $C_{3-20}$ cycloalkyl, $C_{3-20}$ cycloalkenyl, $C_{6-20}$ cycloalkynyl, heterocyclyl, aryl, heteroaryl, $C_{1-12}$ alkyl-cycloalkyl, $C_{1-12}$ alkyl-heterocyclyl, $C_{1-12}$ alkyl-aryl, $C_{1-12}$ alkyl-heteroaryl; $C_{2-12}$ alkenyl-cycloalkyl, $C_{2-12}$ alkenyl-heterocyclyl, $C_{2-12}$ alkenyl-aryl, $C_{2-12}$ alkenyl-heteroaryl; $C_{2-12}$ alkynyl-cycloalkyl, $C_{2-12}$ alkynyl-heterocyclyl, $C_{2-12}$ alkynyl-aryl, $C_{2-12}$ alkynyl-heteroaryl, —CN, —NH$_2$, —CHO, —COR$^a$, —CSR$^a$, —COOR$^a$, —NR$^a$R$^b$, —CONR$^a$NR$^b$R$^c$, —(C=NR$^a$)—NR$^b$R$^c$, —CHS, —COOH, —COCOR$^a$, —CONH$_2$, —CONHNH$_2$, —CSNHNH$_2$, —CONR$^a$R$^b$, —CSNH$_2$, —CSNR$^a$R$^b$, —C(=NOR$^b$)R$^a$—NH$_2$, —NHNH$_2$, —NR$^a$NR$^b$R$^c$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OH or —OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

$R^3$ represents —(CH$_2$)$_p$Z;
Z is selected from —H, halogen, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-20}$ cycloalkyl, $C_{3-20}$ cycloalkenyl, $C_{6-20}$ cycloalkynyl, heterocyclyl, aryl, heteroaryl, —NH$_2$, —CHO, —COR$^a$, —CSR$^a$, —COOR$^a$, —CONR$^a$R$^b$, —CSNR$^a$R$^b$, —NR$^a$R$^b$,
—CONR$^a$NR$^b$R$^c$, —(C=NR$^a$)—NR$^b$R$^c$, —OH or —OR$^a$;
each of which may be optionally substituted at any available position by one or more substituents selected from but not limited to —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$) (CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, halogen, —P(O)R$^a$R$^b$, —P(O)OR$^a$OR$^b$, —P(O)R$^a$OR$^b$, —P(O)NR$^a$OR$^b$ or —P(O)NR$^a$R$^b$;

$R^5$ and $R^6$ are independently selected from —H, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-20}$ cycloalkyl, $C_{3-20}$ cycloalkenyl, $C_{6-20}$ cycloalkynyl, heterocyclyl, aryl, heteroaryl, $C_{1-12}$ alkyl-cycloalkyl, $C_{1-12}$ alkyl-heterocyclyl, $C_{1-12}$ alkyl-aryl, $C_{1-12}$ alkyl-heteroaryl; $C_{2-12}$ alkenyl-cycloalkyl, $C_{2-12}$ alkenyl-heterocyclyl, $C_{2-12}$ alkenyl-aryl, $C_{2-12}$ alkenyl-heteroaryl; $C_{2-12}$ alkynyl-cycloalkyl, $C_{2-12}$ alkynyl-heterocyclyl, $C_{2-12}$ alkynyl-aryl, $C_{2-12}$ alkynyl-heteroaryl, oxo, —NH$_2$, —CHO, —COR$^a$, —CSR$^a$, —COOR$^a$, —CONR$^a$R$^b$, —CSNR$^a$R$^b$, —NR$^a$R$^b$, —CONR$^a$N(R$^b$)$_2$, —(C=NR$^a$)—NR$^b$R$^c$, —(CH$_2$)$_n$—N$_3$, —(CH$_2$)$_n$—NCS, —C(=Y)R$^a$, —C(=Y)OR$^a$, —C(=Y)NR$^a$R$^b$, —(CH$_2$)$_n$YR$^a$, —(CH$_2$)$_n$OP(=O)R$^a$R$^b$, —(CH$_2$)$_n$NHP(=O)R$^a$R$^b$, —(CH$_2$)$_n$OC(=Y)R$^a$, —(CH$_2$)$_n$OC(=Y)OR$^a$, —(CH$_2$)$_n$C(=Y)R$^a$, —(CH$_2$)$_n$C(=Y)NR$^a$R$^b$, —(CH$_2$)$_n$OC(=Y)NR$^a$R$^b$, —(CH$_2$)$_n$C(=Y)OR$^a$, —(CH$_2$)$_n$NR$^a$R$^b$, —(CH$_2$)$_n$NR$^a$C(=Y)R$^b$, —(CH$_2$)$_n$NR$^a$C(=Y)OR$^b$, —(CH$_2$)$_n$NR$^a$C(=Y)NR$^a$R$^b$, —(CH$_2$)$_n$NR$^a$SO$_2$R$^b$, —OH or —OR$^a$; each of which may be optionally substituted at any available position by one or more substituents selected from but not limited to halogen, —CN, —CHO, —COR$^a$, —CHS, —CSR$^a$, COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

or $R_5$ and $R_6$ are joined together to form a 5 to 10 membered heterocyclic ring which can be optionally substituted at any available position with $C_{1-12}$ alkyl, $C_{2-12}$ alkenyl, $C_{2-12}$ alkynyl, $C_{1-12}$ haloalkyl, $C_{3-20}$ cycloalkyl, heterocyclyl, aryl, heteroaryl, oxo, —NH$_2$, —NO$_2$, —N$_3$, —CN, —CHO, —COR$^c$, —CHS, —CSR$^c$, —COOH, —COOR$^c$, —OH, —OR$^c$, —SH or —SR$^c$;

with the proviso that when $R^1$, $R^2$ and $R^3$ represent —H, ring A represents phenyl, m is 1, $R^5$ is —F and $R^6$ is —CH$_2$—NH—CO—CH$_3$,
then $R^4$ cannot be

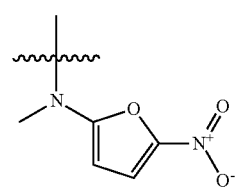 [SMILES: *N(C)c1ccc([N+](=O)[O-])o1]

{N-methyl-N-(5-nitro-furan-2-yl)amino};
Q is independently selected from —CH$_2$—, O, S, SO, SO$_2$, —N(R$^a$)—, —(CO)—, —(CS)—, —CR$^a$(N(R$^b$)$_2$)—, —C(=NR$^a$)—, —CR$^a$(OR$^b$)—, —CR$^a$R$^b$—, —P(O)

R$^a$—, —P(O)(OR$^a$)—, —CR$^a$(SR$^b$)—, —CR$^a$(SO$_3$R$^b$)—, —CR$^a$(SOR$^b$)—, —CR$^a$(SO$_2$R$^b$)— or —CR$^a$(SO$_2$NR$^b$R$^c$)—;

R$^a$ and R$^b$ are same or different and can independently be selected from —H, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, C$_{1-12}$ alkyl-aryl, C$_{1-12}$ alkyl-heteroaryl; C$_{2-12}$ alkenyl-cycloalkyl, C$_{2-12}$ alkenyl-heterocyclyl, C$_{2-12}$ alkenyl-aryl, C$_{2-12}$ alkenyl-heteroaryl; C$_{2-12}$ alkynyl-cycloalkyl, C$_{2-12}$ alkynyl-heterocyclyl, C$_{2-12}$ alkynyl-aryl or C$_{2-12}$ alkynyl-heteroaryl; each of which may be optionally substituted at any available position by one or more substituents selected from but not limited to —CN, —CHO, —COR$^c$, —CHS, —CSR$^c$, —COOH, —COOR$^c$, —COCN, —CONH$_2$, —CONHNH$_2$, —CSNHNH$_2$, —CONR$^c$R$^d$, —CSNH$_2$, —CSNR$^c$R$^d$, —C(=NOR$^c$)R$^d$, oxo, —NH$_2$, —NHNH$_2$, —NR$^c$R$^d$, —NR$^c$N(R$^d$)$_2$, —N$_3$, —NO$_2$, —N(R$^c$)(CO)R$^d$, N(R$^c$)(CO)OR$^d$, —N(R$^c$)(CO)N(R$^d$)$_2$, —N(R$^c$)(CS)R$^d$, —N(R$^c$)(CS)OR$^d$, —N(R$^c$)(CS)N(R$^d$)$_2$, —NR$^a$(C=NR$^a$)NR$^a$R$^b$, —OH, —OR$^c$, —OCOR$^c$, —OCOOR$^c$, —OCONR$^c$R$^d$, —SH, —SR$^c$, —SO$_3$H, —SOR$^c$, —SO$_2$R$^c$, —SO$_2$NR$^c$R$^d$, halogen, —P(O)R$^c$R$^d$, P(O)OR$^c$OR$^d$, —P(O)R$^c$OR$^d$, —P(O)NR$^c$OR$^d$, —P(O)NR$^c$R$^d$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

or

R$^a$ and R$^b$ are joined together to form a C$_{3-20}$ cycloalkyl, C$_{3-20}$ cycloalkenyl, C$_{6-20}$ cycloalkynyl, heterocyclyl, aryl or heteroaryl ring which can be optionally substituted at any available position with Q.

R$^c$ and R$^d$ are same or different and can independently selected from —H, C$_{1-12}$ alkyl, C$_{2-12}$ alkenyl, C$_{2-12}$ alkynyl, C$_{3-20}$ cycloalkyl, heterocyclyl, aryl, heteroaryl, —CN, —CHO, —COOH, —COCN, —CONH$_2$, —CONHNH$_2$, —CSNHNH$_2$, —CSNH$_2$, oxo, —NH$_2$, —NHNH$_2$, —N$_3$, —NO$_2$, —OH, —SH, —SO$_3$H or halogen;

Y is O or S;
m is 0, 1, 2, 3 or 4;
n is 0, 1, 2, 3 or 4;
r is 0, 1, 2, 3 or 4;
p is 0, 1, 2, 3, 4, 5, 6, 7, 8, 9, 10;
s is 0, 1, 2, 3 or 4.

Another aspect of the invention provides processes for the preparation of the novel compounds of Formula I, their pharmaceutically acceptable derivatives, tautomeric forms, stereoisomers including R and S isomers, polymorphs, prodrugs, metabolites, salts or solvates thereof.

A further aspect of the present invention provides pharmaceutical compositions, containing compounds of Formula I, their pharmaceutically acceptable derivatives, tautomeric forms, stereoisomers including R and S isomers, polymorphs, prodrugs, metabolites, salts or solvates thereof in combination with one or more pharmaceutically acceptable carrier(s), adjuvants and vehicles.

Another aspect of the present invention is the use of the compounds of Formula I for the prophylaxis, amelioration and/or treatment of one or more condition(s)/disease(s)/disorder(s) of the central and/or peripheral nervous system or microbial infections.

Yet another aspect of the invention relates to methods of using the compounds of Formula I of the present invention or compositions comprising the compounds of Formula I, for the prophylaxis, amelioration and/or treatment of one or more condition(s)/disease(s)/disorders of the central and/or peripheral nervous system or microbial infections, which comprises administering to a subject in need thereof the compounds of Formula I or compositions comprising a pharmaceutically effective amount of the compounds of Formula I.

A further aspect of the present invention is the use of a compound of Formula I for the manufacture of a medicament for the prophylaxis, amelioration and/or treatment of one or more condition(s)/disease(s)/disorders of the central and/or peripheral nervous system or microbial infections, in a subject in need thereof preferably a mammal including a human.

In another aspect, the present invention provides a method for treating one or more condition(s)/disease(s)/disorders of the central and/or peripheral nervous system or microbial infections, in a mammal by administering a therapeutically effective amount of a compound of Formula I or a pharmaceutically acceptable salt.

The present invention also encompasses prodrugs and active metabolites of the compounds of the Formula I.

Other aspects of the invention will be set forth in the description which follows, and in part will be apparent from the description, or may be learnt by the practice of the invention.

DETAILED DESCRIPTION OF THE INVENTION

The present invention relates to the novel compounds of the Formula I,

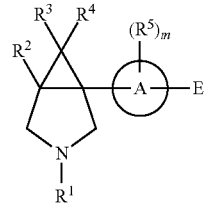

Formula I their pharmaceutically acceptable derivatives, tautomeric forms, stereoisomers including R and S isomers, polymorphs, prodrugs, metabolites, salts or solvates thereof, wherein,
E represents

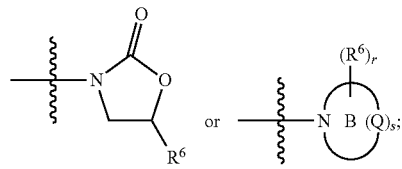

ring A represents either aryl or heteroaryl;
ring B represents heterocyclyl attached to ring A through a nitrogen atom at any available position of ring A, ring B can further be fused to one or more aryl, heteroaryl, cycloalkyl or heterocyclyl rings, with the proviso that ring B cannot be isoxazolyl, —CH$_2$—N-pyrrolyl, 1,1-dioxido-2-isothiazolidinyl, thienyl, thiazolyl, pyridyl or 2-pyrrolidinonyl;
R$^1$, R$^2$ and R$^4$ are independently selected from —H, C$_{1-12}$ alkyl, C$_{2-12}$ alkenyl, C$_{2-12}$ alkynyl, C$_{1-12}$ alkoxyalkyl, C$_{2-12}$ alkoxyalkenyl, C$_{2-12}$ alkoxyalkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, $C_{1-12}$ alkyl-aryl, $C_{1-12}$ alkyl-heteroaryl; $C_{2-12}$ alkenyl-cycloalkyl, $C_{2-12}$ alkenyl-heterocyclyl, $C_{2-12}$ alkenyl-aryl, $C_{2-12}$ alkenyl-heteroaryl; $C_{2-12}$ alkynyl-cycloalkyl, $C_{2-12}$ alkynyl-heterocyclyl, $C_{2-12}$ alkynyl-aryl, $C_{2-12}$ alkynyl-heteroaryl, —CN, —NH$_2$, —CHO, —COR$^a$, —CSR$^a$, —COOR$^a$, —NR$^a$R$^b$, —CONR$^a$NR$^b$R$^c$, —(C=NR$^a$)—NR$^b$R$^c$, —CHS, —COOH, —COCOR$^a$, —CONH$_2$, —CONHNH$_2$, —CSNHNH$_2$, —CONR$^a$R$^b$, —CSNH$_2$, —CSNR$^a$R$^b$, —C(=NOR$^b$)R$^a$—NH$_2$, —NHNH$_2$, —NR$^a$NR$^b$R$^c$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OH or —OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

$R^3$ represents —(CH$_2$)$_p$Z;

Z is selected from —H, halogen, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-20}$ cycloalkyl, $C_{3-20}$ cycloalkenyl, $C_{6-20}$ cycloalkynyl, heterocyclyl, aryl, heteroaryl, —NH$_2$, —CHO, —COR$^a$, —CSR$^a$, —COOR$^a$, —CONR$^a$R$^b$, —CSNR$^a$R$^b$, —NR$^a$R$^b$, —CONR$^a$NR$^b$R$^c$, —(C=NR$^a$)—NR$^b$R$^c$, —OH or —OR$^a$; each of which may be optionally substituted at any available position by one or more substituents selected from but not limited to —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, halogen, —P(O)R$^a$R$^b$, —P(O)OR$^a$OR$^b$, —P(O)R$^a$OR$^b$, —P(O)NR$^a$OR$^b$ or —P(O)NR$^a$R$^b$;

$R^5$ and $R^6$ are independently selected from —H, halogen, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-20}$ cycloalkyl, $C_{3-20}$ cycloalkenyl, $C_{6-20}$ cycloalkynyl, heterocyclyl, aryl, heteroaryl, $C_{1-12}$ alkyl-cycloalkyl, $C_{1-12}$ alkyl-heterocyclyl, $C_{1-12}$ alkyl-aryl, $C_{1-12}$ alkyl-heteroaryl; $C_{2-12}$ alkenyl-cycloalkyl, $C_{2-12}$ alkenyl-heterocyclyl, $C_{2-12}$ alkenyl-aryl, $C_{2-12}$ alkenyl-heteroaryl; $C_{2-12}$ alkynyl-cycloalkyl, $C_{2-12}$ alkynyl-heterocyclyl, $C_{2-12}$ alkynyl-aryl, $C_{2-12}$ alkynyl-heteroaryl, oxo, —NH$_2$, —CHO, —COR$^a$, —CSR$^a$, —COOR$^a$, —CONR$^a$R$^b$, —CSNR$^a$R$^b$, —NR$^a$R$^b$, —CONR$^a$N(R$^b$)$_2$, —(C=NR$^a$)—NR$^b$R$^c$, —(CH$_2$)$_n$—N$_3$, —(CH$_2$)$_n$—NCS, —C(=Y)R$^a$, —C(=Y)OR$^a$, —C(=Y)NR$^a$R$^b$, —(CH$_2$)$_n$YR$^a$, —(CH$_2$)$_n$OP(=O)R$^a$R$^b$, —(CH$_2$)$_n$NHP(=O)R$^a$R$^b$, —(CH$_2$)$_n$OC(=Y)R$^a$, —(CH$_2$)$_n$OC(=Y)OR$^a$, —(CH$_2$)$_n$C(=Y)R$^a$, —(CH$_2$)$_n$C(=Y)NR$^a$R$^b$, —(CH$_2$)$_n$C(=Y)NR$^a$R$^b$, —(CH$_2$)$_n$C(=Y)OR$^a$, —(CH$_2$)$_n$NR$^a$R$^b$, —(CH$_2$)$_n$NR$^a$C(=Y)R$^b$, —(CH$_2$)$_n$NR$^a$C(=Y)OR$^b$, —(CH$_2$)$_n$NR$^a$C(=Y)NR$^a$R$^b$, —(CH$_2$)$_n$NR$^a$SO$_2$R$^b$, —OH or —OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

or $R_5$ and $R_6$ are joined together to form a 5 to 10 membered heterocyclic ring which can be optionally substituted at any available position with $C_{1-12}$ alkyl, $C_{2-12}$ alkenyl, $C_{2-12}$ alkynyl, $C_{1-12}$ haloalkyl, $C_{3-20}$ cycloalkyl, heterocyclyl, aryl, heteroaryl, oxo, —NH$_2$, —NO$_2$, —N$_3$, —CN, —CHO, —COR$^c$, —CHS, —CSR$^c$, —COOH, —COOR$^c$, —OH, —OR$^c$, —SH or —SR$^c$;

with the proviso that when $R^1$, $R^2$ and $R^3$ represent —H, ring A represents phenyl, m is 1, $R^5$ is —F and $R^6$ is —CH$_2$—NH—CO—CH$_3$, then $R^4$ cannot be

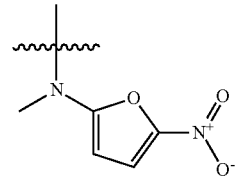 [SMILES: *N(C)c1ccc([N+](=O)[O-])o1]

{N-methyl-N-(5-nitro-furan-2-yl)amino};

Q is independently selected from —CH$_2$—, O, S, SO, SO$_2$, —N(R$^a$)—, —(CO)—, —(CS)—, —CR$^a$(N(R$^b$)$_2$)—, —C(=NR$^a$)—, —CR$^a$(OR$^b$)—, —CR$^a$R$^b$—, —P(O)R$^a$—, —P(O)(OR$^a$)—, —CR$^a$(SR$^b$)—, —CR$^a$(SO$_3$R$^b$)—, —CR$^a$(SOR$^b$)—, —CR$^a$(SO$_2$R$^b$)— or —CR$^a$(SO$_2$NR$^b$R$^c$)—;

$R^a$ and $R^b$ are same or different and can independently be selected from —H, $C_{1-12}$ alkyl, $C_{2-12}$ alkenyl, $C_{2-12}$ alkynyl, $C_{1-12}$ haloalkyl, $C_{2-12}$ haloalkenyl, $C_{2-12}$ haloalkynyl, $C_{3-20}$ cycloalkyl, $C_{3-20}$ cycloalkenyl, $C_{6-20}$ cycloalkynyl, heterocyclyl, aryl, heteroaryl, $C_{1-12}$ alkyl-cycloalkyl, $C_{1-12}$ alkyl-heterocyclyl, $C_{1-12}$ alkyl-aryl, $C_{1-12}$ alkyl-heteroaryl; $C_{2-12}$ alkenyl-cycloalkyl, $C_{2-12}$ alkenyl-heterocyclyl, $C_{2-12}$ alkenyl-aryl, $C_{2-12}$ alkenyl-heteroaryl; $C_{2-12}$ alkynyl-cycloalkyl, $C_{2-12}$ alkynyl-heterocyclyl, $C_{2-12}$ alkynyl-aryl or $C_{2-12}$ alkynyl-heteroaryl; each of which may be optionally substituted at any available position by one or more substituents selected from but not limited to —CN, —CHO, —COR$^c$, —CHS, —CSR$^c$, —COOH, —COOR$^c$, —COCN, —CONH$_2$, —CONHNH$_2$, —CSNHNH$_2$, —CONR$^c$R$^d$, —CSNH$_2$, —CSNR$^c$R$^d$, —C(=NOR$^c$)R$^d$, oxo, —NH$_2$, —NHNH$_2$, —NR$^c$R$^d$, —NR$^c$N(R$^d$)$_2$, —N$_3$, —NO$_2$, —N(R$^c$)(CO)R$^d$, N(R$^c$)(CO)OR$^d$, —N(R$^c$)(CO)N(R$^d$)$_2$, —N(R$^c$)(CS)R$^d$, —N(R$^c$)(CS)OR$^d$, —N(R$^c$)(CS)N(R$^d$)$_2$, —NR$^a$(C=NR$^a$)NR$^a$R$^b$, —OH, —OR$^c$, —OCOR$^c$, —OCOOR$^c$, —OCONR$^c$R$^d$, —SH, —SR$^c$, —SO$_3$H, —SOR$^d$, —SO$_2$R$^c$, —SO$_2$NR$^c$R$^d$, halogen, —P(O)R$^c$R$^d$, —P(O)OR$^c$R$^d$, —P(O)R$^c$OR$^d$, —P(O)NR$^c$OR$^d$, —P(O)NR$^c$R$^d$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

or

R$^a$ and R$^b$ are joined together to form a C$_{3-20}$ cycloalkyl, C$_{3-20}$ cycloalkenyl, C$_{6-20}$ cycloalkynyl, heterocyclyl, aryl or heteroaryl ring which can be optionally substituted at any available position with Q.

R$^c$ and R$^d$ are same or different and can independently selected from —H, C$_{1-12}$ alkyl, C$_{2-12}$ alkenyl, C$_{2-12}$ alkynyl, C$_{3-20}$ cycloalkyl, heterocyclyl, aryl, heteroaryl, —CN, —CHO, —COOH, —COCN, —CONH$_2$, —CONHNH$_2$, —CSNHNH$_2$, —CSNH$_2$, oxo, —NH$_2$, —NHNH$_2$, —N$_3$, —NO$_2$, —OH, —SH, —SO$_3$H or halogen;

Y is O or S;
m is 0, 1, 2, 3 or 4;
n is 0, 1, 2, 3 or 4;
r is 0, 1, 2, 3 or 4;
p is 0, 1, 2, 3, 4, 5, 6, 7, 8, 9, 10;
s is 0, 1, 2, 3 or 4.

One embodiment of the present invention provides compounds of Formula Ia,

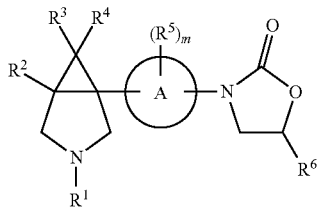

Formula Ia their pharmaceutically acceptable derivatives, tautomeric forms, stereoisomers including R and S isomers, polymorphs, prodrugs, metabolites, salts or solvates thereof, wherein, ring A represents either aryl or heteroaryl;

R$^1$ is selected from C$_{5-12}$ alkyl, C$_{5-12}$ alkenyl, C$_{5-12}$ alkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, C$_{1-12}$ alkyl-aryl, C$_{1-12}$ alkyl-heteroaryl, C$_{2-12}$ alkenyl-cycloalkyl, C$_{2-12}$ alkenyl-heterocyclyl, C$_{2-12}$ alkenyl-aryl, C$_{2-12}$ alkenyl-heteroaryl; C$_{2-12}$ alkynyl-cycloalkyl, C$_{2-12}$ alkynyl-heterocyclyl, C$_{2-12}$ alkynyl-aryl, C$_{2-12}$ alkynyl-heteroaryl, —CN, —NH$_2$, —CHO, —COR$^a$, —CSR$^a$, —COOR$^a$, —NR$^a$R$^b$, —CONR$^a$NR$^b$R$^c$, —(C=NR$^a$)—NR$^b$R$^c$, —OH, OR$^a$, —CHS, —COOH, —COCOR$^a$, —CONH$_2$, —CONHNH$_2$, —CSNHNH$_2$, —CONR$^a$R$^b$, —CSNH$_2$, —CSNR$^a$R$^b$, —C(=NOR$^b$)R$^a$—NH$_2$, —NHNH$_2$, —NR$^a$NR$^b$R$^c$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$ or —P(O)NR$^a$R$^b$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl or heteroaryl;

R$^2$ and R$^4$ are independently selected from —H, C$_{1-12}$ alkyl, C$_{2-12}$ alkenyl, C$_{2-12}$ alkynyl, C$_{1-12}$ alkoxyalkyl, C$_{2-12}$ alkoxyalkenyl, C$_{2-12}$ alkoxyalkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, C$_{1-12}$ alkyl-aryl, C$_{1-12}$ alkyl-heteroaryl; C$_{2-12}$ alkenyl-cycloalkyl, C$_{2-12}$ alkenyl-heterocyclyl, C$_{2-12}$ alkenyl-aryl, C$_{2-12}$ alkenyl-heteroaryl; C$_{2-12}$ alkynyl-cycloalkyl, C$_{2-12}$ alkynyl-heterocyclyl, C$_{2-12}$ alkynyl-aryl, C$_{2-12}$ alkynyl-heteroaryl, —NH$_2$, —CHO, —COR$^a$, —CSR$^a$, —COOR$^a$, —CONR$^a$R$^b$, —CSNR$^a$R$^b$, —NR$^a$R$^b$, —CONR$^a$NR$^b$R$^c$, —(C=NR$^a$)—NR$^b$R$^c$, —OH or OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl or heteroaryl;

R$^3$ is selected from —H or —(CH$_2$)$_p$Z;

Z is selected from —H, halogen, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-20}$ cycloalkyl, C$_{3-20}$ cycloalkenyl, C$_{6-20}$ cycloalkynyl, heterocyclyl, aryl, heteroaryl, —NH$_2$, —CHO, —COR$^a$, —CSR$^a$, —COOR$^a$, —CONR$^a$R$^b$, —CSNR$^a$R$^b$, —NR$^a$R$^b$, —CONR$^a$NR$^b$R$^c$, —(C=NR$^a$)—NR$^b$R$^c$, —OH or —OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$ or —P(O)NR$^a$R$^b$;

R⁵ is selected from —H, halogen or —OR$^a$;

R⁶ represents C$_{1-12}$ alkyl, C$_{2-12}$ alkenyl, C$_{2-12}$ alkynyl, C$_{1-12}$ alkoxyalkyl, C$_{2-12}$ alkoxyalkenyl, C$_{2-12}$ alkoxyalkynyl, C$_{3-20}$ cycloalkyl, C$_{3-20}$ cycloalkenyl, C$_{6-20}$ cycloalkynyl, heterocyclyl, aryl, heteroaryl, —(CH$_2$)$_n$-cycloalkyl, —(CH$_2$)$_n$-heterocyclyl, —(CH$_2$)$_n$-aryl, —(CH$_2$)$_n$-heteroaryl, —(CH$_2$)$_n$—N$_3$, —(CH$_2$)$_n$—NCS, —C(=Y)R$^a$, —C(=Y)OR$^a$, —C(=Y)NR$^a$R$^b$, —(CH$_2$)$_n$YR$^a$, —(CH$_2$)$_n$OP(=O)R$^a$R$^b$, —(CH$_2$)$_n$NHP(=O)R$^a$R$^b$, —(CH$_2$)$_n$OC(=Y)R$^a$, —(CH$_2$)$_n$OC(=Y)OR$^a$, —(CH$_2$)$_n$C(=Y)R$^a$, —(CH$_2$)$_n$C(=Y)NR$^a$R$^b$, —(CH$_2$)$_n$OC(=Y)NR$^a$R$^b$, —(CH$_2$)$_n$C(=Y)OR$^a$, —(CH$_2$)$_n$NR$^a$R$^b$, —(CH$_2$)$_n$NR$^a$C(=Y)R$^b$, —(CH$_2$)$_n$NR$^a$C(=Y)OR$^b$, —(CH$_2$)$_n$NR$^a$C(=Y)NR$^a$R$^b$ or —(CH$_2$)$_n$NR$^a$SO$_2$R$^b$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

with the proviso that when R¹, R² and R³ represent —H, ring A represents phenyl, m is 1, R⁵ is —F and R⁶ is —CH$_2$—NH—CO—CH$_3$, then R⁴ cannot be

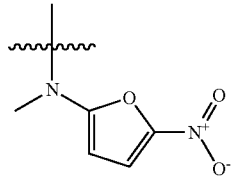 [SMILES: *N(C)c1ccc([N+](=O)[O-])o1]

{N-methyl-N-(5-nitro-furan-2-yl)amino};

R$^a$ and R$^b$ are same or different and are independently selected from —H, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, C$_{1-12}$ alkyl-aryl, C$_{1-12}$ alkyl-heteroaryl; C$_{2-12}$ alkenyl-cycloalkyl, C$_{2-12}$ alkenyl-heterocyclyl, C$_{2-12}$ alkenyl-aryl, C$_{2-12}$ alkenyl-heteroaryl; C$_{2-12}$ alkynyl-cycloalkyl, C$_{2-12}$ alkynyl-heterocyclyl, C$_{2-12}$ alkynyl-aryl or C$_{2-12}$ alkynyl-heteroaryl; each of which may be optionally substituted at any available position by one or more substituents selected from but not limited to halogen, —CN, —CHO, —COR$^c$, —CHS, —CSR$^c$, —COOH, —COOR$^c$, —COCN, —CONH$_2$, —CONHNH$_2$, —CSNHNH$_2$, —CONR$^c$R$^d$, —CSNH$_2$, —CSNR$^c$R$^d$, —C(=NOR$^c$)R$^d$, oxo, —NH$_2$, —NHNH$_2$, —NR$^c$R$^d$, —NR$^c$N(R$^d$)$_2$, —N$_3$, —NO$_2$, —N(R$^c$)(CO)R$^d$, —N(R$^c$)(CO)OR$^d$, —N(R$^c$)(CO)N(R$^d$)$_2$, —N(R$^c$)(CS)R$^d$, —N(R$^c$)(CS)OR$^d$, —N(R$^c$)(CS)N(R$^d$)$_2$, —NR$^a$(C=NR$^a$)NR$^a$R$^b$, —OH, —OR$^c$, —OCOR$^c$, —OCOOR$^c$, —OCONR$^c$R$^d$, —SH, —SR$^c$, —SO$_3$H, —SOR$^c$, —SO$_2$R$^c$, —SO$_2$NR$^c$R$^d$, —P(O)R$^c$R$^d$, —P(O)OR$^c$OR$^d$, —P(O)R$^c$OR$^d$, —P(O)NR$^c$OR$^d$, —P(O)NR$^c$R$^d$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl or heteroaryl;

or

R$^a$ and R$^b$ are joined together to form a C$_{3-20}$ cycloalkyl, C$_{3-20}$ cycloalkenyl, C$_{6-20}$ cycloalkynyl, heterocyclyl, aryl or heteroaryl ring which can be optionally substituted at any available position with Q.

R$^c$ and R$^d$ are same or different and are independently selected from —H, C$_{1-12}$ alkyl, C$_{2-12}$ alkenyl, C$_{2-12}$ alkynyl, C$_{3-20}$ cycloalkyl, heterocyclyl, aryl, heteroaryl, —CN, —CHO, —COOH, —COCN, —CONH$_2$, —CONHNH$_2$, —CSNHNH$_2$, —CSNH$_2$, oxo, —NH$_2$, —NHNH$_2$, —N$_3$, —NO$_2$, —OH, —SH, —SO$_3$H or halogen;

Q is independently selected from —CH$_2$—, O, S, SO, SO$_2$, —N(R$^a$)—, —(CO)—, —(CS)—, —CR$^a$(N(R$^b$)$_2$)—, —C(=NR$^a$)—, —CR$^a$(OR$^b$)—, —CR$^a$R$^b$—, —P(O)R$^a$—, —P(O)(OR$^a$)—, —CR$^a$(SR$^b$)—, —CR$^a$(SO$_3$R$^b$)—, —CR$^a$(SOR$^b$)—, —CR$^a$(SO$_2$R$^b$)— or —CR$^a$(SO$_2$NR$^b$R$^c$)—;

Y is O or S;

m is 0, 1, 2, 3 or 4;

p is 0, 1, 2, 3, 4, 5, 6, 7, 8, 9 or 10;

n is 1, 2, 3, 4, 5 or 6.

Another embodiment of the present invention provides compounds of Formula Ib,

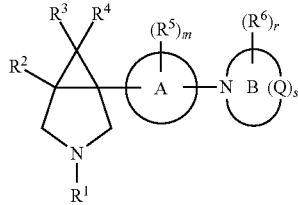

Formula Ib their pharmaceutically acceptable derivatives, tautomeric forms, stereoisomers including R and S isomers, polymorphs, prodrugs, metabolites, salts or solvates thereof, wherein, ring A is either aryl or heteroaryl;

ring B is heterocyclyl attached to ring A through a nitrogen atom at any available position of ring A, ring B can further be fused to one or more aryl, heteroaryl, cycloalkyl or heterocyclyl rings, with the proviso that ring B cannot be isoxazolyl, —CH$_2$—N-pyrrolyl, 1,1-dioxido-2-isothiazolidinyl, thienyl, thiazolyl, pyridyl or 2-pyrrolidinonyl;

R¹, R² and R⁴ are independently selected from —H, C$_{1-12}$ alkyl, C$_{2-12}$ alkenyl, C$_{2-12}$ alkynyl, C$_{1-12}$ alkoxyalkyl, C$_{2-12}$ alkoxyalkenyl, C$_{2-12}$ alkoxyalkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, C$_{1-12}$ alkyl-aryl, C$_{1-12}$ alkyl-heteroaryl; C$_{2-12}$ alkenyl-cycloalkyl, C$_{2-12}$ alkenyl-heterocyclyl, C$_{2-12}$ alkenyl-aryl, C$_{2-12}$ alkenyl-heteroaryl; C$_{2-12}$ alkynyl-cycloalkyl, C$_{2-12}$ alkynyl-heterocyclyl, C$_{2-12}$ alkynyl-aryl, C$_{2-12}$ alkynyl-heteroaryl, —CN, —NH$_2$, —CHO, —COR$^a$, —CSR$^a$, —COOR$^a$, —NR$^a$R$^b$, —CONR$^a$NR$^b$R$^c$, —(C=NR$^a$)—NR$^b$R$^c$, —CHS, —COOH, —COCOR$^a$, —CONH$_2$, —CONHNH$_2$, —CONR$^a$R$^b$, —CSNH$_2$, —CSNR$^a$R$^b$, —C(=NOR$^b$)R$^a$—NH$_2$, —NHNH$_2$, —NR$^a$NR$^b$R$^c$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —OH or —OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

R$^3$ represents —(CH$_2$)$_p$Z;

Z is selected from —H, halogen, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-20}$ cycloalkyl, C$_{3-20}$ cycloalkenyl, C$_{6-20}$ cycloalkynyl, heterocyclyl, aryl, heteroaryl, —NH$_2$, —CHO, —COR$^a$, —CSR$^a$, —COOR$^a$, —CONR$^a$R$^b$, —CSNR$^a$R$^b$, —NR$^a$R$^b$, —CONR$^a$NR$^b$R$^c$, —(C=NR$^a$)—NR$^b$R$^c$, —OH or —OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$;

R$^5$ is independently selected from —H, halogen, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, C$_{1-12}$ alkyl-aryl, C$_{1-12}$ alkyl-heteroaryl; C$_{2-12}$ alkenyl-cycloalkyl, C$_{2-12}$ alkenyl-heterocyclyl, C$_{2-12}$ alkenyl-aryl, C$_{2-12}$ alkenyl-heteroaryl; C$_{2-12}$ alkynyl-cycloalkyl, C$_{2-12}$ alkynyl-heterocyclyl, C$_{2-12}$ alkynyl-aryl, C$_{2-12}$ alkynyl-heteroaryl, oxo, —NH$_2$, —CHO, —COR$^a$, —CSR$^a$, —COOR$^a$, —CONR$^a$R$^b$, —CSNR$^a$R$^b$, —NR$^a$R$^b$, —CONR$^a$N(R$^b$)$_2$, —(C=NR$^a$)—NR$^b$R$^c$, —(CH$_2$)$_n$—N$_3$, —(CH$_2$)$_n$—NCS, —C(=Y)R$^a$, —C(=Y)OR$^a$, —C(=Y)NR$^a$R$^b$, —(CH$_2$)$_n$YR$^a$, —(CH$_2$)$_n$OP(=O)R$^a$R$^b$, —(CH$_2$)$_n$NHP(=O)R$^a$R$^b$, —(CH$_2$)$_n$OC(=Y)R$^a$, —(CH$_2$)$_n$OC(=Y)OR$^a$, —(CH$_2$)$_n$C(=Y)R$^a$, —(CH$_2$)$_n$C(=Y)NR$^a$R$^b$, —(CH$_2$)$_n$OC(=Y)NR$^a$R$^b$, —(CH$_2$)$_n$C(=Y)OR$^a$, —(CH$_2$)$_n$NR$^a$R$^b$, —(CH$_2$)$_n$NR$^a$C(=Y)R$^b$, —(CH$_2$)$_n$NR$^a$C(=Y)OR$^b$, —(CH$_2$)$_n$NR$^a$C(=Y)NR$^a$R$^b$, —(CH$_2$)$_n$NR$^a$SO$_2$R$^b$, —OH or —OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

R$^6$ is independently selected from —H, halogen, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, C$_{1-12}$ alkyl-aryl, C$_{1-12}$ alkyl-heteroaryl; C$_{2-12}$ alkenyl-cycloalkyl, C$_{2-12}$ alkenyl-heterocyclyl, C$_{2-12}$ alkenyl-aryl, C$_{2-12}$ alkenyl-heteroaryl; C$_{2-12}$ alkynyl-cycloalkyl, C$_{2-12}$ alkynyl-heterocyclyl, C$_{2-12}$ alkynyl-aryl, C$_{2-12}$ alkynyl-heteroaryl, oxo, —NH$_2$, —CHO, —COR$^a$, —CSR$^a$, —COOR$^a$, —CONR$^a$R$^b$, —CSNR$^a$R$^b$, —NR$^a$R$^b$, —CONR$^a$N(R$^b$)$_2$, —(C=NR$^a$)—NR$^b$R$^c$, —(CH$_2$)$_n$—N$_3$, —(CH$_2$)$_n$—NCS, —C(=Y)R$^a$, —C(=Y)OR$^a$, —C(=Y)NR$^a$R$^b$, —(CH$_2$)$_n$YR$^a$, —(CH$_2$)$_n$OP(=O)R$^a$R$^b$, —(CH$_2$)$_n$NHP(=O)R$^a$R$^b$, —(CH$_2$)$_n$OC(=Y)R$^a$, —(CH$_2$)$_n$OC(=Y)OR$^a$, —(CH$_2$)$_n$C(=Y)R$^a$, —(CH$_2$)$_n$C(=Y)NR$^a$R$^b$, —(CH$_2$)$_n$OC(=Y)NR$^a$R$^b$, —(CH$_2$)$_n$C(=Y)OR$^a$, —(CH$_2$)$_n$NR$^a$R$^b$, —(CH$_2$)$_n$NR$^a$C(=Y)R$^b$, —(CH$_2$)$_n$NR$^a$C(=Y)OR$^b$, —(CH$_2$)$_n$NR$^a$C(=Y)NR$^a$R$^b$, —OH or —OR$^a$; each of which may be optionally substituted at any available position by one or more substituents selected from but not limited to halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^a$R$^b$, —CSNH$_2$, —CSNR$^a$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, —N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

with the proviso that when ring B is oxazolidinyl and r is 1, then R$_6$ cannot be C$_{1-12}$ alkyl, C$_{2-12}$ alkenyl, C$_{2-12}$ alkynyl, C$_{1-12}$ alkoxyalkyl, C$_{2-12}$ alkoxyalkenyl, C$_{2-12}$ alkoxyalkynyl, C$_{3-20}$ cycloalkyl, C$_{3-20}$ cycloalkenyl, C$_{6-20}$ cycloalkynyl, heterocyclyl, aryl, heteroaryl, —(CH$_2$)$_n$-cycloalkyl, —(CH$_2$)$_n$-heterocyclyl, —(CH$_2$)$_n$-aryl, —(CH$_2$)$_n$-heteroaryl, —(CH$_2$)$_n$—N$_3$, —(CH$_2$)$_n$—NCS, —C(=Y)R$^a$, —C(=Y)OR$^a$, —C(=Y)NR$^a$R$^b$, —(CH$_2$)$_n$YR$^a$, —(CH$_2$)$_n$OP(=O)R$^a$R$^b$, —(CH$_2$)$_n$NHP(=O)R$^a$R$^b$, —(CH$_2$)$_n$OC(=Y)R$^a$, —(CH$_2$)$_n$OC(=Y)OR$^a$, —(CH$_2$)$_n$C(=Y)R$^a$, —(CH$_2$)$_n$C(=Y)NR$^a$R$^b$, —(CH$_2$)$_n$OC(=Y)NR$^a$R$^b$, —(CH$_2$)$_n$C(=Y)OR$^a$, —(CH$_2$)$_n$NR$^a$R$^b$, —(CH$_2$)$_n$NR$^a$C(=Y)R$^b$, —(CH$_2$)$_n$NR$^a$C(=Y)OR$^b$, —(CH$_2$)$_n$NR$^a$C(=Y)NR$^a$R$^b$ or —(CH$_2$)$_n$NR$^a$SO$_2$R$^b$;

or

R$_5$ and R$_6$ are joined together to form a 5 to 10 membered heterocyclic ring which can be optionally substituted at any available position with C$_{1-12}$ alkyl, C$_{2-12}$ alkenyl, C$_{2-12}$ alkynyl, C$_{1-12}$ haloalkyl, C$_{3-20}$ cycloalkyl, heterocyclyl, aryl, heteroaryl, oxo, —NH$_2$, —NO$_2$, —N$_3$, —CN, —CHO, —COR$^c$, —CHS, —CSR$^c$, —COOH, —COOR$^c$, —OH, —OR$^c$, —SH or —SR$^c$;

Q is independently selected from —CH$_2$—, O, S, SO, SO$_2$, —N(R$^a$)—, —(CO)—, —(CS)—, —CR$^a$(N(R$^b$)$_2$)—, —C(=NR$^a$)—, —CR$^a$(OR$^b$)—, —CR$^a$R$^b$—, —P(O)R$^a$—, —P(O)(OR$^a$)—, —CR$^a$(SR$^b$)—, CR$^a$(SO$_3$R$^b$)—, —CR$^a$(SOR$^b$)—, —CR$^a$(SO$_2$R$^b$)— or —CR$^a$(SO$_2$NR$^b$R$^c$)—;

R$^a$ and R$^b$ are same or different and can independently be selected from —H, C$_{1-12}$ alkyl, C$_{2-12}$ alkenyl, C$_{2-12}$ alkynyl, C$_{1-12}$ haloalkyl, C$_{2-12}$ haloalkenyl, C$_{2-12}$ haloalkynyl, C$_{3-20}$ cycloalkyl, C$_{3-20}$ cycloalkenyl, C$_{6-20}$ cycloalkynyl, heterocyclyl, aryl, heteroaryl, C$_{1-12}$ alkyl-cycloalkyl, C$_{1-12}$ alkyl-heterocyclyl, C$_{1-12}$ alkyl-aryl, C$_{1-12}$ alkyl-heteroaryl; C$_{2-12}$ alkenyl-cycloalkyl, C$_{2-12}$ alkenyl-heterocyclyl, C$_{2-12}$ alkenyl-aryl, C$_{2-12}$ alkenyl-heteroaryl; C$_{2-12}$ alkynyl-cycloalkyl, C$_{2-12}$ alkynyl-heterocyclyl, C$_{2-12}$ alkynyl-aryl or C$_{2-12}$ alkynyl-heteroaryl; each of which may be optionally substituted at any available position by one or more substituents selected from but not limited to halogen, —CN, —CHO, —COR$^c$, —CHS, —CSR$^c$, —COOH, —COOR$^c$, —COCN, —CONH$_2$, —CONHNH$_2$, —CSNHNH$_2$, —CONR$^c$R$^d$, —CSNH$_2$, —CSNR$^c$R$^d$, —C(=NOR$^c$)R$^d$, oxo, —NH$_2$, —NHNH$_2$, —NR$^c$R$^d$, —NR$^c$N(R$^d$)$_2$, —N$_3$, —NO$_2$, —N(R$^c$)(CO)R$^d$, —N(R$^c$)(CO)OR$^d$, —N(R$^c$)(CO)N(R$^d$)$_2$, —N(R$^c$)(CS)R$^d$, —N(R$^c$)(CS)OR$^d$, —N(R$^c$)(CS)N(R$^d$)$_2$, —NR$^a$(C=NR$^a$)NR$^a$R$^b$, —OH, —OR$^c$, —OCOR$^c$, —OCOOR$^c$, —OCONR$^c$R$^d$, —SH, —SR$^c$, —SO$_3$H, —SOR$^c$, —SO$_2$R$^c$, —SO$_2$NR$^c$R$^d$, —P(O)R$^c$R$^d$, —P(O)OR$^c$R$^d$, —P(O)R$^c$OR$^d$, —P(O)NR$^c$OR$^d$, —P(O)NR$^c$R$^d$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl, heteroaryl;

or

R$^a$ and R$^b$ are joined together to form a C$_{3-20}$ cycloalkyl, C$_{3-20}$ cycloalkenyl, C$_{6-20}$ cycloalkynyl, heterocyclyl, aryl or heteroaryl ring which can be optionally substituted at any available position with Q;

R$^c$ and R$^d$ are same or different and can independently be selected from —H, C$_{1-12}$ alkyl, C$_{2-12}$ alkenyl, C$_{2-12}$ alkynyl, C$_{3-20}$ cycloalkyl, heterocyclyl, aryl, heteroaryl, —CN, —CHO, —COOH, —COCN, —CONH$_2$, —CONHNH$_2$, —CSNHNH$_2$, —CSNH$_2$, oxo, —NH$_2$, —NHNH$_2$, —N$_3$, —NO$_2$, —OH, —SH, —SO$_3$H or halogen;

Y is O or S;
m is 0, 1, 2, 3 or 4;
n is 0, 1, 2, 3 or 4;
r is 0, 1, 2, 3 or 4;
p is 0, 1, 2, 3, 4, 5, 6, 7, 8, 9 or 10;
s is 0, 1, 2, 3 or 4.

In an embodiment of the compounds of the general Formula Ia, it is preferred that ring A is selected from phenyl, fluorophenyl, difluorophenyl or pyrimidyl.

In a further embodiment of the compounds of the general Formula Ia, it is preferred that R$^1$ is selected from the group consisting of aryl, heteroaryl, C$_{1-12}$ alkyl-heterocyclyl, C$_{1-12}$ alkyl-aryl, C$_{1-12}$ alkyl-heteroaryl, —CN, —COR$^a$, —COOR$^a$, —CONR$^a$R$^b$, —COCOR$^a$, —SO$_2$R$^a$ and —SO$_2$NR$^a$R$^b$; each of which is unsubstituted or substituted, at any available position, with one or more substituents independently selected from the group consisting of halogen, —CN, —CHO, —COR$^a$, —CHS, —CSR$^a$, —COOH, —COOR$^a$, —COCN, —CONH$_2$, —CONHNH$_2$, —CSNHNH$_2$, —CONR$^c$R$^b$, —CSNH$_2$, —CSNR$^c$R$^b$, —C(=NOR$^b$)R$^a$, oxo, —NH$_2$, —NHNH$_2$, —NR$^a$R$^b$, —NR$^a$NR$^b$R$^c$, —N$_3$, —NO$_2$, —N(R$^a$)(CO)R$^b$, —N(R$^a$)(CO)OR$^b$, N(R$^a$)(CO)NR$^a$R$^b$, —N(R$^a$)(CS)R$^b$, —N(R$^a$)(CS)OR$^b$, —N(R$^a$)(CS)NR$^a$R$^b$, —NR$^a$(C=NR$^a$)NR$^a$R$^b$, —OH, —OR$^a$, —OCOR$^a$, —OCOOR$^a$, —OCONR$^a$R$^b$, —SH, —SR$^a$, —SO$_3$H, —SOR$^a$, —SO$_2$R$^a$, —SO$_2$NR$^a$R$^b$, —P(O)R$^a$R$^b$, —P(O)OR$^a$OR$^b$, —P(O)R$^a$OR$^b$, —P(O)NR$^a$OR$^b$, —P(O)NR$^a$R$^b$, —C$_{1-12}$ alkyl, —C$_{2-12}$ alkenyl, —C$_{2-12}$ alkynyl, C$_{3-20}$ cycloalkyl, C$_{3-20}$ cycloalkenyl, C$_{6-20}$ cycloalkynyl, heterocyclyl, aryl or heteroaryl.

In another embodiment of the compounds of the general Formula Ia, it is still more preferred that R$^1$ is selected from the group consisting of —COCH$_3$, —CN, —COCF$_3$, —CON(CH$_3$)$_2$, —COOCH$_3$, —COO$^i$Pr, —COO$^t$Bu, —COOCH$_2$—CH=CH$_2$, —COCH$_2$OH, —COCH$_2$OCOOCH$_2$CH$_3$, —COCH$_2$CH$_2$Ph, —COCH$_2$NHCOCH$_3$, —CH$_2$Ph, —SO$_2$CH$_3$, —SO$_2$CF$_3$, —SO$_2$Ph,

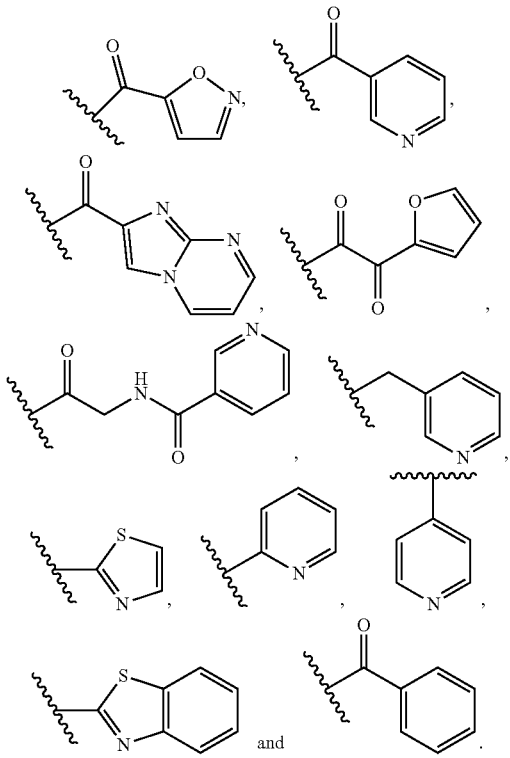

In a further embodiment of the compounds of the general Formula Ia, it is preferred that R$^2$ is selected from hydrogen or alkyl.

In another embodiment of the compounds of the general Formula Ia, R$^3$ is selected from the group consisting of —H, —(CH$_2$)$_p$—OH, —(CH$_2$)$_p$—OR$^a$, —(CH$_2$)$_p$—NR$^a$R$^b$, —C$_{1-12}$ alkyl, heterocyclyl, aryl, heteroaryl and C$_{1-12}$ alkyl-heterocyclyl, wherein p is 0, 1, 2 or 3.

Another embodiment of the present invention provides compounds of the general Formula Ia, wherein R$^4$ is selected from the group consisting of —H, —C$_{1-12}$ alkyl, —C$_{1-12}$ alkoxyalkyl, heterocyclyl, aryl, heteroaryl and C$_{1-12}$ alkyl-heterocyclyl.

In another embodiment of the compounds of the general Formula Ia, it is preferred that R$^5$ is selected from hydrogen or halogen, wherein m is 0, 1 or 2.

In a further embodiment of the compounds of the general Formula Ia, it is more preferred that R$^5$ is selected from hydrogen or fluoro wherein m is 1 or 2.

In another embodiment of the compounds of the general Formula Ia, R$^6$ is selected from the group consisting of —C$_{1-12}$ alkyl, —(CH$_2$)$_n$-heteroaryl, —(CH$_2$)$_n$-heterocyclyl, —(CH$_2$)$_n$YR$^a$, —(CH$_2$)$_n$NR$^a$C(=Y)R$^b$ and —(CH$_2$)$_n$NR$^a$C(=Y)OR$^b$.

In still another embodiment of the compounds of the general Formula Ia, $R^6$ is selected from —$CH_2F$, —$CHF_2$, —$(CH_2)_n NHCOCH_3$, —$(CH_2)_n NHCOOCH_3$, —$(CH_2)_n NHCOOC_2H_5$ or —$(CH_2)_n$-triazolyl.

In an embodiment of the compounds of the general Formula Ib, it is preferred that ring A is selected from the group consisting of phenyl, pyridyl, benzothiophene and naphthyl.

In another embodiment of the compounds of the general Formula Ib, it is preferred that ring B is selected from the group consisting of

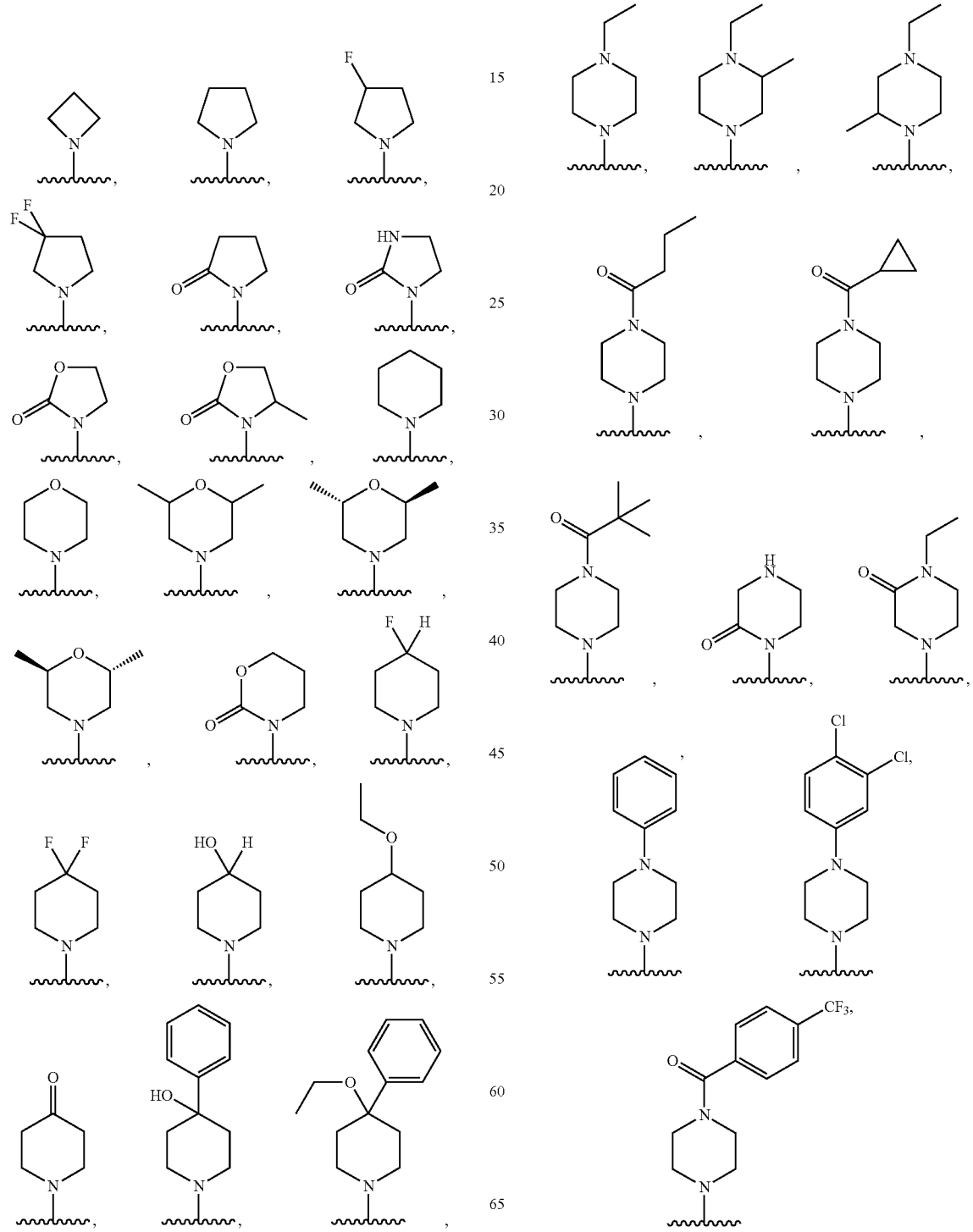

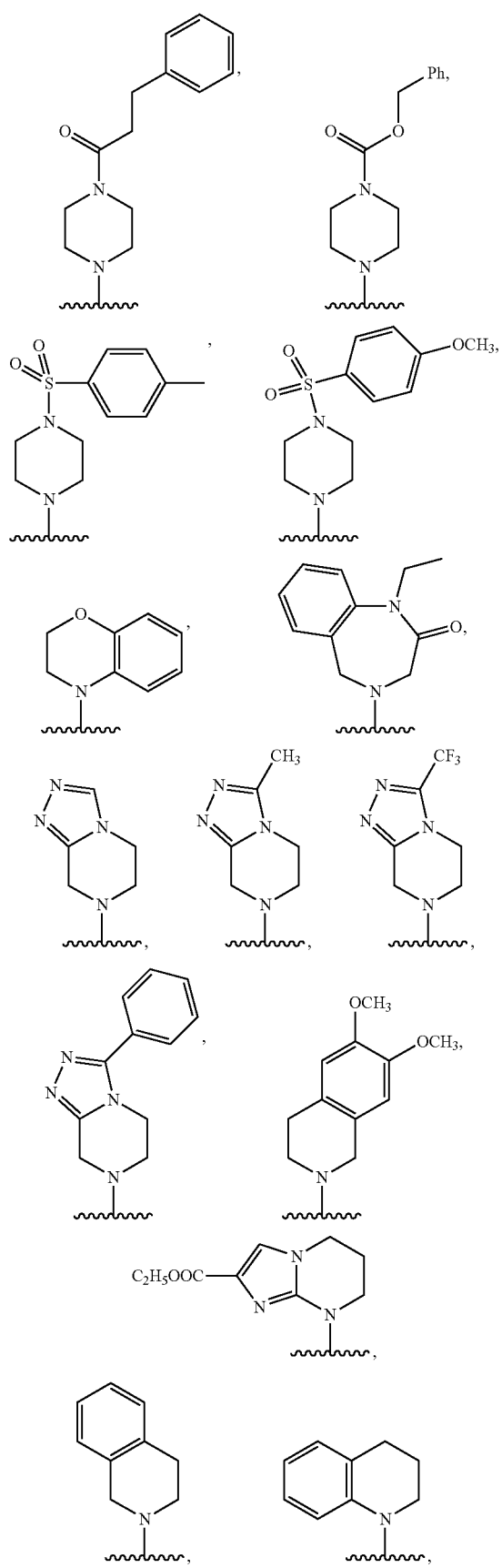

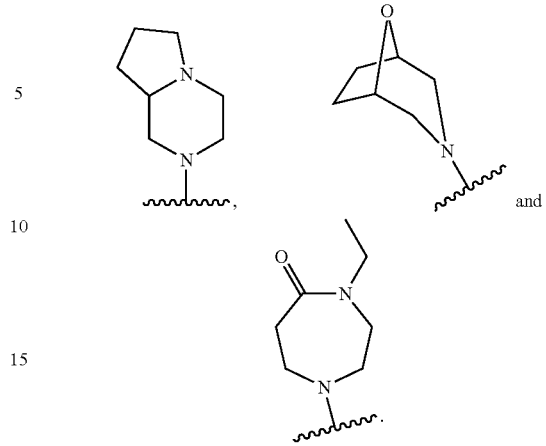

In a further embodiment of the compounds of the general Formula Ib, it is preferred that $R^1$ is selected from the group consisting of —H, $C_{1-4}$ alkyl, $C_{2-4}$ alkenyl, $C_{2-4}$ alkynyl, $C_{1-4}$ alkoxyalkyl, $C_{3-7}$ cycloalkyl, heterocyclyl, aryl, heteroaryl, $C_{3-7}$ alkyl-cycloalkyl, $C_{1-12}$ alkyl-heterocyclyl, $C_{1-12}$ alkyl-aryl, $C_{1-12}$ alkyl-heteroaryl, $OR^a$, —$COOR^a$, —$CONR^aR^b$—$COR^a$ and —$SO_2R^a$; each of which is unsubstituted or substituted, at any available position, with one or more substituents independently selected from the group consisting of —CN, —CHO, —$COR^a$, —CHS, —$CSR^a$, —COOH, —$COOR^a$, —COCN, —$CONH_2$, —$CONHNH_2$, —CS-$NHNH_2$, —$CONR^aR^b$, —$CSNH_2$, —$CSNR^aR^b$, —C(=$NOR^b$)$R^a$, oxo, —$NH_2$, —$NHNH_2$, —$NR^aR^b$, —$NR^aNR^bR^c$, —$N_3$, —$NO_2$, —$N(R^a)(CO)R^b$, —$N(R^a)$(CO)$OR^b$, $N(R^a)(CO)NR^aR^b$, —$N(R^a)(CS)R^b$, —$N(R^a)$(CS)$OR^b$, —$N(R^a)(CS)NR^aR^b$, —$NR^a$(C=$NR^a$)$NR^aR^b$, —OH, —$OR^a$, —$OCOR^a$, —$OCOOR^a$, —$OCONR^aR^b$, —SH, —$SR^a$, —$SO_3H$, —$SOR^a$, —$SO_2R^a$, —$SO_2NR^aR^b$, halogen, —$P(O)R^aR^b$, —$P(O)OR^aOR^b$, —$P(O)R^aOR^b$, —$P(O)NR^aOR^b$, —$P(O)NR^aR^b$, —$C_{1-12}$ alkyl, —$C_{2-12}$ alkenyl, —$C_{2-12}$ alkynyl, $C_{3-20}$ cycloalkyl, $C_{3-20}$ cycloalkenyl, $C_{6-20}$ cycloalkynyl, heterocyclyl, aryl or heteroaryl.

In another embodiment of the compounds of the general Formula Ib, it is more preferred that $R^1$ is selected from the group consisting of —H, $C_{1-4}$ alkyl, $C_{2-4}$ alkenyl, $C_{2-4}$ alkynyl, $C_{1-4}$ alkoxyalkyl, $C_{3-7}$ cycloalkyl, $C_{3-7}$ alkyl-cycloalkyl, —$OR^a$, —$COOR^a$, —$CONR^aR^b$—$COR^a$ and —$SO_2R^a$.

In a further embodiment of the compounds of the general Formula Ib, it is preferred that $R^2$ is selected from hydrogen, alkyl or $C_{1-4}$ alkoxyalkyl.

In another embodiment of the compounds of the general Formula Ib, $R^3$ is selected from the group consisting of hydrogen, —$(CH_2)_p$—CHO, —$(CH_2)_p$—OH, —$(CH_2)_p$—$OR^a$, —$(CH_2)_p$—$COOR^a$, —$(CH_2)_p$—$CONR^aR^b$, —$(CH_2)_p$—$CSNR^aR^b$, —$(CH_2)_p$—$NR^aR^b$, —$(CH_2)_p$—$CONR^aNR^bR^c$, —$(CH_2)_p$—(C=$NR^a$)—$NR^bR^c$ and —$(CH_2)_p$—$NH_2$, wherein p is 0, 1, 2 or 3.

Another embodiment of the compounds of the general Formula Ib, provides that $R^4$ is selected from the group consisting of hydrogen, —CHO, —OH, $OR^a$, $COOR^a$, —$CONR^aR^b$, —$CSNR^aR^b$, —$NR^aR^b$, —$CONR^aNR^bR^c$, —(C=$NR^a$)—$NR^bR^c$ and —$NH_2$.

In another embodiment of the compounds of the general Formula Ib, it is preferred that $R^5$ is selected from —H, $C_{1-4}$ alkyl, $C_{1-2}$ haloalkyl, —$NH_2$, —$NR^aR^b$, —OH, —$OR^a$ or halogen.

In a further embodiment of the compounds of the general Formula Ib, $R^6$ is selected from the group consisting of —H, $C_{1-4}$ alkyl, —OH, oxo, halogen, —$OR^a$, —$NH_2$ and —$NR^aR^b$.

In another embodiment of the compounds of the general Formula Ib, Q is selected from the group consisting of —$CH_2$—, O, S, —C(=$NR^a$)—, —N($R^a$)—, —(CO)— and —$CR^a(OR^b)$—.

DEFINITIONS

Relative to the above description of the compounds of the present invention, the following definitions apply:

Unless specified otherwise, the terms "alkyl", "alkenyl", and "alkynyl" may be straight or branched with 1 to 12 carbon atoms. These groups may further be substituted with one or more substituents selected from but not limited to, for example, halogen, hydroxyl, oxo, carboxyl, amino, nitro, cyano, carboxyalkyl, azido, alkenyl, alkynyl, alkoxy, cycloalkyl, cycloalkynyl, acyl acyloxy, aryl, heterocyclyl and heteroaryl.

The term "alkoxy" refers to an above defined alkyl group attached via an oxygen linkage to the rest of the molecule. Non-limiting examples of such groups include —$OCH_3$, —$OC_2H_5$ and the like.

The term "haloalkyl" refers to an above-defined "alkyl" group, which is substituted with one or more "halogen" groups, as defined herein, at any one or more of the 1 to 12 carbon atoms of the alkyl group. Representative examples of haloalkyl include, but are not limited to chloromethyl, 2-fluoromethyl, trifluoromethyl, trichloromethyl, difluoroethyl, trifluoroethyl, dichloroethyl, and the like.

The term "haloalkoxy" refers to an above defined "haloalkyl" group, appended to the parent molecular moiety through an oxygen atom.

The term "haloalkenyl" refers to at least one halogen as defined herein, appended to the parent molecular moiety through an above defined alkenyl group. Representative examples of haloalkenyl include, but are not limited to, chloroethenyl, 2-fluoroethenyl, trifluorobutenyl and dichloropropenyl.

The term "haloalkynyl" refers to at least one halogen as defined herein, appended to the parent molecular moiety through an above defined alkynyl group. Representative examples of haloalkenyl include, but are not limited to, 2-fluoroethynyl, trifluorobutynyl and dichloropropynyl.

The term "cycloalkyl" refers to cyclic alkyl groups constituting of 3 to 20 carbon atoms having a single cyclic ring or multiple condensed rings, for example, fused or spiro systems, unless otherwise constrained by the definition. Such cycloalkyl groups include, by way of example, single ring structures, for example, cyclopropyl, cyclobutyl, cyclopentenyl, cyclohexyl, cyclooctyl, and the like, or multiple ring structures, for example, adamantyl, and bicyclo[2.2.1]heptane, or cyclic alkyl groups to which is fused an aryl group, heteroaryl group, heterocyclyl group or another cycloalkyl group, for example, indane and the like. The cycloalkyl group may optionally contain one or more heteroatom(s) independently selected from N, O and S. Cycloalkyl groups may further be substituted with one or more substituents selected from but not limited to, for example, halogen, hydroxyl, oxo, carboxy, amino, nitro, cyano, carboxyalkyl, azido, alkenyl, alkynyl, alkoxy, cycloalkyl, cycloalkynyl, acyl acyloxy, aryl, heterocyclyl, heteroaryl.

The term "cycloalkenyl" refers to a cycloalkyl group as defined above which may optionally contain one or more double bonds.

The term "cycloalkynyl" refers to a cycloalkyl group as defined above which may optionally contain one or more triple bonds.

The term "aryl" herein refers to a mono- or poly-carbocyclic aromatic group, for example phenyl or naphthyl ring and the like optionally substituted with one or more substituents selected from but not limited to, for example, halogen, hydroxyl, alkyl, alkenyl, alkynyl, cycloalkyl, alkoxy, acyl, amino, aryloxy, $CF_3$, $COOR^d$ (wherein $R^d$ can be hydrogen, alkyl, alkenyl, cycloalkyl, aralkyl, heterocyclylalkyl or heteroarylalkyl), cyano, nitro, carboxy, heterocyclyl, heteroaryl, heterocyclylalkyl or heteroarylalkyl. The aryl group may optionally be fused with cycloalkyl group, heteroaryl group, heterocyclyl group or another aryl group. The aryl group may be further substituted at any available position with one or more substituents selected from but not limited to, for example, halogen, hydroxyl, oxo, carboxy, amino, nitro, cyano, carboxyalkyl, azido, alkenyl, alkynyl, alkoxy, cycloalkyl, cycloalkynyl, acyl acyloxy, aryl, heterocyclyl, heteroaryl.

The term "heteroaryl" unless and otherwise specified refers to an aromatic monocyclic or polycyclic ring structure, fully or partially unsaturated, containing one to four heteroatoms independently selected from N, O and S. The nitrogen atoms can be optionally quaternerized and the sulphur atoms can be optionally oxidized. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, a heterocyclyl ring and another monocyclic heteroaryl ring. Examples of heteroaryl groups include, but are not limited to, oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, thienyl, isoxazolyl, triazinyl, furanyl, benzofuranyl, indolyl, benzothiazolyl, benzoxazolyl, imidazo[1,2-a]pyrimidine, imidazo[1,2-a]pyrazine, and the like. The bicyclic or tricyclic heteroaryl rings can be attached either through the heteroaryl group itself or the aryl, cycloalkyl, cycloalkenyl or heterocyclyl group to which it is fused. The heteroaryl group may be further substituted at any available position with one or more substituents selected from but not limited to, for example, halogen, hydroxyl, oxo, carboxy, amino, nitro, cyano, carboxyalkyl, azido, alkenyl, alkynyl, alkoxy, cycloalkyl, cycloalkynyl, acyl acyloxy, aryl, heterocyclyl, heteroaryl.

The term "heterocyclyl" unless otherwise specified refers to a non-aromatic monocyclic or polycyclic cycloalkyl group, fully or partially unsaturated, with one or more heteroatom(s) independently selected from N, O and S, and are optionally benzofused or fused heteroaryl of 5-6 ring members and/or are optionally substituted wherein the substituents are selected from but not limited to halogen, hydroxyl, alkyl, alkenyl, alkynyl, cycloalkyl, acyl, carboxy, aryl, alkoxy, aralkyl, cyano, nitro, heterocyclyl, or heteroaryl. Examples of heterocyclyl groups include but are not limited to, morpholinyl, oxazolidinyl, tetrahydrofuranyl, dihydrofuranyl, dihydropyridinyl, dihydroisooxazolyl, dihydrobenzofuryl, azabicyclohexyl, dihydroindonyl, piperidinyl or piperazinyl. The heterocyclyl group may be further substituted at any available position with one or more substituents selected from but not limited to, for example, halogen, hydroxyl, oxo, carboxy, amino, nitro, cyano, carboxyalkyl, azido, alkenyl, alkynyl, alkoxy, cycloalkyl, cycloalkynyl, acyl acyloxy, aryl, heterocyclyl, heteroaryl.

"Halogen" refers to F, Cl, Br or I.

Hydroxy" or "hydroxyl" refers to the group —OH.

In all the above definitions, nitrogen and sulphur heteroatom can optionally be quaternerized or oxidized wherever permissible.

The term "Protecting Group" or "PG" refers to a group which is in a modified form to preclude undesired side reactions at the protected site. The term protecting group, unless otherwise specified, may be used with groups, for example, hydroxyl, amino, carboxyl and examples of such groups are found in T. W. Greene. et al. *"Protecting Groups in Organic Synthesis,"* 3$^{rd}$ Ed, Wiley, New York, which is incorporated herein by reference. The species of the carboxylic protecting groups, amino protecting groups or hydroxyl protecting groups employed are not critical, as long as the derivatised moieties/moiety is/are stable to conditions of subsequent reactions and can be removed without disrupting the remainder of the molecule. Examples of suitable hydroxyl and amino protecting groups include but are not limited to trimethylsilyl, triethylsilyl, o-nitrobenzyloxycarbonyl, p-nitrobenzyloxycarbonyl, t-butyldiphenylsilyl, t-butyldimethylsilyl, acetyl, trifluoroacetyl, benzyloxycarbonyl (CBz), t-butoxycarbonyl (Boc), 9-fluorenylmethylenoxycarbonyl (Fmoc), 2,2,2-trichloroethyloxycarbonyl, allyloxycarbonyl and the like. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl, t-butyl and the like.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity, weight, physical condition and responsiveness of the mammal to be treated, among other factors.

A "pharmaceutically acceptable salt" refers to salts prepared from pharmaceutically acceptable non-toxic bases or acids including inorganic or organic bases and inorganic or organic acids.

Asymmetric centres may exist in the compounds of the present invention. The compounds of Formula I may have one or more stereogenic centres and so can exhibit optical isomerism. All such isomers including enantiomers, diastereomers, and epimers are included within the scope of this invention. Furthermore, the invention includes such compounds as single isomers (R and/or S) and as mixtures, including racemates. If desired, racemic mixtures of the compounds may be separated so that the individual enantiomers are isolated. The separation may be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Starting materials of particular stereochemistry may either be commercially available or may be made by the methods described herein and resolved by techniques well known in the art.

Certain compounds according to Formula I, can also exist as tautomers, which have different points of attachment of hydrogen accompanied by one or more double bond shifts. These tautomers, either separately or as mixtures, are also considered to be within the scope of the invention.

The present invention also encompasses geometrical isomers of compounds of Formula I and the mixtures thereof.

Particularly useful examples of the present invention include but are not limited to the compounds selected from Tables 1 to 3:

One embodiment of the present invention provides compounds of Formula Ia, wherein the compounds are selected from Table 1:

TABLE 1

| Compound No. | Structure | Compound No. | Structure |
|---|---|---|---|
| 1 | 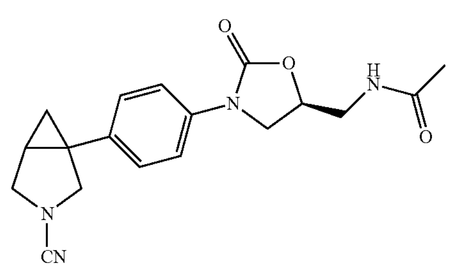 [SMILES: CC(=O)NC[C@H]1CN(c2ccc(C34CC3CN(C#N)C4)cc2)C(=O)O1] | 2 | 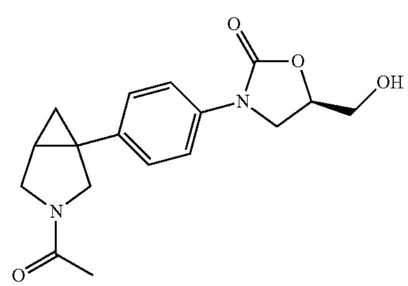 [SMILES: CC(=O)N1CC2CC2(c2ccc(N3C[C@H](CO)OC3=O)cc2)C1] |
| 3 | 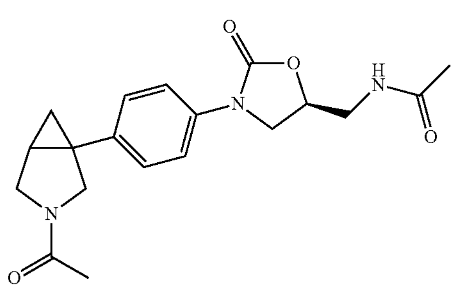 [SMILES: CC(=O)NC[C@H]1CN(c2ccc(C34CC3CN(C(C)=O)C4)cc2)C(=O)O1] | 4 | 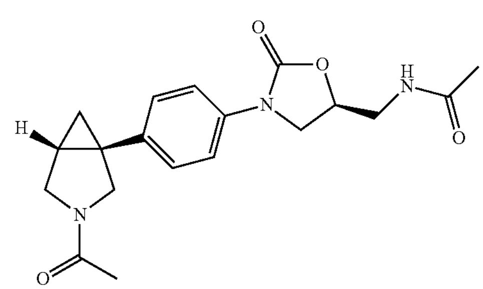 [SMILES: CC(=O)NC[C@H]1CN(c2ccc([C@]34C[C@H]3CN(C(C)=O)C4)cc2)C(=O)O1] |

TABLE 1-continued

| Compound No. | Structure |
|---|---|
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |

TABLE 1-continued
| Compound No. | Structure | Compound No. | Structure |
|---|---|---|---|
| 15 | 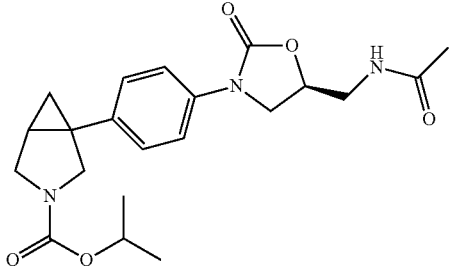 [SMILES: CC(=O)NC[C@H]1CN(c2ccc(C34CC3CN(C(=O)OC(C)C)C4)cc2)C(=O)O1] | 16 | 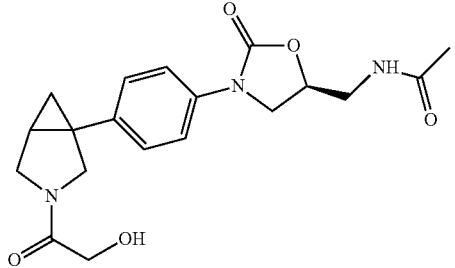 [SMILES: CC(=O)NC[C@H]1CN(c2ccc(C34CC3CN(C(=O)CO)C4)cc2)C(=O)O1] |
| 17 | 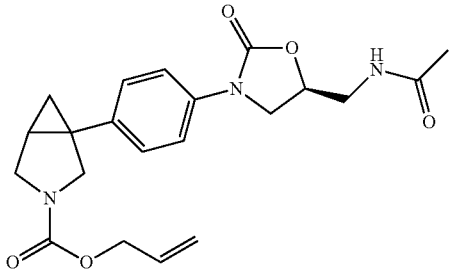 [SMILES: C=CCOC(=O)N1CC2CC2(c2ccc(N3C[C@H](CNC(C)=O)OC3=O)cc2)C1] | 18 | 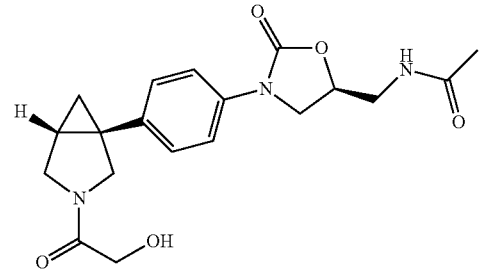 [SMILES: CC(=O)NC[C@H]1CN(c2ccc([C@]34C[C@H]3CN(C(=O)CO)C4)cc2)C(=O)O1] |
| 19 | 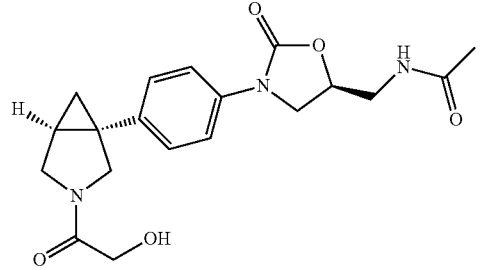 [SMILES: CC(=O)NC[C@H]1CN(c2ccc([C@@]34C[C@@H]3CN(C(=O)CO)C4)cc2)C(=O)O1] | 20 | 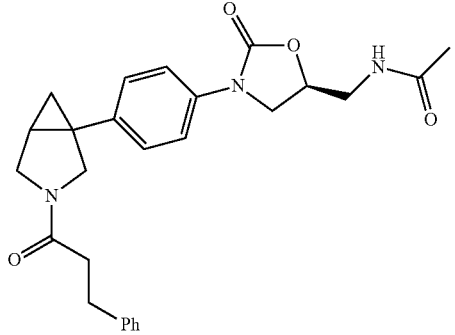 [SMILES: CC(=O)NC[C@H]1CN(c2ccc(C34CC3CN(C(=O)CCc3ccccc3)C4)cc2)C(=O)O1] |
| 21 | 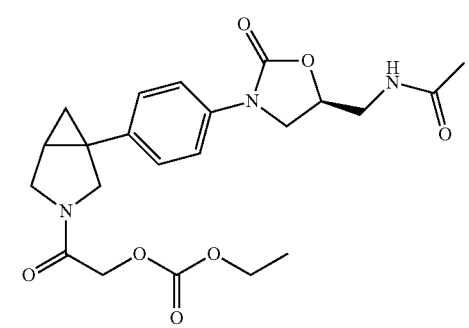 [SMILES: CCOC(=O)OCC(=O)N1CC2CC2(c2ccc(N3C[C@H](CNC(C)=O)OC3=O)cc2)C1] | 22 | 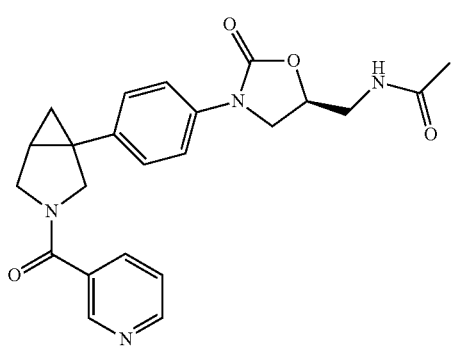 [SMILES: CC(=O)NC[C@H]1CN(c2ccc(C34CC3CN(C(=O)c3cccnc3)C4)cc2)C(=O)O1] |

TABLE 1-continued

| Compound No. | Structure | Compound No. | Structure |
|---|---|---|---|
| 23 | 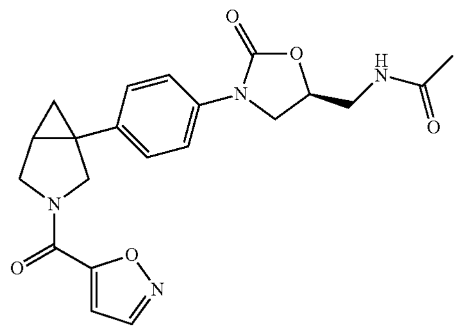 [SMILES: CC(=O)NC[C@H]1CN(c2ccc(C34CC3CN(C(=O)c3ccno3)C4)cc2)C(=O)O1] | 24 | 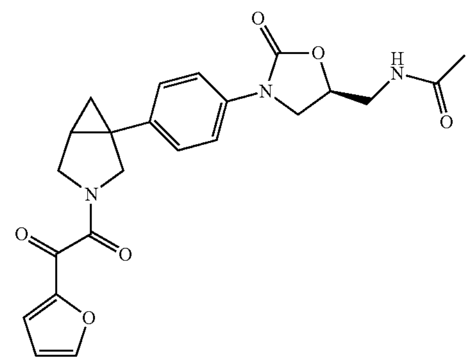 [SMILES: CC(=O)NC[C@H]1CN(c2ccc(C34CC3CN(C(=O)C(=O)c3ccco3)C4)cc2)C(=O)O1] |
| 25 | 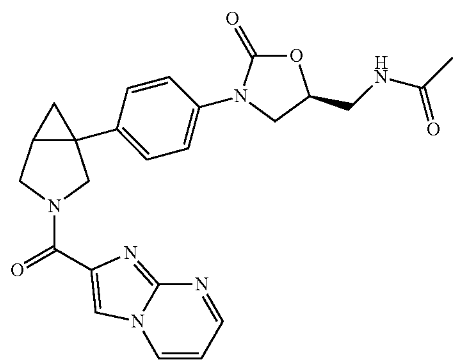 [SMILES: CC(=O)NC[C@H]1CN(c2ccc(C34CC3CN(C(=O)c3cn5cccnc5n3)C4)cc2)C(=O)O1] | 26 | 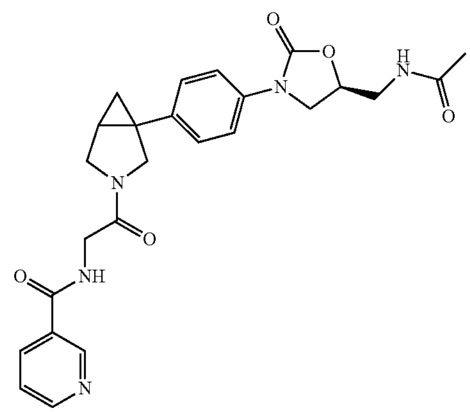 [SMILES: CC(=O)NC[C@H]1CN(c2ccc(C34CC3CN(C(=O)CNC(=O)c3cccnc3)C4)cc2)C(=O)O1] |
| 27 | 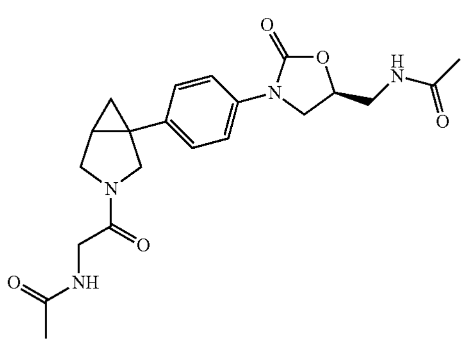 [SMILES: CC(=O)NCC(=O)N1CC2CC2(c2ccc(N3C[C@H](CNC(C)=O)OC3=O)cc2)C1] | 28 | 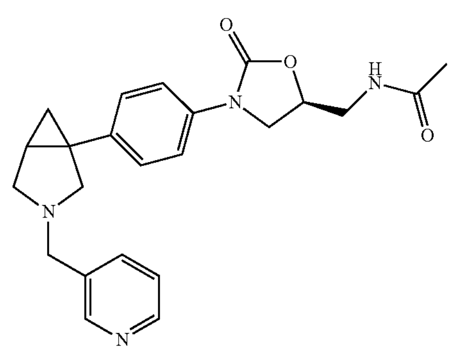 [SMILES: CC(=O)NC[C@H]1CN(c2ccc(C34CC3CN(Cc3cccnc3)C4)cc2)C(=O)O1] |
| 29 | 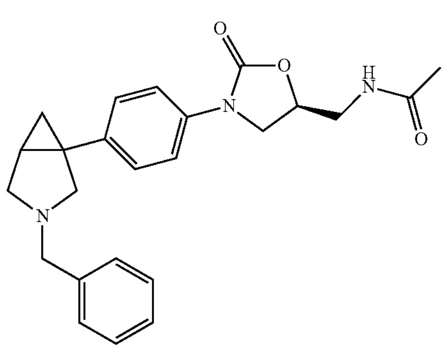 [SMILES: CC(=O)NC[C@H]1CN(c2ccc(C34CC3CN(Cc3ccccc3)C4)cc2)C(=O)O1] | 30 | 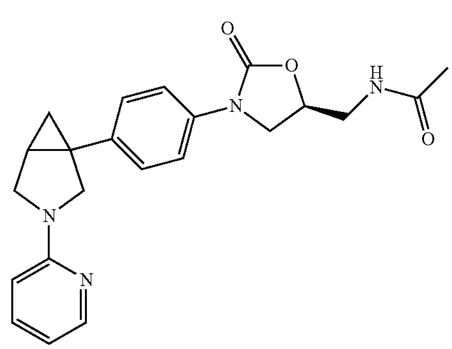 [SMILES: CC(=O)NC[C@H]1CN(c2ccc(C34CC3CN(c3ccccn3)C4)cc2)C(=O)O1] |

TABLE 1-continued

| Compound No. | Structure | Compound No. | Structure |
| --- | --- | --- | --- |
| 31 | 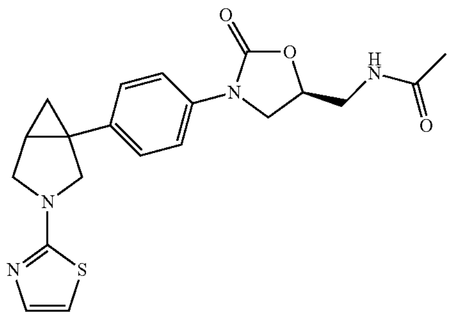 [SMILES: CC(=O)NC[C@H]1CN(c2ccc(C34CC3CN(c3nccs3)C4)cc2)C(=O)O1] | 32 | 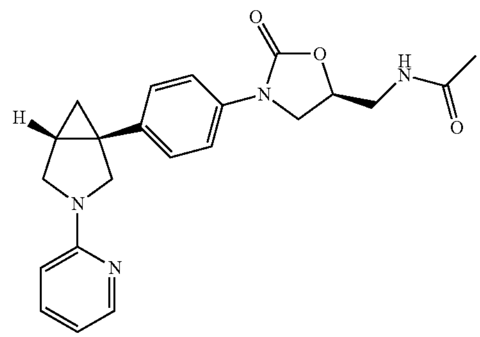 [SMILES: CC(=O)NC[C@H]1CN(c2ccc([C@]34C[C@H]3CN(c3ccccn3)C4)cc2)C(=O)O1] |
| 33 | 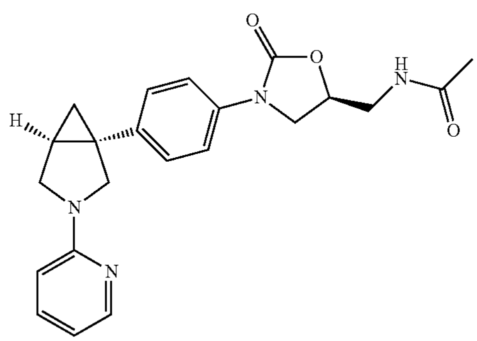 [SMILES: CC(=O)NC[C@H]1CN(c2ccc([C@@]34C[C@@H]3CN(c3ccccn3)C4)cc2)C(=O)O1] | 34 | 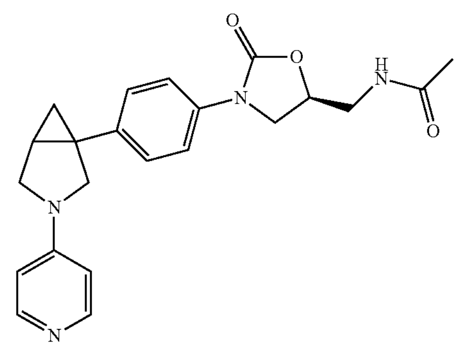 [SMILES: CC(=O)NC[C@H]1CN(c2ccc(C34CC3CN(c3ccncc3)C4)cc2)C(=O)O1] |
| 35 | 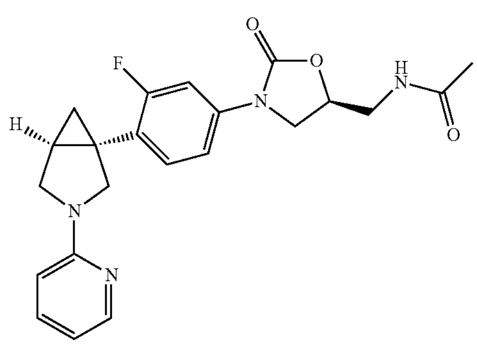 [SMILES: CC(=O)NC[C@H]1CN(c2ccc([C@@]34C[C@@H]3CN(c3ccccn3)C4)c(F)c2)C(=O)O1] | 36 | 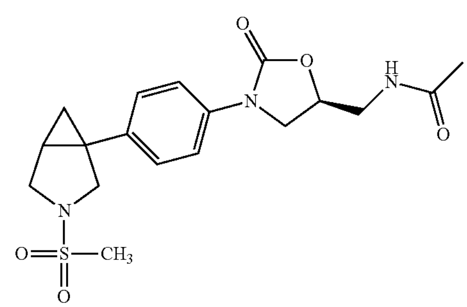 [SMILES: CC(=O)NC[C@H]1CN(c2ccc(C34CC3CN(S(C)(=O)=O)C4)cc2)C(=O)O1] |
| 37 | 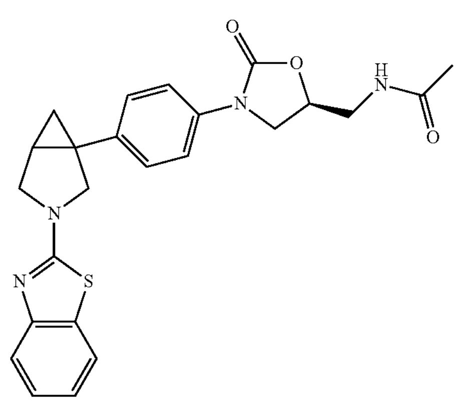 [SMILES: CC(=O)NC[C@H]1CN(c2ccc(C34CC3CN(c3nc5ccccc5s3)C4)cc2)C(=O)O1] | 38 | 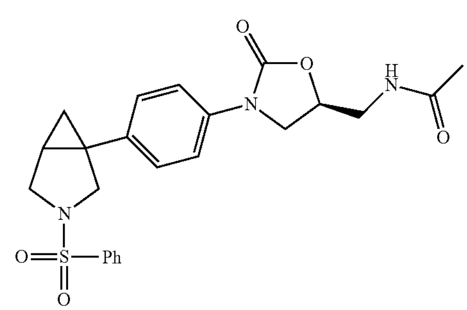 [SMILES: CC(=O)NC[C@H]1CN(c2ccc(C34CC3CN(S(=O)(=O)c3ccccc3)C4)cc2)C(=O)O1] |

TABLE 1-continued

| Compound No. | Structure | Compound No. | Structure |
| --- | --- | --- | --- |
| 39 | (structure) | 40 | (structure) |
| 41 | (structure) | 42 | (structure) |
| 43 | (structure) | 44 | (structure) |
| 45 | (structure) | 46 | (structure) |
| 47 | (structure) | 48 | (structure) |

Another embodiment of the present invention provides compounds of Formula Ib, wherein the compounds are selected from Table 2:

TABLE 2

| Compound No. | Structure | Compound No. | Structure |
|---|---|---|---|
| 49 | 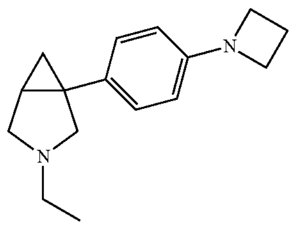 [SMILES: CCN1CC2CC2(c2ccc(N3CCC3)cc2)C1] | 50 | 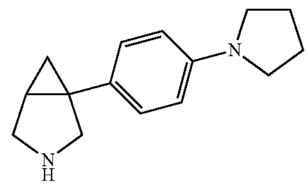 [SMILES: c1cc(C23CNCC2C3)ccc1N1CCCC1] |
| 51 | 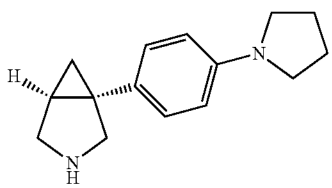 [SMILES: c1cc([C@]23CNC[C@H]2C3)ccc1N1CCCC1] | 52 | 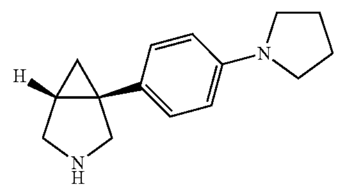 [SMILES: c1cc([C@@]23CNC[C@@H]2C3)ccc1N1CCCC1] |
| 53 | 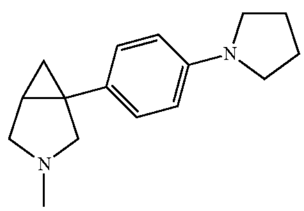 [SMILES: CN1CC2CC2(c2ccc(N3CCCC3)cc2)C1] | 54 | 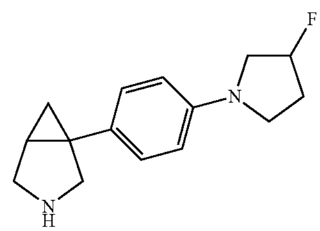 [SMILES: FC1CCN(c2ccc(C34CNCC3C4)cc2)C1] |
| 55 | 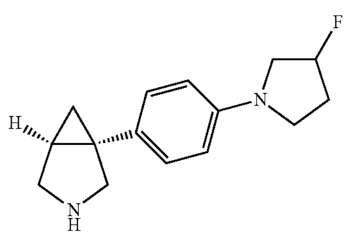 [SMILES: FC1CCN(c2ccc([C@]34CNC[C@H]3C4)cc2)C1] | 56 | 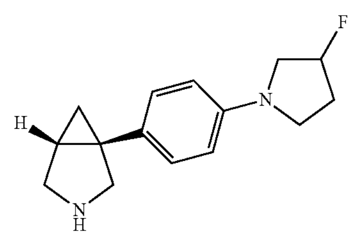 [SMILES: FC1CCN(c2ccc([C@@]34CNC[C@@H]3C4)cc2)C1] |
| 57 | 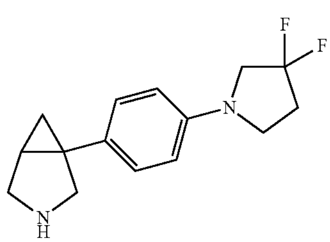 [SMILES: FC1(F)CCN(c2ccc(C34CNCC3C4)cc2)C1] | 58 | 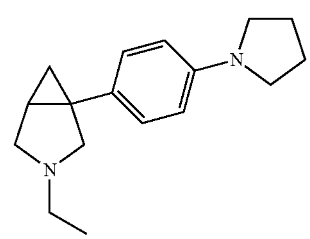 [SMILES: CCN1CC2CC2(c2ccc(N3CCCC3)cc2)C1] |
| 59 | 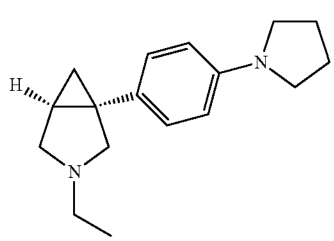 [SMILES: CCN1C[C@H]2C[C@@]2(c2ccc(N3CCCC3)cc2)C1] | 60 | 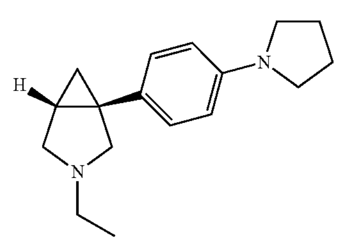 [SMILES: CCN1C[C@@H]2C[C@]2(c2ccc(N3CCCC3)cc2)C1] |

TABLE 2-continued

| Compound No. | Structure | Compound No. | Structure |
|---|---|---|---|
| 61 | 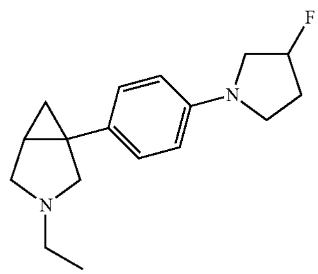 [SMILES: CCN1CC2CC2(c2ccc(N3CCC(F)C3)cc2)C1] | 62 | 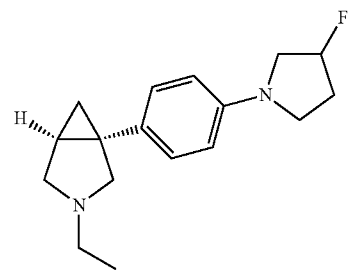 [SMILES: CCN1C[C@H]2C[C@@]2(c2ccc(N3CCC(F)C3)cc2)C1] |
| 63 | 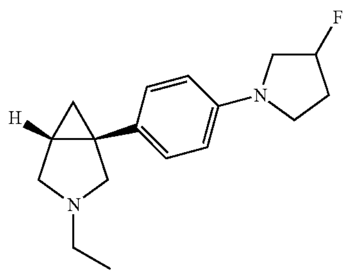 [SMILES: CCN1C[C@@H]2C[C@]2(c2ccc(N3CCC(F)C3)cc2)C1] | 64 | 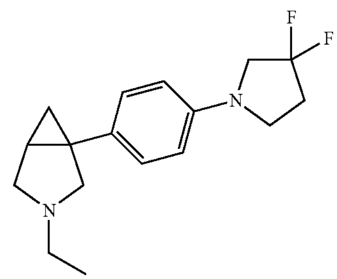 [SMILES: CCN1CC2CC2(c2ccc(N3CCC(F)(F)C3)cc2)C1] |
| 65 | 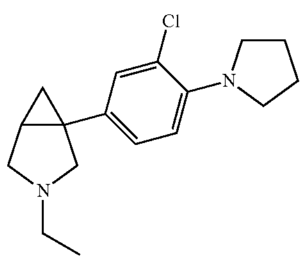 [SMILES: CCN1CC2CC2(c2ccc(N3CCCC3)c(Cl)c2)C1] | 66 | 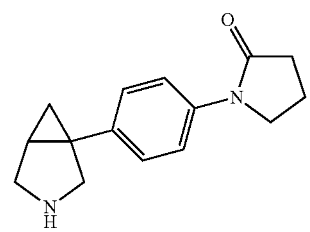 [SMILES: O=C1CCCN1c1ccc(C23CNCC2C3)cc1] |
| 67 | 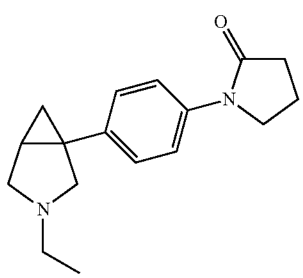 [SMILES: CCN1CC2CC2(c2ccc(N3CCCC3=O)cc2)C1] | 68 | 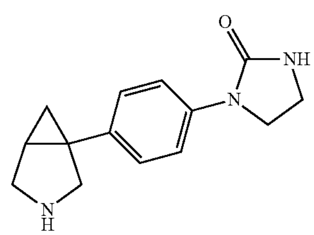 [SMILES: O=C1NCCN1c1ccc(C23CNCC2C3)cc1] |
| 69 | 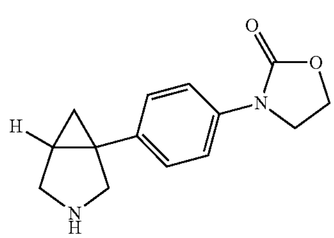 [SMILES: O=C1OCCN1c1ccc(C23CNCC2C3)cc1] | 70 | 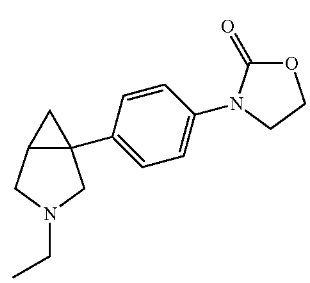 [SMILES: CCN1CC2CC2(c2ccc(N3CCOC3=O)cc2)C1] |

TABLE 2-continued

| Compound No. | Structure | Compound No. | Structure |
|---|---|---|---|
| 71 | 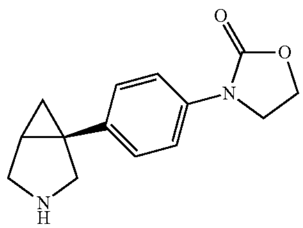 [SMILES: O=C1OCCN1c1ccc([C@@]23CNCC2C3)cc1] | 72 | 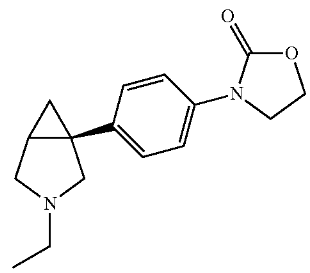 [SMILES: CCN1CC2C[C@]2(c2ccc(N3CCOC3=O)cc2)C1] |
| 73 | 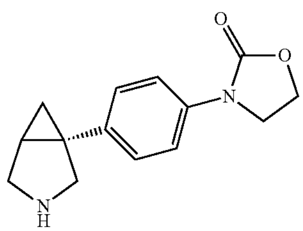 [SMILES: O=C1OCCN1c1ccc([C@]23CNCC2C3)cc1] | 74 | 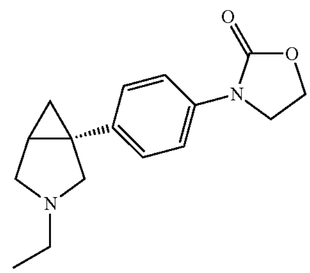 [SMILES: CCN1CC2C[C@@]2(c2ccc(N3CCOC3=O)cc2)C1] |
| 75 | 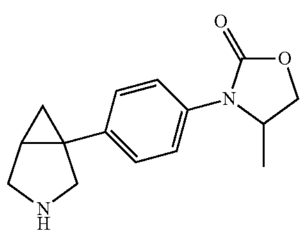 [SMILES: CC1COC(=O)N1c1ccc(C23CNCC2C3)cc1] | 76 | 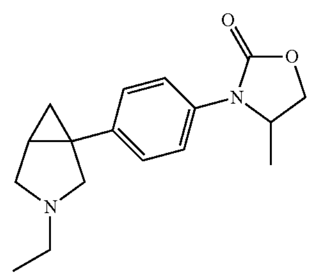 [SMILES: CCN1CC2CC2(c2ccc(N3C(=O)OCC3C)cc2)C1] |
| 77 | 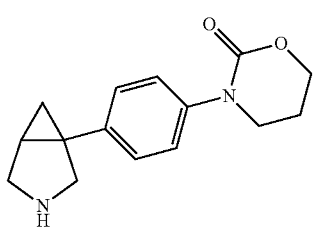 [SMILES: O=C1OCCCN1c1ccc(C23CNCC2C3)cc1] | 78 | 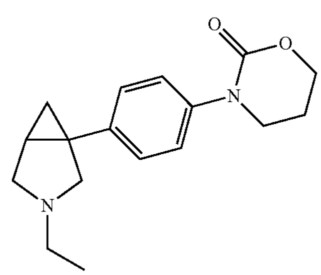 [SMILES: CCN1CC2CC2(c2ccc(N3CCCOC3=O)cc2)C1] |
| 79 | 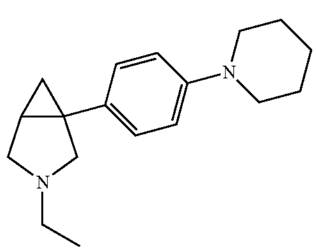 [SMILES: CCN1CC2CC2(c2ccc(N3CCCCC3)cc2)C1] | 80 | 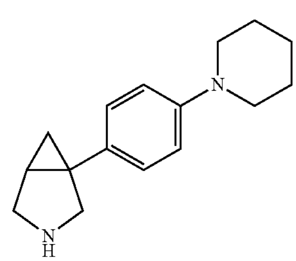 [SMILES: c1cc(C23CNCC2C3)ccc1N1CCCCC1] |

TABLE 2-continued

| Compound No. | Structure | Compound No. | Structure |
|---|---|---|---|
| 81 | 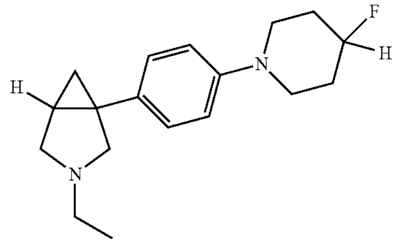 [SMILES: CCN1CC2CC2(c2ccc(N3CCC(F)CC3)cc2)C1] | 82 | 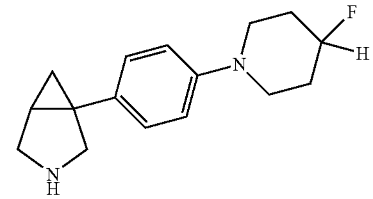 [SMILES: FC1CCN(c2ccc(C34CNCC3C4)cc2)CC1] |
| 83 | 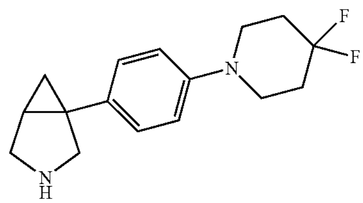 [SMILES: FC1(F)CCN(c2ccc(C34CNCC3C4)cc2)CC1] | 84 | 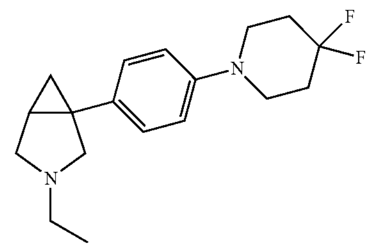 [SMILES: CCN1CC2CC2(c2ccc(N3CCC(F)(F)CC3)cc2)C1] |
| 85 | 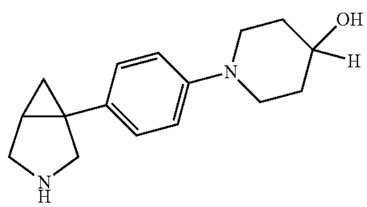 [SMILES: OC1CCN(c2ccc(C34CNCC3C4)cc2)CC1] | 86 | 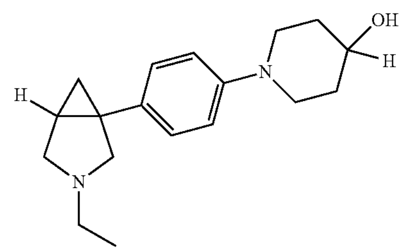 [SMILES: CCN1CC2CC2(c2ccc(N3CCC(O)CC3)cc2)C1] |
| 87 | 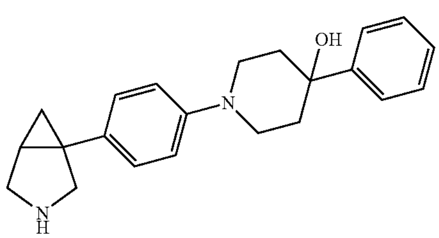 [SMILES: OC1(c2ccccc2)CCN(c2ccc(C34CNCC3C4)cc2)CC1] | 88 | 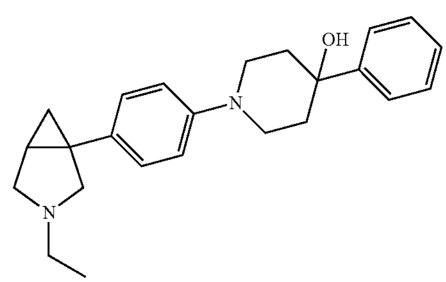 [SMILES: CCN1CC2CC2(c2ccc(N3CCC(O)(c4ccccc4)CC3)cc2)C1] |
| 89 | 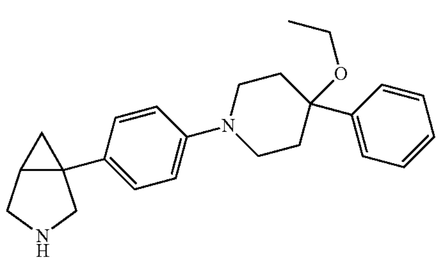 [SMILES: CCOC1(c2ccccc2)CCN(c2ccc(C34CNCC3C4)cc2)CC1] | 90 | 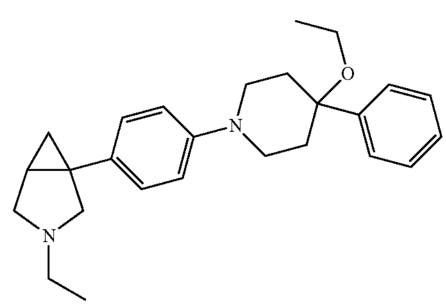 [SMILES: CCOC1(c2ccccc2)CCN(c2ccc(C34CC3CN(CC)C4)cc2)CC1] |

TABLE 2-continued
| Compound No. | Structure | Compound No. | Structure |
| --- | --- | --- | --- |
| 91 | 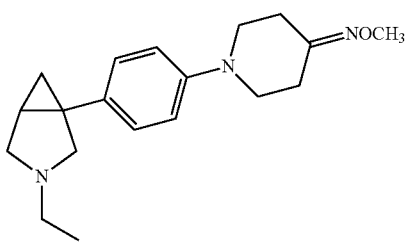 | 92 | 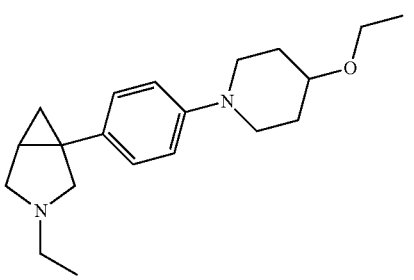 [SMILES: CCOC1CCN(c2ccc(C34CC3CN(CC)C4)cc2)CC1] |
| 93 | 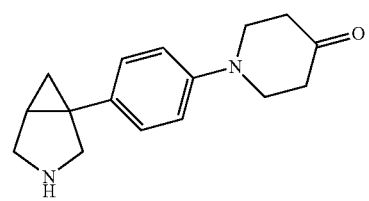 [SMILES: O=C1CCN(c2ccc(C34CNCC3C4)cc2)CC1] | 94 | 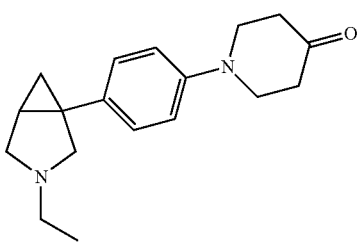 [SMILES: CCN1CC2CC2(c2ccc(N3CCC(=O)CC3)cc2)C1] |
| 95 | 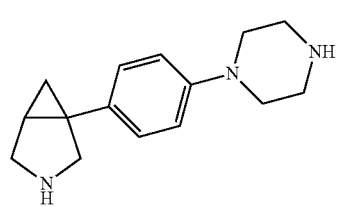 [SMILES: c1cc(C23CNCC2C3)ccc1N1CCNCC1] | 96 | 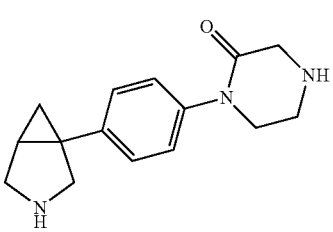 [SMILES: O=C1CNCCN1c1ccc(C23CNCC2C3)cc1] |
| 97 | 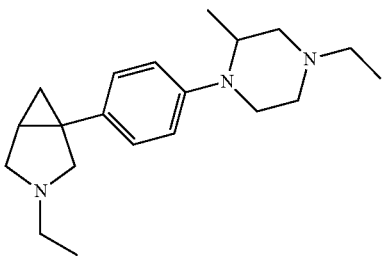 [SMILES: CCN1CCN(c2ccc(C34CC3CN(CC)C4)cc2)C(C)C1] | 98 | 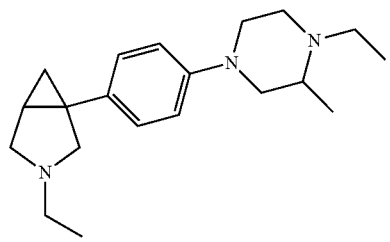 [SMILES: CCN1CC2CC2(c2ccc(N3CCN(CC)C(C)C3)cc2)C1] |
| 99 | 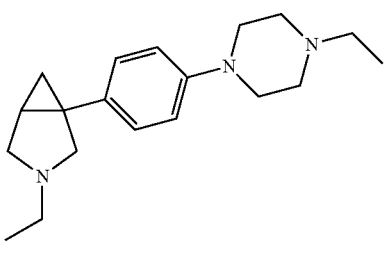 [SMILES: CCN1CCN(c2ccc(C34CC3CN(CC)C4)cc2)CC1] | 100 | 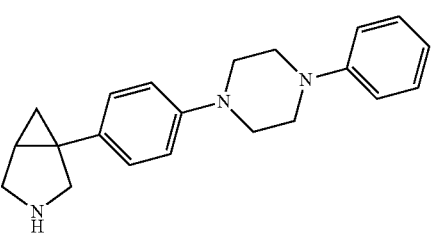 [SMILES: c1ccc(N2CCN(c3ccc(C45CNCC4C5)cc3)CC2)cc1] |
| 101 | 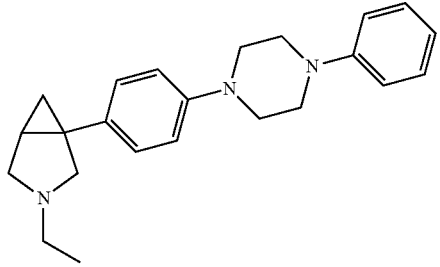 [SMILES: CCN1CC2CC2(c2ccc(N3CCN(c4ccccc4)CC3)cc2)C1] | 102 | 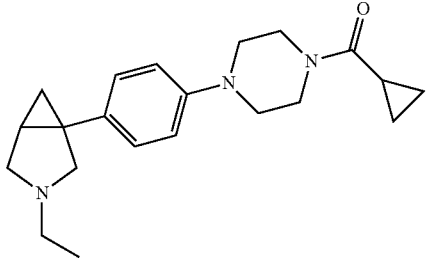 [SMILES: CCN1CC2CC2(c2ccc(N3CCN(C(=O)C4CC4)CC3)cc2)C1] |

TABLE 2-continued

| Compound No. | Structure | Compound No. | Structure |
|---|---|---|---|
| 103 | 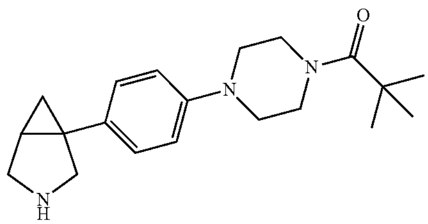 [SMILES: CC(C)(C)C(=O)N1CCN(c2ccc(C34CNCC3C4)cc2)CC1] | 104 | 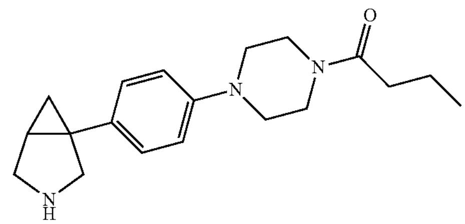 [SMILES: CCCC(=O)N1CCN(c2ccc(C34CNCC3C4)cc2)CC1] |
| 105 | 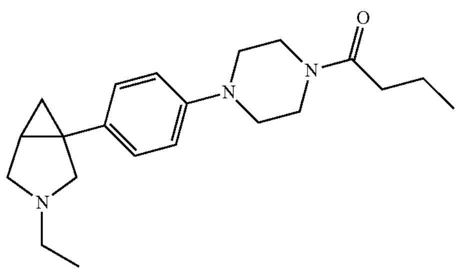 [SMILES: CCCC(=O)N1CCN(c2ccc(C34CC3CN(CC)C4)cc2)CC1] | 106 | 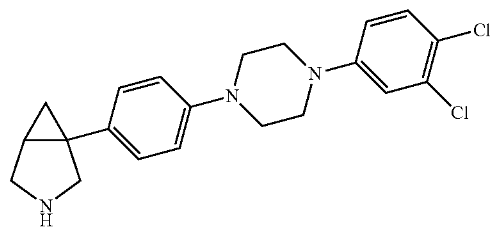 [SMILES: Clc1ccc(N2CCN(c3ccc(C45CNCC4C5)cc3)CC2)cc1Cl] |
| 107 | 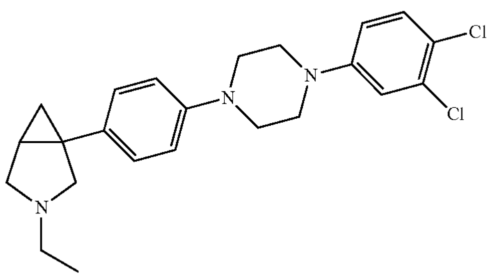 [SMILES: CCN1CC2CC2(c2ccc(N3CCN(c4ccc(Cl)c(Cl)c4)CC3)cc2)C1] | 108 | 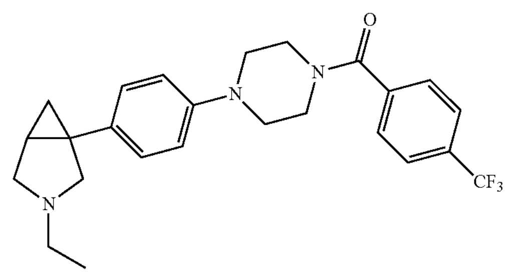 [SMILES: CCN1CC2CC2(c2ccc(N3CCN(C(=O)c4ccc(C(F)(F)F)cc4)CC3)cc2)C1] |
| 109 | 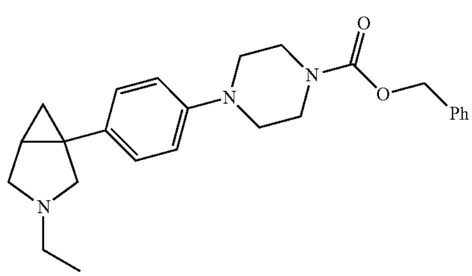 [SMILES: CCN1CC2CC2(c2ccc(N3CCN(C(=O)OCc4ccccc4)CC3)cc2)C1] | 110 | 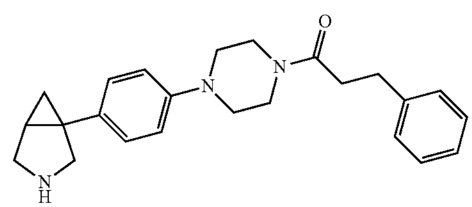 [SMILES: O=C(CCc1ccccc1)N1CCN(c2ccc(C34CNCC3C4)cc2)CC1] |
| 111 | 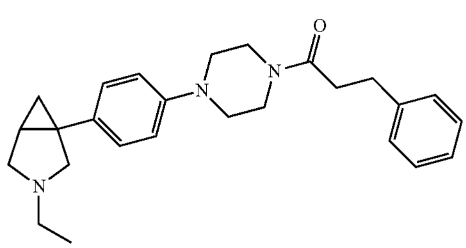 [SMILES: CCN1CC2CC2(c2ccc(N3CCN(C(=O)CCc4ccccc4)CC3)cc2)C1] | 112 | 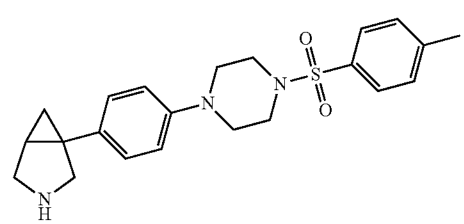 [SMILES: Cc1ccc(S(=O)(=O)N2CCN(c3ccc(C45CNCC4C5)cc3)CC2)cc1] |
| 113 | 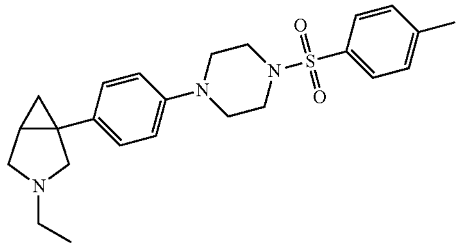 [SMILES: CCN1CC2CC2(c2ccc(N3CCN(S(=O)(=O)c4ccc(C)cc4)CC3)cc2)C1] | 114 | 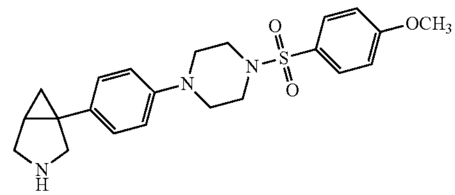 [SMILES: COc1ccc(S(=O)(=O)N2CCN(c3ccc(C45CNCC4C5)cc3)CC2)cc1] |

TABLE 2-continued
| Compound No. | Structure | Compound No. | Structure |
|---|---|---|---|
| 115 | 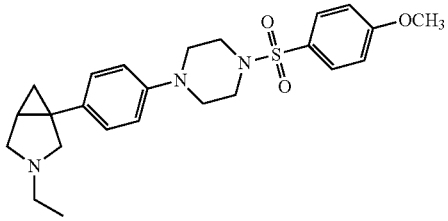 [SMILES: CCN1CC2CC2(c2ccc(N3CCN(S(=O)(=O)c4ccc(OC)cc4)CC3)cc2)C1] | 116 | 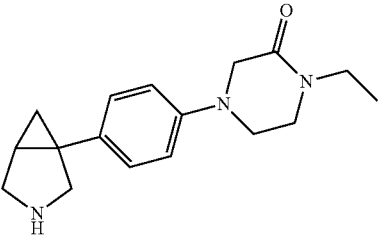 [SMILES: CCN1CCN(c2ccc(C34CNCC3C4)cc2)CC1=O] |
| 117 | 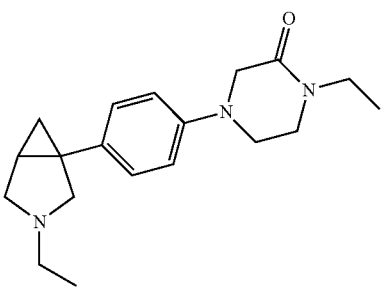 [SMILES: CCN1CC2CC2(c2ccc(N3CCN(CC)C(=O)C3)cc2)C1] | 118 | 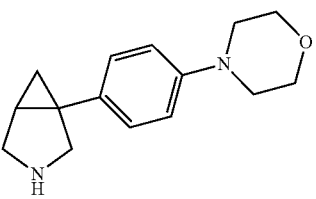 [SMILES: c1cc(C23CNCC2C3)ccc1N1CCOCC1] |
| 119 | 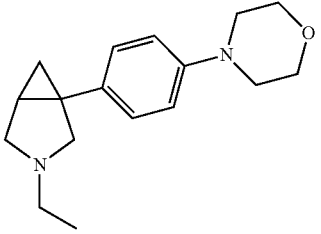 | 120 | 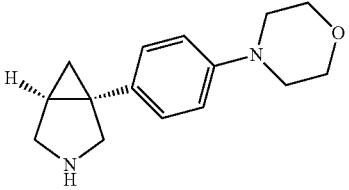 [SMILES: c1cc([C@]23CNC[C@H]2C3)ccc1N1CCOCC1] |
| 121 | 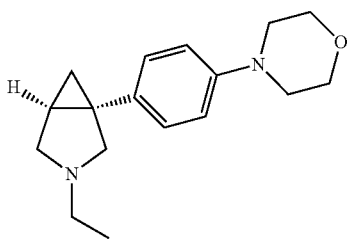 [SMILES: CCN1C[C@H]2C[C@@]2(c2ccc(N3CCOCC3)cc2)C1] | 122 | 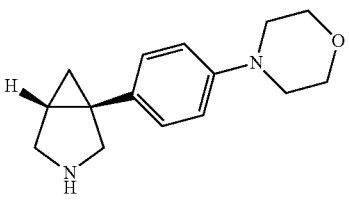 [SMILES: c1cc([C@@]23CNC[C@@H]2C3)ccc1N1CCOCC1] |
| 123 | 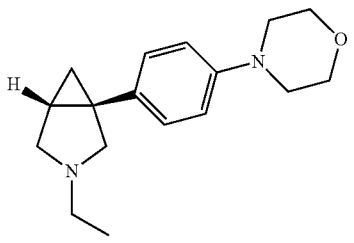 [SMILES: CCN1C[C@@H]2C[C@]2(c2ccc(N3CCOCC3)cc2)C1] | 124 | 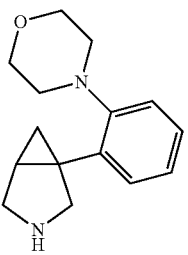 [SMILES: c1ccc(C23CNCC2C3)c(N2CCOCC2)c1] |

TABLE 2-continued

| Compound No. | Structure | Compound No. | Structure |
| --- | --- | --- | --- |
| 125 | 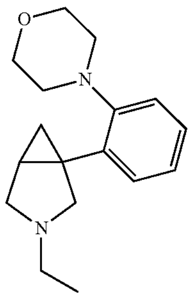 [SMILES: CCN1CC2CC2(c2ccccc2N2CCOCC2)C1] | 126 | 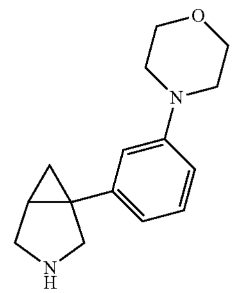 [SMILES: c1cc(N2CCOCC2)cc(C23CNCC2C3)c1] |
| 127 | 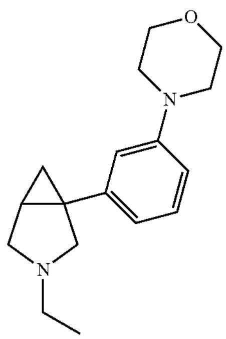 [SMILES: CCN1CC2CC2(c2cccc(N3CCOCC3)c2)C1] | 128 | 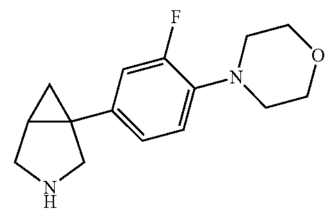 [SMILES: Fc1cc(C23CNCC2C3)ccc1N1CCOCC1] |
| 129 | 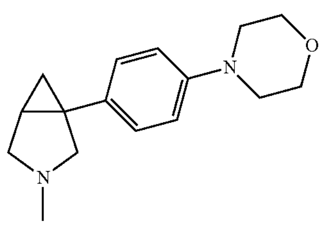 [SMILES: CN1CC2CC2(c2ccc(N3CCOCC3)cc2)C1] | 130 | 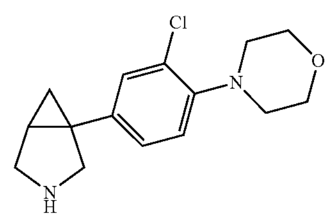 [SMILES: Clc1cc(C23CNCC2C3)ccc1N1CCOCC1] |
| 131 | 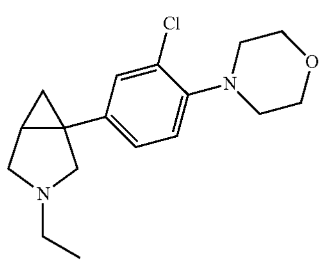 [SMILES: CCN1CC2CC2(c2ccc(N3CCOCC3)c(Cl)c2)C1] | 132 | 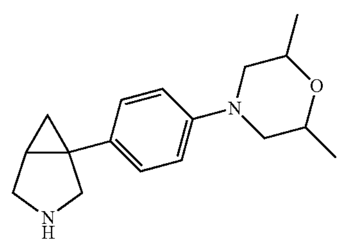 [SMILES: CC1CN(c2ccc(C34CNCC3C4)cc2)CC(C)O1] |
| 133 | 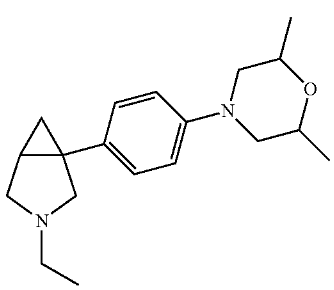 [SMILES: CCN1CC2CC2(c2ccc(N3CC(C)OC(C)C3)cc2)C1] | 134 | 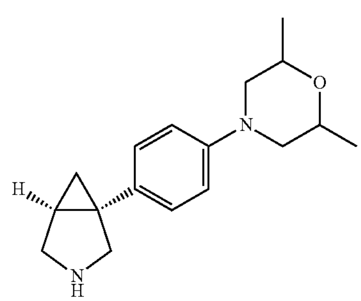 [SMILES: CC1CN(c2ccc([C@]34CNC[C@H]3C4)cc2)CC(C)O1] |

TABLE 2-continued

| Compound No. | Structure | Compound No. | Structure |
|---|---|---|---|
| 135 | 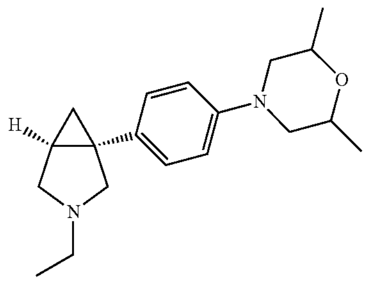 [SMILES: CCN1C[C@H]2C[C@@]2(c2ccc(N3CC(C)OC(C)C3)cc2)C1] | 136 | 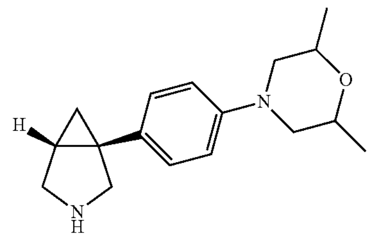 [SMILES: CC1CN(c2ccc([C@@]34CNC[C@@H]3C4)cc2)CC(C)O1] |
| 137 | 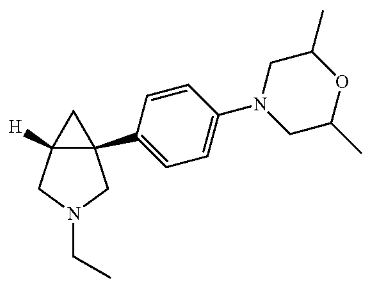 [SMILES: CCN1C[C@@H]2C[C@]2(c2ccc(N3CC(C)OC(C)C3)cc2)C1] | 138 | 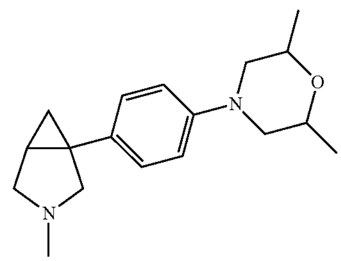 [SMILES: CC1CN(c2ccc(C34CC3CN(C)C4)cc2)CC(C)O1] |
| 139 | 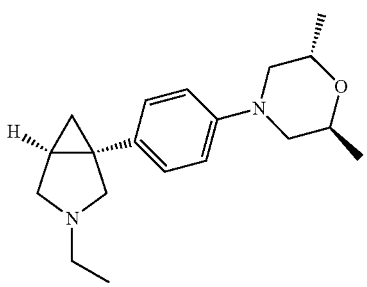 [SMILES: CCN1C[C@H]2C[C@@]2(c2ccc(N3C[C@H](C)O[C@@H](C)C3)cc2)C1] | 140 | 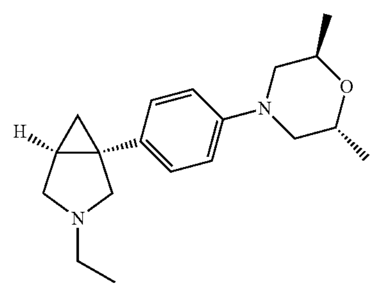 [SMILES: CCN1C[C@H]2C[C@@]2(c2ccc(N3C[C@@H](C)O[C@H](C)C3)cc2)C1] |
| 141 | 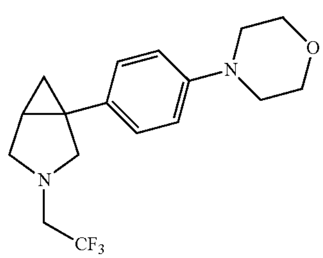 [SMILES: FC(F)(F)CN1CC2CC2(c2ccc(N3CCOCC3)cc2)C1] | 142 | 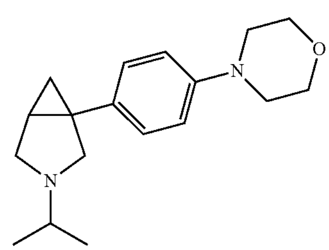 [SMILES: CC(C)N1CC2CC2(c2ccc(N3CCOCC3)cc2)C1] |
| 143 | 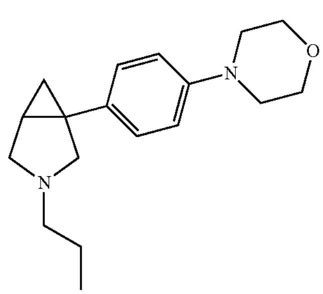 [SMILES: CCCN1CC2CC2(c2ccc(N3CCOCC3)cc2)C1] | 144 | 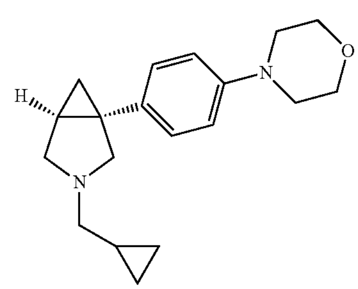 [SMILES: c1cc([C@@]23C[C@@H]2CN(CC2CC2)C3)ccc1N1CCOCC1] |

TABLE 2-continued
| Compound No. | Structure | Compound No. | Structure |
|---|---|---|---|
| 145 | 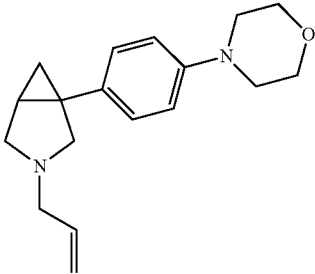 [SMILES: C=CCN1CC2CC2(c2ccc(N3CCOCC3)cc2)C1] | 146 | 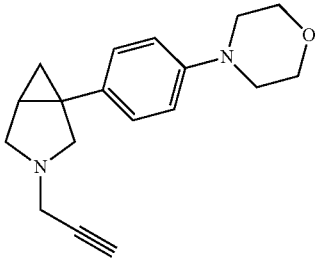 [SMILES: C#CCN1CC2CC2(c2ccc(N3CCOCC3)cc2)C1] |
| 147 | 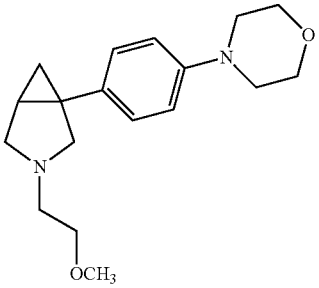 [SMILES: COCCN1CC2CC2(c2ccc(N3CCOCC3)cc2)C1] | 148 | 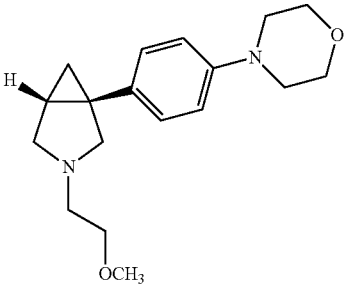 [SMILES: COCCN1C[C@@H]2C[C@]2(c2ccc(N3CCOCC3)cc2)C1] |
| 149 | 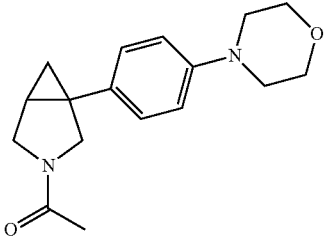 [SMILES: CC(=O)N1CC2CC2(c2ccc(N3CCOCC3)cc2)C1] | 150 | 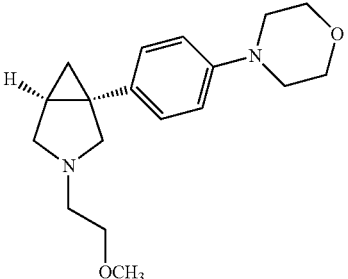 |
| 151 | 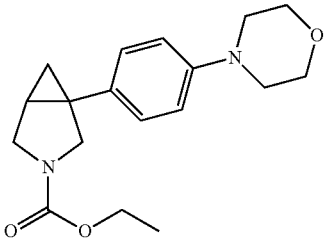 [SMILES: CCOC(=O)N1CC2CC2(c2ccc(N3CCOCC3)cc2)C1] | 152 | 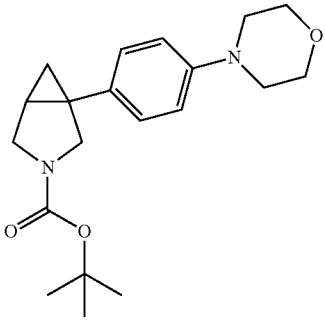 [SMILES: CC(C)(C)OC(=O)N1CC2CC2(c2ccc(N3CCOCC3)cc2)C1] |
| 153 | 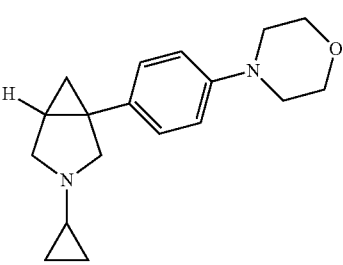 [SMILES: c1cc(C23CC2CN(C2CC2)C3)ccc1N1CCOCC1] | 154 | 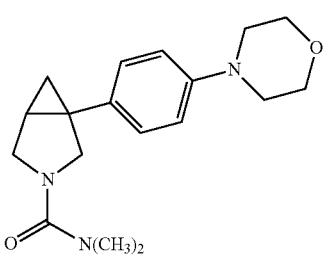 [SMILES: CN(C)C(=O)N1CC2CC2(c2ccc(N3CCOCC3)cc2)C1] |

TABLE 2-continued

| Compound No. | Structure | Compound No. | Structure |
| --- | --- | --- | --- |
| 155 | 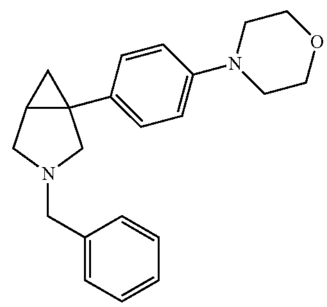 [SMILES: c1ccc(CN2CC3CC3(c3ccc(N4CCOCC4)cc3)C2)cc1] | 156 | 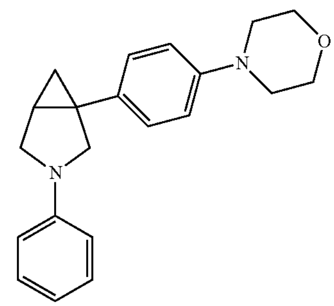 [SMILES: c1ccc(N2CC3CC3(c3ccc(N4CCOCC4)cc3)C2)cc1] |
| 157 | 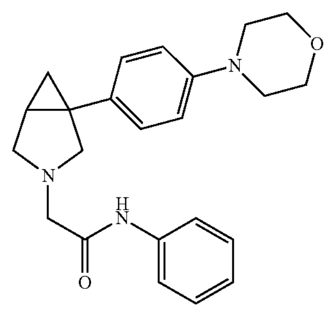 [SMILES: O=C(CN1CC2CC2(c2ccc(N3CCOCC3)cc2)C1)Nc1ccccc1] | 158 | 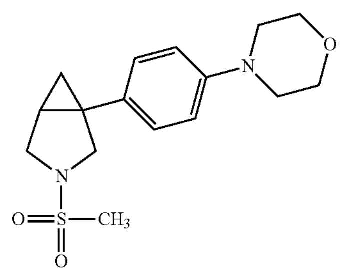 [SMILES: CS(=O)(=O)N1CC2CC2(c2ccc(N3CCOCC3)cc2)C1] |
| 159 | 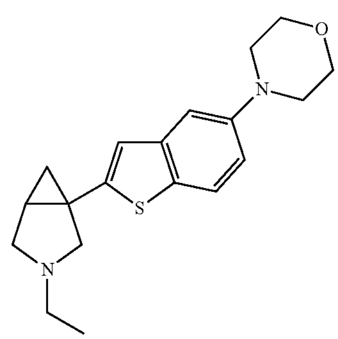 [SMILES: CCN1CC2CC2(c2cc3cc(N4CCOCC4)ccc3s2)C1] | 160 | 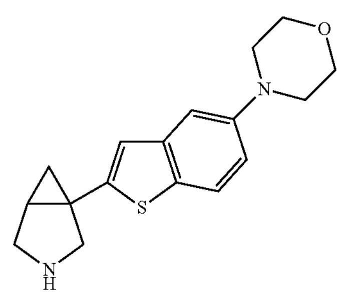 [SMILES: c1cc2sc(C34CNCC3C4)cc2cc1N1CCOCC1] |
| 161 | 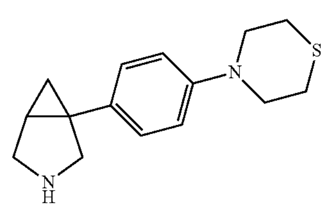 [SMILES: c1cc(C23CNCC2C3)ccc1N1CCSCC1] | 162 | 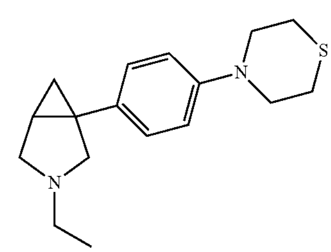 |
| 163 | 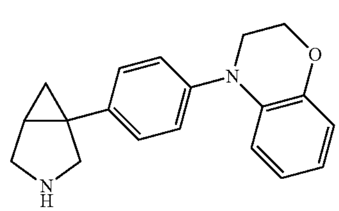 [SMILES: c1ccc2c(c1)OCCN2c1ccc(C23CNCC2C3)cc1] | 164 | 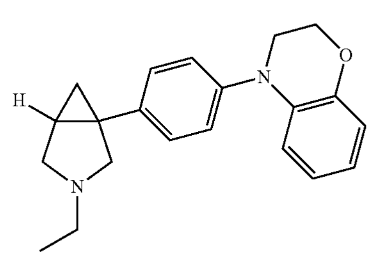 [SMILES: CCN1CC2CC2(c2ccc(N3CCOc4ccccc43)cc2)C1] |

TABLE 2-continued
| Compound No. | Structure | Compound No. | Structure |
|---|---|---|---|
| 165 | 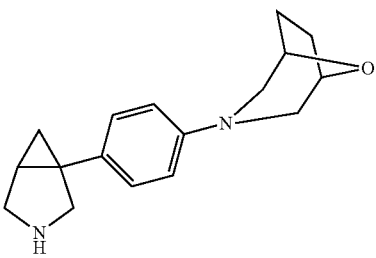 [SMILES: c1cc(C23CNCC2C3)ccc1N1CC2CCC(C1)O2] | 166 | 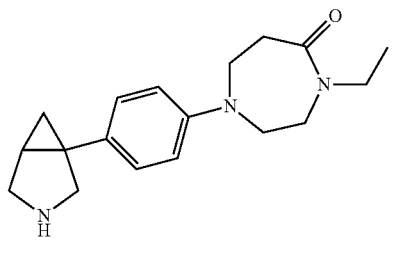 [SMILES: CCN1CCN(c2ccc(C34CNCC3C4)cc2)CCC1=O] |
| 167 | 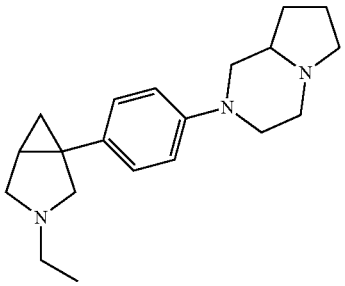 [SMILES: CCN1CC2CC2(c2ccc(N3CCN4CCCC4C3)cc2)C1] | 168 | 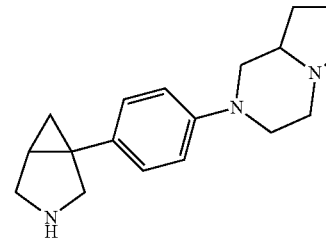 |
| 169 | 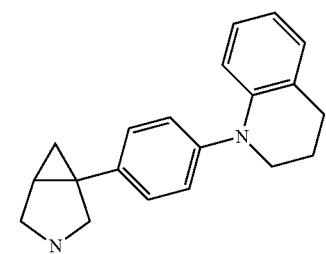 | 170 | 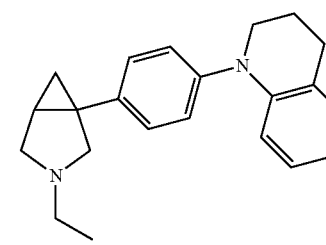 |
| 171 | 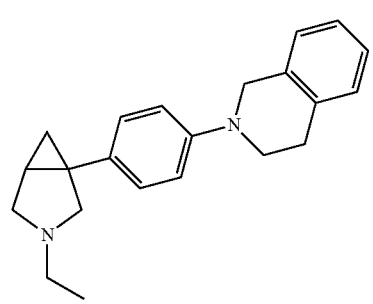 [SMILES: CCN1CC2CC2(c2ccc(N3CCc4ccccc4C3)cc2)C1] | 172 | 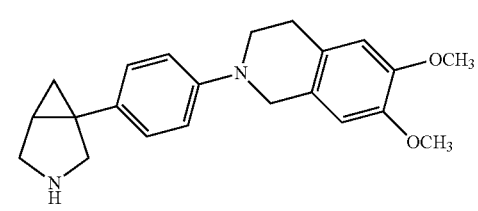 [SMILES: COc1cc2c(cc1OC)CN(c1ccc(C34CNCC3C4)cc1)CC2] |
| 173 | 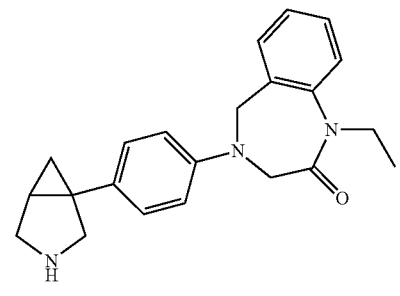 [SMILES: CCN1C(=O)CN(c2ccc(C34CNCC3C4)cc2)Cc2ccccc21] | 174 | 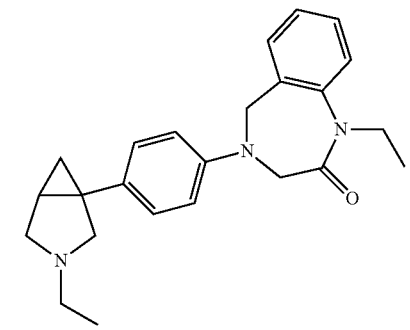 [SMILES: CCN1CC2CC2(c2ccc(N3CC(=O)N(CC)c4ccccc4C3)cc2)C1] |

TABLE 2-continued
| Compound No. | Structure | Compound No. | Structure |
| --- | --- | --- | --- |
| 175 | 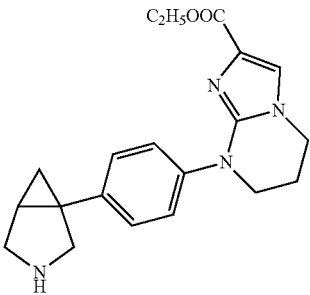 | 176 | 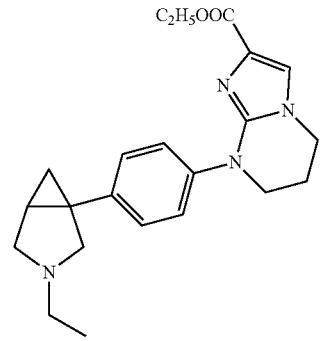 |
| 177 | 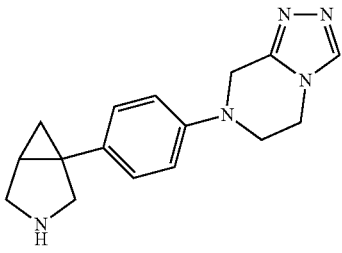 [SMILES: c1cc(C23CNCC2C3)ccc1N1CCn2cnnc2C1] | 178 | 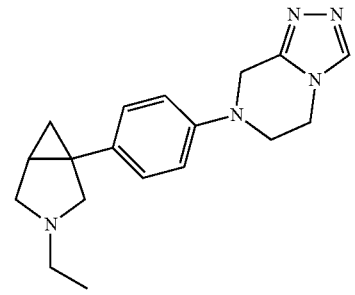 [SMILES: CCN1CC2CC2(c2ccc(N3CCn4cnnc4C3)cc2)C1] |
| 179 | 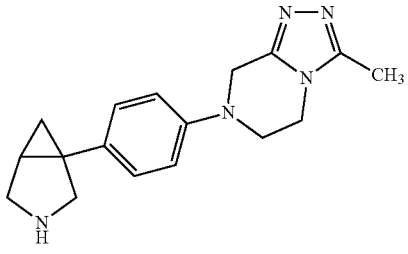 [SMILES: Cc1nnc2n1CCN(c1ccc(C34CNCC3C4)cc1)C2] | 180 | 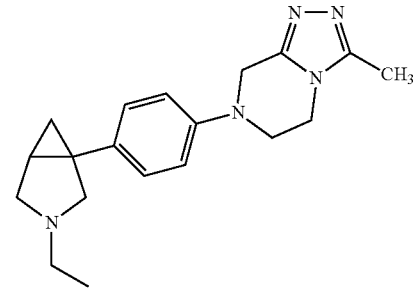 [SMILES: CCN1CC2CC2(c2ccc(N3CCn4c(C)nnc4C3)cc2)C1] |
| 181 | 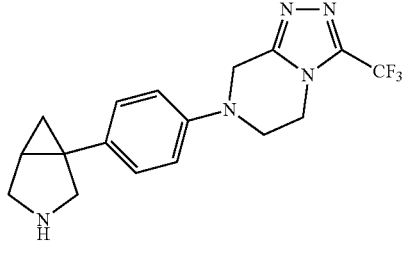 [SMILES: FC(F)(F)c1nnc2n1CCN(c1ccc(C34CNCC3C4)cc1)C2] | 182 | 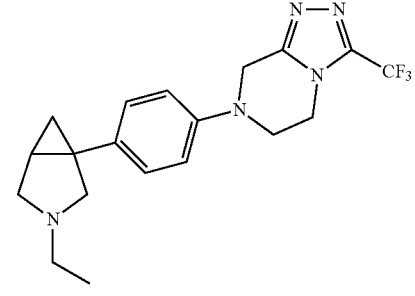 [SMILES: CCN1CC2CC2(c2ccc(N3CCn4c(nnc4C(F)(F)F)C3)cc2)C1] |
| 183 | 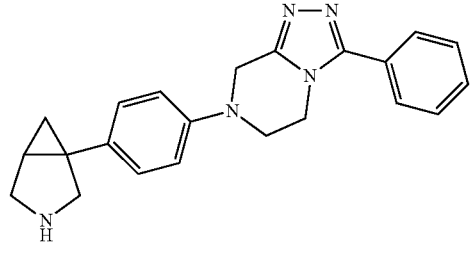 [SMILES: c1ccc(-c2nnc3n2CCN(c2ccc(C45CNCC4C5)cc2)C3)cc1] | 184 | 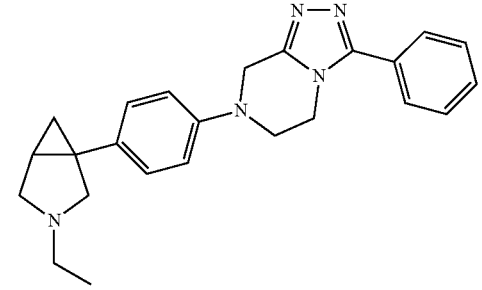 [SMILES: CCN1CC2CC2(c2ccc(N3CCn4c(nnc4-c4ccccc4)C3)cc2)C1] |

A further embodiment of the present invention provides compounds of Formula Ib, wherein the compounds are selected from Table 3:

TABLE 3

| Compound No. | Structure | Compound No. | Structure |
|---|---|---|---|
| 185 | 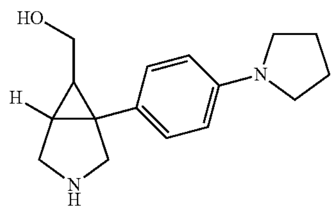 [SMILES: OCC1C2CNCC12c1ccc(N2CCCC2)cc1] | 186 | 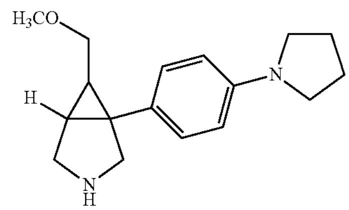 [SMILES: COCC1C2CNCC21c1ccc(N2CCCC2)cc1] |
| 187 | 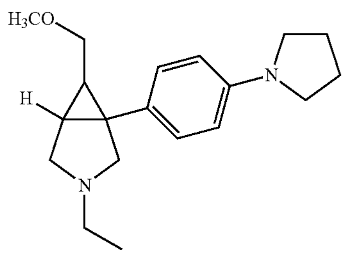 [SMILES: CCN1CC2C(COC)C2(c2ccc(N3CCCC3)cc2)C1] | 188 | 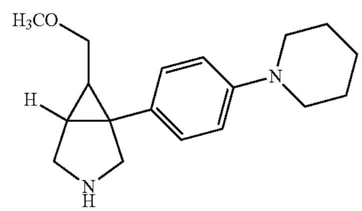 [SMILES: COCC1C2CNCC21c1ccc(N2CCCCC2)cc1] |
| 189 | 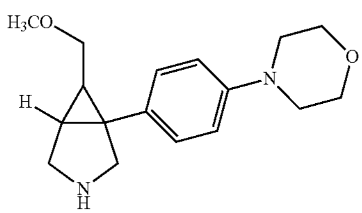 [SMILES: COCC1C2CNCC21c1ccc(N2CCOCC2)cc1] | 190 | 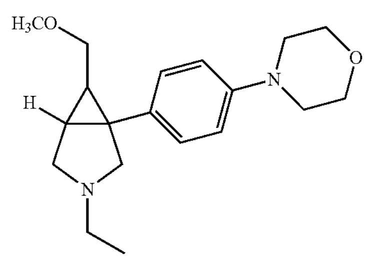 [SMILES: CCN1CC2C(COC)C2(c2ccc(N3CCOCC3)cc2)C1] |
| 191 | 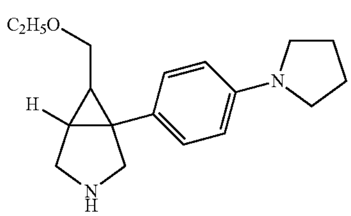 | 192 | 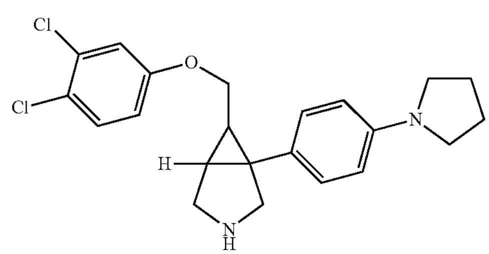 [SMILES: Clc1ccc(OCC2C3CNCC32c2ccc(N3CCCC3)cc2)cc1Cl] |
| 193 | 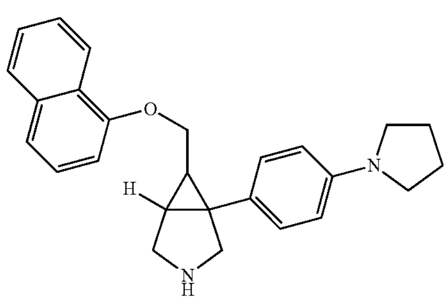 [SMILES: c1ccc2c(OCC3C4CNCC43c3ccc(N4CCCC4)cc3)cccc2c1] | | |

The compounds of the present invention represented by Formula Ia and Formula Ib can be prepared from azabicyclohexane intermediates such as those of Formula II, wherein $R^2$, $R^3$, $R^4$, $R^5$ are the same as defined herein.

Compounds of Formula II can be prepared following procedures reported in *Org. Lett.* 2006, 8, 3885-3888 and PCT application numbers WO 2007016155, WO 2008074716 and WO 2007022935.

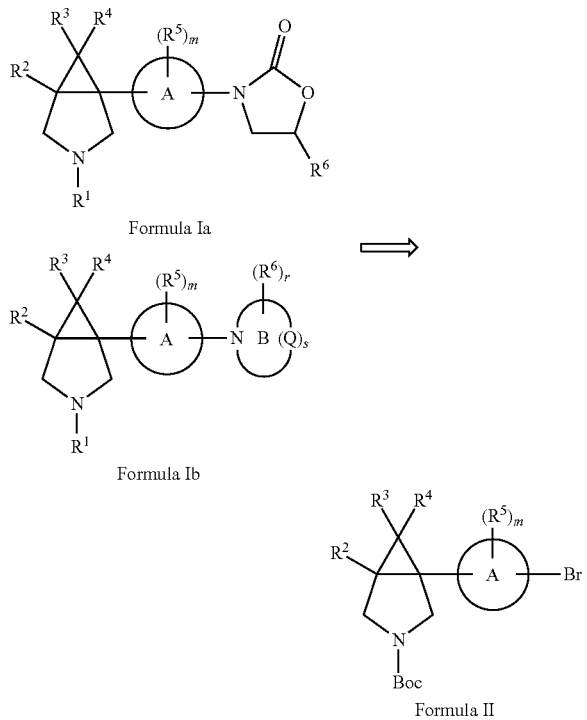

The compounds of Formula Ia can be prepared from the compounds of Formula II (wherein $R^2$, $R^3$, $R^4$, $R^5$ are the same as defined herein) by following the Scheme 1. Compounds of Formula II can be reacted with suitable benzyl amine to give compounds of Formula III by using appropriate coupling reagents like tris(dibenzylideneacetone)dipalladium (0) (Pd$_2$(dba)$_3$) and 2,2'-bis(diphenylphosphino)-1,1'-binaphthyl (BINAP) in the presence of a base and suitable solvent (*J. Org. Chem.*, 2006, 71, 6522-6529). Examples of bases include $^t$BuONa, triethylamine, diisopropylethyl amine and the like. Examples of appropriate solvents include toluene, dioxane, N,N-dimethylformamide (DMF), dimethyl sulfoxide (DMSO) and the like or mixtures thereof. Examples of substituted benzyl amine include but are not limited to p-methoxy benzylamine, 3,4-dimethoxybenzyl amine and the like. Compounds of Formula IV can be prepared from compounds of Formula III by debenzylation. The debenzylation can be carried out using various methods familiar to persons skilled in the art, such as hydrogenation over an appropriate catalyst such as palladium, platinum, or ruthenium on activated charcoal or chemical methods such as reaction with ceric ammonium nitrate (CAN), 2,3-dichloro-5,6-dicyanobenzoquinone (DDQ) and 1-chloroethyl chloroformate. Alternatively, compounds of Formula IV can be prepared directly from compounds of Formula II using other methods familiar to those skilled in the art, like reaction of compound of Formula II with ammonia. The resulting amines of Formula IV can then be treated with benzyl or methyl chloroformate and sodium bicarbonate in presence of water and acetone to form the corresponding benzyl or methyl carbamate derivatives of Formula V which are subsequently deprotonated in the next step using a lithium base such as n-butyllithium followed by the addition of glycidyl butyrate in presence of a suitable solvent such as diethylether or tetrahydrofuran to afford the oxazolidinones of Formula VI. The hydroxymethyl group of compounds of Formula VI can then be converted to $R^6$ (Formula VII) (wherein $R^6$ is as defined herein). The exact nature of the reagents used for this conversion is dependent on the nature of the $R^6$ desired. For example, if $R^6$ is desired to be —CH$_2$—NH(C=O)CH$_3$ group, the hydroxyl group is first converted to amino group which is then acetylated in the presence of suitable acylating reagents such as acetic anhydride, acetyl chloride or the like. If $R^6$ is desired to be —CH$_2$-1,2,3-triazolyl, the hydroxyl group is first converted to the azide and then reacted with a norbornadiene in dioxane. The appropriate conditions and reagents for any particular $R^6$ group can be readily selected by persons skilled in the art. The compounds of Formula VII are then converted to compound of Formula VIII using standard deprotecting reagents, familiar to those skilled in the art for example, trifluoroacetic acid (TFA) or by passing HCl gas in a solution of solvent such as methanol, ethyl acetate, diethyl ether, dioxane and the like. Compounds of Formula VIII are then converted to compounds of Formula Ia (wherein $R^1$ is as defined earlier).

The exact nature of the reagents used for this conversion is dependent on the exact nature of the $R^1$ desired. For example, if $R^1$ is desired to be —(C=O)OCH$_3$ group, compounds of Formula VIII are reacted with methyl chloroformate in the presence of suitable base like triethyl amine (TEA), diisopropyl ethylamine (DIPEA), pyridine or like in suitable solvent like dichloromethane (DCM), chloroform, acetonitrile, toluene and mixture thereof. If $R^1$ is desired to be 2-pyridyl, the compounds of Formula VIII are reacted with 2-bromopyridine in the presence of Pd$_2$(dba)$_3$, BINAP in the presence of suitable base like $^t$BuONa, DIPEA and suitable solvent like toluene or DMF. The appropriate conditions and reagents for any particular $R^1$ group can be readily selected by persons skilled in the art.

Scheme 1

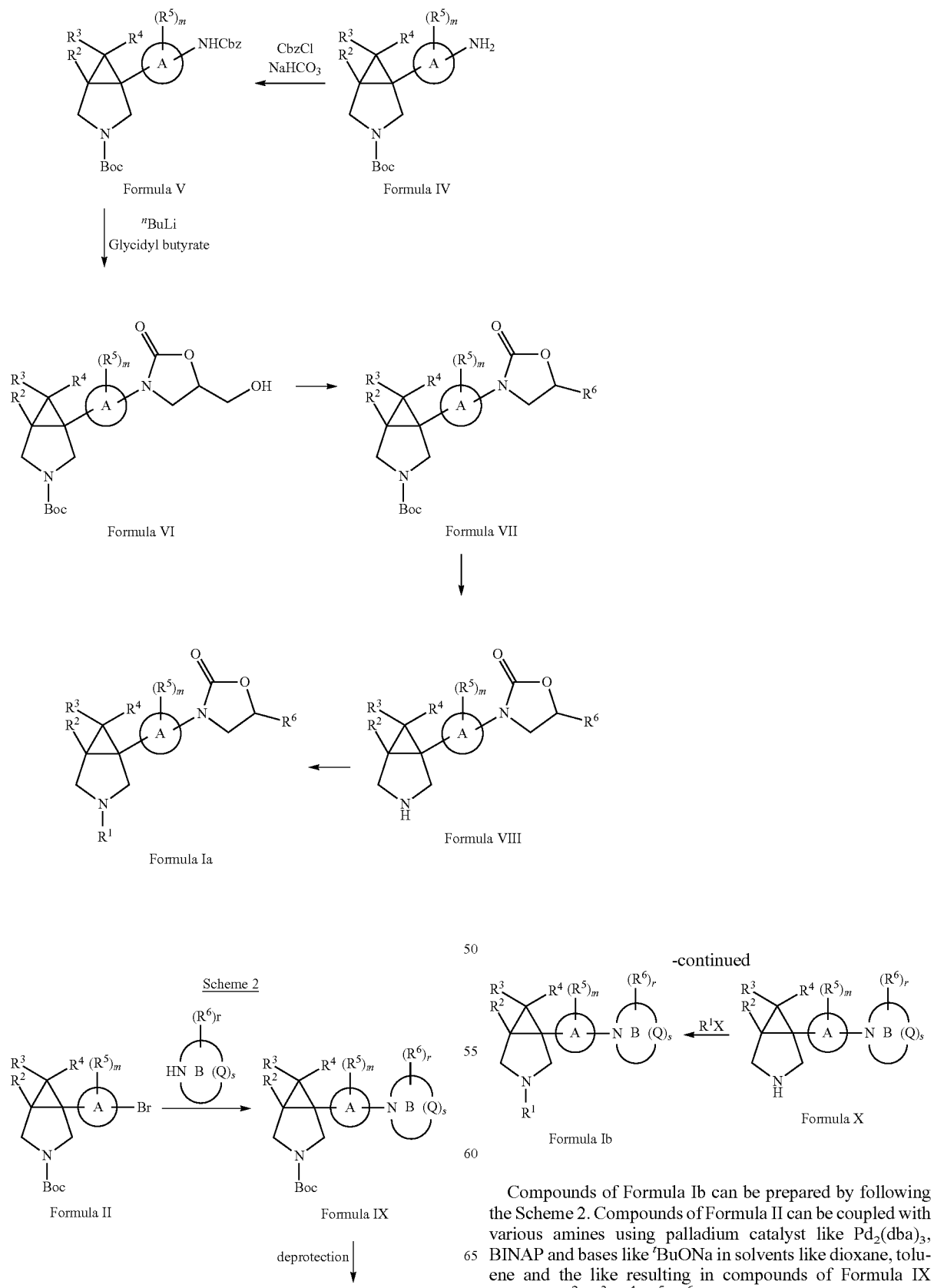
Compounds of Formula Ib can be prepared by following the Scheme 2. Compounds of Formula II can be coupled with various amines using palladium catalyst like $Pd_2(dba)_3$, BINAP and bases like $^tBuONa$ in solvents like dioxane, toluene and the like resulting in compounds of Formula IX (wherein $R^2$, $R^3$, $R^4$, $R^5$, $R^6$ are the same as defined herein).

Compounds of Formula IX can be deprotected by using various deprotecting agents like trifluoroacetic acid, HCl gas, p-toluenesulfonyl chloride (pTSA) or phosphoric acid, to provide compounds of Formula X. Compounds of Formula X are subsequently converted to compounds of Formula Ib, by reaction with appropriate reagent $R^1X$, using various conditions known to persons skilled in the art. Conditions chosen for this conversion will depend upon the exact nature of $R^1$ required.

Compounds of Formula Ib can also be prepared by following the alternate Scheme 3. Compounds of Formula II can be coupled with various cyclic amides using bases selected from but not limited to potassium carbonate ($K_2CO_3$), cesium carbonate ($Cs_2CO_3$) in the presence of CuI and diamines like (±)-trans-cyclohexanediamine, ethylene diamine and the like, using various solvents like dioxane, toluene, DMF (*J. Am. Chem. Soc.* 2001, 123, 7727-7729) to provide compounds of Formula XI (wherein $R^2$, $R^3$, $R^4$, $R^5$, $R^6$, Q, ring B are the same as defined herein). The compounds of Formula XI can be deprotected by various deprotecting reagents like TFA, HCl gas, pTSA or phosphoric acid and the like, to provide compounds of Formula XII. Compounds of Formula XII are subsequently converted to compounds of Formula XIII, by reaction with appropriate reagent $R^1X$, using various conditions known to persons skilled in the art. Conditions chosen for this conversion will depend upon the exact nature of $R^1$ required. Compounds of Formula XIII are then converted to compounds of Formula Ib via reduction of ring B, using reducing agents like lithium aluminum hydride (LAH), borane dimethyl sulfide complex solution ($BH_3.Me_2S$), borane tetrahydrofuran complex solution ($BH_3.THF$) and the like in the presence of solvents like tetrahydrofuran (THF), ether and the like.

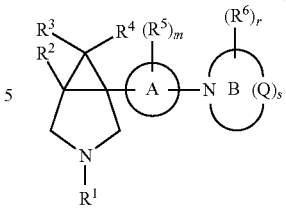

Formula Ib

It is understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations. The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. The salts may be prepared during the final isolation and purification of the compounds or separately by making basic or acidic addition salts. Representative salts of basic compounds of the present invention can be prepared by reacting free base form of the compound with a suitable acid, including, but not limited to acetate, trifluoroacetate, adipate, citrate, aspartate, benzoate, benzenesulphonate, bisulfate, besylate, butyrate, camphorsulphonate, difluconae, hemisulfate, heptanoate, formate, fumarate, lactate, maleate, methanesulfonate, naphthylsulfonate, nicotinate, oxalate, picrate, pivalate, succinate, tartrate, tirchloracetat, glutamate, p-toluenesulphonate, hydrochloric, hydrobromic, sulphuric, phosphoric and the like. Representative salts of acidic compounds of the present invention can be prepared by reacting free acid form of the compound with a suitable base, including, but not limited to ammonium, calcium, magnesium, potassium, sodium salts, salts of primary, secondary and tertiary amines, substituted amines including naturally occurring ones e.g., arginine, betaine, caffeine, choline, glucamine, glucosamine, histidine, lysine, morpholine, piperazine, piperidine, purine, triethylamine and the like. Compounds of the present invention that contain a carboxylic acid (—COOH) or alcohol group, their pharmaceutically acceptable esters of carboxylic acids such as methyl, ethyl and the like, or acyl derivatives of alcohols such as acetate and the like, can be employed. Compounds of the present invention that comprise basic nitrogen atom may be quaternized with alkyl halides, alkyl sulfates and the like. Such salts permit the preparation of both water soluble and oil soluble compounds of the present invention. It should be recognized that the free base or free acid forms will typically differ from their respective salt forms somewhat in physical properties such as solubility in polar solvents, but otherwise the salts are equivalent to their respective free forms for the purpose of the invention.

The "pharmaceutically acceptable solvates" refer to solvates with water (i.e., hydrates) or pharmaceutically acceptable solvents, for example, ethanol and the like.

The invention also encompasses "prodrugs" of the compounds of the present invention which upon in-vivo administration undergo chemical conversion by metabolic processes before becoming active pharmacological substances. In general such prodrugs will be functional derivatives of a compound of the invention which are readily convertible in vivo into the compound of the invention. Conventional pro- Scheme 3

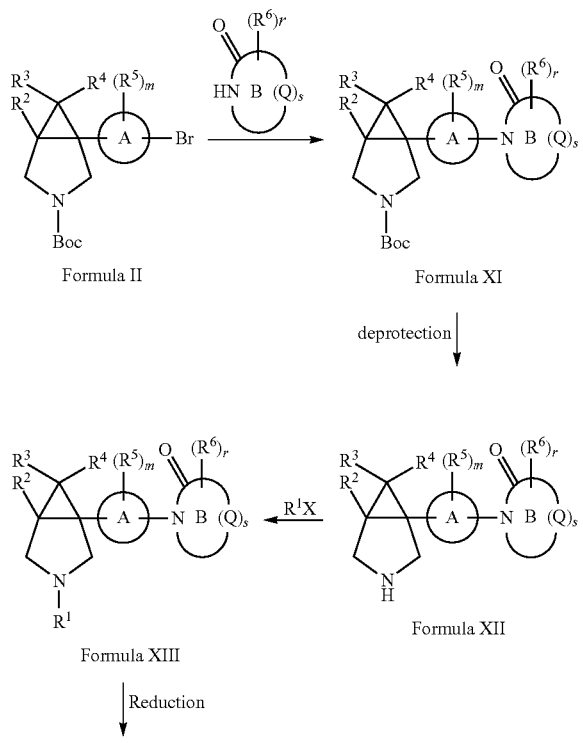

cedures for the selection and preparation of suitable prodrug derivatives are described, for example, in "Targeted prodrug design to optimize drug delivery", *AAPS PharmaSci* (2000), 2(1), E6.

The invention also encompasses active "metabolites" of the compound of the present invention. An active metabolite is an active derivative of a compound of Formula I, produced when the compound of Formula I is metabolized.

Various "polymorphs" of a compound of general Formula I forming part of this invention may be prepared by crystallization of a compound of Formula I under different conditions. For example, by using different solvents commonly used or their mixtures for recrystallization; crystallizations at different temperatures; various modes of cooling, ranging from very fast to very slow cooling during crystallizations, heating or melting the compound followed by gradual or fast cooling may also obtain polymorphs. The presence of polymorphs may be determined by solid probe NMR spectroscopy, IR spectroscopy, differential scanning calorimetry, powder X-ray diffraction or such other techniques.

The present invention also provides pharmaceutical compositions, comprising compounds of the present invention or their pharmaceutically acceptable derivatives, tautomeric forms, stereoisomers, polymorphs, prodrugs, metabolites, salts or solvates thereof optionally in combination with one or more pharmaceutically acceptable carriers comprising excipients and auxiliaries. The pharmaceutical compositions may be in any form known in the art, such as tablets, capsules, powders, syrups, solutions, suspensions and the like, may contain flavourants, sweeteners etc in suitable solid or liquid carriers or diluents, or in suitable sterile media to form injectable solutions or suspensions. Such compositions typically contain active compound optionally in combination with pharmaceutically acceptable carriers, diluents or solvents.

The pharmaceutical compositions of the present invention can be manufactured by processes well known in the art, for example, by means of conventional mixing, dissolving, dry granulation, wet granulation, dragee-making, levigating, emulsifying, encapsulating, entrapping, lyophilizing processes or spray drying. The compounds or the pharmaceutical compositions comprising such compounds of the present invention may be administered in the form of any pharmaceutical formulation. The pharmaceutical formulation will depend upon the nature of the active compound and its route of administration. Any route of administration may be used, for example oral, buccal, pulmonary, topical, parenteral (including subcutaneous, intramuscular and intravenous), transdermal, ocular (ophthalmic), by inhalation, intranasal, transmucosal, implant or rectal administration. Preferably the compounds of the present invention are administered orally, parenterally or topically.

In an embodiment, the amount of the novel compounds having the Formula I according to the present invention to be incorporated into the pharmaceutical compositions of the present invention can vary over a wide range depending on known factors such as, for example, the disorder to be treated, the severity of the disorder, the patient's body weight, the dosage form, the chosen route of administration and the number of administration per day. Typically, the amount of the compound of Formula I in the pharmaceutical compositions of the present invention will range from approximately 0.01 mg to about 5000 mg. In an embodiment, the daily dose of composition comprising the novel compounds having the Formula I is in the range of about 0.01 mg/kg to about 100 mg/kg based on the body weight of the subject in need thereof which may be administered as a single or multiple doses.

In an embodiment, the novel compounds having the Formula I according to the present invention are particularly useful for the treatment of disease(s) or disorder(s) which are particularly acute in nature and which require a short term but mild to moderate treatment, or even some chronic conditions which favorably respond to or are alleviated by the novel compounds having the Formula I or compositions comprising them. The compositions comprising the novel compounds having the Formula I are useful prophylactically or therapeutically depending upon the pathological condition intended to be prevented or treated respectively.

In one embodiment compounds of general Formula I are useful in the prophylaxis, amelioration and/or treatment of one or more condition(s)/disease(s)/disorder(s), in a subject in need thereof preferably a mammal including a human.

In another embodiment compounds of general Formula Ia are useful in the prophylaxis, amelioration and/or treatment of one or more condition(s)/disease(s)/disorder(s), as antimicrobial agents, in a subject in need thereof preferably a mammal including a human.

In a further embodiment compounds of general Formula Ia are useful in the prophylaxis, amelioration and/or treatment of one or more condition(s)/disease(s)/disorder(s), as antibacterial agents, effective against a number of aerobic and/or anaerobic Gram positive and/or Gram negative pathogens such as multi drug resistant species of *Staphylococcus, Streptococcus, Enterococcus, Bacterioides, Clostridia, H. influenza, Moraxella*, acid-fast organisms such as *Mycobacterium tuberculosis* and the like, in a subject in need thereof preferably a mammal including a human.

In another embodiment compounds of general Formula Ib are useful in the prophylaxis, amelioration and/or treatment of one or more condition(s)/disease(s)/disorder(s) of the central and/or peripheral nervous system, in a subject in need thereof preferably a mammal including a human.

In further embodiment compounds of general Formula Ib are useful in the prophylaxis, amelioration and/or treatment of one or more condition(s)/disease(s)/disorder(s) of the central and/or peripheral nervous system that are responsive to modulation of neurological and/or psychiatric targets (GPCR and/or non-GPCR), in a subject in need thereof preferably a mammal including a human.

The condition(s)/disease(s)/disorder(s) of the central and/or peripheral nervous system that may be treated, controlled, or in some cases prevented, by treatment with compounds of general Formula Ib include, but are not limited to, for example, depression, psychotic disorders, mood disorders, bipolar disorders, personality disorders, eating disorders, aggressive behavior, schizophrenia, inflammatory bowel disorders, irritable bowel syndrome, pain, chronic neuropathic pain, addiction disorders including cocaine abuse, urinary incontinence, dementia, Alzheimer's memory loss, Parkinsonism, stroke, anxiety, attention-deficit disorder, social phobia, pathological crying and/or laughing, obsessive compulsive disorder, substance (like nicotine, alcohol and opium) abuse and withdrawal (substance related disorder), cognitive disorders, fibromyalgia, Interstitial cystitis, Nocturnal enuresis, Ciguatera poisoning, Body dysmorphic disorder, Lichen simplex chronicus, chronic hiccups and sleep disorders. Included among these disorders are disorders related to depression, such as pseudodementia, migraine pain or headache, bulimia, obesity, pre-menstrual syndrome or late luteal phase syndrome, tobacco abuse, smoking, panic disorder, memory loss, dementia of ageing, acquired immunodeficiency syndrome dementia complex, memory dysfunction in ageing, anti-attention deficit hyperactivity disorder (ADHD), chronic fatigue syndrome, premature ejaculation, erectile difficulty, anorexia nervosa, narcolepsy, Gilles de la Tourettes disease, presenile dementia, senile dementia, cognition impairment, sexual dysfunctions, disorders of sleep or autism, mutism or trichotillomania.

All of the various forms and sub-forms of the disorders mentioned herein are contemplated as part of the present invention.

The neurological and/or psychiatric targets (GPCR and/or non-GPCR) which may be modulated with compounds of general Formula Ib for treatment, control, or in some cases prevention of the aforementioned disorders include, but are not limited to, for example biogenic amine transport, HPA axis, hippocampus dysfunction, neurotrophic mechanism of modulating neuroplasticity; Acetycholine (muscarinic) $M_1$, $M_2$, $M_4$, $M_5$ or Glutamatergic receptors namely, ionotropic receptors (NMDA, AMPA, and kainate receptors) and metabotropic receptors (G-protein coupled receptors); Adenosine $A_1$; Adrenoceptor $\alpha_{1B}$, $\alpha_{2A}$, $\beta_{1, 2, 3}$; Bombesin BB2; Bradykinin B2; Cannabinoid CB1; Chemokine CCR2B, CXCR3; Cholecystokinin CCK1, CCK2; Dopamine D1, D2L, D5; $GABA_A$; Galanin GAL1, GAL2; Glucagon GLP-1, Secretin receptor; Glutamate(metabotropic) mGlu, NMDA, AMPA, Kainate; Glycoprotein hormone TSH; Histamine H1, H2, H3; Lysophospholipid S1P1, SIPS, LPA1; Neuropeptide Y2; NPY acting via Y1 receptors; Neurotensin NTR1; N-formylpeptide FPR1, FPRL1; Nicotinic acid GPR109A; Melatonin MT1 and MT2 receptor; Opioid Delta, Mu, NOP/ORL1, OX1; P2Y P2RY1; Platelet Activating Factor; Prolactin-releasing peptide; Prostanoid EP1, EP2; Serotonin $5-HT_{1A}$, $5-HT_{2C}$, $5-HT_{2A}$, $5-HT_3$, $5-HT_6$, $5-HT_7$; Somatostatin SST2, SST4; Tachykinin/neurokinin NK1, NK2, NK3; VIP/PACAP PAC1 long isoform, VPAC1, VPAC2; Adrenoceptor alpha2A; Corticotropin releasing factor CRF1, CRF2; Lysophospholipid LPA1; Melanin-concentrating hormone MCHR1; Opiods (Delta, mu, kappa & NOP/ORL1); Orexin OX1, OX2; Vasopressin V(1b); Sigma $\delta_1$; Melatonin MT1, MT2; BDNF, TrkB; Phospodiesterase; Beta adrenoceptor β-1,2,3; Glucorticoid receptor antagonists; Calcium channels, glycine receptors; MAO; Nitric Oxide Synthase; and various other GPCRs targeting neurological and psychiatric disorders.

In still another embodiment of the present invention is provided use of the dosage form compositions comprising the novel compounds of Formula I for the treatment of one or more condition(s)/disease(s)/disorder(s), which comprises administrating to a subject in need thereof a pharmaceutically effective amount of the composition.

In still another embodiment of the present invention is provided use of the dosage form compositions comprising the novel compounds of Formula Ia as antimicrobial agents, for the treatment of one or more condition(s)/disease(s)/disorder(s), which comprises administrating to a subject in need thereof a pharmaceutically effective amount of the composition.

In still another embodiment of the present invention is provided use of the dosage form compositions comprising the novel compounds of Formula Ia as antibacterial agents, effective against a number of aerobic and/or anaerobic Gram positive and/or Gram negative pathogens for the treatment of one or more condition(s)/disease(s)/disorder(s), which comprises administrating to a subject in need thereof a pharmaceutically effective amount of the composition.

In another embodiment of the present invention is provided use of the dosage form compositions comprising the novel compounds of Formula Ib for the treatment of one or more condition(s)/disease(s)/disorder(s) of the central and/or peripheral nervous system, which comprises administrating to a subject in need thereof a pharmaceutically effective amount of the composition.

A further embodiment of the present invention is provided use of the dosage form compositions comprising the novel compounds of Formula Ib for the treatment of one or more condition(s)/disease(s)/disorder(s) of the central and/or peripheral nervous system that are responsive to modulation of neurological and/or psychiatric targets (GPCR and/or non-GPCR), which comprises administrating to a subject in need thereof a pharmaceutically effective amount of the composition.

Another embodiment of the present invention is the use of a compound of Formula I for the manufacture of a medicament for the prophylaxis, amelioration and/or treatment of one or more condition(s)/disease(s)/disorder(s), in a subject in need thereof preferably a mammal including a human.

A further embodiment of the present invention is the use of a compound of Formula Ia for the manufacture of a medicament for the prophylaxis, amelioration and/or treatment of bacterial infections in a subject in need thereof preferably a mammal including a human.

In still another embodiment of the present invention is the use of a compound of Formula Ib for the manufacture of a medicament for the prophylaxis, amelioration and/or treatment of one or more condition(s)/disease(s)/disorder(s) of the central and/or peripheral nervous system, in a subject in need thereof preferably a mammal including a human.

In another embodiment of the present invention is the use of a compound of Formula Ib for the manufacture of a medicament for the prophylaxis, amelioration and/or treatment of one or more condition(s)/disease(s)/disorder(s) of the central and/or peripheral nervous system that are responsive to modulation of neurological and/or psychiatric targets (GPCR and/or non-GPCR), in a subject in need thereof preferably a mammal including a human.

An embodiment of the present invention relates to methods of using the compounds of Formula I of the present invention or compositions comprising the compounds of Formula I for the prophylaxis, amelioration and/or treatment of any one or more condition(s)/disease(s)/disorder(s), which comprises administering to a subject in need thereof the compounds of Formula I or compositions comprising a pharmaceutically effective amount of the compounds of Formula I.

Another embodiment of the present invention relates to methods of using the compounds of Formula Ia of the present invention or compositions comprising the compounds of Formula Ia, as antimicrobial agents, for the prophylaxis, amelioration and/or treatment of one or more condition(s)/disease(s)/disorder(s), which comprises administering to a subject in need thereof the compounds of Formula Ia or compositions comprising a pharmaceutically effective amount of the compounds of Formula Ia.

Further an embodiment of the present invention relates to methods of using the compounds of Formula Ib of the present invention or compositions comprising the compounds of Formula Ib for the prophylaxis, amelioration and/or treatment of one or more condition(s)/disease(s)/disorder(s) of the central and/or peripheral nervous system, which comprises administering to a subject in need thereof the compounds of Formula Ib or compositions comprising a pharmaceutically effective amount of the compounds of Formula Ib.

Still another embodiment of the present invention relates to methods of using the compounds of Formula Ib of the present invention or compositions comprising the compounds of Formula Ib for the prophylaxis, amelioration and/or treatment of one or more condition(s)/disease(s)/disorder(s) of the central and/or peripheral nervous system, that are responsive to modulation of neurological and/or psychiatric targets (GPCR and/or non-GPCR), which comprises administering to a subject in need thereof the compounds of Formula Ib or compositions comprising a pharmaceutically effective amount of the compounds of Formula Ib.

An embodiment of the present invention provides methods for the prophylaxis, amelioration and/or treatment of one or more one or more condition(s)/disease(s)/disorder(s), in a subject in need thereof preferably a mammal including a human, that comprises administering a therapeutically effective amount of compound of Formula I.

Another embodiment of the present invention further provides methods for the prophylaxis, amelioration and/or treatment of one or more one or more condition(s)/disease(s)/disorder(s), in a subject in need thereof preferably a mammal including a human, that comprises administering a therapeutically effective amount of compound of Formula Ia as antimicrobial agent.

Another embodiment of the present invention further provides methods for the prophylaxis, amelioration and/or treatment of one or more one or more condition(s)/disease(s)/disorder(s), in a subject in need thereof preferably a mammal including a human, that comprises administering a therapeutically effective amount of compound of Formula Ia as antibacterial agents, effective against a number of aerobic and/or anaerobic Gram positive and/or Gram negative pathogens for the treatment of one or more condition(s)/disease(s)/disorder(s).

Another embodiment of the present invention further provides methods for the prophylaxis, amelioration and/or treatment of one or more one or more condition(s)/disease(s)/disorder(s) of the central and/or peripheral nervous system, in a subject in need thereof preferably a mammal including a human, that comprises administering a therapeutically effective amount of compound of Formula Ib.

A further embodiment of the present invention provides methods for the prophylaxis, amelioration and/or treatment of one or more one or more condition(s)/disease(s)/disorder(s) of the central and/or peripheral nervous system that are responsive to modulation of neurological and/or psychiatric targets (GPCR and/or non-GPCR), in a subject in need thereof preferably a mammal including a human, that comprises administering a therapeutically effective amount of compound of Formula Ib.

In an embodiment, compounds of the general Formula Ib may be useful as analgesics to relieve pain. For example they may be useful in the treatment of conditions which include but are not limited to chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain, sympathetically maintained pain myositis, pain associated with cancer and fibromyalgia; pain associated with migraine; pain associated with influenza or other viral infections, such as common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

In a further embodiment compounds of general Formula Ib may be useful in the treatment of neuropathic pain which includes, but is not limited to, diabetic neuropathy, sciatica, non-specific lower back pain, multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. Neuropathic pain may be spontaneous shooting and lancinating pain; ongoing, burning pain; pain associated with normally non-painful sensations such as "pins and needles" (paraesthesias and dysesthesias), increased sensitivity to touch (hyperesthesia) and; pain associated with painful sensation following innocuous stimulation (dynamic, static or thermal allodynia), increased sensitivity to noxious stimuli (thermal, cold, mechanical hyperalgesia), continuing pain sensation after removal of stimulation (hyperpathia) or an absence of or deficit in selective sensory pathways (hypoalgesia).

In another embodiment compounds of the general Formula Ib may be useful in the treatment of depression which includes, but is not limited to, Depression and mood disorders including Major Depressive Episode, Manic Episode, Mixed Episode and Hypomanic Episode; Depressive Disorders including Major Depressive Disorder, Dysthymic Disorder, Depressive Disorder not otherwise specified; Other Mood Disorders including Mood Disorder due to a general medical condition which includes the subtypes with depressive features, with major depressive-like episode, with manic features and mixed features, Substance-induced Mood Disorder (including the subtypes with depressive features, with manic features and with mixed features), dysthymia and mood disorders not otherwise specified; Bipolar Disorders including Bipolar I Disorder, Bipolar II Disorder (Recurrent Major Depressive Episodes with Hypomanic Episodes), Cylothymic disorder, and Bipolar Disorder not otherwise specified; Neuralgia (neuropathic pain) and fibromyalgia.

In an embodiment compounds of the general Formula Ib may be useful in the treatment of anxiety which includes, but is not limited to, anxiety disorders including Panic Attack, Panic Disorder in Panic Disorder without Agoraphobia and panic disorder with Agoraphobia; Agoraphobia; Agoraphobia without history of panic disorder, specific phobia including the subtypes Animal Type, Natural Environment Type, blood-injection-injury type, situational type and other type; Social phobia (Social Anxiety Disorder), Obsessive-Compulsive Disorder, Personality disorders such as borderline personality disorder (BPD), attention-deficit hyperactivity disorder (ADHD) and personality disorder not otherwise specified; Posttraumatic stress disorder, acute stress disorder, generalized anxiety disorder, depression related anxiety, anxiety disorder due to a general medical condition, substance-induced anxiety disorder, Separation anxiety disorder, adjustment disorder with anxiety, and anxiety disorder not otherwise specified.

In a further embodiment compounds of the general Formula Ib may be useful in the treatment of substance related disorders which include, but are not limited to, substance-related disorders including substance use disorders such as Substance Dependence, Substance craving and substance abuse; substance-induced Disorders such as Substance Intoxication, Substance Withdrawal, substance-induced Delirium, substance-induced persisting dementia, substance-induced persisting amnestic disorder, substance-induced psychotic disorder, substance-induced mood disorder, substance-induced Mood disorder, substance-induced anxiety disorder, substance-induced sexual dysfunction, substance-induced sleep disorder and hallucinogen persisting perception disorder (Flashbacks); Alcohol-related disorders such as alcohol dependence, alcohol abuse, alcohol intoxication, alcohol withdrawal, alcohol intoxication delirium, alcohol withdrawal delirium, alcohol-induced persisting dementia, alcohol-induced persisting amnestic disorder, alcohol-induced psychotic disorder, alcohol-induced mood disorder, alcohol-induced anxiety disorder, alcohol-induced sexual dysfunction, alcohol-induced sleep disorder and alcohol related disorder not otherwise specified; Amphetamine (or Amphetamine like)-related disorder such as Amphetamine dependence, Amphetamine abuse, Amphetamine intoxication, Amphetamine withdrawal, Amphetamine intoxication delirium, Amphetamine-induced psychotic disorder, Amphetamine-induced mood disorder, Amphetamine-induced anxiety disorder, Amphetamine-induced sexual dysfunction, Amphetamine-induced sleep disorder and Amphetamine related disorder not otherwise specified; Caffeine related disorders such as caffeine intoxication, caffeine induced anxiety disorder, caffeine induced sleep disorder and caffeine related disorder not otherwise specified; *Cannabis*-related disorders such as *cannabis* dependence, *cannabis* abuse, *cannabis* intoxication, *cannabis* intoxication delirium, *cannabis* induced psychotic disorder, *cannabis* induced anxiety disorder and *cannabis* related disorder not otherwise specified; Cocaine-related disorders such as Cocaine dependence, Cocaine abuse, Cocaine intoxication, Cocaine withdrawal, Cocaine intoxication delirium, Cocaine induced psychotic disorder, Cocaine induced mood disorder, Cocaine induced anxiety disorder, Cocaine induced sexual dysfunction, Cocaine induced sleep disorder and Cocaine related disorder not otherwise specified; Hallucinogen-related disorders such as Hallucinogen dependence, Hallucinogen abuse, Hallucinogen intoxication, Hallucinogen persisting perception disorder (Flashbacks), Hallucinogen intoxication delirium, Hallucinogen induced psychotic disorder, Hallucinogen induced mood disorder, Hallucinogen induced anxiety disorder and Hallucinogen related disorder not otherwise specified; Inhalant-related disorders such as Inhalant dependence, Inhalant abuse, Inhalant intoxication, Inhalant intoxication delirium, Inhalant induced persisting dementia, Inhalant induced psychotic disorder, Inhalant induced mood disorder, Inhalant induced anxiety disorder and Inhalant related disorder not otherwise specified; Nicotine-related disorders such as Nicotine dependence, Nicotine withdrawal and Nicotine related disorder not otherwise specified; Opiod-related disorders such as Opiod dependence, Opiod abuse, Opiod intoxication, Opiod withdrawal, Opiod intoxication delirium, Opiod induced psychotic disorder, Opiod induced mood disorder, Opiod induced anxiety disorder, Opiod induced sexual dysfunction, Opiod induced sleep disorder and Opiod related disorder not otherwise specified; Phencyclidine (or Phencyclidine like)-related disorder such as Phencyclidine dependence, Phencyclidine abuse, Phencyclidine intoxication, Phencyclidine intoxication delirium, Phencyclidine-induced psychotic disorder, Phencyclidine-induced mood disorder, Phencyclidine-induced anxiety disorder and Phencyclidine related disorder not otherwise specified; Sedative-, Hypnotic-, or Anxiolytic-related disorder such as Sedative, Hypnotic, or Anxiolytic dependence, Sedative, Hypnotic, or Anxiolytic abuse, Sedative, Hypnotic, or Anxiolytic intoxication, Sedative, Hypnotic, or Anxiolytic withdrawal, Sedative, Hypnotic, or Anxiolytic intoxication delirium, Hypnotic, or Anxiolytic withdrawal delirium, Sedative-, Hypnotic-, or Anxiolytic-Persisting Dementia, Sedative-, Hypnotic-, or Anxiolytic-persisting amnestic disorder, Sedative, Hypnotic, or Anxiolytic-induced psychotic disorder, Sedative, Hypnotic, or Anxiolytic-induced mood disorder, Sedative, Hypnotic, or Anxiolytic-induced anxiety disorder, Sedative, Hypnotic, or Anxiolytic-induced sexual dysfunction, Sedative, Hypnotic, or Anxiolytic-induced sleep disorder and Sedative, Hypnotic, or Anxiolytic related disorder not otherwise specified; Polysubstance related disorder such as polysubstance dependence; and other (or unknown) substance related disorders such as anabolic steroids, nitrate inhalants and nitrous oxide.

In still another embodiment compounds of the general Formula Ib may be useful in the treatment of sleep disorders which include, but are not limited to, sleep disorders including primary sleep disorders such as Dyssomnias such as Primary Insomnia, Primary Hypersomnia, Narcolepsy, Breathing-related sleep disorders, circadian rhythm sleep disorder and dyssomnia not otherwise specified; primary sleep disorders such as Parasomniaa such as nightmare disorder, sleep tenor disorder, sleepwalking disorder and parasomnia not otherwise specified; Sleep disorder related to another mental disorder such as Insomnia related to another mental disorder and Hypersomnia related to another mental disorder; sleep disorder due to a general medical condition; and substance-induced sleep disorder including the subtypes insomnia type, hypersomnia type, parasomnia type and mixed type.

In a further embodiment compounds of the general Formula Ib may be useful in the treatment of eating disorders which include, but are not limited to, eating disorders such as Anorexia Nervosa including subtypes restricting type and binge-eating/purging type; Bulimia Nervosa including the subtypes purging type and nonpurging type; obesity; compulsive eating disorder; binge eating disorder and eating order not otherwise specified.

In still another embodiment compounds of the general Formula Ib may be useful in the treatment of Attention deficit/hyperactivity disorder which includes, but is not limited to, Attention Deficit/Hyperactivity Disorder including the subtypes Attention Deficit/Hyperactivity Disorder combined type, Attention Deficit/Hyperactivity Disorder Hyperactive-impulse type and Attention Deficit/Hyperactivity Disorder not otherwise specified; Hyperkinetic disorder; disruptive behavior disorders such as conduct disorder including the subtypes childhood-onset type, adolescent-onset type and unspecified onset, oppositional defiant disorder and disruptive behavior disorder not otherwise specified; and Tic disorders such as Tourette's Disorder.

In an embodiment compounds of the general Formula Ib may be useful in the treatment of Cognition impairment which includes, but is not limited to, cognition impairment including cognition impairment in other diseases such as schizophrenia, bipolar disorder, depression, other psychiatric disorders and psychotic conditions associated with cognitive impairment, e.g. Alzheimer's disease.

In another embodiment compounds of the general Formula Ib may be useful in the treatment of Sexual Dysfunction which includes, but is not limited to, sexual dysfunctions including sexual desire disorders such as hypoactive sexual desire disorder, and sexual aversion disorder; sexual arousal disorders such as Female sexual arousal disorder and male erectile disorder; orgasmic disorders such as female orgasmic disorder, male orgasmic disorder and premature ejaculation; sexual pain disorder such as dyspareunia and vaginismus; sexual function not otherwise specified; paraphilias such as exhibitionism, fetishism, frotteurism, pedophilia, sexual masochism, sexual sadism, transvestic fetishism, voyeurism and paraphilia not otherwise specified; gender identity disorders such as Gender identity disorder in children and gender identity disorder in adolescents or adults; and sexual disorder not otherwise specified.

In still another embodiment compounds of the general Formula Ib may be useful in the treatment of obsessive compulsive disorder which includes, but is not limited to, obsessive compulsive disorder including obsessive compulsive disorders, somatoform disorders including body dysmorphic disorder and hyperchondriasis, bulimia nervosa and anorexia nervosa, eating disorders not elsewhere classified such as binge eating, impulse control disorders not elsewhere classified (including intermitted explosive disorder, compulsive buying or shopping, repetitive self-mutilation, onychophagia, psychogenic excoriation, kleptomania, pathological gambling, trichotillomania and internet addiction), paraphilia and nonparaphilic sexual addictions, sydeham's chorea, torticollis, autistic disorders, compulsive hoarding and movement disorders, including Tourett's syndrome.

In yet another embodiment, the compounds or their pharmaceutically acceptable salts according to the general Formula I are useful in the treatment of the diseases, disorders and conditions mentioned herein, in combination with at least one other therapeutic agent. The compounds of the general Formula I may be used in combination with one or more other therapeutic agents in the treatment, prevention, suppression or amelioration of diseases or conditions for which compounds of the general Formula I or other therapeutic agents may have utility, where the combination of drugs together are safer or more effective than either drug alone or where incorporation of another drug might reduce the dose of the compound of Formula I.

The other therapeutic agents suitable for combination with the compounds of the general Formula Ia include, but are not limited to, quinolines, β-lactams e.g., cephalosporins, penicillins, penams, penems and the like.

The other therapeutic agents suitable for combination with the compounds of the general Formula Ib include, but are not limited to, other antidepressants, mood stabilizers, antiemetics, testosterone receptor antagonists, testosterone agonists, stimulants, anti-anxiolytic agents, anti-psychotic drugs, anti-obesity drugs, NMDA receptor antagonists, GABA receptor agonists, opioid receptor antagonists, anti-attention deficit hyperactivity disorder agents, anti-addictive disorder agents, anti-alcohol agents, anti-nicotine agents, anti-opiate agents, anti-cocaine agents, opioid mu receptor agonist/opioid kappa receptor antagonist, vasodilatory antihypertensives, anti-Parkinson's-disease agent, anti-schizophernia agent, anti-epilepsy agents, benzodiazepines, non-benzodiazepine hypnotics, barbiturates, other sedative hypnotics, appetite stimulants, zinc, premenstral agents, phosphodiesterase V inhibitors, alpha adrenoreceptor antagonists, prostaglandin agonists, serotonin transport inhibitors, noradrenaline transport inhibitors, 5-$HT_{1A}$ agonists, estrogen agonists, drugs for extrapyramidal side effects and cognitive enhancers.

Examples of suitable cognitive enhancers for use in combination with the compounds of the general Formula Ib include but are not limited to cholinesterase inhibitors, appetite suppressants, anti-inflammatory agents, anti-diabetic agents, anti-hypertensive agents, anti-lysergic acid diethylamide ("anti-LCD") agent and anti-phencyclidine ("anti-PCP") agent.

It is believed that the use of the compounds of the general Formula I in combination with at least one or more of the other therapeutic agents mentioned herein may provide results greater than that possible from each of these medicaments alone or greater than the combined additive effects produced by these medicaments.

EXAMPLES

The invention is explained in detail in the following examples which are given solely for the purpose of illustration only and therefore should not be construed to limit the scope of the invention. All of the starting materials are either commercially available or can be prepared by procedures that would be well known to one of ordinary skill in organic chemistry. Solvents were dried prior to use wherever necessary by standard methods (Perrin, D. D.; Armarego, W. L. F. Purification of Laboratory Chemicals, Pergamon Press: Oxford, 1988). Mass spectra (MS) were obtained by electron spray ionization (ESI) eV using Applied biosystem 4000 Q TRAP. $^1$H NMR were recorded on Bruker 400 MHz Avance II NMR spectrometer. Chemical shifts are reported as δ values in parts per million (ppm), relative to TMS as internal standard. All coupling constants (J) values are given in Hz.

ABBREVIATIONS

The following abbreviations are employed in the examples and elsewhere herein:

| | |
|---|---|
| $^1$H NMR | proton nuclear magnetic resonance |
| $BF_3 \cdot OEt_2$ | boron trifluoride diethyl ether complex |
| $BH_3 \cdot Me_2S$ | borane dimethyl sulfide complex |
| $BH_3 \cdot THF$ | borane tetrahydrofuran complex |
| Boc | tert-butoxycarbonyl |
| bs | broad singlet |
| BINAP | 2,2'-bis(diphenylphosphino)-1,1'-binaphthyl |
| C | centigrade |
| CAN | ceric ammonium nitrate |
| CbzCl | benzyloxycarbonylchloride |
| $CDCl_3$ | deuterated chloroform |
| $CD_3OD$ | deuterated methanol |
| $CHCl_3$ | chloroform |
| cm | centimeter |
| $Cs_2CO_3$ | cesium carbonate |
| CuI | copper iodide |
| CuCl | copper (I) chloride |
| $CuCl_2$ | copper (II) chloride |
| DCM | dichloromethane |
| d | doublet |
| dd | doublet of doublet |
| DDQ | 2,3-dichloro-5,6-dicyanobenzoquinone |
| DIPEA | N,N-diisopropylethylamine |
| DMAP | 4-dimethylaminopyridine |
| DMF | dimethylformamide |
| DMSO | dimethylsulfoxide |
| EDC | N-(3-dimethylaminopropyl)-N-ethylcarbodiiimide hydrochloride |
| ESIMS | electron spray ionization mass Spectroscopy |
| EtOAc | ethylacetate |
| g | gram(s) |
| h | hour(s) |
| HCl | hydrochloric acid |
| HOBT | 1-hydroxybenzotriazole |
| Hz | hertz |
| J | coupling constant |
| $K_2CO_3$ | potassium carbonate |
| KOH | potassium hydroxide |
| LAH | lithium aluminum hydride |
| m | multiplet |
| M | molar |
| MeOH | methanol |
| mg | milligram |
| MHz | mega hertz |
| min | minutes |
| mL | milliliter |
| mmol | millimoles |
| NaOH | sodium hydroxide |
| $Na_2SO_4$ | sodium sulphate |
| $NaHCO_3$ | sodium bicarbonate |
| NaHMDS | sodium hexamethyldisilazide |
| $^n$BuLi | n-Butyl lithium |
| $NH_4Cl$ | ammonium chloride |
| NMM | N-methyl morpholine |
| NMR | nuclear magnetic resonance |
| $NaNO_2$ | sodium nitrite |
| Pd/C | palladium on carbon |
| $Pd_2(dba)_3$ | tris(dibenzylideneacetone)dipalladium (0) |

| Pet. ether | petroleum ether |
|---|---|
| PG | protecting group |
| pH | potential hydrogen |
| ppm | parts per million |
| pTSA | p-toluenesulfonyl chloride |
| r. t. | room temperature |
| s | singlet |
| t | triplet |
| ᵗBuONa | sodium tert-butoxide |
| TEA | triethyl amine |
| TFA | trifluoroacetic acid |
| THF | tetrahydrofuran |
| TLC | thin layer chromatography |
| μg | microgram |

EXAMPLES

Intermediate I: Preparation of 1-(4-bromo-phenyl)-3-aza-bicyclo[3.1.0]hexane-3-carboxylic acid tert-butyl ester Step 1: Preparation of 1-(4-bromo-phenyl)-2-hydroxymethyl-cyclopropanecarbonitrile To a solution of NaHMDS (23 g, 127.5 mmol) in THF (80 mL), was added a solution of 4-bromophenylacetonitrile (10 g, 51.0 mmol) in THF (80 mL) at −10° C. and stirred for 10 min. Epichlorohydrin (4.7 mL, 56.11 mmol) was added to the reaction mixture at −10° C. and then stirred the mixture at r.t. for 4 h. After completion of the reaction as indicated by TLC, the reaction mixture was quenched with 2:1 dioxane:hydrochloric acid (10 mL) at 0° C. and extracted with diethyl ether (3×200 mL). The combined organic layers were dried over anhydrous sodium sulphate and concentrated to yield the title compound (12.8 g, 100%) as brown oil which was used as such in the next step.

ESIMS (m/z): 251.8 (M+1, $^{79}$Br isotope), 252.9 (M+1, $^{81}$Br isotope)

Step 2: preparation of [2-aminomethyl-2-(4-bromo-phenyl)-cyclopropyl]-methanol

To a solution of 1-(4-bromo-phenyl)-2-hydroxymethyl-cyclopropanecarbonitrile (12.8 g, 51.0 mmol) in anhydrous THF (150 mL) was added BF$_3$.OEt$_2$ (10.15 mL, 0.2 mL per mmol) and the reaction mixture was heated at 80° C. Borondimethylsulphide complex (63.4 mL, 126.9 mmol, 2M in THF) was added to the reaction mixture and heated 80° C. for 4 h. Reaction mixture was quenched by 10% hydrochloric acid at 0° C. till effervescence vanishes. The reaction mixture was washed with diethyl ether (2×70 mL) and the aqueous layer was neutralized with solid sodium bicarbonate till pH 8. The neutralized aqueous layer was extracted with ethyl acetate (3×200 mL), dried over anhydrous sodium sulphate and concentrated to yield the title compound (9.49 g, 73%) as brown oil which was used as such in the next step.

ESIMS (m/z): 256.6 (M+1, $^{79}$Br isotope), 258.5 (M+1, $^{81}$Br isotope)

Step 3: Preparation of 1-(4-bromo-phenyl)-3-aza-bicyclo[3.1.0]hexane

To a solution of [2-aminomethyl-2-(4-bromo-phenyl)-cyclopropyl]-methanol (9.49 g, 37.02 mmol) in dichloroethane (120 mL), was added thionylchloride (3.2 mL, 44.4 mmol) at 0° C. and stirred for 2 h at r.t. After completion of the reaction as indicated by TLC, the reaction mixture was quenched with water (30 mL) at 0° C. Dichloroethane layer was separated from the acidic layer and discarded. The acidic layer was neutralized with sodium bicarbonate at 0° C. till pH=8 and extracted with 5% methanol in DCM (3×300 mL). The combined organic layers were dried over anhydrous sodium sulphate and concentrated to yield the title compound in crude form (5.20 g, 59%) as white gel, which was used as such in the next step.

ESIMS (m/z): 238.5 (M+1, $^{79}$Br isotope), 240.0 (M+1, $^{81}$Br isotope)

Step 4: Preparation of 1-(4-bromo-phenyl)-3-aza-bicyclo[3.1.0]hexane-3-carboxylic acid tert-butyl ester To a solution of 1-(4-bromo-phenyl)-3-aza-bicyclo[3.1.0]hexane (5.20 g, 21.8 mmol) in DCM (60 mL), were added triethylamine (6.06 mL, 43.6 mmol) and di-tert-butyl dicarbonate (7.7 mL, 32.7 mmol) at 0° C. and stirred for 2 h. After completion of the reaction as indicated by TLC, the solvents were evaporated under reduced pressure and the crude compound was purified by column chromatography (silica gel, 0.5:9.5 EtOAc:hexane) to yield the title compound (6.2 g, 84%) as colourless viscous liquid.

$^1$H NMR (400 MHz, CDCl$_3$): δ 0.85-0.87 (m, 1H), 1.03-1.07 (m, 1H), 1.46 (s, 9H), 1.77-1.79 (m, 1H), 3.52-3.55 (m, 2H), 3.65 (dd, J=10.4 and 41.6 Hz, 1H), 3.90 (dd, J=10.4 and 41.6 Hz, 1H), 7.02-7.06 (m, 2H), 7.41 (d, J=8.3 Hz, 2H)

ESIMS (m/z): 338.8 (M+1, $^{79}$Br isotope), 340.7 (M+1, $^{81}$Br isotope)

Intermediate II: Preparation of (1S,5R)-tert-butyl 1-(4-bromophenyl)-3-azabicyclo[3.1.0]hexane-3-carboxylate Intermediate II was prepared following the procedure as reported in Intermediate I. (R)-isomer of epichlorohydrin was used in the synthesis.

$^1$H NMR (400 MHz, CDCl$_3$): δ 0.86 (t, J=4.5 Hz, 1H), 1.03-1.07 (m, 1H), 1.46 (s, 9H), 1.77-1.82 (m, 1H), 3.50-3.55 (m, 2H), 3.68 (dd, J=10.7 and 36.8 Hz, 1H), 3.94 (dd, J=10.5 and 41.3 Hz, 1H), 7.04 (t, J=7.9 Hz, 2H), 7.41 (d, J=8.5 Hz, 2H)

ESIMS (m/z): 338.8 (M+1, $^{79}$Br isotope), 340.8 (M+1, $^{81}$Br isotope)

Intermediate III: Preparation of (1R,5S)-tert-butyl 1-(4-bromophenyl)-3-azabicyclo[3.1.0]hexane-3-carboxylate Intermediate III was prepared following the procedure as reported in Intermediate I. (S)-isomer of epichlorohydrin was used in the synthesis.

$^1$H NMR (400 MHz, CDCl$_3$): δ 0.85-0.88 (m, 1H), 1.01-1.03 (m, 1H), 1.46 (s, 9H), 1.77-1.81 (m, 1H), 3.49-3.62 (m, 2H), 3.83 (dd, J=10.6 and 53.1 Hz, 1H), 4.11 (dd, J=8.8 and 64.4 Hz, 1H), 7.04 (t, J=8.1 Hz, 2H), 7.41 (d, J=8.5 Hz, 2H)

ESIMS (m/z): 338.9 (M+1, $^{79}$Br isotope), 340.9 (M+1, $^{81}$Br isotope)

Intermediate IV: Preparation of hydrochloride salt of N-{3-[4-(3-Aza-bicyclo[3.1.0]hex-1-yl)-phenyl]-2-oxo-oxazolidin-5-(S)-yl-methyl}-acetamide Step 1: Preparation of 1-(4-Benzylamino-phenyl)-3-aza-bicyclo[3.1.0]hexane-3-carboxylic acid tert-butyl ester To a solution of 1-(4-bromo-phenyl)-3-aza-bicyclo[3.1.0]hexane-3-carboxylic acid tert-butyl ester (Intermediate I, 3.5 g, 10.4 mmol) in toluene (20 mL) were added Pd$_2$(dba)$_3$ (47 mg, 0.05 mmol), BINAP (97 mg, 0.16 mmol), sodium tert-butoxide (2.0 g, 20.7 mmol) and benzyl amine (1.2 mL, 11.4 mmol). The resulting solution was refluxed for 4 h. After the completion of the reaction, the reaction mixture was adsorbed on silica gel and purified by column chromatography (silica gel, 4:6 EtOAc:Pet. ether) to yield the title compound (3.0 g, 80%) as yellow solid.

ESIMS (m/z): 387.6 (M+23), 366.7 (M+2), 365.4 (M+1)

Step 2: Preparation of 1-(4-Amino-phenyl)-3-aza-bicyclo[3.1.0]hexane-3-carboxylic acid tert-butyl ester To a solution of 1-(4-benzylamino-phenyl)-3-aza-bicyclo[3.1.0]hexane-3-carboxylic acid tert-butyl ester (3.0 g, 8.2 mmol) in methanol (20 mL) was added 10% Pd/C (600 mg, 20% by weight). Flask was evacuated and hydrogen was introduced. The reaction mixture was stirred under hydrogen and progress of the reaction was monitored by TLC. On completion, the reaction mixture was filtered through celite pad using methanol as solvent. The filtrate was evaporated to provide the title compound (2.2 g, 97%) as brown solid and subjected to further reaction without any purification.

ESIMS (m/z): 297.8 (M+23), 275.7 (M+1)

Step 3: Preparation of 1-(4-Benzyloxycarbonylamino-phenyl)-3-aza-bicyclo[3.1.0]hexane-3-carboxylic acid tert-butyl ester To a solution of 1-(4-amino-phenyl)-3-aza-bicyclo[3.1.0]hexane-3-carboxylic acid tert-butyl ester (1.5 g, 5.5 mmol), in 1:1 acetone:water (12 mL) was added sodium bicarbonate (1.2 g, 13.7 mmol). The resulting solution was cooled to 0° C. and benzyl chloroformate (2.8 mL, 8.2 mmol, 50% solution in toluene) was added dropwise. The reaction mixture was stirred at r.t. and progress of the reaction was monitored by TLC. On completion, solvent was evaporated under reduced pressure and the residue was dissolved in ethyl acetate (50 mL). The organic layer was washed with water (2×10 mL), brine (10 mL), dried over anhydrous sodium sulphate and concentrated in vacuo. The residue was purified by column chromatography (silica gel, 5:5 EtOAc:Pet. ether) to provide the title compound (2.05 g, 92%) as off white solid.

ESIMS (m/z): 407.9 (M−1)

Step 4: Preparation of 1-[4-(5R)-Hydroxymethyl-2-oxo-oxazolidin-3-yl)-phenyl]-3-aza-bicyclo[3.1.0]hexane-3-carboxylic acid tert-butyl ester To a solution of 1-(4-benzyloxycarbonylamino-phenyl)-3-aza-bicyclo[3.1.0]hexane-3-carboxylic acid tert-butyl ester (2.0 g, 4.9 mmol), in dry THF (15 mL) was added "BuLi (5.5 mL, 8.8 mmol, 1.6 M solution in hexane) dropwise under nitrogen atmosphere at −78° C. The reaction mixture was stirred at the same temperature for 1 h and then (R)-glycidyl butyrate (0.75 mL, 5.4 mmol) was added dropwise over a period of 5 min. The reaction mixture was stirred at −78° C. for additional 2 h and then warmed to r.t. The progress of reaction was monitored by TLC and on completion, the reaction mixture was quenched with saturated NH$_4$Cl solution (10 mL) and extracted with ethyl acetate (4×20 mL). The organic layer was washed with brine (10 mL), dried over anhydrous sodium sulphate and concentrated in vacuo. The residue was purified by column chromatography (silica gel, 0.31:9.69 MeOH:CHCl$_3$) to provide the title compound (1.8 g, 96%) as off white solid.

ESIMS (m/z): 373.8 (M−1)

Step 5: Preparation of 1-[4-{(5R)-Methanesulfonyloxymethyl-2-oxo-oxazolidin-3-yl}-phenyl]-3-aza-bicyclo[3.1.0]hexane-3-carboxylic acid tert-butyl ester To a solution of 1-[4-{(5R)-hydroxymethyl-2-oxo-oxazolidin-3-yl}-phenyl]-3-aza-bicyclo[3.1.0]hexane-3-carboxylic acid tert-butyl ester (1.7 g, 4.5 mmol), in DCM (10 mL) was added triethylamine (1.92 mL, 13.7 mmol). The reaction mixture was cooled to 0° C. and methanesulfonyl chloride (0.7 mL, 6.8 mmol) was added dropwise. The reaction mixture was stirred at r.t. and progress of the reaction was monitored by TLC. On completion, the reaction mixture was diluted with DCM (10 mL). The organic layer was washed with water (10 mL), brine (10 mL), dried over anhydrous sodium sulphate and concentrated in vacuo. The title compound in crude form (1.8 g, 89%) was obtained as brown solid and subjected to further reaction without any purification.

ESIMS (m/z): 475.7 (M+23), 453.7 (M+1)

Step 6: Preparation of 1-[4-{(5R)-Azidomethyl-2-oxo-oxazolidin-3-yl}-phenyl]-3-aza-bicyclo[3.1.0]hexane-3-carboxylic acid tert-butyl ester To a solution of 1-[4-(5R)-methanesulfonyloxymethyl-2-oxo-oxazolidin-3-yl)-phenyl]-3-aza-bicyclo[3.1.0]hexane-3-carboxylic acid tert-butyl ester (1.8 g, 4.0 mmol), in DMF (5 mL) was added sodium azide (786 mg, 12.1 mmol). The reaction mixture was stirred at 110° C. and progress of the reaction was monitored by TLC. On completion, the reaction mixture was diluted with water (10 mL) and extracted with ethyl acetate (2×20 mL). The organic layer was washed with brine (10 mL), dried over anhydrous sodium sulphate and concentrated in vacuo. The title compound in crude form (1.6 g, 99%) was obtained as yellow solid and subjected to further reaction without any purification.

ESIMS (m/z): 422.7 (M+23), 400.7 (M+1)

Step 7: Preparation of 1-{4-[5S)-(Acetylamino-methyl)-2-oxo-oxazolidin-3-yl]-phenyl}-3-aza-bicyclo[3.1.0]hexane-3-carboxylic acid tert-butyl ester To 1-[4-{(5R)-azidomethyl-2-oxo-oxazolidin-3-yl}-phenyl]-3-aza-bicyclo[3.1.0]hexane-3-carboxylic acid tert-butyl ester (1.5 g, 3.8 mmol) was added thioacetic acid (0.3 mL, 4.1 mmol) and the reaction mixture was stirred at r.t. for 16 h. The reaction mixture was then adsorbed on silica gel and purified by column chromatography (silica gel, 0.25:9.75 MeOH:CHCl$_3$) to yield the title compound (710 mg, 39%) as white solid.

ESIMS (m/z): 416.4 (M+1)

Step 8: Preparation of hydrochloride salt of N-{3-[4-(3-Aza-bicyclo[3.1.0]hex-1-yl)-phenyl]-2-oxo-oxazolidin-5-(S)-yl-methyl}-acetamide To a solution of 1-{4-[(5S)-(acetylamino-methyl)-2-oxo-oxazolidin-3-yl]-phenyl}-3-aza-bicyclo[3.1.0]hexane-3-carboxylic acid tert-butyl ester (710 mg, 1.7 mmol) in diethyl-ether (10 mL) was passed HCl gas and progress of the salt formation was monitored by TLC. The solvent was evaporated under reduced pressure to obtain the title compound (510 mg, 85%) as off white solid.

$^1$H NMR (400 MHz, CD$_3$OD): δ1.24-1.26 (m, 2H), 1.34-1.38 (m, 1H), 2.01 (s, 3H), 3.37-3.39 (m, 2H), 3.53-3.58 (m, 3H), 3.71 (d, J=11.3 Hz, 1H), 3.77-3.85 (m, 1H), 4.07-4.12 (m, 1H), 4.77-4.80 (m, 1H), 7.24 (d, J=8.7 Hz, 2H), 7.49 (d, J=8.7 Hz, 2H)

ESIMS (m/z): 316.8 (M+1)

Intermediate V: Preparation of hydrochloride salt of N—(((S)-3-(4-((1S,5R)-3-azabicyclo[3.1.0]hexan-1-yl)phenyl)-2-oxooxazolidin-5-yl)methyl)acetamide Intermediate V was prepared following the procedure as reported in Intermediate IV. Intermediate II was used in the place of Intermediate I.

$^1$H NMR (400 MHz, CD$_3$OD): δ1.07-1.09 (m, 1H), 1.24-1.28 (m, 1H), 1.95 (s, 3H), 2.10-2.15 (m, 1H), 3.50-3.55 (m, 4H), 3.57-3.65 (m, 1H), 3.67 (d, J=11.3 Hz, 1H), 3.72-3.80 (m, 1H), 4.14 (d, J=9.0 Hz, 1H), 4.75-4.80 (m, 1H), 7.33 (dd, J=2.1 and 6.8 Hz, 2H), 7.54 (dd, J=2.0 and 6.8 Hz, 2H)

ESIMS (m/z): 338.8 (M+23), 317.6 (M+2), 316.3 (M+1)

Intermediate VI: Preparation of hydrochloride salt of N—(((S)-3-(4-((1R,5S)-3-azabicyclo[3.1.0]hexan-1-yl)phenyl)-2-oxooxazolidin-5-yl)methyl)acetamide Intermediate VI was prepared following the procedure as reported in Intermediate IV. Intermediate III was used in the place of Intermediate I.

$^1$H NMR (400 MHz, CD$_3$OD): δ1.08-1.11 (m, 1H), 1.35-1.38 (m, 1H), 1.95 (s, 3H), 2.12-2.15 (m, 1H), 3.51 (d, J=11.5 Hz, 1H), 3.55-3.58 (m, 3H), 3.67-3.69 (m, 1H), 3.73 (d, J=11.3 Hz, 1H), 3.80-3.85 (m, 1H), 4.14 (t, J=9.0 Hz, 1H), 4.77-4.85 (m, 1H), 7.33 (dd, J=2.0 and 6.7 Hz, 2H), 7.55 (dd, J=2.0 and 6.8 Hz, 2H)

ESIMS (m/z): 338.7 (M+23), 316.5 (M+1)

Intermediate VII: Preparation of 1-(4-bromo-2-fluoro-phenyl)-3-aza-bicyclo[3.1.0]hexane-3-carboxylic acid tert-butyl ester

Step 1: Preparation of 3-(4-Bromo-2-fluoro-phenyl)-pyrrole-2,5-dione

To a solution of 4-bromo-2-fluoroaniline (10.0 g, 52.6 mmol) in aqueous HCl (50 mL) was added aqueous NaNO$_2$ (4.0 g, 57.9 mmol) at 0° C. The reaction mixture was stirred for 30 min. To this was added a solution of maleimide (7.65 g, 78.9 mmol) in acetone (50 mL). The pH was adjusted to 3-3.5 by addition of sodium acetate. To the resultant reaction mixture was added CuCl (1.05 g, 7.9 mmol) and it was stirred at 0° C. for 1 h and at r.t. for 6 h. Finally acetone was evaporated and the reaction mixture was diluted with water (20 mL) and extracted with DCM (2×50 mL). The organic layer was washed with brine (20 mL), dried over anhydrous sodium sulphate and concentrated in vacuo. The crude was purified by column chromatography (silica gel, 1:9 EtOAc:Pet. ether) to provide the title compound (2.6 g, 18%) as brown solid.

ESIMS (m/z): 271.0 (M+1)

Step 2: Preparation of 1-(4-Bromo-2-fluoro-phenyl)-3-aza-bicyclo[3.1.0]hexane-2,4-dione To a solution of trimethylsulfoxonium iodide (3.18 g, 14.5 mmol) in DMSO (15 mL) was added KOH (1.08 g, 19.3 mmol) at r.t. The reaction mixture was stirred at r.t. for 30 min followed by addition of 3-(4-bromo-2-fluoro-phenyl)-pyrrole-2,5-dione (2.60 g, 9.6 mmol). The reaction mixture was stirred at r.t. and progress of the reaction was monitored by TLC. On completion, the reaction mixture was quenched with saturated NH$_4$Cl (10 mL) and extracted with ethyl acetate (2×20 mL). The organic layer was washed with brine (10 mL), dried over anhydrous sodium sulphate and concentrated in vacuo. The title compound was obtained as brown solid in crude form (2.51 g, 92%) and was as such used in the next step.

ESIMS (m/z): 285.0 (M+1)

Step 3: Preparation of 1-(4-Bromo-2-fluoro-phenyl)-3-aza-bicyclo[3.1.0]hexane To a solution of 1-(4-bromo-2-fluoro-phenyl)-3-aza-bicyclo[3.1.0]hexane-2,4-dione (2.5 g, 8.8 mmol) in THF (20 mL) were added BF$_3$.OEt$_2$ (1.8 mL, 1.8 mmol) and BH$_3$.Me$_2$S (11.0 mL, 22.0 mmol) at r.t. The reaction mixture was refluxed for 3 h and progress of the reaction was monitored by TLC. On completion, the reaction mixture was quenched with 20% HCl (10 mL) and solvent evaporated, residue was washed with diethylether (10 mL). The aqueous layer was neutralized with sodium carbonate and extracted with DCM (2×20 mL). The organic layer was washed with brine (10 mL), dried over anhydrous sodium sulphate and concentrated in vacuo. The title compound was obtained as brown liquid in crude form (1.22 g, 54%) and was as such used in the next step.

ESIMS (m/z): 258.7 (M+2), 257.5 (M+1)

Step 4: Preparation of 1-(4-bromo-2-fluoro-phenyl)-3-aza-bicyclo[3.1.0]hexane-3-carboxylic acid tert-butyl ester To a solution of 1-(4-bromo-2-fluoro-phenyl)-3-aza-bicyclo[3.1.0]hexane (1.22 g, 4.8 mmol) in DCM (10 mL) were added triethylamine (1.66 mL, 11.9 mmol) and di-tert-butyl-dicarbonate (1.56 g, 7.2 mmol) at r.t. The reaction mixture was stirred at r.t. and progress of the reaction was monitored by TLC. On completion, the reaction mixture was diluted with water (10 mL) and extracted with ethyl acetate (2×20 mL). The organic layer was washed with brine (10 mL), dried over anhydrous sodium sulphate and concentrated in vacuo. The crude was purified by column chromatography (silica gel, 2:8 EtOAc:Pet. ether) to provide the title compound as brown liquid (2.01 g, 42%).

$^1$H NMR (400 MHz, CDCl$_3$): δ0.83-0.95 (m, 1H), 0.95-1.10 (m, 1H), 1.44 (s, 9H), 1.75-1.77 (m, 1H), 3.37-3.41 (m, 1H), 3.50-3.60 (m, 1H), 3.60-3.90 (m, 2H), 7.11 (t, J=8.2 Hz, 1H), 7.20-7.25 (m, 2H)

ESIMS (m/z): 354.6 (M+1, $^{79}$Br isotope), 356.5 (M+1, $^{81}$Br isotope)

Intermediate VIII: Preparation of hydrochloride salt of N-{3-[4-(3-Aza-bicyclo[3.1.0]hex-1-yl)-3-fluoro-phenyl]-2-oxo-oxazolidin-5(S)-ylmethyl}-acetamide Intermediate VIII was prepared following the procedure as reported in Intermediate IV. Intermediate VII was used in the place of Intermediate I.

$^1$H NMR (400 MHz, CD$_3$OD): δ1.00-1.10 (m, 1H), 1.15-1.30 (m, 1H), 1.95 (s, 3H), 2.10-2.20 (m, 1H), 3.40-3.60 (m, 4H), 3.67 (d, J=11.4 Hz, 2H), 3.81 (dd, J=6.3 and 9.2 Hz, 1H), 4.13 (t, dd, J=9.0 Hz, 1H), 4.70-4.80 (m, 1H), 7.26 (dd, J=2.2 and 8.5 Hz, 1H), 7.37 (t, J=8.5 Hz, 1H), 7.56 (dd, J=2.2 and 13.1 Hz, 1H)

ESIMS (m/z): 334.5 (M+1)

Intermediate IX: Preparation of tert-butyl 1-(4-bromophenyl)-6-(methoxymethyl)-3-aza-bicyclo[3.1.0]hexane-3-carboxylate

Step 1: Preparation of 3-(4-bromophenyl)-1H-pyrrole-2,5-dione

A solution of hydrochloric acid (37%, 13 mL) in water (5.5 mL) was added to 4-bromoaniline (7.48 g, 43.52 mmol) at r.t. with vigorous stirring and the formed precipitate was allowed to stir for 30 min. The reaction mixture was cooled to 0° C. and a solution of sodium nitrite (3.30 g, 47.87 mmol) in water (9 mL) was added dropwise. At the end of diazotization, a clear yellow solution was obtained. Maleimide (8.45 g, 87.05 mmol) in acetone (35 mL) was added dropwise at 0° C. and then the pH of the solution was adjusted to 3-3.5 by adding sodium acetate. CuCl$_2$ (0.88 g, 6.57 mmol) was added to the vigorously stirred mixture. The reaction mixture was stirred at 0° C. for 1 h and overnight at r.t. After completion of the reaction as confirmed by TLC, solvents were removed in vacuo to afford the crude compound, which was purified by column chromatography (silica gel, 4:6 EtOAc:Pet. ether) to afford the title compound as a yellow solid (5.8 g, 57%).

ESIMS (m/z): 252.3 (M+1)

Step 2: Preparation of ethyl 1-(4-bromophenyl)-2,4-dioxo-3-aza-bicyclo[3.1.0]hexane-6-carboxylate To a solution of 3-(4-bromophenyl)-1H-pyrrole-2,5-dione (3.45 g, 13.74 mmol) obtained in Step 1 of Intermediate IX, in toluene (50 mL) was added ethyldiazoacetate (4.27 mL, 41.23 mmol). The reaction mixture was heated to reflux for 18 h. After completion of the reaction as confirmed by TLC, solvent was removed in vacuo to afford crude product which was purified by column chromatography (silica gel, 4:6 EtOAc:Pet. ether) to afford the title compound as a yellow solid (2.66 g, 57%).

ESIMS (m/z): 338.7 (M+1)

Step 3: Preparation of 1-[(4-bromophenyl)-3-azabicyclo[3.1.0]hex-6-yl]methanol

To a solution of ethyl 1-(4-bromophenyl)-2,4-dioxo-3-azabicyclo[3.1.0]hexane-6-carboxylate (2.66 g, 7.89 mmol), obtained in Step 2 of Intermediate IX, in dry THF (30 mL), was added BH$_3$.Me$_2$S (31.51 mL, 63.14 mmol, 2M solution in THF). The mixture was heated to reflux for 6 h. After completion of the reaction as confirmed by TLC, methanol (10 mL) was added slowly and the reaction mixture was heated to reflux for 1 h. The solvents were removed in vacuo to afford the title compound in crude form (2.10 g), which was used for the next step without any purification.

ESIMS (m/z): 268.3 (M+1)

Step 4: Preparation of tert-butyl-1-(4-bromophenyl)-6-(hydroxymethyl)-3-aza-bicyclo[3.1.0]hexane-3-carboxylate To a solution of 1-(4-bromophenyl)-3-azabicyclo[3.1.0]hex-6-yl]methanol (2.10 g, 7.86 mmol), obtained in Step 3 of Intermediate IX, in DCM (30 mL), was added triethylamine (5.99 mL, 39.45 mmol) and di-tert-butyl dicarbonate (2.05 g, 9.43 mmol). The reaction mixture was stirred at r.t. overnight. After completion of the reaction as confirmed by TLC, the solvent was removed in vacuo to afford the crude compound, which was purified by column chromatography (silica gel, 3:7 EtOAc:Pet. ether) to afford pure the title compound (1.14 g, 39%) as a gummy solid.

ESIMS (m/z): 490.6 (M+23)

Step 5: Preparation of tert-butyl 1-(4-bromophenyl)-6-(methoxymethyl)-3-aza-bicyclo[3.1.0]hexane-3-carboxylate To a solution of tert-butyl 1-(4-bromophenyl)-6-(hydroxymethyl)-3-aza-bicyclo[3.1.0]hexane-3-carboxylate (1.10 g, 2.99 mmol), obtained in Step 4 of Intermediate IX, in DMF (5 mL) was added sodium hydride (358 mg, 3.97 mmol, 60% suspension in mineral oil) at 0° C. under nitrogen atmosphere. The reaction mixture was stirred at the same temperature for 30 min followed by the addition of methyl iodide (0.22 mL, 3.59 mmol). The reaction mixture was stirred at r.t. overnight. After completion of the reaction as confirmed by TLC, the reaction mixture was quenched by saturated solution of ammonium chloride and the crude compound was extracted with ethyl acetate. The organic layer was washed with water, separated, dried over anhydrous sodium sulphate and concentrated in vacuo to afford the title compound (1.0 g) as a viscous oil which was used without any purification for the next step.

ESIMS (m/z): 404.9 (M+23), 381.8 (M+1)

$^1$H NMR (400 MHz, CD$_3$OD): δ 1.21-1.24 (m, 1H), 1.44 (s, 9H), 1.91-1.92 (m, 1H), 2.92-3.15 (m, 2H), 3.13 (s, 3H), 3.25-3.59 (m, 2H), 3.67 (d, J=10.8 Hz, 1H), 3.95 (d, J=10.4 Hz, 1H), 7.25 (d, J=8.4 Hz, 2H), 7.47 (d, J=8.4 Hz, 2H)

Example I

Preparation of N-(((5S)-3-(4-(3-acetyl-3-azabicyclo[3.1.0]hexan-1-yl)phenyl)-2-oxooxazolidin-5-yl)methyl)acetamide

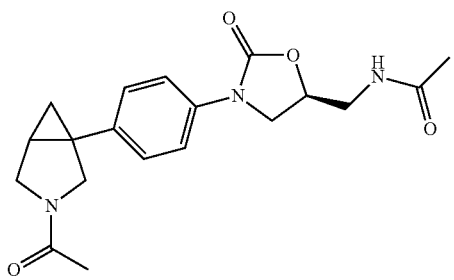 [SMILES: CC(=O)NC[C@H]1CN(c2ccc(C34CC3CN(C(C)=O)C4)cc2)C(=O)O1]

To a solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (80 mg, 0.23 mmol) in DCM (2 mL) were added triethylamine (0.13 mL, 0.92 mmol) and acetyl chloride (0.02 mL, 0.34 mmol) at 0° C. and progress of the reaction was monitored by TLC. On completion, the reaction mixture was diluted with water (10 mL) and extracted with DCM (2×20 mL). The organic layer was washed with brine (10 mL), dried over anhydrous sodium sulphate and concentrated in vacuo. The residue was purified by column chromatography (silica gel, 0.83:9.17 MeOH:CHCl$_3$) to provide the title compound (42 mg, 51%) as white solid.

$^1$H NMR (400 MHz, CDCl$_3$): δ0.82-0.85 (m, 1H), 1.10-1.20 (m, 1H), 1.30-1.45 (m, 1H), 2.02 (s, 3H), 2.03 (s, 3H), 3.42-3.49 (m, 1H), 3.57-3.74 (m, 2H), 3.76-3.82 (m, 3H), 3.88-4.08 (m, 2H), 4.75-4.85 (m, 1H), 6.05-6.20 (m, 1H), 7.17-7.24 (m, 2H), 7.45-7.52 (m, 2H)

ESIMS (m/z): 380.6 (M+23), 358.5 (M+1)

Example II

Preparation of N-(((5S)-3-(4-(3-acetyl-3-azabicyclo[3.1.0]hexan-1-yl)-3-fluorophenyl)-2-oxooxazolidin-5-yl)methyl)acetamide

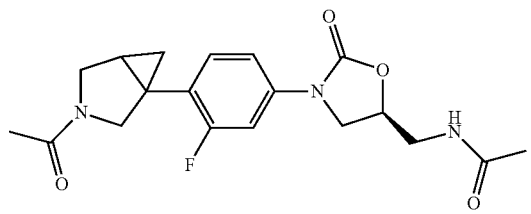 [SMILES: CC(=O)NC[C@H]1CN(c2ccc(C34CC3CN(C(C)=O)C4)c(F)c2)C(=O)O1]

The title compound was prepared following the procedure as reported in Example I. Intermediate VIII was used in place of Intermediate IV.

¹H NMR (400 MHz, CDCl₃): δ 0.70-0.85 (m, 1H), 1.05-1.15 (m, 1H), 1.80-1.95 (m, 1H), 2.02 (two merging s, 6H), 3.35-3.45 (m, 0.5H), 3.55-3.85 (m, 4.5H), 3.95-4.20 (m, 2H), 4.70-4.85 (m, 1H), 5.95-6.05 (m, 1H), 7.05-7.15 (m, 1H), 7.15-7.25 (m, 1H), 7.35-7.45 (m, 1H)

ESIMS (m/z): 398.1 (M+23), 376.3 (M+1)

Example III

Preparation of N-(((5S)-2-oxo-3-(4-(3-(2,2,2-trifluoroacetyl)-3-azabicyclo[3.1.0]hexan-1-yl)phenyl)oxazolidin-5-yl)methyl)acetamide

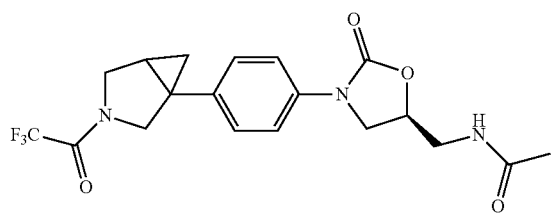 [SMILES: CC(=O)NC[C@H]1CN(c2ccc(C34CC3CN(C(=O)C(F)(F)F)C4)cc2)C(=O)O1]

To a solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (350 mg, 1.0 mmol), in DCM (25 mL) was added DIPEA (0.7 mL, 4.0 mmol). The resulting solution was cooled to 0° C. and trifluoroacetic anhydride (0.21 mL, 1.5 mmol) was added dropwise. The reaction mixture was stirred at r.t. and progress of the reaction was monitored by TLC. On completion, the reaction mixture was diluted with DCM (100 mL). The organic layer was washed with water (25 mL), brine (25 mL), dried over anhydrous sodium sulphate and concentrated in vacuo. The residue was purified by column chromatography (silica gel, 0.2:9.8 MeOH:CHCl₃) to provide the title compound (225 mg, 55%) as white solid.

¹H NMR (400 MHz, CDCl₃): δ 0.75-0.90 (m, 1H), 1.10-1.20 (m, 1H), 1.85-2.00 (m, 1H), 2.02 (s, 3H), 3.55-3.65 (m, 1H), 3.65-3.75 (m, 2H), 3.75-3.80 (m, 1H), 3.80-4.00 (m, 1.5H), 4.05-4.15 (m, 1.5H), 4.16 (d, J=9.5 Hz, 0.5H), 4.28 (d, J=12.2 Hz, 0.5H), 4.75-4.85 (m, 1H), 6.00-6.10 (m, 1H), 7.22 (t, J=8.4 Hz, 2H), 7.48 (dd, J=1.7 and 8.6 Hz, 2H)

ESIMS (m/z): 412.7 (M+1)

Example IV

Preparation of methyl 1-(4-((S)-5-(acetamidomethyl)-2-oxooxazolidin-3-yl)phenyl)-3-azabicyclo[3.1.0]hexane-3-carboxylate

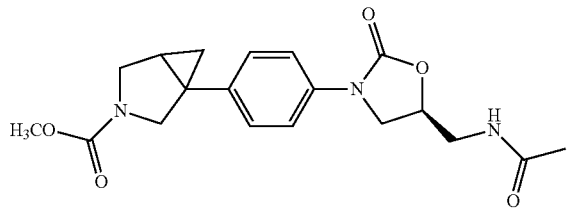 [SMILES: COC(=O)N1CC2CC2(c2ccc(N3C[C@H](CNC(C)=O)OC3=O)cc2)C1]

To a solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (200 mg, 0.57 mmol) in DCM (25 mL), was added triethyl amine (0.3 mL, 2.27 mmol). The resulting solution was cooled to 0° C. and methyl chloroformate (0.07 mL, 0.86 mmol) was added dropwise. The reaction mixture was stirred at r.t. and progress of the reaction was monitored by TLC. On completion, the reaction mixture was diluted with DCM (100 mL). The organic layer was washed with water (25 mL), brine (25 mL), dried over anhydrous sodium sulphate and concentrated in vacuo. The residue was purified by column chromatography (silica gel, 0.2:9.8 MeOH:CHCl₃) to provide the title compound (160 mg, 74%) as white solid.

¹H NMR (400 MHz, CDCl₃): δ 0.85 (t, J=4.4 Hz, 1H), 1.07 (dd, J=2.4 and J=7.6 Hz, 1H), 1.75-1.90 (m, 1H), 2.02 (s, 3H), 3.50-3.69 (m, 4H), 3.70 (s, 3H), 3.71-3.85 (m, 2H), 3.92 (d, J=10.3 Hz, 0.5H), 4.00-4.10 (m, 1.5H), 4.70-4.80 (m, 1H), 6.05 (t, J=5.9 Hz, 1H), 7.17 (d, J=8.7 Hz, 2H), 7.45 (d, J=8.7 Hz, 2H)

ESIMS (m/z): 374.6 (M+1)

Example V

Preparation of (1S,5R)-methyl 1-(4-((S)-5-(acetamidomethyl)-2-oxooxazolidin-3-yl)phenyl)-3-azabicyclo[3.1.0]hexane-3-carboxylate

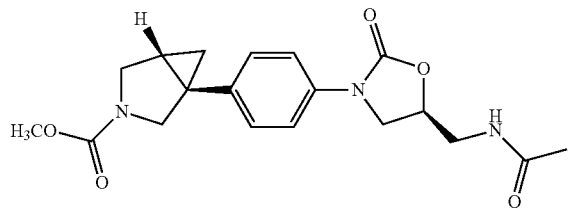 [SMILES: COC(=O)N1C[C@@H]2C[C@]2(c2ccc(N3C[C@H](CNC(C)=O)OC3=O)cc2)C1]

The title compound was prepared following the procedure as reported in Example IV. Intermediate V was used in place of Intermediate IV.

¹H NMR (400 MHz, CDCl₃): δ 0.85 (t, J=4.3 Hz, 1H), 1.07 (dd, J=5.0 and 7.9 Hz, 1H), 1.75-1.90 (m, 1H), 2.02 (s, 3H), 3.50-3.70 (m, 4H), 3.71 (s, 3H), 3.72-3.85 (m, 2H), 3.92 (d, J=10.4 Hz, 0.5H), 4.00-4.10 (m, 1.5H), 4.70-4.80 (m, 1H), 6.00 (t, J=6.3 Hz, 1H), 7.17 (d, J=8.7 Hz, 2H), 7.45 (d, J=8.8 Hz, 2H)

ESIMS (m/z): 396.6 (M+23), 374.8 (M+1)

Example VI

Preparation of (1R,5S)-methyl 1-(4-((S)-5-(acetamidomethyl)-2-oxooxazolidin-3-yl)phenyl)-3-azabicyclo[3.1.0]hexane-3-carboxylate

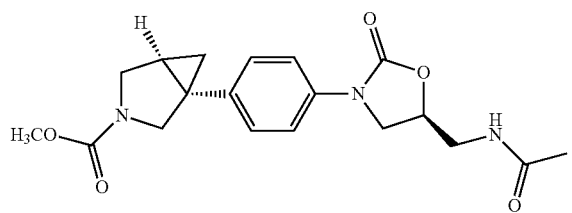 [SMILES: COC(=O)N1C[C@H]2C[C@@]2(c2ccc(N3C[C@H](CNC(C)=O)OC3=O)cc2)C1]

The title compound was prepared following the procedure as reported in Example IV. Intermediate VI was used in place of Intermediate IV.

¹H NMR (400 MHz, CDCl₃): δ 0.85 (t, J=4.3 Hz, 1H), 1.07 (dd, J=5.1 and 8.1 Hz, 1H), 1.75-1.90 (m, 1H), 2.02 (s, 3H), 3.50-3.70 (m, 4H), 3.71 (s, 3H), 3.72-3.85 (m, 2H), 3.90-4.10 (m, 2H), 4.70-4.85 (m, 1H), 6.05 (t, J=6.1 Hz, 1H), 7.17 (d, J=8.7 Hz, 2H), 7.45 (d, J=8.8 Hz, 2H)

ESIMS (m/z): 396.8 (M+23), 374.5 (M+1)

Example VII

Preparation of 1-{4-[5(S)-(Acetylamino-methyl)-2-oxo-oxazolidin-3-yl]-2-fluoro-phenyl}-3-aza-bicyclo[3.1.0]hexane-3-carboxylic acid methyl ester

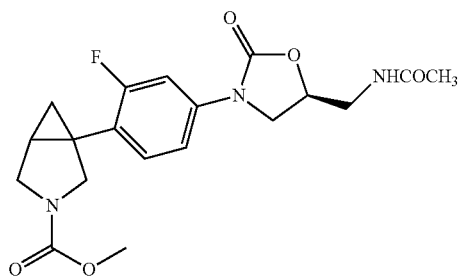

The title compound was prepared following the procedure as reported in Example IV. Intermediate VIII was used in place of Intermediate IV.

¹H NMR (400 MHz, CDCl₃): δ 0.75-0.85 (m, 1H), 1.00-1.10 (m, 1H), 1.77-1.81 (m, 1H), 2.02 (s, 3H), 3.42-3.49 (m, 1H), 3.51-3.80 (m, 8H), 3.80-3.96 (m, 1H), 4.04 (t, J=9.0 Hz, 1H), 4.76-4.79 (m, 1H), 5.97-5.98 (m, 1H), 7.05-7.15 (m, 1H), 7.15-7.30 (m, 1H), 7.42 (d, J=12.5 Hz, 1H)

ESIMS (m/z): 393.6 (M+2), 392.6 (M+1)

Example VIII

Preparation of 1-{4-[5(S)-(Acetylamino-methyl)-2-oxo-oxazolidin-3-yl]-phenyl}-3-aza-bicyclo[3.1.0]-hexane-3-carboxylic acid allyl ester

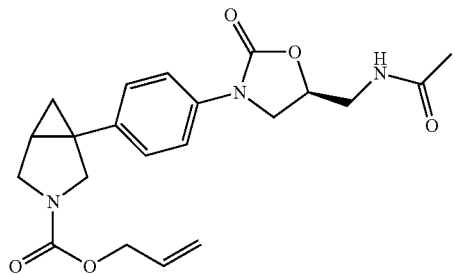 [SMILES: C=CCOC(=O)N1CC2CC2(c2ccc(N3C[C@H](CNC(C)=O)OC3=O)cc2)C1]

To a solution of hydrochloride salt of N-{3-[4-(3-aza-bicyclo[3.1.0]hex-1-yl)-phenyl]-2-oxo-oxazolidin-5(S)-ylmethyl}-acetamide (Intermediate IV) (100 mg, 0.28 mmol) in dry DCM (5 mL) were added triethylamine (0.16 mL, 1.12 mmol) and allyl chloroformate (0.05 mL, 0.42 mmol) at r.t. and progress of the reaction was monitored by TLC. On completion, the reaction mixture was diluted with water (10 mL) and extracted with DCM (2×20 mL). The organic layer was washed with brine (10 mL), dried over anhydrous sodium sulphate and concentrated in vacuo. The residue was purified by column chromatography (silica gel, 0.3:9.7 MeOH: CHCl₃) to provide the title compound (55 mg, 50%) as white solid.

¹H NMR (400 MHz, CDCl₃): δ 0.86 (bs, 1H), 1.10-1.07 (m, 1H), 1.82-1.84 (m, 1H), 2.02 (s, 3H), 3.62-3.64 (m, 3H), 3.69-3.80 (m, 3H), 3.96-4.08 (m, 2H), 4.60 (d, J=5.0 Hz, 2H), 4.75-4.80 (m, 1H), 5.22 (dd, J=1.3 and 10.5 Hz, 1H), 5.31 (dd, J=1.4 and 17.2 Hz, 1H), 5.90-5.98 (m, 1H), 6.08 (s, 1H), 7.18 (d, J=8.2 Hz, 2H), 7.45 (d, J=8.7 Hz, 2H)

ESIMS (m/z): 401.7 (M+2), 400.8 (M+1)

Example IX

Preparation of N-{3-[4-(3-Methanesulfonyl-3-aza-bicyclo[3.1.0]hex-1-yl)-phenyl]-2-oxo-oxazolidin-5(S)-ylmethyl}-acetamide

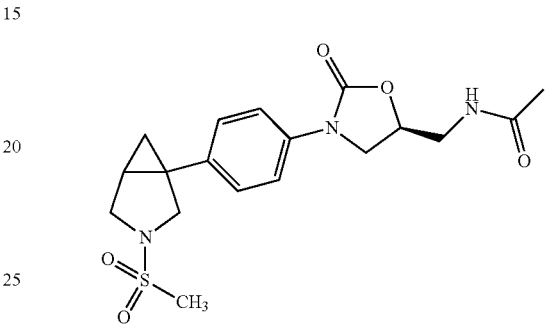

To a solution of hydrochloride salt of N-{3-[4-(3-aza-bicyclo[3.1.0]hex-1-yl)-phenyl]-2-oxo-oxazolidin-5(S)-ylmethyl}-acetamide (Intermediate IV) (100 mg, 0.28 mmol) in dry DCM (5 mL) were added triethylamine (0.15 mL, 1.12 mmol) and methane sulfonyl chloride (0.03 mL, 0.42 mmol) at r.t. and progress of the reaction was monitored by TLC. On completion, the reaction mixture was diluted with water (10 mL) and extracted with DCM (2×20 mL). The organic layer was washed with brine (10 mL), dried over anhydrous sodium sulphate and concentrated in vacuo. The residue was purified by column chromatography (silica gel, 0.3:9.7 MeOH: CHCl₃) to provide the title compound (22 mg, 21.4%) as white solid.

¹H NMR (400 MHz, CDCl₃): δ 1.04-1.07 (m, 1H), 1.18 (t, J=4.8 Hz, 1H), 1.86-1.90 (m, 1H), 2.02 (s, 3H), 2.88 (s, 3H), 3.48-3.53 (m, 2H), 3.59-3.66 (m, 1H), 3.68-3.73 (m, 2H), 3.76-3.80 (m, 1H), 3.88 (d, J=9.1 Hz, 1H), 4.05 (t, J=8.9 Hz, 1H), 4.74-4.80 (m, 1H), 5.93-5.95 (m, 1H), 7.17 (dd, J=2.0 and 6.8 Hz, 2H), 7.46 (dd, J=2.0 and 6.8 Hz, 2H)

ESIMS (m/z): 395.6 (M+2), 394.6 (M+1)

Example X

Preparation of N-(3-{4-[3-(2-Hydroxy-acetyl)-3-aza-bicyclo[3.1.0]hex-1-yl]-phenyl}-2-oxo-oxazolidin-5(S)-ylmethyl)-acetamide

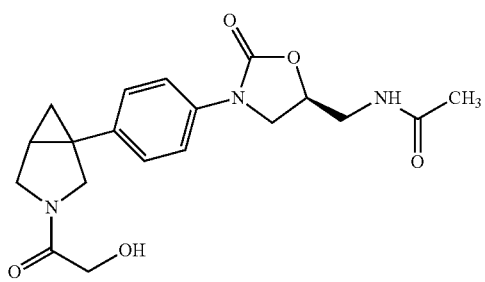 [SMILES: CC(=O)NC[C@H]1CN(c2ccc(C34CC3CN(C(=O)CO)C4)cc2)C(=O)O1]

To a solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (300 mg, 0.72 mmol), in DCM (5 mL), were added EDC (180 mg, 0.94 mmol), HOBt (127 mg, 0.94 mmol) and NMM (0.32 mL, 2.89 mmol) and glycolic acid (60.4 mg, 0.79 mmol), at 0° C. The reaction mixture was stirred at r.t. and progress of the reaction was monitored by TLC. On completion, the reaction mixture was diluted with DCM (20 mL). The organic layer was washed with water (10 mL), brine (10 mL), dried over anhydrous sodium sulphate and concentrated in vacuo. The residue was purified by column chromatography (silica gel, 0.35:9.65 MeOH:CHCl$_3$) to provide the title compound (160 mg, 59%) as off white solid.

$^1$H NMR (400 MHz, CDCl$_3$): δ 0.78-0.82 (m, 1H), 1.15-1.19 (m, 1H), 1.88-1.95 (m, 1H), 2.02 (m, 3H), 3.49-3.51 (m, 1H), 3.60-3.74 (m, 4H), 3.78-3.82 (m, 1H), 4.01-4.27 (m, 4H), 4.75-4.81 (m, 1H), 6.21-6.24 (m, 1H), 7.18-7.22 (m, 2H), 7.47 (dd, J=2.6 and 8.8 Hz, 2H)

ESIMS (m/z): 396.6 (M+23), 376.8 (M+2), 374.5 (M+1)

Example XI

Preparation of Carbonic acid 2-(1-{4-[5(S)-(acetylamino-methyl)-2-oxo-oxazolidin-3-yl]-phenyl}-3-aza-bicyclo[3.1.0]hex-3-yl)-2-oxo-ethyl ester ethyl ester

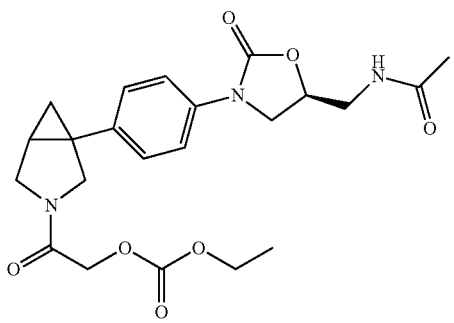 [SMILES: CCOC(=O)OCC(=O)N1CC2CC2(c2ccc(N3C[C@H](CNC(C)=O)OC3=O)cc2)C1]

To a solution of N-(3-{4-[3-(2-hydroxy-acetyl)-3-aza-bicyclo[3.1.0]hex-1-yl]-phenyl}-2-oxo-oxazolidin-5(S)-ylmethyl)-acetamide (Example X) (200 mg, 0.54 mmol) in THF (5 mL) were added triethylamine (0.19 mL, 1.35 mmol) and ethyl chloroformate (0.07 mL, 0.7 mmol) at 0° C. and progress of the reaction was monitored by TLC. On completion, the reaction mixture was diluted with water (10 mL) and extracted with DCM (2×20 mL). The organic layer was washed with brine (10 mL), dried over anhydrous sodium sulphate and concentrated in vacuo. The residue was purified by column chromatography (silica gel, 0.3:9.7 MeOH:CHCl$_3$) to provide the title compound (72 mg, 30%) as white solid.

$^1$H NMR (400 MHz, CDCl$_3$): δ 0.85 (bs, 1H), 1.10-1.20 (m, 1H), 1.34 (t, J=7.0 Hz, 3H), 1.86-1.94 (m, 1H), 2.02 (s, 3H), 3.60-3.84 (m, 7H), 3.99-4.08 (m, 1H), 4.25 (dd, J=7.2 and 14.3 Hz, 2H), 4.63 (dd, J=15.0 and 24.0 Hz, 2H), 4.78 (bs, 1H), 6.08 (bs, 1H), 7.18-7.22 (m, 2H), 7.46-7.49 (m, 2H)

ESIMS (m/z): 468.8 (M+23), 447.8 (M+2), 446.5 (M+1)

Example XII

Preparation of N-{2-Oxo-3-[4-(3-pyridin-2-yl-3-aza-bicyclo[3.1.0]hex-1-yl)-phenyl]-oxazolidin-5(S)-ylmethyl}-acetamide

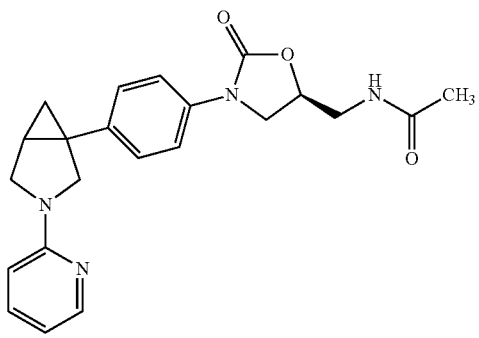 [SMILES: CC(=O)NC[C@H]1CN(c2ccc(C34CC3CN(c3ccccn3)C4)cc2)C(=O)O1]

To a solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (0.4 g, 1.1 mmol) in DCM (5 mL) were added DIPEA (0.5 mL, 3.4 mmol) and 2-bromopyridine (0.9 mL, 5.7 mmol) at r.t. The reaction mixture was stirred at 90° C. and progress of the reaction was monitored by TLC. On completion, the reaction mixture was diluted with water (10 mL) and extracted with DCM (2×20 mL). The organic layer was washed with brine (10 mL), dried over anhydrous sodium sulphate and concentrated in vacuo. The crude was purified by column chromatography (silica gel, 0.2:9.8 MeOH:CHCl$_3$) to provide the title compound (0.3 g, 67%) as white solid.

$^1$H NMR (400 MHz, CDCl$_3$): δ 1.00 (t, J=4.5 Hz, 1H), 1.11-1.19 (m, 1H), 1.99 (t, J=4.0 Hz, 1H), 2.02 (s, 3H), 3.58-3.65 (m, 3H), 3.70-3.76 (m, 1H), 3.78-3.84 (m, 2H), 4.07 (t, J=8.9 Hz, 1H), 4.11 (d, J=9.7 Hz, 1H), 4.76-4.78 (m, 1H), 5.95-5.97 (m, 1H), 6.40 (d, J=8.5 Hz, 1H), 6.57-6.59 (m, 1H), 7.27-7.28 (m, 3H), 7.43-7.48 (m, 3H)

ESIMS (m/z): 415.6 (M+23), 395.8 (M+3), 393.3 (M+1)

Example XIII

Preparation of N-{3-[4-(3-Cyano-3-aza-bicyclo[3.1.0]hex-1-yl)-phenyl]-2-oxo-oxazolidin-5(S)-ylmethyl}-acetamide

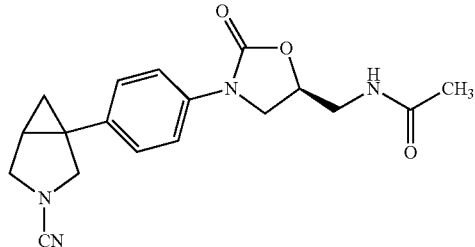 [SMILES: CC(=O)NC[C@H]1CN(c2ccc(C34CC3CN(C#N)C4)cc2)C(=O)O1]

To a solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (0.2 g, 0.57 mmol) in DMF (5 mL) were added DIPEA (0.3 mL, 1.7 mmol) and cyanogen bromide (0.18 g, 1.1 mmol) at r.t. The reaction mixture was stirred at 100° C. and progress of the reaction was monitored by TLC. On completion, the reaction mixture was diluted with water (10 mL) and extracted with ethyl acetate (2×20 mL). The organic layer was washed with brine (10 mL), dried over anhydrous sodium sulphate and concentrated in vacuo. The crude was purified by column chromatography (silica gel, 0.2:9.8 MeOH:CHCl₃) to provide the title compound (0.05 g, 26%) as white solid.

¹H NMR (400 MHz, CDCl₃): δ 1.04 (t, J=5.0 Hz, 1H), 1.19-1.62 (m, 1H), 1.80-1.82 (m, 1H), 2.01 (s, 3H), 3.54 (d, J=9.6 Hz, 1H), 3.58-3.67 (m, 1H), 3.68-3.74 (m, 3H), 3.75-3.80 (m, 2H), 4.05 (t, J=8.9 Hz, 1H), 4.75-4.79 (m, 1H), 6.00-6.10 (m, 1H), 7.17 (d, J=8.7 Hz, 2H), 7.47 (dd, J=1.9 and 6.8 Hz, 2H)

ESIMS (m/z): 363.8 (M+23), 342.8 (M+2), 341.8 (M+1)

Example XIV

Preparation of N-(((5S)-3-(4-(3-(isoxazole-5-carbonyl)-3-azabicyclo[3.1.0]hexan-1-yl)phenyl)-2-oxooxazolidin-5-yl)methyl)acetamide

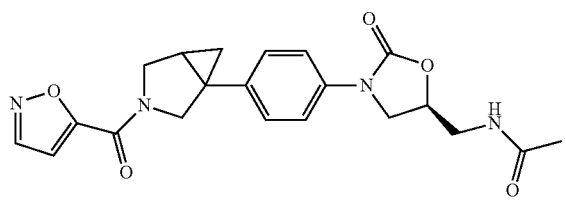 [SMILES: CC(=O)NC[C@H]1CN(c2ccc(C34CC3CN(C(=O)c3ccno3)C4)cc2)C(=O)O1]

To a solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (200 mg, 0.57 mmol), in DMF (10 mL), were added isoxazole-5-carboxylic acid (71 mg, 0.63 mmol), EDC (130 mg, 0.68 mmol), HOBt (89 mg, 0.68 mmol) and NMM (0.19 mL, 1.71 mmol) at 0° C. The reaction mixture was stirred at r.t. and progress of the reaction was monitored by TLC. On completion, DMF was evaporated in vacuo and residue was dissolved in chloroform (50 mL). The organic layer was washed with water (25 mL), brine (25 mL), dried over anhydrous sodium sulphate and concentrated in vacuo. The residue was purified by column chromatography (silica gel, 0.4:9.6 MeOH:CHCl₃) to provide the title compound (156 mg, 67%) as white solid.

¹H NMR (400 MHz, CDCl₃): δ 0.80-0.90 (m, 1H), 1.15-1.25 (m, 1H), 1.85-2.02 (m, 1H), 2.03 (s, 3H), 3.55-3.65 (m, 1H), 3.65-3.75 (m, 1H), 3.75-3.85 (m, 2H), 4.07 (t, J=9.0 Hz, 1H), 4.08-4.20 (m, 1H), 4.23 (dd, J=9.1 and 17.6 Hz, 1H), 4.46 (dd, J=9.1 and 16.9 Hz, 1H), 4.70-4.85 (m, 1H), 6.00-6.15 (bs, 1H), 6.91 (d, J=1.7 Hz, 1H), 7.15-7.25 (m, 2H), 7.48 (d, J=8.7 Hz, 2H), 8.33 (t, J=1.8 Hz, 1H)

ESIMS (m/z): 411.3 (M+1)

Example XV

Preparation of N-(((5S)-2-oxo-3-(4-(3-(pyridin-3-ylmethyl)-3-azabicyclo[3.1.0]hexan-1-yl)phenyl)oxazolidin-5-yl)methyl)acetamide

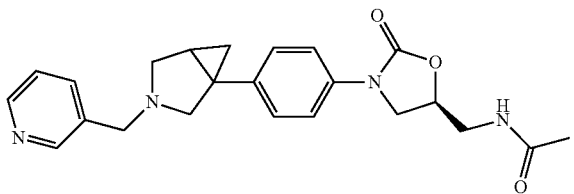 [SMILES: CC(=O)NC[C@H]1CN(c2ccc(C34CC3CN(Cc3cccnc3)C4)cc2)C(=O)O1]

To a stirred solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (210 mg, 0.6 mmol), in dichloroethane (25 mL), were added 3-pyridinecarboxaldehyde (0.06 mL, 0.6 mmol), triethyl amine (0.17 mL, 1.2 mmol) and sodium triacetoxyborohydride (254 mg, 1.2 mmol) at 0° C. under nitrogen atmosphere. The reaction mixture was stirred at r.t. and progress of the reaction was monitored by TLC. On completion, the reaction mixture was quenched by adding saturated aq. NaHCO₃ solution (20 mL) and product was extracted with DCM (3×25 mL). The organic layer was washed with water (25 mL), brine (25 mL), dried over anhydrous sodium sulphate and concentrated in vacuo. The residue was purified by column chromatography (silica gel, 0.5:9.5 MeOH:CHCl₃) to provide the title compound (98 mg, 40%) as off white solid.

¹H NMR (400 MHz, CDCl₃): δ 0.77 (dd, J=3.8 and 7.7 Hz, 1H), 1.49 (t, J=3.6 Hz, 1H), 1.60-1.75 (m, 1H), 2.02 (s, 3H), 2.45-2.55 (m, 1H), 2.59 (d, J=8.3 Hz, 1H), 3.05 (d, J=8.5 Hz, 1H), 3.24 (d, J=8.4 Hz, 1H), 3.55-3.65 (m, 2H), 3.55-3.85 (m, 4H), 4.04 (t, J=8.9 Hz, 1H), 4.65-4.80 (m, 1H), 6.03 (t, J=5.7 Hz, 1H), 7.12 (d, J=8.6 Hz, 2H), 7.20-7.30 (m, 1H), 7.41 (d, J=8.6 Hz, 2H), 7.65 (d, J=7.9 Hz, 2H), 8.50 (d, J=3.8 Hz, 1H), 8.54 (s, 1H)

ESIMS (m/z): 445.8 (M+39), 429.7 (M+23), 407.9 (M+1)

Example XVI

Preparation of N-(((5S)-3-(4-(3-(2-(furan-2-yl)-2-oxoacetyl)-3-azabicyclo[3.1.0]hexan-1-yl)phenyl)-2-oxooxazolidin-5-yl)methyl)acetamide

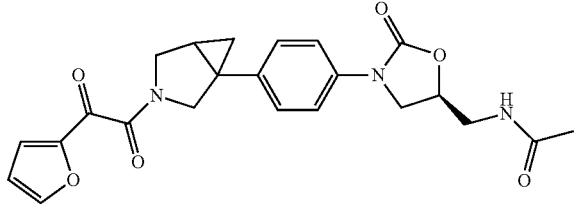 [SMILES: CC(=O)NC[C@H]1CN(c2ccc(C34CC3CN(C(=O)C(=O)c3ccco3)C4)cc2)C(=O)O1]

To a stirred solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (163 mg, 0.46 mmol), in DMF (20 mL), were added α-oxo-2-furanacetic acid (65 mg, 0.46 mmol), EDC (97 mg, 0.51 mmol), HOBt (69 mg, 0.51 mmol) and NMM (0.11 mL, 1.02 mmol) at 0° C. The reaction mixture was stirred at r.t. and progress of the reaction was monitored by TLC. On completion, DMF was evaporated in vacuo and residue was dissolved in chloroform (50 mL). The organic layer was washed with water (25 mL), brine (25 mL), dried over anhydrous sodium sulphate and concentrated in vacuo. The residue was purified by column chromatography (silica gel, 0.4:9.6 MeOH:CHCl₃) to provide the title compound (140 mg, 69%) as white solid.

¹H NMR (400 MHz, CDCl₃): δ 0.87 (dd, J=5.2 and 10.0 Hz, 1H), 1.48 (dd, J=5.5 and 6.7 Hz, 1H), 1.85-1.95 (m, 1H), 2.02 (two s in the ratio 1:1, 3H), 3.55-3.65 (m, 1H), 3.70-3.90 (m, 3.5H), 3.95-4.05 (m, 1H), 4.05-4.15 (m, 1.5H), 4.16 (d, J=12.2 Hz, 0.5H), 4.39 (d, J=12.1 Hz, 0.5H), 4.70-4.85 (m, 1H), 5.95-6.05 (m, 1H), 6.55-6.65 (m, 1H), 7.10-7.25 (m, 2H), 7.40-7.60 (m, 3H), 7.73 (t, J=0.8 Hz, 1H)

ESIMS (m/z): 460.7 (M+23), 438.6 (M+1)

Example XVII

Preparation of N-(3-{4-[3-(2-Acetylamino-acetyl)-3-aza-bicyclo[3.1.0]hex-1-yl]-phenyl}-2-oxo-oxazolidin-(5S)-ylmethyl)-acetamide

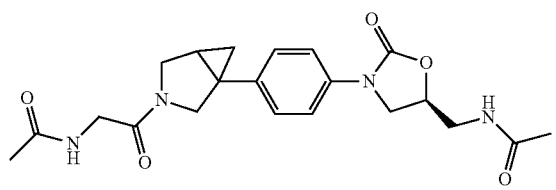 [SMILES: CC(=O)NCC(=O)N1CC2CC2(c2ccc(N3C[C@H](CNC(C)=O)OC3=O)cc2)C1]

Step 1: Preparation of [2-(1-{4-[(5S)-(Acetylamino-methyl)-2-oxo-oxazolidin-3-yl]-phenyl}-3-aza-bicyclo[3.1.0]hex-3-yl)-2-oxo-ethyl]-carbamic acid tert-butyl ester To a solution of hydrochloride salt of N-{3-[4-(3-aza-bicyclo[3.1.0]hex-1-yl)-phenyl]-2-oxo-oxazolidin-5(S)-yl-methyl}-acetamide (Intermediate IV) (450 mg, 1.28 mmol), in DCM (40 mL), were added N-(tert-butoxycarbonyl)glycine (245 mg, 1.41 mmol), EDC (269 mg, 1.41 mmol), HOBt (190 mg, 1.41 mmol) and NMM (3.1 mL, 2.8 mmol) at 0° C. The reaction mixture was stirred at r.t. and progress of the reaction was monitored by TLC. On completion, the reaction mixture was diluted with DCM (100 mL). The organic layer was washed with water (50 mL), brine (50 mL), dried over anhydrous sodium sulphate and concentrated in vacuo. The residue was purified by column chromatography (silica gel, 0.2:9.8 MeOH:CHCl$_3$) to provide the title compound (480 mg, 80%) as white solid.

ESIMS (m/z): 511.8 (M+39), 495.9 (M+23), 473.9 (M+1)

Step 2: Preparation of 2-(1-{4-[(5S)-(Acetylamino-methyl)-2-oxo-oxazolidin-3-yl]-phenyl-}-3-aza-bicyclo[3.1.0]hex-3-yl)-2-oxo-ethyl-ammonium; trifluoro-acetate To a stirred solution of compound (450 mg, 0.95 mmol) obtained in Step 1, in DCM (2 mL) at 0° C. under nitrogen atmosphere was added TFA (3 mL) dropwise. The reaction mixture was stirred at 0° C. and progress of the reaction was monitored by TLC. On completion, excess TFA and DCM were evaporated under reduced pressure to obtain the title compound (455 mg, 98%) as white solid and subjected to further reaction without any purification.

ESIMS (m/z): 395.6 (M+23), 373.7 (M+1)

Step 3: Preparation of N-(3-{4-[3-(2-Acetylamino-acetyl)-3-aza-bicyclo[3.1.0]hex-1-yl]-phenyl}-2-oxo-oxazolidin-(5S)-ylmethyl)-acetamide To a stirred solution of compound (200 mg, 0.41 mmol) obtained in Step 2, in DCM (25 mL), was added pyridine (0.1 mL, 1.24 mmol). The resulting solution was cooled to 0° C. and acetic anhydride (0.06 mL, 0.62 mmol) was added dropwise. The reaction mixture was stirred at r.t. and progress of the reaction was monitored by TLC. On completion, the reaction mixture was diluted with DCM (100 mL). The organic layer was washed with water (25 mL), brine (25 mL), dried over anhydrous sodium sulphate and concentrated in vacuo. The residue was purified by column chromatography (silica gel, 0.4:9.6 MeOH:CHCl$_3$) to provide the title compound (110 mg, 65%) as white solid.

$^1$H NMR (400 MHz, CDCl$_3$): δ 0.75-0.85 (m, 1H), 1.10-1.20 (m, 1H), 1.85-2.00 (m, 1H), 2.03 (s, 3H), 2.06 (s, 3H), 3.55-3.65 (m, 2.5H), 3.65-3.80 (m, 3H), 3.85-4.15 (m, 4H), 4.21 (d, J=11.6 Hz, 0.5H), 4.70-4.85 (m, 1H), 6.02 (t, J=5.8 Hz, 1H), 6.45-6.55 (m, 1H), 7.10-7.20 (m, 2H), 7.45-7.55 (m, 2H)

ESIMS (m/z): 453.8 (M+39), 437.7 (M+23), 415.7 (M+1)

Example XVIII

Preparation of N-(2-(1-(4-((S)-5-(acetamidomethyl)-2-oxooxazolidin-3-yl)phenyl)-3-azabicyclo[3.1.0]hexan-3-yl)-2-oxoethyl)nicotinamide

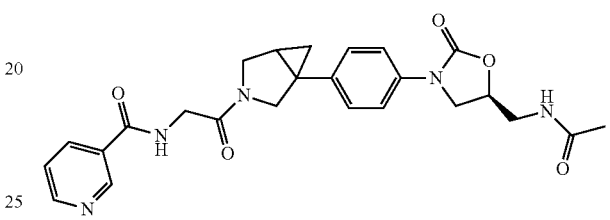

To a solution of compound (225 mg, 0.46 mmol) obtained in Step 2 Example XVII, in DMF (10 mL), were added nicotinic acid (63 mg, 0.51 mmol), EDC (97 mg, 0.51 mmol), HOBt (69 mg, 0.51 mmol) and NMM (0.11 mL, 1.02 mmol) at 0° C. The reaction mixture was stirred at r.t. and progress of the reaction was monitored by TLC. On completion, DMF was evaporated in vacuo and residue was dissolved in chloroform (50 mL). The organic layer was washed with water (25 mL), brine (25 mL), dried over anhydrous sodium sulphate and concentrated in vacuo. The residue was purified by column chromatography (silica gel, 0.3:9.7 MeOH:CHCl$_3$) to provide the title compound (143 mg, 68%) as white solid.

$^1$H NMR (400 MHz, CDCl$_3$): δ 0.75-0.90 (m, 1H), 1.10-1.25 (m, 1H), 1.90-2.01 (m, 1H), 2.02 (s, 3H), 3.60-3.90 (m, 5H), 3.90-4.40 (m, 5H), 4.70-4.85 (m, 1H), 6.06 (bs, 1H), 7.20-7.25 (m 2H), 7.32 (bs, 1H), 7.41 (dd, J=4.9 and 8.0 Hz, 1H), 7.45-7.55 (m, 2H), 8.10-8.20 (m, 1H), 8.75 (d, J=3.6 Hz, 1H), 9.08 (s, 1H)

ESIMS (m/z): 516.9 (M+39), 500.7 (M+23), 478.6 (M+1)

Example XIX

Preparation of 1-{4-[5(S)-(Methoxycarbonylamino-methyl)-2-oxo-oxazolidin-3-yl]-phenyl}-3-aza-bicyclo[3.1.0]-hexane-3-carboxylic acid methyl ester

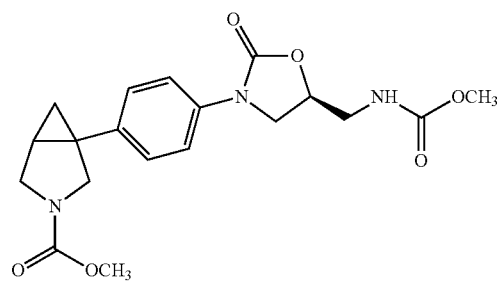 [SMILES: COC(=O)NC[C@H]1CN(c2ccc(C34CC3CN(C(=O)OC)C4)cc2)C(=O)O1]

Step 1: Preparation of 1-[4-(5(S)-Aminomethyl-2-oxo-oxazolidin-3-yl)-phenyl]-3-aza-bicyclo[3.1.0]hexane-3-carboxylic acid tert-butyl ester A mixture of 1-[4-{5(R)-azidomethyl-2-oxo-oxazolidin-3-yl}-phenyl]-3-aza-bicyclo[3.1.0]hexane-3-carboxylic acid tert-butyl ester (Intermediate IV, Step 6) (750 mg, 1.95 mmol) and triphenylphosphine (700 mg, 2.1 mmol) in THF (30 mL) was stirred at r.t. for 6 h. Water (1.5 mL) was added and the reaction mixture was stirred at 80° C. for 12 h. The reaction mixture was then diluted with water (100 mL) and extracted with ethyl acetate (3×100 mL). The organic layer was washed with brine (100 mL), dried over anhydrous sodium sulphate and concentrated in vacuo. The residue was purified by column chromatography (silica gel, 0.5:9.5 MeOH:CHCl$_3$) to provide the title compound (450 mg, 62%) as off white solid.
ESIMS (m/z): 396.7 (M+23), 374.7 (M+1)

Step 2: Preparation of 1-{4-[5(S)-(Methoxycarbonylamino-methyl)-2-oxo-oxazolidin-3-yl]-phenyl}-3-aza-bicyclo[3.1.0]hexane-3-carboxylic acid tert-butyl ester To a solution of solution of compound (400 mg, 1.1 mmol) obtained in Step 1, in THF (20 mL) was added triethylamine (0.45 mL, 3.2 mmol). The resulting solution was cooled to 0° C. and methyl chloroformate (0.12 mL, 1.6 mmol) was added dropwise. The reaction mixture was stirred at r.t. and progress of the reaction was monitored by TLC. On completion, the reaction mixture was diluted with DCM (60 mL). The organic layer was washed with water (25 mL), brine (25 mL), dried over anhydrous sodium sulphate and concentrated in vacuo. The residue was purified by column chromatography (silica gel, 2:8 EtOAc:Pet. ether) to provide the title compound (320 mg, 70%) as white solid.
ESIMS (m/z): 454.7 (M+23), 432.7 (M+1)

Step 3: Preparation of hydrochloride salt of {3-[4-(3-aza-bicyclo[3.1.0]hex-1-yl)-phenyl]-2-oxo-oxazolidin-5(S)-ylmethyl}-carbamic acid methyl ester To a solution of compound (310 mg, 0.72 mmol) obtained in Step 2, in diethylether (10 mL) was passed HCl gas for about 30 min. at r.t. The solid precipitates were washed with diethylether (10 mL) and ethyl acetate (10 mL) and dried under reduced pressure to give the title compound.
ESIMS (m/z): 332.7 (M+1)

Step 4: Preparation of 1-{4-[5(S)-(Methoxycarbonylamino-methyl)-2-oxo-oxazolidin-3-yl]-phenyl}-3-aza-bicyclo[3.1.0]-hexane-3-carboxylic acid methyl ester To a solution of compound (250 mg, 0.58 mmol) obtained in Step 3, in THF (5 mL) were added triethylamine (0.24 mL, 1.74 mmol) and methyl chloroformate (0.07 mL, 0.87 mmol) at 0° C. The reaction mixture was stirred at r.t. and progress of the reaction was monitored by TLC. On completion, the reaction mixture was diluted with water (10 mL) and extracted with DCM (2×20 mL). The organic layer was washed with brine (10 mL), dried over anhydrous sodium sulphate and concentrated in vacuo. The residue was purified by column chromatography (silica gel, 0.3:9.7 MeOH:CHCl$_3$) to provide the title compound (80 mg, 35.5%) as off white solid.
$^1$H NMR (400 MHz, CDCl$_3$): δ 0.84-0.85 (m, 1H), 1.06-1.09 (m, 1H), 1.81 (d, J=3.7 Hz, 1H), 3.49-3.63 (m, 4H), 3.68 (s, 3H), 3.70 (s, 3H), 3.70-3.83 (m, 2H), 3.91-4.08 (m, 2H), 4.76-4.77 (m, 1H), 5.16-5.17 (m, 1H), 7.18 (d, J=8.7 Hz, 2H), 7.46 (d, J=8.7 Hz, 2H)
ESIMS (m/z): 396.6 (M+23), 376.8 (M+2), 374.5 (M+1)

Example XX

Preparation of methyl 1-(4-((R)-5-((1H-1,2,3-triazol-1-yl)methyl)-2-oxooxazolidin-3-yl)phenyl)-3-azabicyclo[3.1.0]hexane-3-carboxylate

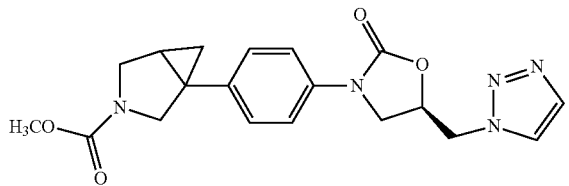 [SMILES: COC(=O)N1CC2CC2(c2ccc(N3C[C@H](Cn4ccnn4)OC3=O)cc2)C1]

Step 1: Preparation of 1-[4-(2-Oxo-(5R)-[1,2,3]triazol-1-ylmethyl-oxazolidin-3-yl)-phenyl]-3-aza-bicyclo[3.1.0]hexane-3-carboxylic acid tert-butyl ester To a solution of 1-[4-((5R)-azidomethyl-2-oxo-oxazolidin-3-yl)-phenyl]-3-aza-bicyclo[3.1.0]hexane-3-carboxylic acid tert-butyl ester (Intermediate IV, Step 6) (2 g, 5 mmol), in dioxane (25 mL) was added bicyclo[2.2.1]hepta-2,5-diene (5.1 mL, 50 mmol) and the resulting solution was stirred at 60° C. for 8 h. The solvent was evaporated and the residue was purified by column chromatography (silica gel, 0.4:9.6 MeOH:CHCl$_3$) to provide the title compound (1.6 g, 75%) as white solid.
ESIMS (m/z): 426.6 (M+1)

Step 2: Preparation of hydrochloride salt of 3-[4-(3-Aza-bicyclo[3.1.0]hex-1-yl)-phenyl]-(5R)-[1,2,3]triazol-1-ylmethyl-oxazolidin-2-one To a stirred solution of compound (1.5 g, 3.53 mmol), obtained in Step 1, in diethyl ether (20 mL) was passed HCl gas. The progress of the reaction was monitored by TLC. On completion, solvent was evaporated under reduced pressure and the residue obtained was washed with diethyl ether (2×20 mL) to provide the title compound (1.2 g, 94%) as off white solid.
ESIMS (m/z): 326.5 (M+1)

Step 3: Preparation of methyl 1-(4-((R)-5-(1H-1,2,3-triazol-1-yl)methyl)-2-oxooxazolidin-3-yl)phenyl)-3-azabicyclo[3.1.0]hexane-3-carboxylate To a stirred solution of compound (300 mg, 0.83 mmol), obtained in Step 2, in DCM (30 mL) was added triethyl amine (0.46 mL, 3.32 mmol). The resulting solution was cooled to 0° C. and methyl chloroformate (0.1 mL, 1.29 mmol) was added dropwise. The reaction mixture was stirred at r.t. and progress of the reaction was monitored by TLC. On completion, the reaction mixture was diluted with DCM (100 mL). The organic layer was washed with water (25 mL), brine (25 mL), dried over anhydrous sodium sulphate and concentrated in vacuo. The residue was purified by column chromatography (silica gel, 0.2:9.8 MeOH:CHCl$_3$) to provide the title compound (245 mg, 77%) as white solid.

$^1$H NMR (400 MHz, CDCl$_3$): δ 0.75-0.85 (m, 1H), 1.00-1.10 (m, 1H), 1.75-1.90 (m, 1H), 3.45-3.65 (m, 2H), 3.67 (d, J=10.8 Hz, 0.5H), 3.70 (s, 3H), 3.77 (d, J=10.8 Hz, 0.5H), 3.85-3.95 (m, 1.5H), 4.00 (d, J=10.6 Hz, 0.5H), 4.16 (t, J=9.0 Hz, 1H), 4.70-4.80 (m, 2H), 5.00-5.10 (m, 1H), 7.14 (d, J=8.7 Hz, 2H), 7.32 (d, J=8.6 Hz, 2H), 7.75 (s, 1H), 7.80 (s, 1H)

ESIMS (m/z): 384.5 (M+1)

Example XXI

Preparation of dihydrochloride salt of 1-(4-morpholin-4-yl-phenyl)-3-aza-bicyclo[3.1.0]hexane

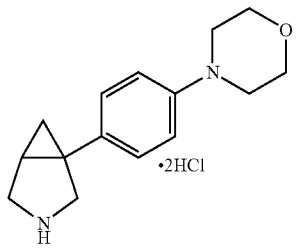 [SMILES: c1cc(C23CNCC2C3)ccc1N1CCOCC1]

Step 1: Preparation of 1-(4-morpholin-4-yl-phenyl)-3-aza-bicyclo[3.1.0]hexane-3-carboxylic acid tert-butyl ester To a solution of 1-(4-bromo-phenyl)-3-aza-bicyclo[3.1.0]hexane-3-carboxylic acid tert-butyl ester (Intermediate I, 680 mg, 2.01 mmol) in anhydrous toluene (20 mL) were added Pd$_2$(dba)$_3$ (4.6 mg, 0.005 mmol), BINAP (9.4 mg, 0.015 mmol), sodium tert-butoxide (232 mg, 2.41 mmol) and morpholine (0.2 mL, 2.21 mmol) at r.t. and reaction mixture was stirred at 90° C. for 4 h. Reaction mixture was then concentrated and crude product was purified by column chromatography (silica gel, 1:9 EtOAc:Pet. ether) to afford the title compound as white solid (456 mg, 66%).

ESIMS (m/z): 367.3 (M+23), 345.3 (M+1)

Step 2: Preparation of dihydrochloride salt of 1-(4-morpholin-4-yl-phenyl)-3-aza-bicyclo[3.1.0]hexane HCl gas was bubbled through a solution of 1-(4-morpholin-4-yl-phenyl)-3-aza-bicyclo[3.1.0]hexane-3-carboxylic acid tert-butyl ester (150 mg, 0.44 mmol), in dry diethylether (3 mL). Progress of the reaction was monitored by TLC. On completion, solvent was removed in vacuo, washings were given with diethylether (2×3 mL) and ethylacetate (3 mL) and dried in vacuo to afford the title compound (115 mg, 93.2%) as white hygroscopic solid.

$^1$H NMR (400 MHz, CD$_3$OD): δ 1.18-1.23 (m, 1H), 1.30-1.35 (m, 1H), 2.20-2.35 (m, 1H), 3.56 (d, J=11.6 Hz, 1H), 3.60-3.75 (m, 6H), 3.83 (d, J=11.4 Hz, 1H), 4.10-4.20 (m, 4H), 7.50-7.60 (m, 2H), 7.60-7.80 (m, 2H)

ESIMS (m/z): 245.7 (M+1)

Example XXII

Preparation of dihydrochloride salt of (1R,5S)-3-Ethyl-1-(4-morpholin-4-yl-phenyl)-3-aza-bicyclo[3.1.0]hexane

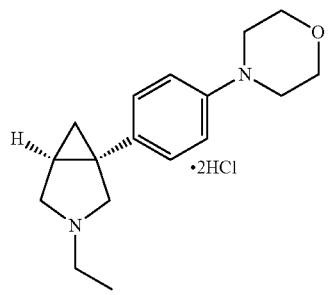 [SMILES: CCN1C[C@H]2C[C@@]2(c2ccc(N3CCOCC3)cc2)C1]

Step 1: Preparation of (1R,5S)-1-(4-morpholin-4-yl-phenyl)-3-aza-bicyclo[3.1.0]hexane-3-carboxylic acid tert-butyl ester The title compound was prepared following the procedure as reported in Step 1, Example XXI. Intermediate III was used instead of Intermediate I.

ESIMS (m/z): 367.3 (M+23), 345.3 (M+1)

Step 2: Preparation of dihydrochloride salt of (1R,5S)-1-(4-morpholin-4-yl-phenyl)-3-aza-bicyclo[3.1.0]hexane The title compound was prepared following the procedure as reported in Step 2, Example XXI. ESIMS (m/z): 245.7 (M+1)

Step 3: Preparation of (1R,5S)-3-ethyl-1-(4-morpholin-4-yl-phenyl)-3-aza-bicyclo[3.1.0]hexane To a solution of dihydrochloride salt of (1R,5S)-(4-morpholin-4-yl-phenyl)-3-aza-bicyclo[3.1.0]hexane (5.0 g, 17.8 mmol) in DMF (20 mL) were added DIPEA (12.7 mL, 71.3 mmol) and ethyl iodide (2.14 mL, 26.7 mmol) at r.t. and progress of the reaction was monitored by TLC. On completion, the reaction mixture was diluted with water (10 mL) and extracted with ethyl acetate (3×20 mL). The organic layer was washed with brine (2×10 mL), dried over anhydrous sodium sulphate and concentrated in vacuo. The residue was purified by column chromatography (silica gel, 0.2:9.8 MeOH:CHCl$_3$) to provide the title compound as viscous liquid (2.3 g, 47%).

ESIMS (m/z): 274.5 (M+2), 273.3 (M+1)

Step 4: Preparation of dihydrochloride salt of (1R,5S)-3-ethyl-1-(4-morpholin-4-yl-phenyl)-3-aza-bicyclo[3.1.0]hexane HCl gas was bubbled through a solution of (1R,5S)-(3-(2-methoxy-ethyl)-1-(4-morpholin-4-yl-phenyl)-3-aza-bicyclo[3.1.0]hexane (2.3 g, 8.45 mmol) in dry diethylether (15 mL). After completion of the reaction as confirmed by TLC, solvent was removed in vacuo, given washings with diethylether (3×5 mL) and ethyl acetate (2×5 mL) and dried in vacuo to afford the title compound (2.5 g, 96%) as white hygroscopic solid.

¹H NMR (400 MHz, CD₃OD): δ 1.26-1.31 (m, 1H), 1.37 (t, J=7.28 Hz, 1H), 1.41-1.35 (m, 1H), 2.23-2.27 (m, 1H), 3.33-3.36 (m, 2H), 3.58-3.61 (m, 6H), 3.82 (d, J=11.3 Hz, 1H), 4.05 (t, J=4.8 Hz, 4H), 4.09 (d, J=11.2 Hz, 2H), 7.50 (d, J=8.9 Hz, 2H), 7.57 (d, J=8.7 Hz, 2H)

ESIMS (m/z): 273.5 (M+1)

Example XXIII

Preparation of dihydrochloride salt of 1-(4-morpholin-4-yl-phenyl)-3-(2,2,2-trifluoro-ethyl)-3-aza-bicyclo[3.1.0]hexane

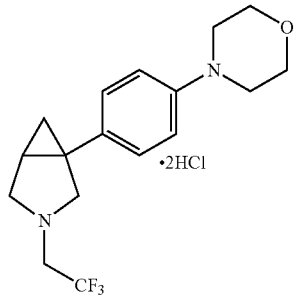 [SMILES: FC(F)(F)CN1CC2CC2(c2ccc(N3CCOCC3)cc2)C1]

Step 1: Preparation of 1-(4-morpholin-4-yl-phenyl)-3-(2,2,2-trifluoro-ethyl)-3-aza-bicyclo[3.1.0]hexane To a solution of dihydrochloride salt of 1-(4-morpholin-4-yl-phenyl)-3-aza-bicyclo[3.1.0]hexane (Example XXI) (250 mg, 0.89 mmol) in dry toluene (5 mL) were added triethylamine (0.5 mL, 3.56 mmol) and 2,2,2-trifluoro-ethyltrifluoromethanesulfonate (413 mg, 1.78 mmol) at r.t. and reaction mixture was refluxed for 3 h. Progress of the reaction was monitored by TLC. On completion, reaction mixture was then concentrated and the crude product was purified by column chromatography (silica gel, 0.35:9.65 MeOH:CHCl₃) to afford the title compound as viscous liquid (135 mg, 46%).

ESIMS (m/z): 327.5 (M+1)

Step 2: Preparation of dihydrochloride salt of 1-(4-morpholin-4-yl-phenyl)-3-(2,2,2-trifluoro-ethyl)-3-aza-bicyclo[3.1.0]hexane HCl gas was bubbled through a solution of 1-(4-morpholin-4-yl-phenyl)-3-(2,2,2-trifluoro-ethyl)-3-aza-bicyclo[3.1.0]hexane (135 mg, 0.41 mmol) obtained in Step 1 of Example XXIII, in dry diethylether (4 mL). After completion of the reaction as confirmed by TLC, solvent was removed in vacuo, given washings with diethylether (2×3 mL) and ethylacetate (3 mL) and dried in vacuo to afford the title compound (145 mg, 98%) as white hygroscopic solid.

¹H NMR (400 MHz, CDCl₃): δ1.29-1.33 (m, 1H), 1.51-1.54 (m, 1H), 2.28-2.30 (m, 1H), 3.64-3.66 (m, 4H), 3.79 (br, 3H), 4.06-4.09 (m, 5H), 4.17-4.24 (m, 2H), 7.54 (d, J=8.8 Hz, 2H), 7.64 (d, J=8.6 Hz, 2H)

ESIMS (m/z): 327.8 (M+1)

Example XXIV

Preparation of dihydrochloride salt of 3-(2-methoxy-ethyl)-1-(4-morpholin-4-yl-phenyl)-3-aza-bicyclo[3.1.0]hexane

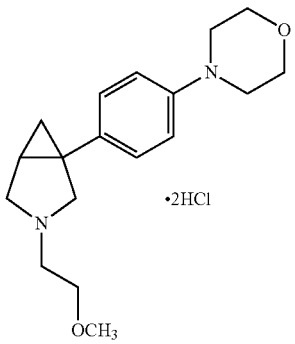 [SMILES: COCCN1CC2CC2(c2ccc(N3CCOCC3)cc2)C1]

Step 1: Preparation of 3-(2-methoxy-ethyl)-1-(4-morpholin-4-yl-phenyl)-3-aza-bicyclo[3.1.0]hexane To a solution of dihydrochloride salt of 1-(4-morpholin-4-yl-phenyl)-3-aza-bicyclo[3.1.0]hexane (Example XXI) (250 mg, 0.89 mmol) in anhydrous DMF (5 mL) were added DIPEA (0.63 mL, 3.56 mmol) and 2-methoxyethyl chloride (0.12 mL, 1.3 mmol) at r.t. and reaction mixture was stirred at 100° C. for 16 h. Progress of the reaction was monitored by TLC. On completion, reaction mixture was then concentrated and the crude product was purified by column chromatography (silica gel, 0.25:9.75 MeOH:CHCl₃) to afford the title compound as viscous liquid (100 mg, 37%).

ESIMS (m/z): 304.7 (M+2), 303.8 (M+1)

Step 2: Preparation of dihydrochloride salt of 3-(2-methoxy-ethyl)-1-(4-morpholin-4-yl-phenyl)-3-aza-bicyclo[3.1.0]hexane HCl gas was bubbled through a solution of 3-(2-methoxy-ethyl)-1-(4-morpholin-4-yl-phenyl)-3-aza-bicyclo[3.1.0]hexane (100 mg, 0.33 mmol) obtained in Step 1 of Example XXIV, in dry diethylether (4 mL). After completion of the reaction as confirmed by TLC, solvent was removed in vacuo, given washings with diethylether (2×3 mL) and ethyl acetate (3 mL) and dried in vacuo to afford the title compound (85 mg, 76%) as white hygroscopic solid.

¹H NMR (400 MHz, CDCl₃): δ1.24-1.29 (m, 1H), 1.37-1.39 (m, 1H), 2.20-2.21 (m, 1H), 3.41 (s, 3H), 3.47-3.51 (m, 6H), 3.58-3.68 (m, 4H), 3.80-3.86 (m, 1H), 4.04-4.06 (m, 5H), 7.44 (br, 4H)

ESIMS (m/z): 304.5 (M+2), 303.4 (M+1)

Example XXV

Preparation of dihydrochloride salt of 1-(4-pyrrolidin-1-yl-phenyl)-3-aza-bicyclo[3.1.0]hexane

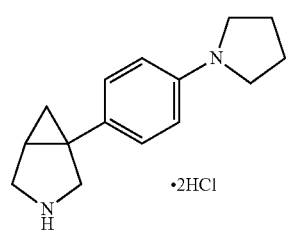 [SMILES: c1cc(C23CNCC2C3)ccc1N1CCCC1]

Step 1: Preparation of 1-(4-pyrrolidin-1-yl-phenyl)-3-aza-bicyclo[3.1.0]hexane-3-carboxylic acid tert-butyl ester To a solution of 1-(4-bromo-phenyl)-3-aza-bicyclo[3.1.0]hexane-3-carboxylic acid tert-butyl ester (Intermediate I, 200 mg, 0.592 mmol) in anhydrous toluene (15 mL) were added $Pd_2(dba)_3$ (1.35 mg, 0.002 mmol), BINAP (2.76 mg, 0.004 mmol), sodium tert-butoxide (68.20 mg, 0.710 mmol) and pyrrolidine (0.05 mL, 0.651 mmol) at r.t. and reaction mixture was stirred for 8 h at 80° C. Reaction mixture was then concentrated and the crude product was purified by column chromatography (silica gel, 0.4:9.6 EtOAc:Pet. ether) to afford the title compound as viscous liquid (140 mg, 72%).
ESIMS (m/z): 330.7 (M+2), 329.8 (M+1)

Step 2: Preparation of dihydrochloride salt of 1-(4-pyrrolidin-1-yl-phenyl)-3-aza-bicyclo[3.1.0]hexane HCl gas was bubbled through a solution of 1-(4-pyrrolidin-1-yl-phenyl)-3-aza-bicyclo[3.1.0]hexane-3-carboxylic acid tert-butyl ester (140 mg, 0.43 mmol) obtained in Step 1 of Example XXV, in dry diethylether (4 mL). After completion of the reaction as confirmed by TLC, solvent was removed in vacuo, given washings with diethylether (2×3 mL) and ethyl acetate (3 mL) and dried in vacuo to afford the title compound (80.0 mg, 70%) as white hygroscopic solid.
$^1$H NMR (400 MHz, $CD_3OD$): δ 1.10-1.16 (m, 1H), 1.26-1.30 (m, 1H), 2.15-2.22 (m, 5H), 3.52 (d, J=11.3 Hz, 1H), 3.59-3.65 (m, 6H), 3.76 (d, J=11.5 Hz, 1H), 7.36-7.45 (m, 4H)
ESIMS (m/z): 229.4 (M+1)

Example XXVI

Preparation of dihydrochloride salt of 1-[4-(3-fluoro-pyrrolidin-1-yl)-phenyl]-3-aza-bicyclo[3.1.0]hexane

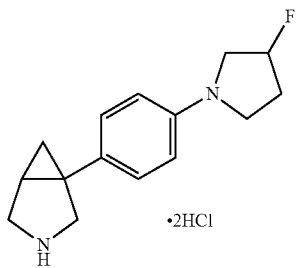 [SMILES: FC1CCN(c2ccc(C34CNCC3C4)cc2)C1]

·2HCl

Step 1: Preparation of 1-[4-(3-fluoro-pyrrolidin-1-yl)-phenyl]-3-aza-bicyclo[3.1.0]hexane-3-carboxylic acid tert-butyl ester To a solution of 1-(4-bromo-phenyl)-3-aza-bicyclo[3.1.0]hexane-3-carboxylic acid tert-butyl ester (Intermediate I, 400 mg, 1.2 mmol) in anhydrous toluene (5 mL) were added $Pd_2(dba)_3$ (5.6 mg, 0.006 mmol), BINAP (11.2 mg, 0.018 mmol), sodium tert-butoxide (230 mg, 2.4 mmol) and 3-fluoro-pyrrolidine hydrochloride (170 mg, 1.32 mmol) at r.t. and reaction mixture was refluxed for 3 h. Reaction mixture was then concentrated and the crude product was purified by column chromatography (silica gel, 2:8 EtOAc:Pet. ether) to afford the title compound as viscous liquid (90 mg, 22%).
ESIMS (m/z): 347.9 (M+1)

Step 2: Preparation of dihydrochloride salt of 1-[4-(3-fluoro-pyrrolidin-1-yl)-phenyl]-3-aza-bicyclo[3.1.0]hexane HCl gas was bubbled through a solution of 1-[4-(3-fluoro-pyrrolidin-1-yl)-phenyl]-3-aza-bicyclo[3.1.0]hexane-3-carboxylic acid tert-butyl ester (90 mg, 0.26 mmol) obtained in Step 1 of Example XXVI, in dry diethylether (3 mL). After completion of the reaction as confirmed by TLC, solvent was removed in vacuo, given washings with diethylether (2×3 mL) and ethyl acetate (3 mL) and dried in vacuo to afford the title compound (60 mg, 82%) as white hygroscopic solid.
$^1$H NMR (400 MHz, $CD_3OD$): δ 1.03 (t, J=5.4 Hz, 1H), 1.21 (t, J=7.4 Hz, 1H), 2.00-2.06 (m, 1H), 2.22-2.37 (m, 2H), 3.48-3.56 (m, 5H), 3.59-3.69 (m, 3H), 6.87 (dd, J=2.9 and 8.7 Hz, 2H), 7.23 (d, J=7.9 Hz, 2H)
ESIMS (m/z): 247.7 (M+1)

Example XXVII

Preparation of hydrochloride salt of 1-[4-(3-aza-bicyclo[3.1.0]hex-1-yl)-phenyl]-pyrrolidin-2-one

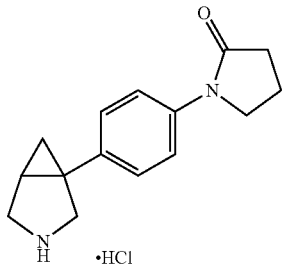 [SMILES: O=C1CCCN1c1ccc(C23CNCC2C3)cc1 ; Cl]

·HCl

Step 1: Preparation of 1-[4-(2-oxo-pyrrolidin-1-yl)-phenyl]-3-aza-bicyclo[3.1.0]hexane-3-carboxylic acid tert-butyl ester To a stirring suspension of potassium carbonate (1.23 g, 8.95 mmol) and CuI (42.5 mg, 0.22 mmol) in anhydrous toluene (10 mL) were added 1-(4-bromo-phenyl)-3-aza-bicyclo[3.1.0]hexane-3-carboxylic acid tert-butyl ester (Intermediate I, 1.6 g, 4.5 mmol) dissolved in toluene (10 mL) followed by addition of pyrrolidinone (0.5 mL, 6.2 mmol) and ethylene diamine (0.03 mL, 0.45 mmol). Reaction mixture was refluxed for 16 h. Reaction mixture was then concentrated and the crude product was purified by column chromatography (silica gel, 4:6 EtOAc:Pet. ether) to afford the title compound as white solid (800 mg, 52%).
ESIMS (m/z): 365.7 (M+23), 343.8 (M+1)

Step 2: Preparation of hydrochloride salt of 1-[4-(3-aza-bicyclo[3.1.0]hex-1-yl)-phenyl]-pyrrolidin-2-one HCl gas was bubbled through a solution of 1-[4-(2-oxo-pyrrolidin-1-yl)-phenyl]-3-aza-bicyclo[3.1.0]hexane-3-carboxylic acid tert-butyl ester 800 mg, 2.34 mmol) obtained in Step 1 of Example XXVII, in dry diethylether (10 mL). After completion of the reaction as confirmed by TLC, solvent was removed in vacuo, given washings with diethylether (2×5 mL) and ethyl acetate (5 mL) and dried in vacuo to afford the title compound (600 mg, 92%) as white hygroscopic solid.
$^1$H NMR (400 MHz, $D_2O$): δ 1.10-1.13 (m, 1H), 1.32-1.34 (m, 1H), 2.10-2.25 (m, 3H), 2.63-2.66 (m, 2H), 3.60 (d, J=11.6 Hz, 1H), 3.69-3.74 (m, 2H), 3.83 (d, J=11.4 Hz, 1H), 3.91-3.94 (m, 2H), 7.39-7.41 (m, 2H), 7.46-7.49 (m, 2H)
ESIMS (m/z): 244.3 (M+2), 242.9 (M+1)

Example XXVIII

Preparation of dihydrochloride salt of 1-(4-Thiomorpholin-4-yl-phenyl)-3-aza-bicyclo[3.1.0]hexane

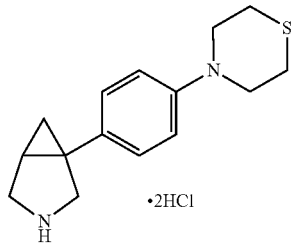 [SMILES: c1cc(C23CNCC2C3)ccc1N1CCSCC1 ; "·2HCl"]

Step 1: Preparation of 1-(4-thiomorpholin-4-yl-phenyl)-3-aza-bicyclo[3.1.0]hexane-3-carboxylic acid tert-butyl ester To a solution of 1-(4-bromo-phenyl)-3-aza-bicyclo[3.1.0]hexane-3-carboxylic acid tert-butyl ester (Intermediate I, 200 mg, 0.59 mmol) in anhydrous toluene (2 mL) were added $Pd_2(dba)_3$ (1.3 mg, 0.002 mmol), BINAP (2.8 mg, 0.004 mmol), sodium tert-butoxide (85 mg, 0.89 mmol) and thiomorpholine (0.07 mL, 0.65 mmol) at r.t. and reaction mixture was refluxed for 17 h. Reaction mixture was then concentrated and the crude product was purified by column chromatography (silica gel, 2:8 EtOAc:Pet. ether) to afford the title compound as viscous liquid (66 mg, 31%).

ESIMS (m/z): 330.7 (M+2), 329.8 (M+1)

Step 2: Preparation of dihydrochloride salt of 1-(4-thiomorpholin-4-yl-phenyl)-3-aza-bicyclo[3.1.0]hexane HCl gas was bubbled through a solution of 1-(4-thiomorpholin-4-yl-phenyl)-3-aza-bicyclo[3.1.0]hexane-3-carboxylic acid tert-butyl ester (60 mg, 0.17 mmol) obtained in Step 1 of Example XXVIII, in methanol (2 mL). After completion of the reaction as confirmed by TLC, solvent was removed in vacuo, given washings with diethylether (2×3 mL) and ethyl acetate (3 mL) and dried in vacuo to afford the title compound (42.0 mg, 83.5%) as white hygroscopic solid.

$^1$H NMR (400 MHz, $CD_3OD$): δ 1.15-1.20 (m, 1H), 1.30 (t, J=7.6 Hz, 1H), 2.15-2.25 (m, 1H), 3.05-3.20 (m, 4H), 3.53 (d, J=11.2 Hz, 1H), 3.60-3.75 (m, 2H), 3.75-3.85 (m, 5H), 7.42-7.71 (m, 4H)

ESIMS (m/z): 261.5 (M+1)

Example XXIX

Preparation of dihydrochloride salt of 1-[4-(3-aza-bicyclo[3.1.0]hex-1-yl)-phenyl]-4-ethyl-[1,4]diazepan-5-one

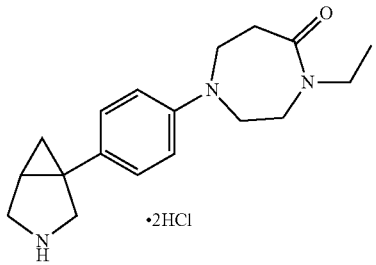 [SMILES: CCN1CCN(c2ccc(C34CNCC3C4)cc2)CCC1=O ; "·2HCl"]

Step 1: Preparation of 1-[4-(4-ethyl-5-oxo-[1,4]diazepan-1-yl)-phenyl]-3-aza-bicyclo[3.1.0]hexane-3-carboxylic acid tert-butyl ester To a solution of 1-(4-bromo-phenyl)-3-aza-bicyclo[3.1.0]hexane-3-carboxylic acid tert-butyl ester (Intermediate I, 250 mg, 0.74 mmol) in anhydrous toluene (5 mL) were added $Pd_2(dba)_3$ (1.65 mg, 0.002 mmol), BINAP (3.42 mg, 0.006 mmol), sodium tert-butoxide (106.56 mg, 1.11 mmol) and 4-ethyl-[1,4]diazepan-5-one (210.2 mg, 1.48 mmol, prepared by the procedure as described in WO2008136754) at r.t. and reaction mixture was refluxed for 3 h. Reaction mixture was then concentrated and the crude product was purified by column chromatography (silica gel, 0.3:9.7 MeOH:$CHCl_3$) to afford the title compound as viscous liquid (60 mg, 20.3%).

ESIMS (m/z): 400.7 (M+1)

Step 2: Preparation of dihydrochloride salt of 1-[4-(3-aza-bicyclo[3.1.0]hex-1-yl)-phenyl]-4-ethyl-[1,4]diazepan-5-one HCl gas was bubbled through a solution of 1-[4-(4-ethyl-5-oxo-[1,4]diazepan-1-yl)-phenyl]-3-aza-bicyclo[3.1.0]hexane-3-carboxylic acid tert-butyl ester (60 mg, 0.15 mmol) obtained in Step 1 of Example XXIX, in methanol (3 mL). After completion of the reaction as confirmed by TLC, solvent was removed in vacuo, given washings with diethylether (2×3 mL) and ethyl acetate (3 mL) and dried in vacuo to afford the title compound (45 mg, 86.7%) as white hygroscopic solid.

$^1$H NMR (400 MHz, $CD_3OD$): δ 1.16-1.19 (m, 3H), 1.28-1.30 (m, 2H), 2.25 (bs, 1H), 3.13 (bs, 2H), 3.53-3.55 (m, 3H), 3.64-3.70 (m, 2H), 3.82 (bs, 5H), 4.01 (bs, 2H), 7.53 (bs, 2H), 7.74 (bs, 2H)

ESIMS (m/z): 300.9 (M+1)

Example XXX

Preparation of dihydrochloride salt of 7-[4-(3-aza-bicyclo[3.1.0]hex-1-yl)-phenyl]-3-trifluoromethyl-5,6,7,8-tetrahydro-[1,2,4]tri-azolo[4,3-a]pyrazine

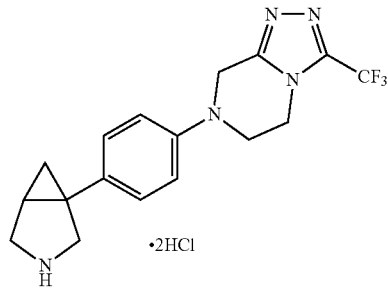 [SMILES: FC(F)(F)c1nnc2n1CCN(c1ccc(C34CNCC3C4)cc1)C2 ; "·2HCl"]

Step 1: Preparation of 1-[4-(3-trifluoromethyl-5,6-dihydro-8H-[1,2,4]triazolo[4,3-a]pyrazin-7-yl)-phenyl]-3-aza-bicyclo[3.1.0]hexane-3-carboxylic acid tert-butyl ester To a solution of 1-(4-bromo-phenyl)-3-aza-bicyclo[3.1.0]hexane-3-carboxylic acid tert-butyl ester (Intermediate I, 400 mg, 1.18 mmol) in anhydrous toluene (5 mL) were added $Pd_2(dba)_3$ (5.4 mg, 0.006 mmol), BINAP (11.0 mg, 0.018 mmol), sodium tert-butoxide (227 mg, 2.34 mmol) and 3-trifluoromethyl-5,6,7,8-tetrahydro-[1,2,4]triazolo[4,3-a]pyrazine (prepared by the procedure as described in reference *J. Med. Chem.*, 2005, 48, 141-151) (340 mg, 1.77 mmol) at r.t. and reaction mixture was refluxed for 6 h. Reaction mixture was then concentrated and the crude product was purified by column chromatography (silica gel, 6:4 EtOAc:Pet. ether) to afford the title compound as white solid (330 mg, 62%).

ESIMS (m/z): 472.9 (M+23), 451.9 (M+2), 450.8 (M+1).

Step 2: Preparation of dihydrochloride salt of 7-[4-(3-aza-bicyclo[3.1.0]hex-1-yl)-phenyl]-3-trifluoromethyl-5,6,7,8-tetrahydro-[1,2,4]tri-azolo[4,3-a]pyrazine HCl gas was bubbled through a solution of 1-[4-(3-trifluoromethyl-5,6-dihydro-8H-[1,2,4]triazolo[4,3-a]pyrazin-7-yl)-phenyl]-3-aza-bicyclo[3.1.0]hexane-3-carboxylic acid tert-butyl ester (330 mg, 0.74 mmol) obtained in Step 1 of Example XXX, in dry diethylether (5 mL). After completion of the reaction as confirmed by TLC, solvent was removed in vacuo, given washings with diethylether (2×5 mL) and ethyl acetate (5 mL) and dried in vacuo to afford the title compound (270 mg, 95%) as white hygroscopic solid.

$^1$H NMR (400 MHz, CD$_3$OD): δ 1.05-1.08 (m, 1H), 1.20-1.23 (m, 1H), 2.06-2.09 (m, 1H), 3.49-3.57 (m, 2H), 3.64-3.72 (m, 2H), 3.81 (t, J=5.5 Hz, 2H), 4.32 (t, J=5.4 Hz, 2H), 4.66 (s, 2H), 7.09 (d, J=8.8 Hz, 2H), 7.27 (d, J=8.8 Hz, 2H)

ESIMS (m/z): 350.6 (M+1)

Example XXXI

Preparation of trihydrochloride salt of 1-(4-(4-phenylpiperazin-1-yl)phenyl)-3-azabicyclo[3.1.0]hexane

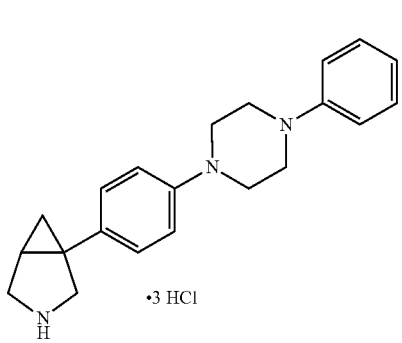 [SMILES: c1ccc(N2CCN(c3ccc(C45CNCC4C5)cc3)CC2)cc1 ; "·3 HCl"]

Step 1: Preparation of (1-[4-{4-Phenyl-piperazin-1-yl)-phenyl]-3-azabicyclo[3.1.0]hexane-3-carboxylic acid tert-butyl ester To a solution of 1-(4-bromo-phenyl)-3-aza-bicyclo[3.1.0] hexane-3-carboxylic acid tert-butyl ester (2 g, 5.91 mmol) in anhydrous toluene (20 mL) were added Pd$_2$(dba)$_3$ (27 mg, 0.029 mmol), BINAP (36 mg, 0.059 mmol), sodium tert-butoxide (230 mg, 2.4 mmol) and 1-phenyl piperazine (1.05 g, 6.5 mmol) and reaction mixture was refluxed at 120° C. for 2 days. After the completion of reaction as confirmed by the TLC, excess solvent was evaporated under reduced pressure to afford crude compound which was purified by column chromatography (silica gel 0.8:9.2 EtOAc:Pet. ether) to afford pure title compound, (1.0 g, 2.38 mmol, 40%) as a thick gel.

$^1$H NMR (400 MHz, CDCl$_3$): δ 0.88 (t, J=6.3 Hz, 1H), 1.03-1.06 (m, 1H), 1.46 (s, 9H), 1.70-1.74 (m, 1H), 3.33 (s, 8H), 3.52-3.56 (m, 2H), 3.65 (dd, J=10.4 and 45.0 Hz, 1H), 3.88 (dd, J=8.7 and 44.0 Hz, 1H), 6.98 (d, J=7.9 Hz, 2H), 7.12 (t, J=8.1 Hz, 2H), 7.29-7.38 (m, 2H), 7.40-7.42 (m, 1H)

ESIMS (m/z): 420.6 (M+1)

Step 2: Preparation of trihydrochloride salt of 1-(4-(4-phenylpiperazin-1-yl)phenyl)-3-azabicyclo[3.1.0] hexane To a solution of 1-[4-{4-Phenyl-piperazin-1-yl)-phenyl]-3-azabicyclo[3.1.0]hexane-3-carboxylic acid tert-butyl ester (1.0 g, 2.38 mmol), in a mixture of dry DCM (5 mL) and dry diethyl ether (10 mL), dry HCl gas was passed for 2 h at 0° C. After completion of reaction as confirmed by TLC, the precipitates of the compound were allowed to settle down at r.t. and excess of solvents were decanted. The solid compound was given washings of dry diethyl ether (3×5 mL) to remove excess of HCl and then dried under reduced pressure to obtain the title compound (0.92 g, 90%) as white solid.

$^1$H NMR (400 MHz, CD$_3$OD): δ 1.11-1.14 (m, 1H), 1.23-1.28 (m, 1H), 2.13-2.16 (m, 1H), 3.33 (s, 8H), 3.50-3.61 (m, 2H), 3.66-3.76 (m, 6H), 3.81-3.84 (m, 4H), 7.27-7.38 (m, 2H), 7.40-7.44 (m, 3H), 7.53-7.58 (m, 4H)

ESIMS (m/z): 320.8 (M+1)

Example XXXII

Preparation of trihydrochloride salt of 3-ethyl-1-(4-(4-phenylpiperazin-1-yl)phenyl)-3-azabicyclo[3.1.0] hexane

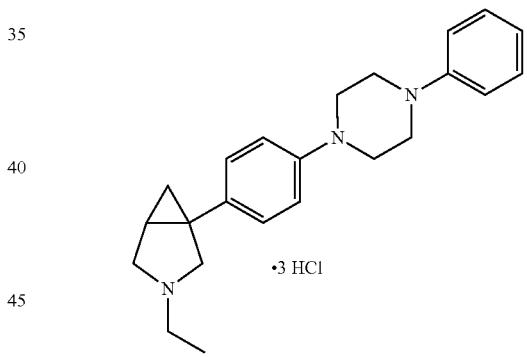

Step 1: Preparation of 3-ethyl-1-(4-(4-phenylpiperazin-1-yl)phenyl)-3-azabicyclo[3.1.0]hexane To a solution of trihydrochloride salt of 1-(4-(4-phenylpiperazin-1-yl)phenyl)-3-azabicyclo[3.1.0]hexane (0.92 g, 2.19 mmol) in dry DMF (6 mL) was added DIPEA (1.21 g, 6.44 mmol)) followed by addition of ethyl iodide (0.197 mL, 2.4 mmol). The reaction was stirred at r.t. for 3 h under argon. After completion of reaction as confirmed by TLC, crude compound was extracted with ethyl acetate (60 mL) and was given water washings (3×30 mL). The combined organic layers were dried over Na$_2$SO$_4$ and the solvents were removed in vacuo to afford the crude compound which was purified by column chromatography (silica gel 0.8:9.2 MeOH:DCM) to afford pure title compound (0.61 g, 74%).

$^1$H NMR (400 MHz, CDCl$_3$): δ1.05 (t, J=7.9 Hz, 1H), 1.23-1.29 (m, 5H), 1.92-1.95 (m, 1H), 3.02 (t, J=7.2 Hz, 2H), 3.18 (t, J=8.3 Hz, 2H), 3.52 (d, J=10.5 Hz, 1H), 3.72 (d,

J=10.3 Hz, 1H), 6.87 (t, J=7.3 Hz, 1H), 6.99-7.03 (m, 4H), 7.19 (d, J=8.7 Hz, 2H), 7.26 (t, J=8.7 Hz, 2H)
ESIMS (m/z): 348.5 (M+1)

Step 2: Preparation of trihydrochloride salt of 3-ethyl-1-(4-(4-phenylpiperazin-1-yl)phenyl)-3-azabicyclo[3.1.0]hexane To a solution of 3-ethyl-1-(4-(4-phenylpiperazin-1-yl)phenyl)-3-azabicyclo[3.1.0]hexane (0.61 g, 1.77 mmol), a mixture of dry DCM (3 mL) and dry diethyl ether (5 mL), dry HCl gas was passed for 2 h at 0° C. After completion of the reaction as indicated by TLC, excess of solvents were decanted and compound was given washings of dry diethyl ether (2×5 mL) to remove excess of HCl. The compound was dried under reduced pressure to obtain the title compound (0.69 g, 86.9%) as a white hygroscopic solid.
$^1$H NMR (400 MHz, CDCl$_3$): δ1.28-1.21 (m, 2H), 1.35-1.40 (m, 4H), 2.16 (m, 1H), 3.33 (d, J=7.3 Hz, 2H), 3.57-3.61 (m, 2H), 3.74 (bs, 4H), 3.79-3.85 (m, 5H), 4.04 (d, J=11.2 Hz, 1H), 7.28-7.30 (m, 2H), 7.39-7.44 (m, 3H), 7.53-7.61 (m, 4H)
ESIMS (m/z): 348.5 (M+1)

Example XXXIII

Preparation of dihydrochloride salt of 6-(methoxymethyl)-1-(4-(pyrrolidin-1-yl)phenyl)-3-azabicyclo[3.1.0]hexane

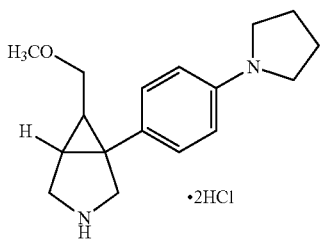 [SMILES: COCC1C2CNCC21c1ccc(N2CCCC2)cc1 ; "·2HCl"]

Step 1: Preparation of tert-butyl 6-(methoxymethyl)-1-(4-(2-oxopyrrolidin-1-yl)phenyl)-3-aza-bicyclo[3.1.0]hexane-3-carboxylate To a solution of tert-butyl 1-(4-bromophenyl)-6-(methoxymethyl)-3-aza-bicyclo[3.1.0]hexane-3-carboxylate (Intermediate IX, 890 mg, 2.33 mmol) in 1,4-dioxane (15 mL), was added 2-pyrrolidinone (0.177 mL, 2.33 mmol), (±)-trans-1,2-diamine (0.139 mL, 1.16 mmol), CuI (221.3 mg, 1.16 mmol) and potassium carbonate (643 mg, 4.66 mmol) under nitrogen atmosphere. The reaction mixture was heated at 120° C. for 36 h. After completion of the reaction as confirmed by TLC, the solvent was removed in vacuo to afford the crude compound, which was purified by column chromatography (silica gel, 2:8 EtOAc:Pet. ether) to afford pure tert-butyl 6-(methoxymethyl)-1-(4-(2-oxopyrrolidin-1-yl)phenyl)-3-aza-bicyclo[3.1.0]hexane-3-carboxylate (600 mg, 66%) as a viscous oil.
ESIMS (m/z): 409.7 (M+23), 387.8 (M+1)

Step 2: Preparation of tert-butyl 6-(methoxymethyl)-1-(4-(pyrrolidin-1-yl)phenyl)-3-aza-bicyclo[3.1.0]hexane-3-carboxylate To a solution of tert-butyl 6-(methoxymethyl)-1-(4-(2-oxopyrrolidin-1-yl)phenyl)-3-aza-bicyclo[3.1.0]hexane-3-carboxylate (500 mg, 1.29 mmol) obtained in Step 2 of Example XXXIII, in dry THF (10 mL), was added BH$_3$.Me$_2$S complex (3.23 mL, 6.47 mmol, 2M in THF) at 0° C. under nitrogen atmosphere. The reaction mixture was refluxed for 4 h. After completion of the reaction as confirmed by TLC, methanol (20 mL) was added and the reaction mixture was heated to reflux for 1 h. The solvents were removed in vacuo to afford the crude compound, which was purified by column chromatography (silica gel, 3:7 EtOAc:Pet. ether) to afford the title compound (400 mg, 86%) as a viscous oil.
ESIMS (m/z): 373.4 (M+1)

Step 3: Preparation of dihydrochloride salt of 6-(methoxymethyl)-1-(4-(pyrrolidin-1-yl)phenyl)-3-azabicyclo[3.1.0]hexane HCl gas was bubbled through a solution of tert-butyl 6-(methoxymethyl)-1-(4-(pyrrolidin-1-yl)phenyl)-3-aza-bicyclo[3.1.0]hexane-3-carboxylate (400 mg, 1.11 mmol) obtained in Step 2 of Example XXXIII, in dry DCM (15 mL). After completion of the reaction as confirmed by TLC, the reaction mixture was purged with excess of nitrogen. Solvent was removed in vacuo to afford the title compound (340 mg, 88%) as a white hygroscopic solid.
$^1$H NMR (400 MHz, CD$_3$OD): δ 1.59-1.65 (m, 1H), 2.25-2.32 (m, 5H), 3.03-3.09 (m, 1H), 3.12 (s, 3H), 3.15-3.21 (m, 1H), 3.30-3.38 (m, 1H), 3.56-3.58 (m, 1H), 3.70-3.75 (m, 5H), 3.80-3.82 (m, 1H), 7.44-7.57 (m, 4H)
ESIMS (m/z): 273.4 (M+1)

Example XXXIV

Preparation of dihydrochloride salt of 3-ethyl-6-(methoxymethyl)-1-(4-(pyrrolidin-1-yl)phenyl)-3-azabicyclo[3.1.0]hexane

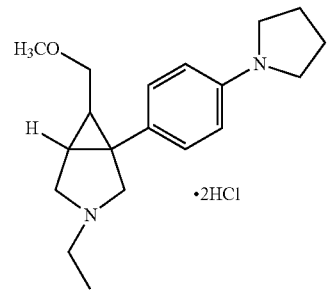 [SMILES: CCN1CC2C(COC)C2(c2ccc(N3CCCC3)cc2)C1 ; "·2HCl"]

Step 1: Preparation of 1-(4-(3-acetyl-6-(methoxymethyl)-3-aza-bicyclo[3.1.0]hexan-1-yl)phenyl)pyrrolidin-2-one To a solution of tert-butyl 6-(methoxymethyl)-1-(4-(2-oxopyrrolidin-1-yl)phenyl)-3-aza-bicyclo[3.1.0]hexane-3-carboxylate (Example XXXIII, Step 1, 500 mg, 1.29 mmol) in dry DCM (10 mL), was added trifluoroacetic acid (3.87 mL, 3 mL/mmol). The reaction mixture was stirred at r.t. for 1 h. after the completion of the reaction as confirmed by TLC, excess of trifluoroacetic acid and DCM were evaporated in vacuo to afford a gummy solid (442 mg). To a solution of this gummy solid in DCM (10 mL), was added triethyl amine (0.614 mL, 4.42 mmol), DMAP (26.9 mg, 0.22 mmol) and acetic anhydride (0.135 mmol, 1.43 mmol) under nitrogen atmosphere. After the completion of the reaction as confirmed by TLC, the reaction mixture was diluted with DCM, washed sequentially with 5% HCl and saturated solution of sodium bicarbonate. The organic layer was separated and washed with water, dried over $Na_2SO_4$ and concentrated in vacuo to afford the title compound (360 mg, 99%) which was used for next step without any purification.

ESIMS (m/z): 351.7 (M+23), 329.5 (M+1)

Step 2: Preparation of 3-ethyl-6-(methoxymethyl)-1-(4-(pyrrolidin-1-yl)phenyl)-3-aza-bicyclo[3.1.0]hexane To a solution of 1-(4-(3-acetyl-6-(methoxymethyl)-3-aza-bicyclo[3.1.0]hexan-1-yl)phenyl)pyrrolidin-2-one (360 mg, 1.097 mmol) obtained in Step 1 of Example XXXIV, in dry THF (10 mL), was added $BF_3.OEt_2$ (0.027 mL, 0.21 mmol) at 40° C. The reaction mixture was heated at the same temperature for 20 min followed by the addition of $BH_3.Me_2S$ (2.79 mL, 5.48 mmol, 2M solution). Reaction mixture was heated to reflux for 6 h. After the completion of the reaction as confirmed by TLC, methanol (15 mL) was added to the cold solution and refluxed further for 1 h. The solvents were removed in vacuo to afford the crude compound, which was purified by column chromatography (silica gel, 1:9 MeOH: DCM) to afford pure title compound (150 mg, 45%).

ESIMS (m/z): 301.4 (M+1)

Step 3: Preparation of dihydrochloride salt of 3-ethyl-6-(methoxymethyl)-1-(4-(pyrrolidin-1-yl)phenyl)-3-azabicyclo[3.1.0]hexane HCl gas was bubbled through a solution of 3-ethyl-6-(methoxymethyl)-1-(4-(pyrrolidin-1-yl)phenyl)-3-aza-bicyclo[3.1.0]hexane (150 mg, 10.5 mmol) obtained in Step 2 of Example XXXIV in dry DCM (10 mL). After the completion of the reaction as confirmed by TLC, the reaction mixture was purged with excess of nitrogen. The solvent was removed in vacuo to afford a gummy solid which was titrated with hexane to afford the title compound (180 mg, 98%) as a white hygroscopic solid.

$^1$H NMR (400 MHz, $CD_3OD$): δ 1.34 (t, J=7.2 Hz, 3H), 1.84-1.89 (m, 1H), 2.27-2.30 (m, 5H), 3.01-3.18 (m, 1H), 3.15 (s, 3H), 3.12-3.40 (m, 5H), 3.76 (m, 4H), 3.87 (d, J=11.6 Hz, 1H), 4.15 (d, J=11.2 Hz, 1H), 7.59-7.64 (m, 4H)

ESIMS (m/z): 301.5 (M+1)

Example XXXV

Preparation of dihydrochloride salt of 6-((3,4-dichlorophenoxy)methyl)-1-(4-(pyrrolidin-1-yl)phenyl)-3-azabicyclo[3.1.0]hexane

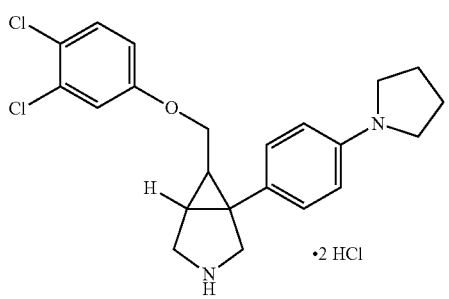 [SMILES: Clc1ccc(OCC2C3CNCC32c2ccc(N3CCCC3)cc2)cc1Cl ; "·2 HCl"]

Step 1: Preparation of tert-butyl 6-((3,4-dichlorophenoxy)methyl)-1-(4-bromophenyl)-3-aza-bicyclo[3.1.0]hexane-3-carboxylate To a solution of tert-butyl 1-(4-bromophenyl)-6-(hydroxymethyl)-3-aza-bicyclo[3.1.0]hexane-3-carboxylate (500 mg, 1.31 mmol) obtained in Step 4 of Intermediate IX, in dry THF (10 mL), were sequentially added 3,4-dichlorophenol (428.0 mg, 2.62 mmol), triphenylphosphine (688.4 mg, 2.62 mmol) and diethyl azodicarboxylate (0.414 mL, 2.62 mmol) at 0° C. under nitrogen atmosphere. The reaction mixture was stirred at r.t. overnight. After the completion of the reaction as confirmed by TLC, the reaction mixture was quenched with 1N NaOH (3 mL). The compound was extracted with ethylacetate. The organic layer was washed with water, separated, dried over $Na_2SO_4$ and concentrated in vacuo to afford the crude compound, which was purified by column chromatography (silica gel, 2:8 EtOAc:Pet. ether) to afford the title compound (500 mg, 74%) as a viscous oil.

ESIMS (m/z): 512.3 (M+1)

Step 2: Preparation of tert-butyl 6-((3,4-dichlorophenoxy)methyl)-1-(4-(2-oxopyrrolidin-1-yl)phenyl)-3-aza-bicyclo[3.1.0]hexane-3-carboxylate The title compound was prepared from tert-butyl 6-((3,4-dichlorophenoxy)methyl)-1-(4-bromophenyl)-3-aza-bicyclo[3.1.0]hexane-3-carboxylate obtained in Step 1 of Example XXXV and 2-pyrrolidinone using the method described for Step 1 (Example XXXIII)

ESIMS (m/z): 518.7 (M+1)

Step 3: Preparation of tert-butyl 6-((3,4-dichlorophenoxy)methyl)-1-(4-(pyrrolidin-1-yl)phenyl)-3-aza-bicyclo[3.1.0]hexane-3-carboxylate The title compound was prepared from tert-butyl 6-((3,4-dichlorophenoxy)methyl)-1-(4-(2-oxopyrrolidin-1-yl)phenyl)-3-aza-icyclo[3.1.0]hexane-3-carboxylate obtained in Step 2 of Example XXXV by using the method described for Step 2 (Example XXXIII).

ESIMS (m/z): 504 (M+1)

Step 4: Preparation of dihydrochloride salt of 6-((3,4-dichlorophenoxy)methyl)-1-(4-(pyrrolidin-1-yl)phenyl)-3-azabicyclo[3.1.0]hexane HCl gas was bubbled through a solution of tert-butyl 6-((3,4-dichlorophenoxy)methyl)-1-(4-(pyrrolidin-1-yl)phenyl)-3-aza-bicyclo[3.1.0]hexane-3-carboxylate (190 mg, 0.366 mmol) obtained in Step 3 of Example XXXV, in dry DCM (10 mL). After the completion of the reaction as confirmed by TLC, the reaction mixture was purged with excess of nitrogen. The solvent was removed in vacuo to afford a gummy solid which was titrated with hexane to afford dihydrochloride salt of the title compound (160 mg, 91%) as a white hygroscopic solid.

$^1$H NMR (400 MHz, $CD_3OD$): δ 1.90 (m, 1H), 2.25-2.29 (m, 4H), 2.47 (m, 1H), 3.42-3.45 (m, 1H), 3.51-3.55 (m, 1H), 3.63-3.68 (m, 4H), 3.75-3.82 (m, 2H), 3.93-4.04 (m, 2H), 6.65 (m, 1H), 6.86 (d, J=2.8 Hz, 1H), 7.31 (d, J=9.2 Hz, 1H), 7.44-7.66 (m, 4H)

ESIMS (m/z): 404.5 (M+1)

Example XXXVI

Preparation of dihydrochloride salt of 4-(6-(methoxymethyl)-3-azabicyclo[3.1.0]hexan-1-yl)phenyl)morpholine

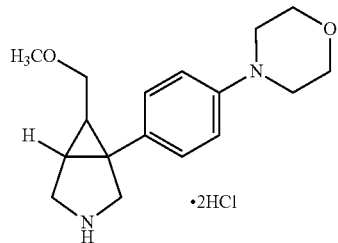 [SMILES: COCC1C2CNCC21c1ccc(N2CCOCC2)cc1 ; "·2HCl"]

The title compound was prepared as white hygroscopic solid starting from tert-butyl 1-(4-bromophenyl)-6-(methoxymethyl)-3-aza-bicyclo[3.1.0]hexane-3-carboxylate obtained in of Step 5 of Intermediate IX and morpholine as described for preparation of Example XXI.

$^1$H NMR (400 MHz, CD$_3$OD): δ 1.44-1.45 (m, 1H) 2.02-2.04 (m, 1H), 3.08-3.16 (m, 9H), 3.22 (d, J=11.2 Hz, 1H), 3.48-3.65 (m, 2H), 3.67 (d, J=11.2 Hz, 1H), 3.80-3.82 (m, 4H), 6.93 (d, J=2.0 Hz, 2H), 7.23 (d, J=2.40 Hz, 2H)

ESIMS (m/z): 290 (M+2)

Example XXXVII

Preparation of dihydrochloride salt of 4-(3-ethyl-6-(methoxymethyl)-3-azabicyclo[3.1.0]hexan-1-yl)phenyl)morpholine

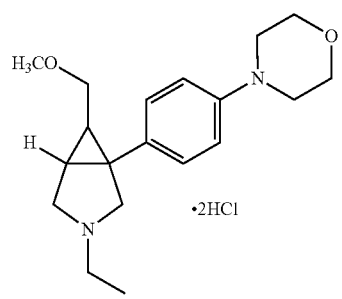 [SMILES: CCN1CC2C(COC)C2(c2ccc(N3CCOCC3)cc2)C1 ; "·2HCl"]

The title compound was prepared following the procedure as reported in the Example XXII from hydrochloride salt of 4-(6-(methoxymethyl)-3-azabicyclo[3.1.0]hexan-1-yl)phenyl)morpholine obtained in Example XXXVI.

$^1$H NMR (400 MHz, CD$_3$OD): δ 1.33 (t, J=7.2 Hz, 3H), 1.73-1.81 (m, 1H), 2.25 (m, 1H), 2.95-3.0 (m, 1H), 3.12 (s, 3H), 3.10-3.15 (m, 1H), 3.11-3.39 (m, 3H), 3.60-3.64 (m, 4H), 3.67-3.69 (m, 1H), 3.86 (d, J=11.6 Hz, 1H), 4.07 (m, 4H), 4.13 (d, J=11.6 Hz, 1H) 7.52-7.59 (m, 4H)

ESIMS (m/z): 318 (M+2)

The compounds listed in Tables 4 to 6 were prepared essentially following the procedures described for Examples I to XXXVII:

TABLE 4

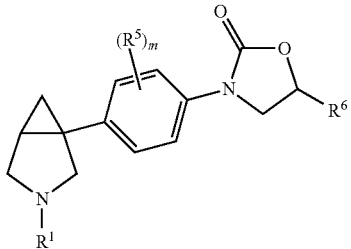

| Example No. | —R$^1$ | —R$^5$ | —R$^6$ | ESIMS (m/z) |
|---|---|---|---|---|
| 1. | COCH$_3$ | H | CH$_2$OH | 318.7 (M + 2), 317.4 (M + 1) |
| 2. | CON(CH$_3$)$_2$ | H | CH$_2$NHCOCH$_3$ | 387.1 (M + 1) |
| 3. | COO$^i$Pr | H | CH$_2$NHCOCH$_3$ | 424.7 (M + 23), 402.5 (M + 1) |
| 4. | COO$^t$Bu | H | CH$_2$NHCOCH$_3$ | 438.9 (M + 23), 416 (M + 1) |
| 5. | COCH$_2$CH$_2$Ph | H | CH$_2$NHCOCH$_3$ | 470.6 (M + 23), 448.6 (M + 1) |
| 6. | ![pyridine-3-carbonyl] | H | CH$_2$NHCOCH$_3$ | 421.6 (M + 1) |

TABLE 4-continued
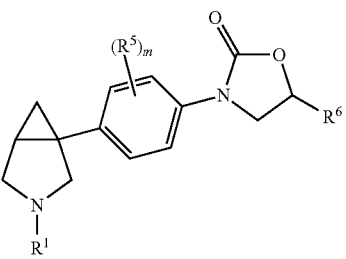
| Example No. | —R¹ | —R⁵ | —R⁶ | ESIMS (m/z) |
|---|---|---|---|---|
| 7. | 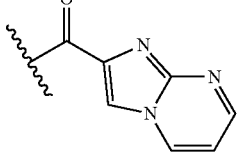 | H | CH$_2$NHCOCH$_3$ | 483.7 (M + 23), 461.6 (M + 1) |
| 8. | CH$_2$Ph | H | CH$_2$NHCOCH$_3$ | 428.6 (M + 23), 406.2 (M + 1) |
| 9. | 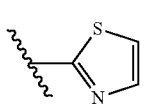 [SMILES: *c1nccs1] | H | CH$_2$NHCOCH$_3$ | 399.5 (M + 1) |
| 10. | 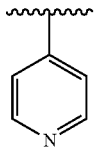 | H | CH$_2$NHCOCH$_3$ | 393.5 (M + 1) |
| 11. | 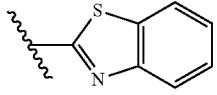 [SMILES: *c1nc2ccccc2s1] | H | CH$_2$NHCOCH$_3$ | 471.8 (M + 23), 449.4 (M + 1) |
| 12. | SO$_2$CF$_3$ | H | CH$_2$NHCOCH$_3$ | 448.6 (M + 1) |
| 13. | SO$_2$Ph | H | CH$_2$NHCOCH$_3$ | 478.7 (M + 23), 456.7 (M + 1) |
| 14. | COCH$_3$ | H | CH$_2$NHCOOCH$_3$ | 374.4 (M + 1) |
| 15. | COCH$_3$ | H | CH$_2$NHCOOC$_2$H$_5$ | 388.9 (M + 1) |
| 16. | 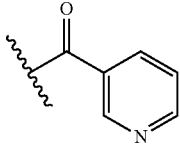 [SMILES: *C(=O)c1cccnc1] | H | CH$_2$NHCOOCH$_3$ | 459.6 (M + 23), 437.4 (M + 1) |
| 17. | H | H | 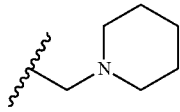 [SMILES: *CN1CCCCC1] | 342.5 (M + 1) |
| 18. | COCH$_3$ | H | 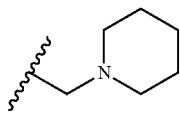 [SMILES: *CN1CCCCC1] | 384.4 (M + 1) |
| 19. | COCH$_3$ | H | 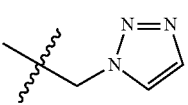 [SMILES: *Cn1ccnn1] | 390.8 (M + 23), 368.6 (M + 1) |

TABLE 4-continued
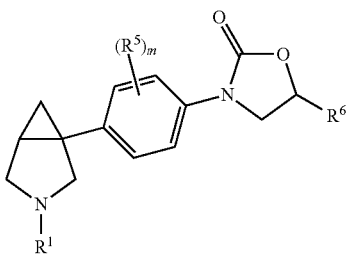
| Example No. | —R¹ | —R⁵ | —R⁶ | ESIMS (m/z) |
|---|---|---|---|---|
| 20. | (3-pyridinylcarbonyl) | H | (2-methyl-2-(1H-1,2,3-triazol-1-ylmethyl)) | 431.5 (M + 1) |
| 21. | (methoxycarbonylmethyl) | 2-F, 6-F | CH₂NHCOCH₃ | 410.6 (M + 1) |
TABLE 5
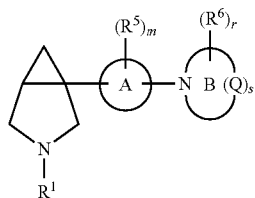
| Example No. | —R¹ | Ring A | Ring B | ESIMS (m/z) |
|---|---|---|---|---|
| 22. | CH₂CH₃ | phenylene | azetidinyl | 243.2 (M + 1) |
| 23. | H | phenylene | pyrrolidinyl | 229.5 (M + 1) |
| 24. | CH₃ | phenylene | pyrrolidinyl | 243.6 (M + 1) |
| 25. | H | phenylene | 3,3-difluoropyrrolidinyl | 265.8 (M + 1) |
| 26. | C₂H₅ | phenylene | pyrrolidinyl | 257.4 (M + 1) |

TABLE 5-continued

| Example No. | —R¹ | Ring A | Ring B | ESIMS (m/z) |
|---|---|---|---|---|
| 27. | C₂H₅ | phenylene | 3-fluoropyrrolidin-1-yl | 275.4 (M + 1) |
| 28. | C₂H₅ | phenylene | 3,3-difluoropyrrolidin-1-yl | 293.4 (M + 1) |
| 29. | C₂H₅ | 3-chlorophenylene | pyrrolidin-1-yl | 291.3 (M + 1) |
| 30. | C₂H₅ | phenylene | 2-oxopyrrolidin-1-yl | 271.5 (M + 1) |
| 31. | H | phenylene | 2-oxoimidazolidin-1-yl | 279.5 (M + 1) |
| 32. | H | phenylene | 2-oxooxazolidin-3-yl | 245.6 (M + 1) |
| 33. | C₂H₅ | phenylene | 2-oxooxazolidin-3-yl | 273.3 (M + 1) |
| 34. | H | phenylene | 4-methyl-2-oxooxazolidin-3-yl | 259.5 (M + 1) |
| 35. | C₂H₅ | phenylene | 4-methyl-2-oxooxazolidin-3-yl | 287.2 (M + 1) |

TABLE 5-continued

| Example No. | —R¹ | Ring A | Ring B | ESIMS (m/z) |
|---|---|---|---|---|
| 36. | H | phenyl (1,4) | 1,3-oxazinan-2-one (N-linked) | 260.5 (M + 1) |
| 37. | C₂H₅ | phenyl (1,4) | 1,3-oxazinan-2-one (N-linked) | 287.2 (M + 1) |
| 38. | C₂H₅ | phenyl (1,4) | piperidin-1-yl | 271.5 (M + 1) |
| 39. | H | phenyl (1,4) | piperidin-1-yl | 243.3 (M + 1) |
| 40. | C₂H₅ | phenyl (1,4) | 4-fluoropiperidin-1-yl | 289.4 (M + 1) |
| 41. | H | phenyl (1,4) | 4-fluoropiperidin-1-yl | 261.4 (M + 1) |
| 42. | H | phenyl (1,4) | 4,4-difluoropiperidin-1-yl | 279.1 (M + 1) |
| 43. | C₂H₅ | phenyl (1,4) | 4,4-difluoropiperidin-1-yl | 307.5 (M + 1) |
| 44. | H | phenyl (1,4) | 4-hydroxypiperidin-1-yl | 259.8 (M + 1) |
| 45. | C₂H₅ | phenyl (1,4) | 4-hydroxypiperidin-1-yl | 287.4 (M + 1) |
| 46. | H | phenyl (1,4) | 4-hydroxy-4-phenylpiperidin-1-yl | 335.4 (M + 1) |

TABLE 5-continued
| Example No. | —R¹ | Ring A | Ring B | ESIMS (m/z) |
|---|---|---|---|---|
| 47. | C₂H₅ | 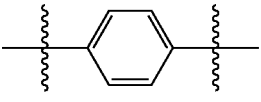 | 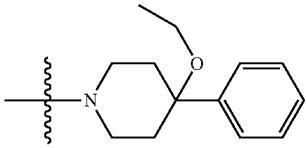 [SMILES: *N1CCC(OCC)(c2ccccc2)CC1] | 363.5 (M + 1) |
| 48. | C₂H₅ | 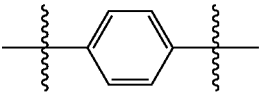 [SMILES: *c1ccc(*)cc1] | 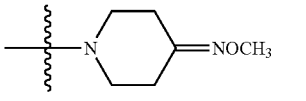 | 413.4 (M + 23), 390.8 (M + 1) |
| 49. | C₂H₅ | 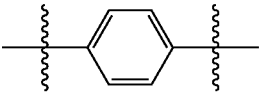 [SMILES: *c1ccc(*)cc1] | 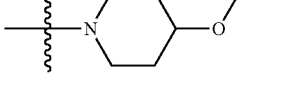 | 314.3 (M + 1) |
| 50. | C₂H₅ | 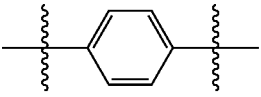 [SMILES: *c1ccc(*)cc1] | 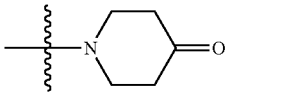 | 315.2 (M + 1) |
| 51. | H | 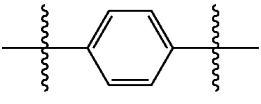 [SMILES: *c1ccc(*)cc1] | 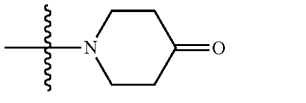 | 257.5 (M + 1) |
| 52. | C₂H₅ | 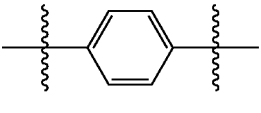 [SMILES: *c1ccc(*)cc1] | 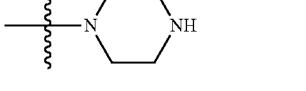 | 285.8 (M + 1) |
| 53. | H | 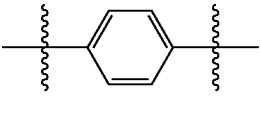 | 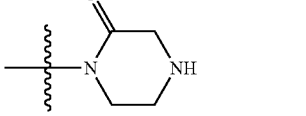 | 244.9 (M + 1) |
| 54. | H | 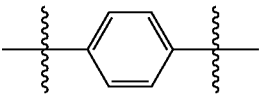 [SMILES: *c1ccc(*)cc1] | 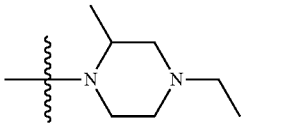 | 258.8 (M + 1) |
| 55. | C₂H₅ | 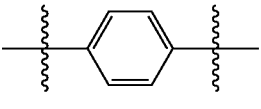 [SMILES: *c1ccc(*)cc1] | 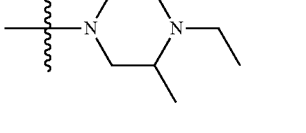 | 314.9 (M + 1) |
| 56. | C₂H₅ | 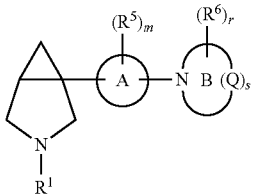 | 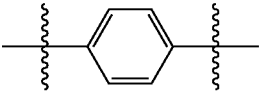 [SMILES: *c1ccc(*)cc1] | 314.6 (M + 1) |
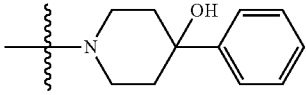

TABLE 5-continued

| Example No. | —R¹ | Ring A | Ring B | ESIMS (m/z) |
|---|---|---|---|---|
| 57. | C₂H₅ | 1,4-phenylene | N-piperazinyl-N'-ethyl | 300.5 (M + 1) |
| 58. | C₂H₅ | 1,4-phenylene | N-piperazinyl-N'-(cyclopropylcarbonyl) | 341.1 (M + 1) |
| 59. | H | 1,4-phenylene | N-piperazinyl-N'-(pivaloyl) | 328 (M + 1) |
| 60. | H | 1,4-phenylene | N-piperazinyl-N'-butyryl | 314.7 (M + 1) |
| 61. | C₂H₅ | 1,4-phenylene | N-piperazinyl-N'-butyryl | 342.3 (M + 1) |
| 62. | H | 1,4-phenylene | N-piperazinyl-N'-(3,4-dichlorophenyl) | 389.5 (M + 1) |
| 63. | C₂H₅ | 1,4-phenylene | N-piperazinyl-N'-(3,4-dichlorophenyl) | 417.8 (M + 1) |
| 64. | C₂H₅ | 1,4-phenylene | N-piperazinyl-N'-(4-trifluoromethylbenzoyl) | 445.1 (M + 2) |
| 65. | C₂H₅ | 1,4-phenylene | N-piperazinyl-N'-(benzyloxycarbonyl) | 420.6 (M + 1) |

TABLE 5-continued

| Example No. | —R¹ | Ring A | Ring B | ESIMS (m/z) |
|---|---|---|---|---|
| 66. | H | p-phenylene | piperazine-C(O)CH₂CH₂-phenyl | 376.1 (M + 1) |
| 67. | C₂H₅ | p-phenylene | piperazine-C(O)CH₂CH₂-phenyl | 404.5 (M + 1) |
| 68. | H | p-phenylene | piperazine-SO₂-(4-methylphenyl) | 398.6 (M + 1) |
| 69. | C₂H₅ | p-phenylene | piperazine-SO₂-(4-methylphenyl) | 426.3 (M + 1) |
| 70. | H | p-phenylene | piperazine-SO₂-(4-OCH₃-phenyl) | 414.5 (M + 1) |
| 71. | C₂H₅ | p-phenylene | piperazine-SO₂-(4-OCH₃-phenyl) | 442.5 (M + 1) |
| 72. | H | p-phenylene | 4-ethyl-3-oxopiperazine | 286.5 (M + 1) |
| 73. | C₂H₅ | p-phenylene | 4-ethyl-3-oxopiperazine | 214.5 (M + 1) |
| 74. | H | o-phenylene | morpholine | 245.4 (M + 1) |

TABLE 5-continued
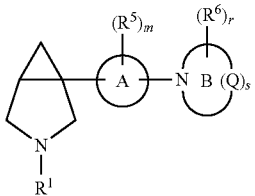
| Example No. | —R[1] | Ring A | Ring B | ESIMS (m/z) |
|---|---|---|---|---|
| 75. | C[2]H[5] | 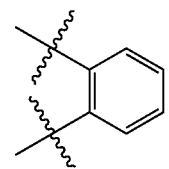 [SMILES: *c1ccccc1*] | 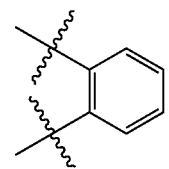 [SMILES: *c1ccccc1*] | 273.4 (M + 1) |
| 76. | H | 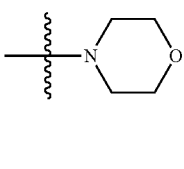 | 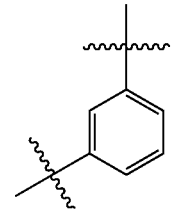 [SMILES: *c1cccc(*)c1] | 245.4 (M + 1) |
| 77. | C[2]H[5] | 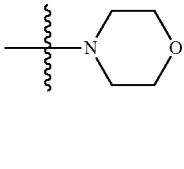 | 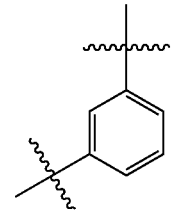 [SMILES: *c1cccc(*)c1] | 273.4 (M + 1) |
| 78. | H | 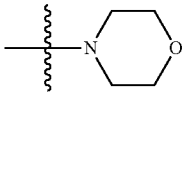 | 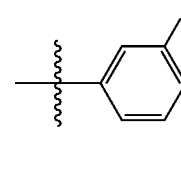 | 263.5 (M + 1) |
| 79. | CH[3] | 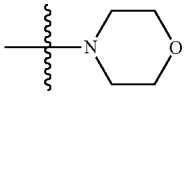 | 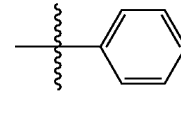 | 259.5 (M + 1) |
| 80. | H | 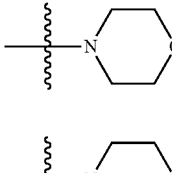 | 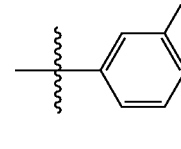 | 281.2 (M + 1) |
| 81. | C[2]H[5] | 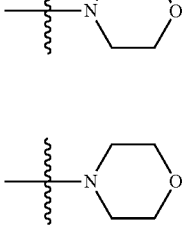 | 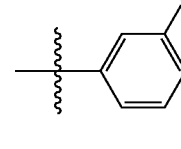 | 307.6 (M + 1) |

TABLE 5-continued

| Example No. | —R¹ | Ring A | Ring B | ESIMS (m/z) |
|---|---|---|---|---|
| 82. | H | phenylene | 2,6-dimethylmorpholine | 273.9 (M + 1) |
| 83. | C₂H₅ | phenylene | 2,6-dimethylmorpholine | 301.5 (M + 1) |
| 84. | CH₃ | phenylene | 2,6-dimethylmorpholine | 287.6 (M + 1) |
| 85. | CH(CH₃)₂ | phenylene | morpholine | 287.5 (M + 1) |
| 86. | C₃H₇ | phenylene | morpholine | 287 (M + 1) |
| 87. | CH₂-cyclopropyl | phenylene | morpholine | 299.9 (M + 1) |
| 88. | CH₂CH₂CH=CH₂ | phenylene | morpholine | 285.6 (M + 1) |
| 89. | CH₂C≡CH | phenylene | morpholine | 283.6 (M + 1) |
| 90. | C(=O)CH₃ | phenylene | morpholine | 243.2 (M + 1) |

TABLE 5-continued
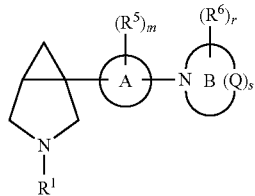
| Example No. | —$R^1$ | Ring A | Ring B | ESIMS (m/z) |
|---|---|---|---|---|
| 91. | ethyl ester group | phenylene | morpholino | 317.5 (M + 1) |
| 92. | tert-butyl ester group | phenylene | morpholino | 367.3 (M + 23), 345.3 (M + 1) |
| 93. | cyclopropyl | phenylene | morpholino | 285.4 (M + 1) |
| 94. | —C(O)N(CH$_3$)$_2$ | phenylene | morpholino | 338.8 (M + 23), 316.5 (M + 1) |
| 95. | benzyl | phenylene | morpholino | 335.6 (M + 1) |
| 96. | phenyl | phenylene | morpholino | 321.6 (M + 1) |
| 97. | —CH$_2$C(O)NHPh | phenylene | morpholino | 378.4 (M + 1) |

TABLE 5-continued

| Example No. | —R¹ | Ring A | Ring B | ESIMS (m/z) |
|---|---|---|---|---|
| 98. | —S(=O)(=O)CH₃ | 1,4-phenylene | morpholin-4-yl | 323.3 (M + 1) |
| 99. | C₂H₅ | benzo[b]thiophene-2,5-diyl | morpholin-4-yl | 329.8 (M + 1) |
| 100. | H | benzo[b]thiophene-2,5-diyl | morpholin-4-yl | 301.4 (M + 1) |
| 101. | C₂H₅ | 1,4-phenylene | thiomorpholin-4-yl | 289.4 (M + 1) |
| 102. | H | 1,4-phenylene | 3,4-dihydro-2H-benzo[b][1,4]oxazin-4-yl | 293.4 (M + 1) |
| 103. | C₂H₅ | 1,4-phenylene | 3,4-dihydro-2H-benzo[b][1,4]oxazin-4-yl | 321.4 (M + 1) |
| 104. | H | 1,4-phenylene | 8-oxa-3-azabicyclo[3.2.1]octan-3-yl | 271.5 (M + 1) |
| 105. | C₂H₅ | 1,4-phenylene | octahydropyrrolo[1,2-a]pyrazin-2-yl | 312.5 (M + 1) |

TABLE 5-continued
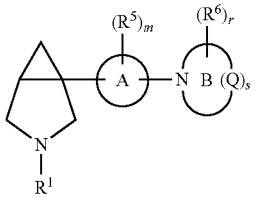
| Example No. | —R¹ | Ring A | Ring B | ESIMS (m/z) |
|---|---|---|---|---|
| 106. | H | 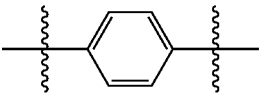 [SMILES: *c1ccc(*)cc1] | 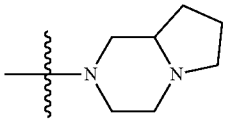 [SMILES: *N1CCN2CCCC2C1] | 284.5 (M + 1) |
| 107. | H | 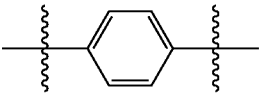 [SMILES: *c1ccc(*)cc1] | 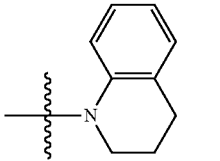 [SMILES: *N1CCCc2ccccc21] | 291.8 (M + 1) |
| 108. | C₂H₅ | 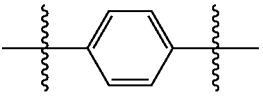 | 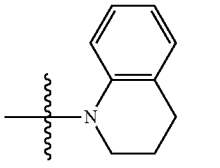 [SMILES: *N1CCCc2ccccc21] | 319.8 (M + 1) |
| 109. | C₂H₅ | 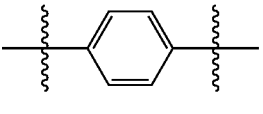 | 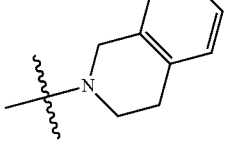 | 321.9 (M + 23), 319.4 (M + 1) |
| 110. | H | 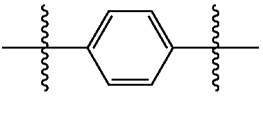 [SMILES: *c1ccc(*)cc1] | 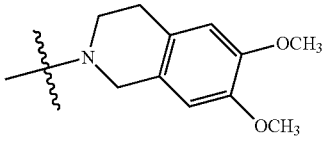 | 351.5 (M + 1) |
| 111. | H | 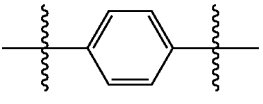 [SMILES: *c1ccc(*)cc1] | 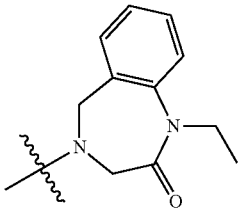 [SMILES: *N1CC(=O)N(CC)c2ccccc2C1] | 348.7 (M + 1) |
| 112. | C₂H₅ | 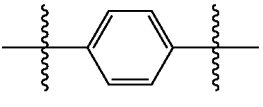 [SMILES: *c1ccc(*)cc1] | 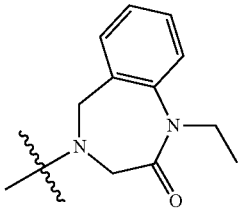 [SMILES: *N1CC(=O)N(CC)c2ccccc2C1] | 376.7 (M + 1) |

TABLE 5-continued

| Example No. | —R¹ | Ring A | Ring B | ESIMS (m/z) |
|---|---|---|---|---|
| 113. | H | phenyl (1,4) | C₂H₅OOC-imidazo[1,2-a]tetrahydropyrimidine | 353.4 (M + 1) |
| 114. | C₂H₅ | phenyl (1,4) | C₂H₅OOC-imidazo[1,2-a]tetrahydropyrimidine | 403.9 (M + 23), 381.5 (M + 1) |
| 115. | H | phenyl (1,4) | 5,6,7,8-tetrahydro-[1,2,4]triazolo[4,3-a]pyrazine | 282.5 (M + 1) |
| 116. | C₂H₅ | phenyl (1,4) | 5,6,7,8-tetrahydro-[1,2,4]triazolo[4,3-a]pyrazine | 332.9 (M + 23), 310.3 (M + 1) |
| 117. | H | phenyl (1,4) | 3-methyl-5,6,7,8-tetrahydro-[1,2,4]triazolo[4,3-a]pyrazine | 296 (M + 1) |
| 118. | C₂H₅ | phenyl (1,4) | 3-methyl-5,6,7,8-tetrahydro-[1,2,4]triazolo[4,3-a]pyrazine | 346.2 (M + 23), 323.8 (M + 1) |
| 119. | C₂H₅ | phenyl (1,4) | 3-CF₃-5,6,7,8-tetrahydro-[1,2,4]triazolo[4,3-a]pyrazine | 378.4 (M + 1) |

TABLE 5-continued

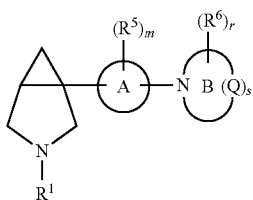

| Example No. | —R¹ | Ring A | Ring B | ESIMS (m/z) |
|---|---|---|---|---|
| 120. | H | 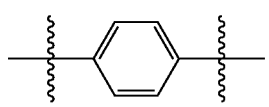 [SMILES: *c1ccc(*)cc1] | 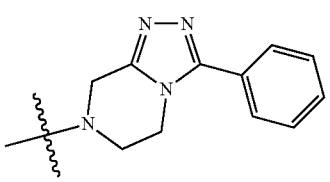 [SMILES: *N1CCn2c(nnc2-c2ccccc2)C1] | 358.4 (M + 1) |
| 121. | C₂H₅ | 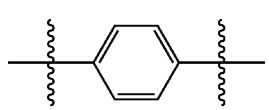 | 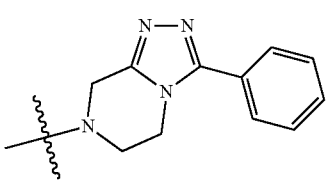 [SMILES: *N1CCn2c(nnc2-c2ccccc2)C1] | 386.5 (M + 1) |

TABLE 6

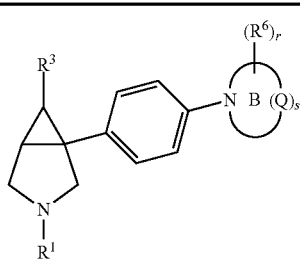

| Example No. | —R¹ | —R³ | Ring B | ESIMS (m/z) |
|---|---|---|---|---|
| 122. | H | CH₂OH | 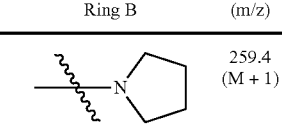 | 259.4 (M + 1) |
| 123. | H | CH₂OCH₃ | 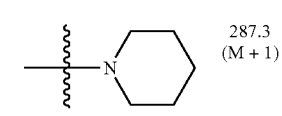 | 287.3 (M + 1) |
| 124. | H | CH₂OCH₂CH₃ | 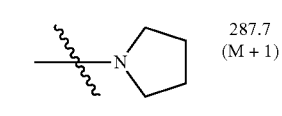 | 287.7 (M + 1) |
| 125. | H | 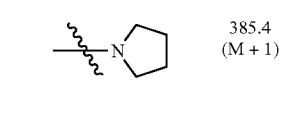 | 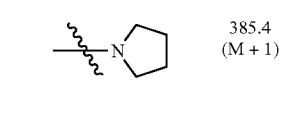 | 385.4 (M + 1) |

In Vitro Studies

In-Vitro Antibacterial Activity:

The in-vitro antibacterial activity of the compounds of the present invention (as described in Table 7) was determined by a broth microdilution following the guidelines prescribed by the Clinical and Laboratory Standards Institute (CLSI). This method is described in the CLSI Document M7-A7, Vol. 26, No. 2, "*Methods for Dilution Antimicrobial Susceptibility Test for Bacteria that Grow Aerobically; Approved Standard-Seventh Edition*", which is incorporated herein by reference. Minimum Inhibitory Concentration (MIC) is defined as the minimum concentration of test compound which inhibits the growth of bacteria as visible or seen by the naked eye. This test can also be carried out by agar dilution method.

The compounds of the present invention were tested against a panel of standard microorganisms obtained from ATCC (American type culture collection). Linezolid was used as comparator in all the tests.

| Organism | Culture No. | Type |
|---|---|---|
| *Staphylococcus aureus* | ATCC 29213 | MSSA (Methicillin sensitive) |
| *Staphylococcus aureus* | ATCC 33591 | MRSA (Methicillin resistant) |
| *Enterococcus faecalis* | ATCC 29212 | Vancomycin Sensitive |
| *Enterococcus faecium* | ATCC 700221 | VRE (Vancomycin resistant *E. faecium*) |

In the broth microdilution method, the compound was dissolved in dimethylsulfoxide and two fold serial dilutions were carried out in 96 well microtitre plates. The inoculum was prepared by adjusting the turbidity of actively growing broth culture and added to the wells to obtain a final bacterial count of ~2-5×10⁴ CFU/well. The microtitre plates were incubated at 35±2° C. for 16-20 h and then read visually. MIC (µg/mL) values of some of the compounds of Formula Ia are presented in the Table 7.

TABLE 7

| | In-vitro antibacterial activity MICs (μg/mL) | | | |
|---|---|---|---|---|
| | MIC(μg/mL) | | | |
| Compound | ATCC 29213 | ATCC 33591 | ATCC 29212 | ATTC 700221 |
| (structure) | 2 | 1 | 2 | 2 |
| (structure) | 2 | 1 | 2 | 1 |
| (structure) | 4 | 2 | 4 | 4 |
| (structure) | 2 | 1 | 2 | 2 |

TABLE 7-continued

In-vitro antibacterial activity MICs (μg/mL)

| Compound | MIC(μg/mL) | | | |
|---|---|---|---|---|
| | ATCC 29213 | ATCC 33591 | ATCC 29212 | ATTC 700221 |
| *(structure)* | 2 | 2 | 1 | 1 |
| *(structure)* | 2 | 1 | 2 | 1 |
| *(structure)* | 2 | 1 | 2 | 1 |
| *(structure)* | 1 | 1 | 1 | 0.5 |

TABLE 7-continued

In-vitro antibacterial activity MICs (μg/mL)

| Compound | MIC(μg/mL) | | | |
|---|---|---|---|---|
| | ATCC 29213 | ATCC 33591 | ATCC 29212 | ATTC 700221 |
| (structure) | 0.5 | 0.5 | 0.5 | 0.5 |
| (structure) | 1 | 1 | 1 | 1 |
| (structure) | 4 | 1 | 0.5 | 0.25 |
| (structure) | 2 | 1 | 0.5 | 0.5 |
| (structure) | 1 | 0.5 | 0.5 | 1 |

TABLE 7-continued

In-vitro antibacterial activity MICs (μg/mL)

| Compound | MIC(μg/mL) | | | |
|---|---|---|---|---|
| | ATCC 29213 | ATCC 33591 | ATCC 29212 | ATTC 700221 |
| *[structure]* | 0.5 | 0.5 | 1 | 0.5 |
| *[structure]* | 1 | 0.5 | 0.5 | 0.5 |
| *[structure]* | 2 | 1 | 2 | 1 |
| *[structure]* | 1 | 2 | 2 | 1 |
| *[structure]* | 1 | 0.5 | 2 | 1 |

TABLE 7-continued
In-vitro antibacterial activity MICs (μg/mL)
| Compound | MIC(μg/mL) | | | |
|---|---|---|---|---|
| | ATCC 29213 | ATCC 33591 | ATCC 29212 | ATTC 700221 |
| 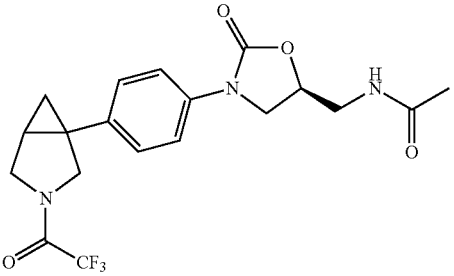 [SMILES: CC(=O)NC[C@H]1CN(c2ccc(C34CC3CN(C(=O)C(F)(F)F)C4)cc2)C(=O)O1] | 2 | 2 | 2 | 1 |
| 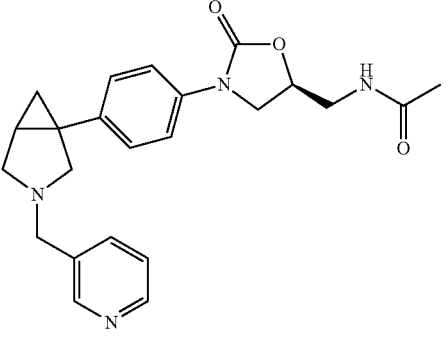 [SMILES: CC(=O)NC[C@H]1CN(c2ccc(C34CC3CN(Cc3cccnc3)C4)cc2)C(=O)O1] | 4 | 4 | 8 | 2 |
| 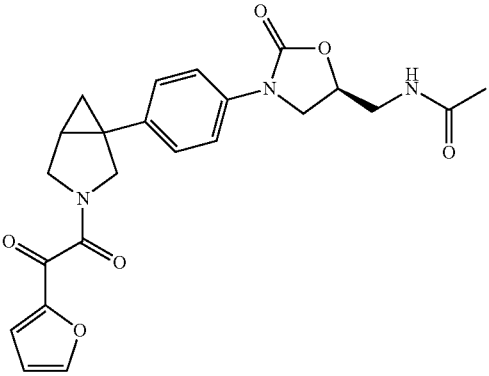 [SMILES: CC(=O)NC[C@H]1CN(c2ccc(C34CC3CN(C(=O)C(=O)c3ccco3)C4)cc2)C(=O)O1] | 1 | 1 | 1 | 0.5 |
| 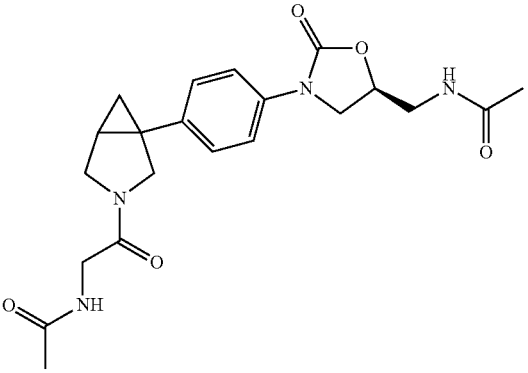 [SMILES: CC(=O)NCC(=O)N1CC2CC2(c2ccc(N3C[C@H](CNC(C)=O)OC3=O)cc2)C1] | 4 | 4 | 2 | 4 |

TABLE 7-continued

In-vitro antibacterial activity MICs (μg/mL)

| Compound | MIC(μg/mL) | | | |
|---|---|---|---|---|
| | ATCC 29213 | ATCC 33591 | ATCC 29212 | ATTC 700221 |
| *(structure)* | 1 | 0.5 | 1 | 0.5 |
| *(structure)* | 2 | 1 | 1 | 1 |
| *(structure)* | 1 | 0.5 | 1 | 0.5 |
| *(structure)* | 0.5 | 0.25 | 0.125 | 0.5 |

TABLE 7-continued

In-vitro antibacterial activity MICs (µg/mL)

| Compound | MIC(µg/mL) | | | |
|---|---|---|---|---|
| | ATCC 29213 | ATCC 33591 | ATCC 29212 | ATTC 700221 |
| *(structure: oxazolidinone with fluoropyridine-substituted azabicyclic phenyl group)* | 1 | 0.5 | 1 | 0.5 |
| *(structure: oxazolidinone with benzothiazole-substituted azabicyclic phenyl group)* | 1 | 0.5 | 1 | 0.25 |
| Linezolid | 2 | 1 | 2 | 1 |

In Vivo Studies

Forced Swim Test:

This test was conducted according to the method of Porsolt et al. (Porsolt, R. D., et al., Behavioural despair in mice: A primary screening test for antidepressants. Arch. in Pharmacodyn. Ther., 229, pp 327-336 (1977)).

A test compound was suspended in deionized water, unless otherwise specified, and this suspension was orally administered to male SWISS albino mice (7 to 9 week old). 15 min later, the mice were placed in a water tank having a water depth of 15 cm and a water temperature of 25±1° C. and immediately thereafter allowed to swim for 6 min. Then, a time during which the mouse was immobile (immobility time) was measured for the last 4 min.

In this experiment, the animals treated with the test compounds exhibited a reduction in immobility time. This demonstrates that the test compounds are useful as antidepressants.

TABLE 8

Forced Swim Test results

| Compound | % decrease in immobility time | |
|---|---|---|
| | (dose 32 mg/kg) | (dose 64 mg/kg) |
|  | — | 37.6 ± 14.5 |

TABLE 8-continued
| | Forced Swim Test results | |
|---|---|---|
| | % decrease in immobility time | |
| Compound | (dose 32 mg/kg) | (dose 64 mg/kg) |
| 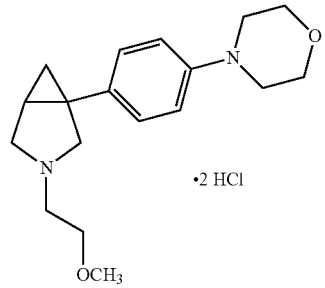 [SMILES: COCCN1CC2CC2(c2ccc(N3CCOCC3)cc2)C1] •2 HCl | — | 62.4 ± 16.3 |
| 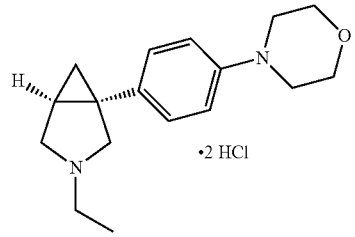 [SMILES: CCN1C[C@H]2C[C@@]2(c2ccc(N3CCOCC3)cc2)C1] •2 HCl | 87.7 ± 6.0 | — |
| 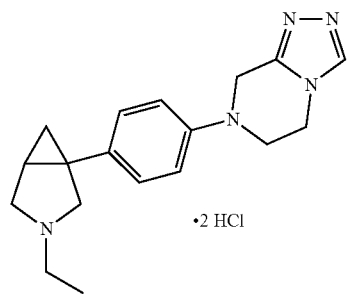 [SMILES: CCN1CC2CC2(c2ccc(N3CCn4cnnc4C3)cc2)C1] •2 HCl | — | 89.6 ± 10.4 |
| 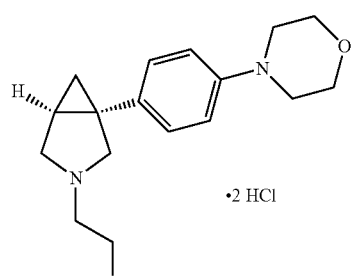 •2 HCl | — | 79.2 ± 14.9 |
| 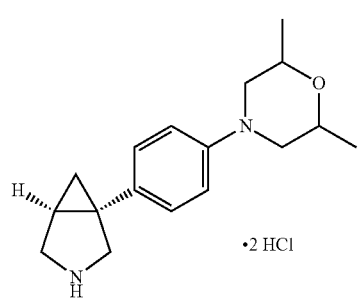 [SMILES: CC1CN(c2ccc([C@]34CNC[C@H]3C4)cc2)CC(C)O1] •2 HCl | — | 63.9 ± 4.8 |

TABLE 8-continued
| | Forced Swim Test results | |
| | % decrease in immobility time | |
| Compound | (dose 32 mg/kg) | (dose 64 mg/kg) |
| 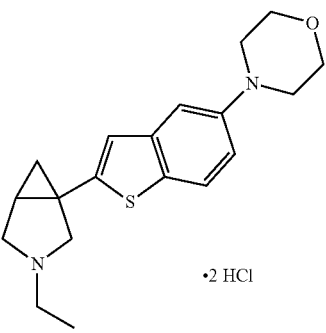 [SMILES: CCN1CC2CC2(c2cc3cc(N4CCOCC4)ccc3s2)C1] •2 HCl | — | 38.4 ± 2.7 |
| 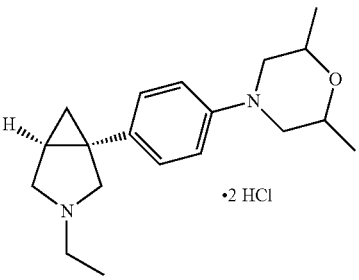 [SMILES: CCN1C[C@H]2C[C@@]2(c2ccc(N3CC(C)OC(C)C3)cc2)C1] •2 HCl | — | 92.4 ± 7.6 |
| 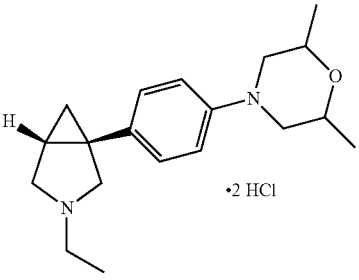 [SMILES: CCN1C[C@@H]2C[C@]2(c2ccc(N3CC(C)OC(C)C3)cc2)C1] •2 HCl | 80.9 ± 8.7 | — |
| 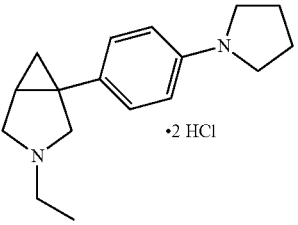 [SMILES: CCN1CC2CC2(c2ccc(N3CCCC3)cc2)C1] •2 HCl | 99.9 ± 0.1 | — |
| 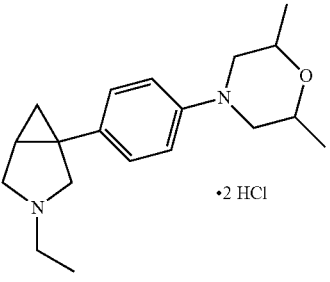 [SMILES: CCN1CC2CC2(c2ccc(N3CC(C)OC(C)C3)cc2)C1] •2 HCl | 81.6 ± 10.1 | — |

TABLE 8-continued
| | Forced Swim Test results | |
|---|---|---|
| | % decrease in immobility time | |
| Compound | (dose 32 mg/kg) | (dose 64 mg/kg) |
| 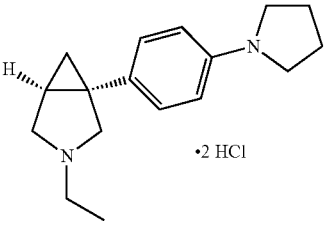 [SMILES: CCN1C[C@H]2C[C@@]2(c2ccc(N3CCCC3)cc2)C1] •2 HCl | 97.7 ± 2.3 | — |
| 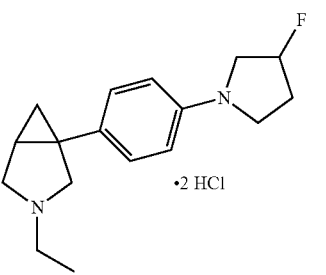 [SMILES: CCN1CC2CC2(c2ccc(N3CCC(F)C3)cc2)C1] •2 HCl | 77.1 ± 11.2 | — |
| 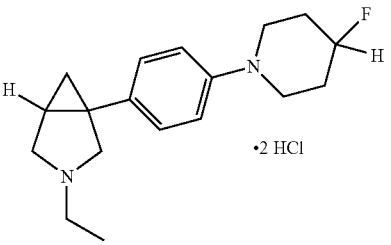 [SMILES: CCN1CC2CC2(c2ccc(N3CCC(F)CC3)cc2)C1] •2 HCl | 62.8 ± 23.4 | — |
| 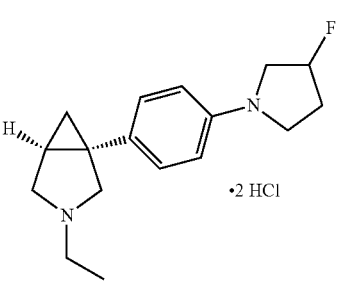 [SMILES: CCN1C[C@H]2C[C@@]2(c2ccc(N3CCC(F)C3)cc2)C1] •2 HCl | 75.5 ± 12.9 | — |
| 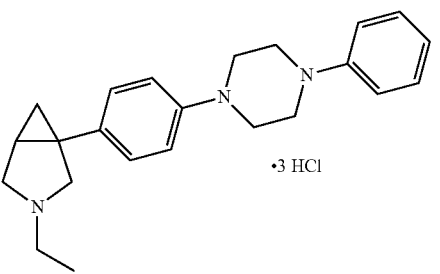 [SMILES: CCN1CC2CC2(c2ccc(N3CCN(c4ccccc4)CC3)cc2)C1] •3 HCl | — | 65.8 ± 9.9 |

TABLE 8-continued
| | Forced Swim Test results | |
|---|---|---|
| | % decrease in immobility time | |
| Compound | (dose 32 mg/kg) | (dose 64 mg/kg) |
| 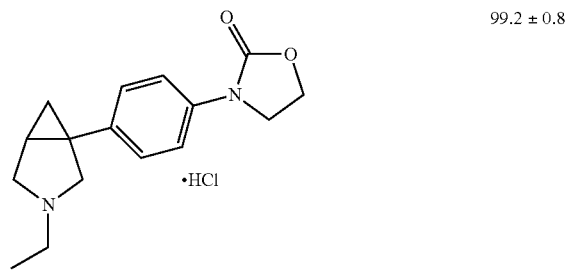 | 99.2 ± 0.8 | |
| 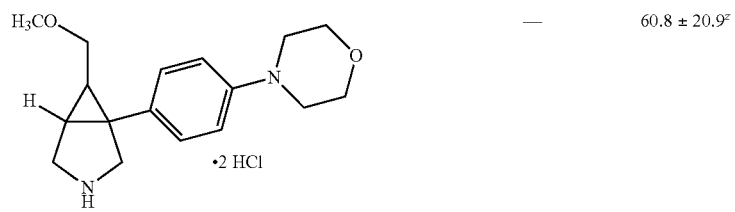 | — | 60.8 ± 20.9[z] |
| 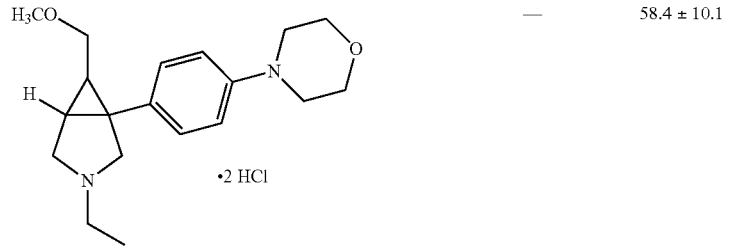 | — | 58.4 ± 10.1 |
| 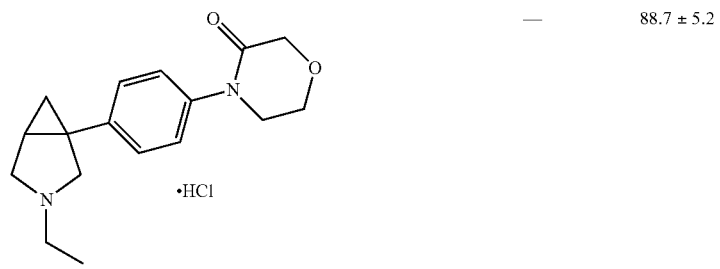 | — | 88.7 ± 5.2 |
| 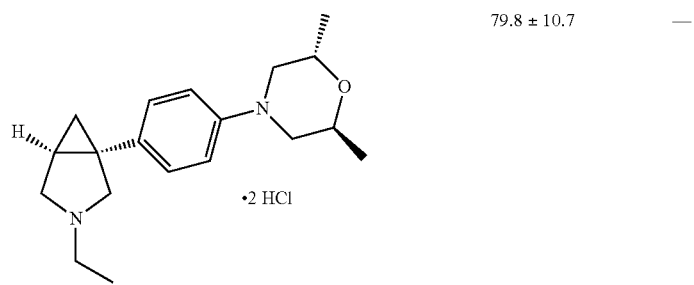 | 79.8 ± 10.7 | — |

TABLE 8-continued

Forced Swim Test results

| Compound | % decrease in immobility time | |
|---|---|---|
| | (dose 32 mg/kg) | (dose 64 mg/kg) |
| 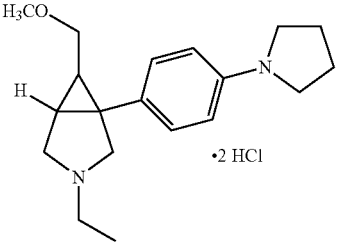 [SMILES: CCN1CC2C(COC)C2(c2ccc(N3CCCC3)cc2)C1] ·2 HCl | 97.2 ± 1.2 | — |
| 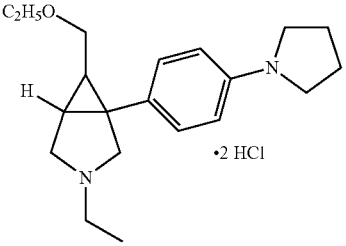 ·2 HCl | 80.6 ± 13.7 | — |

$^z$Vehicle—0.25% CMC

Depending upon the selection of different types of substituents in compounds of Formula I the specificity or affinity for the different targets varied. The compounds of the Formula Ia show antimicrobial activity whereas compounds of Formula Ib show activity against central and/or peripheral nervous system disorders, selectively. The selected few compounds of the Formula Ia when screened for activity against central and/or peripheral nervous system disorders and the selected few compounds of Formula Ib when screened for antimicrobial activity, were found to be inactive. The results are given in Table 9.

TABLE 9

In-vitro antimicrobial activity MICs (µg/mL)/Forced Swim Test results time Table

| Compound | Antimicrobial activity (in vitro MIC in µg/mL) | | | | CNS Activity (in vivo FST) % decrease in immobility time (dose 32 mg/kg) |
|---|---|---|---|---|---|
| | ATCC 29213 | ATCC 33591 | ATCC 29212 | ATCC 700221 | |
| 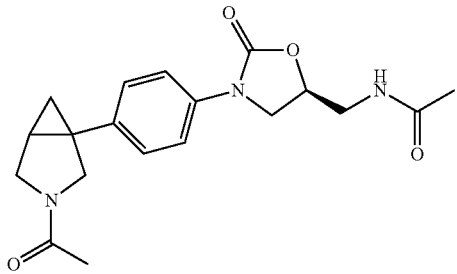 [SMILES: CC(=O)NC[C@H]1CN(c2ccc(C34CC3CN(C(C)=O)C4)cc2)C(=O)O1] | 2 | 1 | 2 | 2 | NE* |

TABLE 9-continued

In-vitro antimicrobial activity MICs (μg/mL)/Forced Swim Test results time Table

| Compound | Antimicrobial activity (in vitro MIC in μg/mL) | | | | CNS Activity (in vivo FST) % decrease in immobility time (dose 32 mg/kg) |
|---|---|---|---|---|---|
| | ATCC 29213 | ATCC 33591 | ATCC 29212 | ATCC 700221 | |
| [structure: 1-acetyl-azabicyclic-phenyl-oxazolidinone-CH2OH] | 4 | 2 | 4 | 4 | 5.1 ± 1.4 |
| [structure: N-ethyl-azabicyclic-phenyl-pyrrolidine] · 2 HCl | >32 | >32 | >32 | >32 | 99.9 ± 0.1 |
| [structure: N-ethyl-azabicyclic-phenyl-morpholine] · 2 HCl | >32 | >32 | >32 | >32 | 81.0 ± 7.1* |
| [structure: NH-azabicyclic-phenyl-morpholine] · 2 HCl | >32 | >32 | >32 | >32 | 84.8* |
| [structure: H3CO-CH2-cyclopropyl-N-ethyl-azabicyclic-phenyl-pyrrolidine] · 2 HCl | >32 | >32 | >32 | >32 | 97.2 ± 1.2 |

TABLE 9-continued

In-vitro antimicrobial activity MICs (μg/mL)/Forced Swim Test results time Table

| Compound | Antimicrobial activity (in vitro MIC in μg/mL) | | | | CNS Activity (in vivo FST) % decrease in immobility time (dose 32 mg/kg) |
|---|---|---|---|---|---|
| | ATCC 29213 | ATCC 33591 | ATCC 29212 | ATCC 700221 | |
| [structure] ·HCl | >32 | >32 | >32 | >32 | 99.2 ± 0.8 |

*dose 64 mg/kg/p.o

The invention claimed is:

1. A compound of Formula Ib,

Formula Ib

[structure]

or its tautomeric forms, stereoisomers including R and S isomers, or pharmaceutically acceptable salts thereof, wherein:

ring A is phenyl;

ring B is morphonilyl, attached to ring A through a nitrogen atom at any available position of ring A, ring B can further be fused to one or more aryl;

$R^1$, $R^2$ and $R^4$ are independently selected from —H, $C_{1-12}$ alkyl, $C_{2-12}$ alkenyl, $C_{2-12}$ alkynyl, $C_{1-12}$ alkoxyalkyl, $C_{3-20}$ cycloalkyl, —$COR^a$, —$COOR^a$, —$CONR^aR^b$, and —$SO_2R^a$ each of which may be optionally substituted at any available position by one or more substituents selected from but not limited to halogen, —$OR^a$;

$R^3$ represents —$(CH_2)_pZ$;

Z is selected from —H or —$OR^a$;

$R^5$ is independently selected from —H, halogen;

$R^6$ is independently selected from —H or $C_{1-12}$ alkyl;

Q is O;

$R^a$ and $R^b$ are same or different and can independently be selected from —H, $C_{1-12}$ alkyl, $C_{3-20}$ cycloalkyl, heterocyclyl, aryl, heteroaryl;

m is 0, 1, 2, 3 or 4;

r is 0, 1, 2, 3 or 4;

p is 0, 1, 2, 3, 4, 5, 6, 7, 8, 9 or 10;

s is 0, 1, 2, 3 or 4.

2. The compound according to claim 1 having the Formula Ib, wherein ring B is selected from the group consisting of

[structures of morpholine variants] and [structure]

3. The compound according to claim 1 having the Formula Ib, wherein $R^1$ is selected from the group consisting of —H, $C_{1-4}$ alkyl, $C_{2-4}$ alkenyl, $C_{2-4}$ alkynyl, $C_{1-4}$ alkoxyalkyl, $C_{3-7}$ cycloalkyl, $COOR^a$, —$CONR^aR^b$—$COR^a$ and —$SO_2R^a$.

4. The compound according to claim 1 having the Formula Ib, wherein $R^2$ is hydrogen.

5. The compound according to claim 1 having the Formula Ib, wherein $R^3$ is hydrogen.

6. The compound according to claim 1 having the Formula Ib, wherein $R^4$ is hydrogen.

7. The compound according to claim 1 having the Formula Ib, wherein $R^5$ is selected from —H or halogen.

8. The compound according to claim 1 having the Formula Ib, wherein $R^6$ is selected from the group consisting of —H and $C_{1-4}$ alkyl.

9. A compound which is selected from the group consisting of:

[structure]

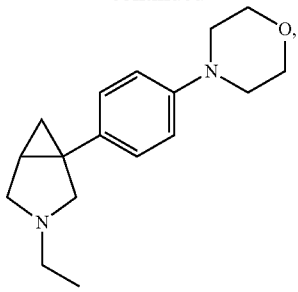
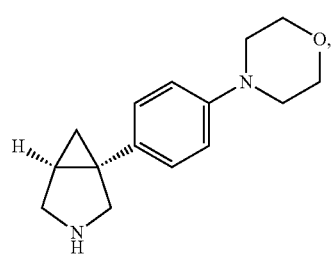
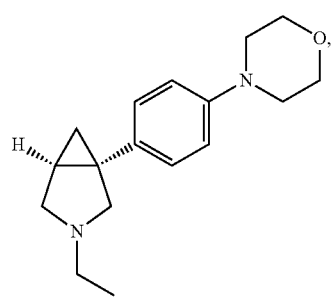
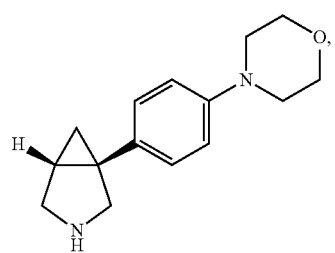
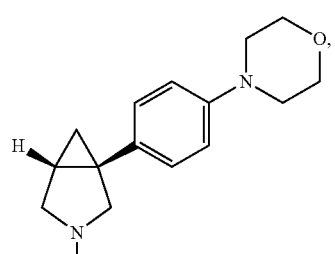
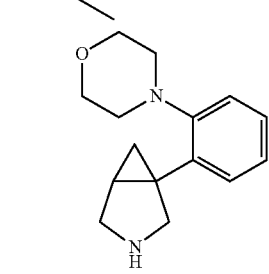
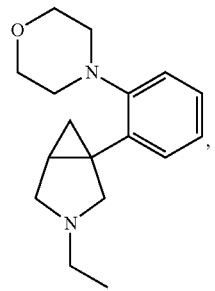
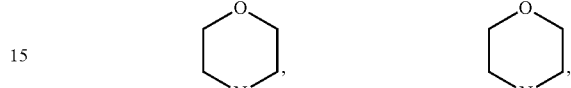
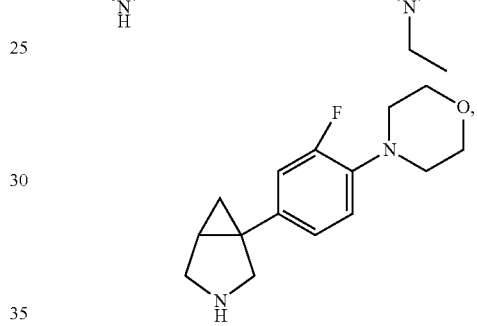
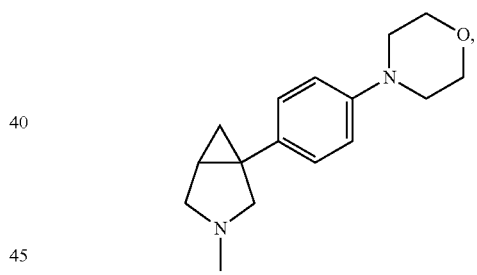
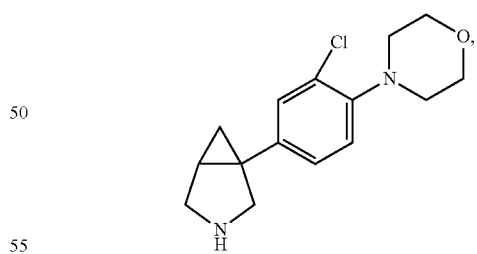
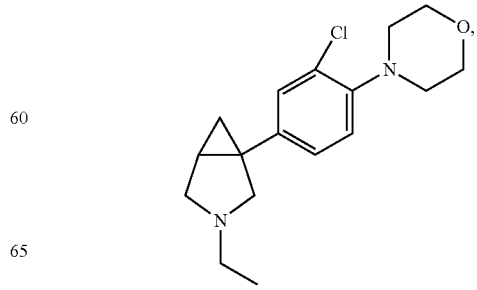

173
-continued
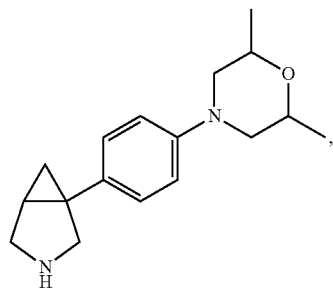
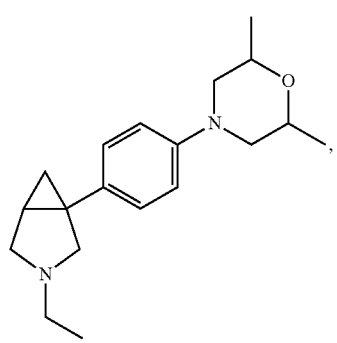
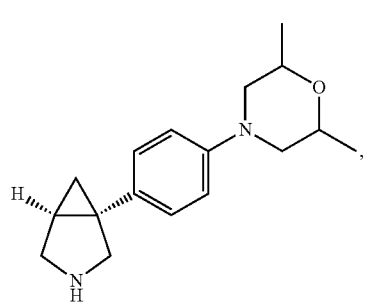
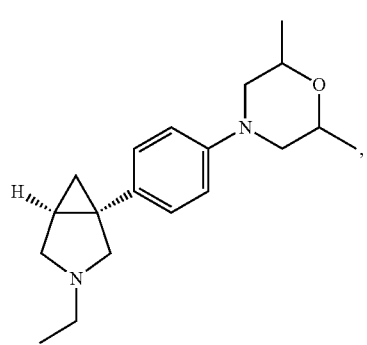
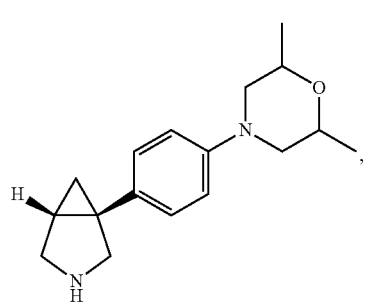
174
-continued
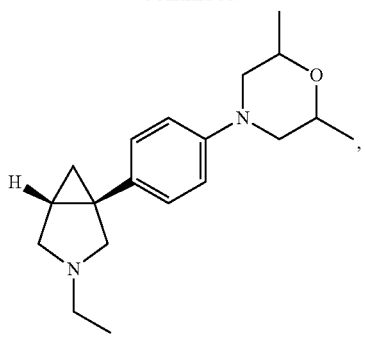
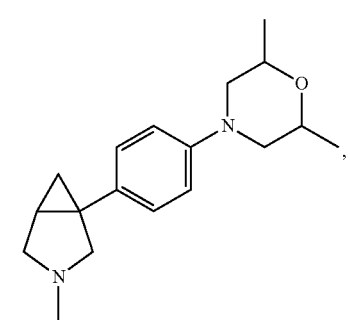
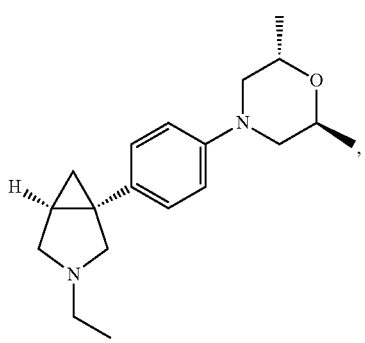
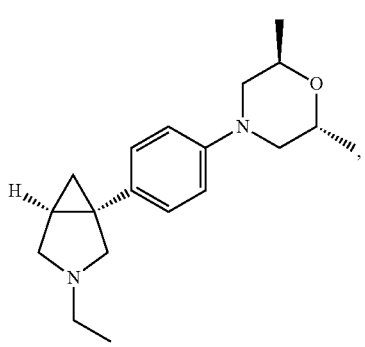
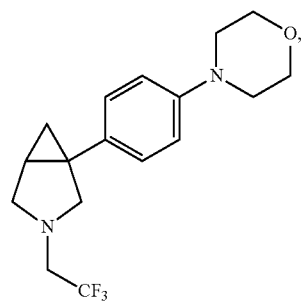

-continued
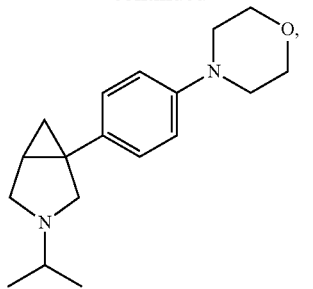
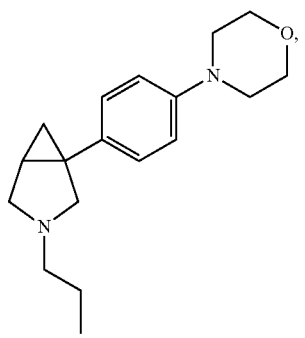
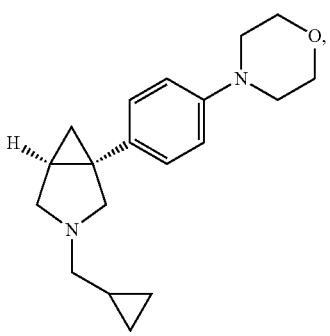
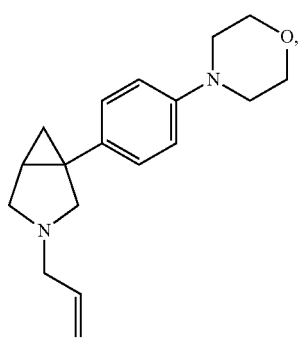
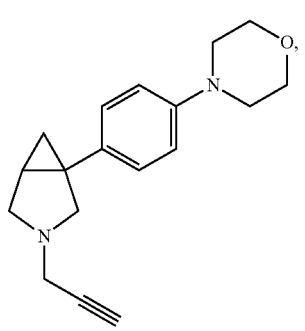
-continued
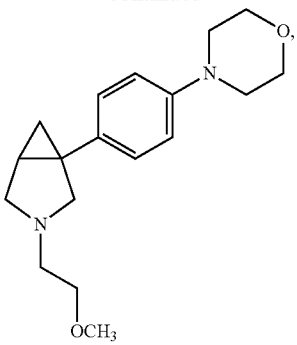
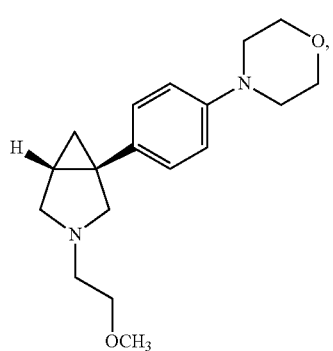
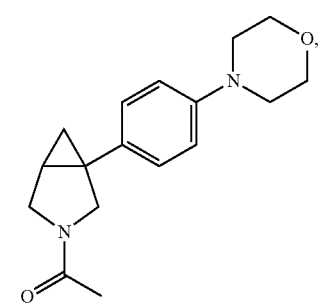
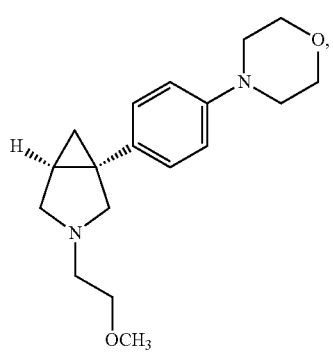
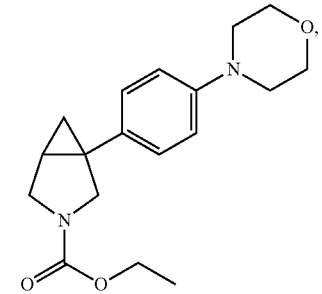

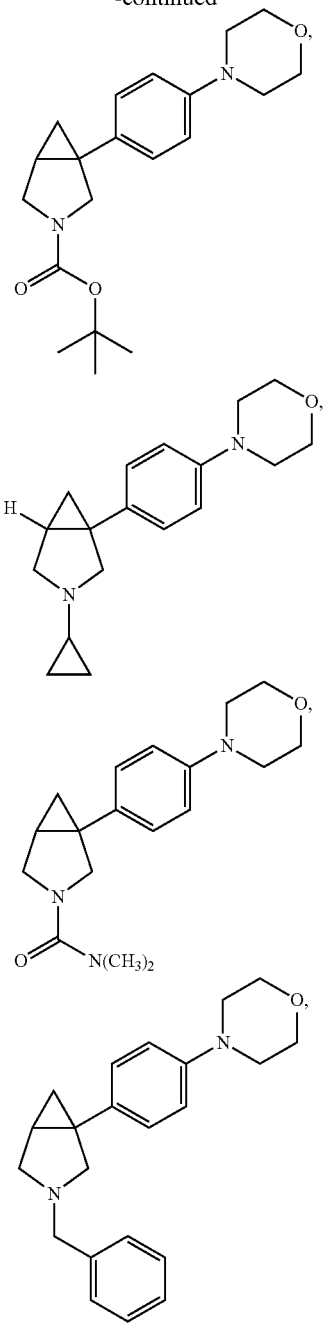

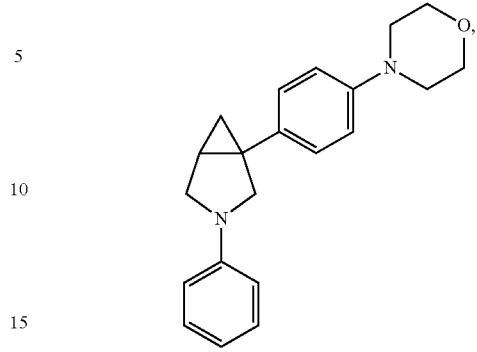

and its pharmaceutically acceptable salts thereof.

10. A compound which is selected from the group consisting of:

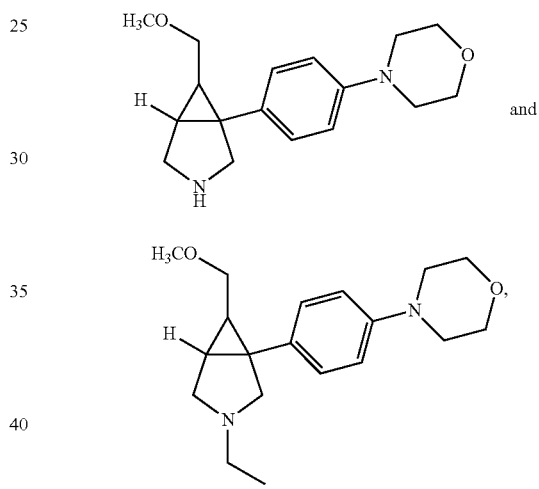

and its pharmaceutically acceptable salts or solvates thereof.

11. A pharmaceutical composition, comprising a compound according to claim 1, or its tautomeric forms, stereoisomers or pharmaceutically acceptable salts thereof, optionally in combination with one or more pharmaceutically acceptable carrier(s).

* * * * *